US012636372B2

(12) United States Patent
Blake et al.

(10) Patent No.: US 12,636,372 B2
(45) **Date of Patent: *May 26, 2026**

(54) IMMOLATIVE CELL-PENETRATING COMPLEXES FOR NUCLEIC ACID DELIVERY TO THE LUNG

(71) Applicant: The Board of Trustees of the Leland Stanford Junior University, Stanford, CA (US)

(72) Inventors: Tim R. Blake, Stanford, CA (US); Paul Wender, Stanford, CA (US); Robert Waymouth, Stanford, CA (US); Ronald Levy, Stanford, CA (US); Ole Haabeth, Stanford, CA (US); Rebecca Mcclellan, Stanford, CA (US); Adrienne Sallets, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 18/428,147

(22) Filed: Jan. 31, 2024

(65) Prior Publication Data

US 2024/0277854 A1 Aug. 22, 2024

Related U.S. Application Data

(63) Continuation of application No. 17/427,362, filed as application No. PCT/US2020/016281 on Jan. 31, 2020, now Pat. No. 11,931,416.

(Continued)

(51) Int. Cl.

*A61K 47/59* (2017.01)
*A61K 9/00* (2006.01)

(Continued)

(52) U.S. Cl.

CPC ............ *A61K 47/593* (2017.08); *A61K 9/007* (2013.01); *A61K 47/549* (2017.08);

(Continued)

(58) Field of Classification Search

None

See application file for complete search history.

(56) References Cited

U.S. PATENT DOCUMENTS

| | | | |
|---|---|---|---|
| 5,034,506 | A | 7/1991 | Summerton |
| 5,235,033 | A | 8/1993 | Summerton |

(Continued)

FOREIGN PATENT DOCUMENTS

| | | | |
|---|---|---|---|
| CN | 101180395 A | 5/2008 | |
| WO | 2013036532 A1 | 3/2013 | |

(Continued)

OTHER PUBLICATIONS

Adams et al., "Highly Specific in Vivo Tumor Targeting by Monovalent and Divalent Forms of 741F8 Anti-c-erbB-2 Single-Chain Fv", Cancer Research, 53(17):4026-4034 (Sep. 1, 1993).

(Continued)

*Primary Examiner* — Rachel Kahn
(74) *Attorney, Agent, or Firm* — KDW Firm PLLC

(57) ABSTRACT

There are provided herein, inter alia, complexes, compositions and methods for the delivery of therapeutic, diagnostic and imaging agents, including nucleic acid, into a cell. The complexes, compositions and methods may facilitate complexation, protection, delivery and release of oligonucleotides and polyanionic cargos into lung cells and lung tissue, both in vitro and in vivo.

20 Claims, 41 Drawing Sheets

REVERSE BLOCK (TYPE A):

FORWARD BLOCK (TYPE B):

Related U.S. Application Data

(60) Provisional application No. 62/800,406, filed on Feb. 1, 2019.

(51) Int. Cl.

| | |
|---|---|
| ***A61K 47/54*** | (2017.01) |
| ***A61K 48/00*** | (2006.01) |
| ***C08G 63/08*** | (2006.01) |
| ***C08G 63/64*** | (2006.01) |
| ***C08G 63/685*** | (2006.01) |
| ***C08G 73/02*** | (2006.01) |

(52) U.S. Cl.

CPC .......... *A61K 48/0041* (2013.01); *C08G 63/08* (2013.01); *C08G 63/64* (2013.01); *C08G 63/685* (2013.01); *C08G 73/028* (2013.01); *C08G 73/0293* (2013.01)

(56) References Cited

U.S. PATENT DOCUMENTS

| | | | |
|---|---|---|---|
| 2003/0185788 | A1 | 10/2003 | Rothbard |
| 2008/0234183 | A1 | 9/2008 | Hallbrink |
| 2015/0239947 | A1 | 8/2015 | Brinkmann |
| 2018/0028688 | A1 | 2/2018 | Waymouth |

FOREIGN PATENT DOCUMENTS

| | | | |
|---|---|---|---|
| WO | 2018022930 | A1 | 2/2018 |
| WO | 2020160511 | A1 | 8/2020 |

OTHER PUBLICATIONS

Benner, Nancy L et al. "Functional DNA Delivery Enabled by Lipid-Modified Charge-Altering Releasable Transporters (CARTs)." Biomacromolecules vol. 19,7 (2018): 2812-2824. doi:10.1021/acs.biomac.8b00401.

Berge et al., "Pharmaceutical Salts", Journal of Pharmaceutical Sciences, 66(1):1-19 (Jan. 1977).

Blake et al., "Organocatalytic Ring-Opening Polymerization of Morpholinones: New Strategies to Functionalized Polyesters", Journal of the American Chemical Society, 136(26):9252-9255 (Jun. 19, 2014).

Cooley et al., "Oligocarbonate Molecular Transporters: Oligomerization-based Syntheses and Cell-penetrating Studies", Journal of the American Chemical Society, 131(45):16401-16403 (Nov. 18, 2009).

Dove et al., "Thiourea-Based Bifunctional Organocatalysis: Supramolecular Recognition for Living Polymerization", Journal of the American Chemical Society, 127(40):13798-13799 (Oct. 1, 2005).

European Search Report and Written Opinion for the Application No. EP20747817, mailed Sep. 29, 2022, 9 pages.

Ford et al., "Protein Transduction: An Alternative to Genetic Intervention", Gene Therapy, 8(1):1-4 (Jan. 2001).

Geihe et al., "Designed Guanidinium-Rich Amphipathic Oligocarbonate Molecular Transporters Complex, Deliver and Release Sirna in Cells", Proceedings of the National Academy of Sciences of the United States of America, 109 (33):13171-13176 (Aug. 14, 2012).

Gruber et al., "Efficient Tumor Cell Lysis Mediated by a Bispecific Single Chain Antibody Expressed in *Escherichia coli*", The Journal of Immunology, 152(11):5368-5374 (Jun. 1, 1994).

Holliger et al., "Diabodies": Small Bivalent and Bispecific Antibody Fragments, Proceedings of the National Academy of Sciences of the United States of America, 90(14):6444-6448 (Jul. 15, 1993).

Hu et al., "Minibody: A Novel Engineered Anti-Carcinoembryonic Antigen Antibody Fragment (Single- Chain Fv-CH3) Which Exhibits Rapid, High-Level Targeting of Xenografts", Cancer Research, 56:3055-3061 (Jul. 1, 1996).

Kostelny et al., "Formation of A Bispecific Antibody by the Use of Leucine Zippers", Journal of Immunology, 148(5):1547-1553 (Mar. 1, 1992).

Mccafferty et al., "Phage Antibodies: Filamentous Phage Displaying Antibody Variable Domains", Nature, 348(6301):552-554 (Dec. 6, 1990).

Mccartney et al., "Engineering Disulfide-linked Single-chain Fv Dimers [(Sfv)2] with Improved Solution and Targeting Properties: Anti-digoxin 26-10 (Sfv)2 and Anti-c-erbb-2 741f8 (Sfv)2 Made by Protein Folding and Bonded Through C-terminal Cysteinyl Peptides", Protein Engineering, 8(3):301-314 (Mar. 1995).

Mckinlay et al. "Charge-Altering Releasable Transporters (CARTs) for the Delivery and Release of Mrna in Living Animals", Proceedings of the National Academy of Sciences of the United States of America, 114(4): E448-E456 (Jan. 9, 2017).

Pack et al., "Miniantibodies: Use of Amphipathic Helices to Produce Functional, Flexibly Linked Dimeric Fv Fragments With High Avidity in *Escherichia coli*", Biochemistry, 31(6):1579-1584 (Feb. 18, 1992).

Pratt et al., "Tagging Alcohols With Cyclic Carbonate: A Versatile Equivalent of (Meth)acrylate For Ring-opening Polymerization", Chemical Communication, 1:114-116 (2008).

Pratt et al., "Exploration, Optimization, and Application of Supramolecular Thiourea-Amine Catalysts for the Synthesis of Lactide (Co)polymers", Macromolecules, 39(23):7863-7871 (Oct. 18, 2006).

Prochiantz et al., "For Protein Transduction, Chemistry Can Win Over Biology", Nature Methods, 4 (2):119-120 (Feb. 2007).

Zhu et al., "Remodeling Domain Interfaces to Enhance Heterodimer Formation", Protein Science, 6:781-788 (1997).

POLY(N-HYDROXYETHYL LYSINE)

DKP

N-HYDROXYETHYL GLYCINE

POLY(N-HYDROXYETHYL LYSINE)

N-HYDROXYETHYL LYSINE

CART-GLY

CART-LYS

CART-MIX (1:1 RATIO)

237+/-4.5 nm

145+-33 nm

168+- 21.6 nm

BDK-CART-LYS

BDK-CART-GLY

CART 12: R=DODECYL, R'=none

| ENTRY | DP (DOD) (n) | DP (ORN) (m) | FORWARD OR REVERSE | END GROUP |
|---|---|---|---|---|
| 1 | 31 | 10 | REVERSE | H |
| 2 | 15 | 5 | REVERSE | H |
| 3 | 14 | 7 | REVERSE | H |
| 4 | 16 | 15 | FORWARD | ACETYL |

IMMOLATIVE CELL-PENETRATING COMPLEXES FOR NUCLEIC ACID DELIVERY TO THE LUNG

CROSS REFERENCE TO RELATED APPLICATIONS

This application is a continuation of U.S. application Ser. No. 17/427,362 filed Jul. 30, 2021, which is a 371 of international application no. PCT/US2020/16281 filed Jan. 31, 2020 which claims the benefit of U.S. Provisional Application No. 62/800,406, filed Feb. 1, 2019, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under contract CA197353 awarded by the National Institutes of Health. The Government has certain rights in the invention.

BACKGROUND

There is a need for new materials and strategies that enable or enhance the delivery of therapeutic agents, diagnostic probes and/or research tools across the plasma membrane of cells and other biological barriers, as required for a wide range of clinical, diagnostic and/or research applications. The delivery of such cargo, e.g., nuclei acids, has considerable clinical potential in connection with vaccination strategies for infectious diseases, cancer immunotherapy, protein therapy and gene editing. Provided herein are solutions to these and other problems in the art.

BRIEF SUMMARY

In a first aspect, a cell-penetrating complex including a nucleic acid non-covalently bound to a cationic amphipathic polymer is provided, the cationic amphipathic polymer including a pH-sensitive immolation domain and a lipophilic polymer domain, wherein the cationic amphipathic polymer has the formula:

(XII)

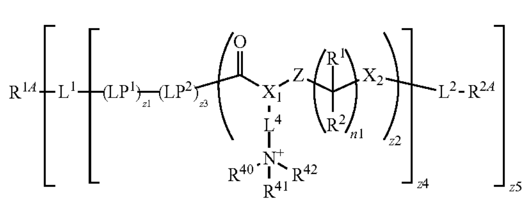

or (XIII)

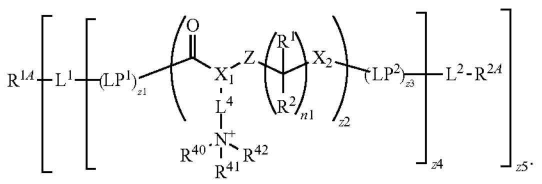

In Formula (XII) and (XIII), $R^{1A}$ is hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ is hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$LP^1$ and $LP^2$ are independently a lipophilic polymer domain.

$X^1$ is a bond, $—C(R^5)(R^6)—$, $—C(R^5)(R^6)—C(R^7)(R^8)—$, $—O—C(R^5)(R^6)—$, or $—O—C(R^5)(R^6)—C(R^7)(R^8)—$.

$X^2$ is —O— or —S—.

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$L^4$ is a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene.

$R^{40}$, $R^{41}$, and $R^{42}$ are independently hydrogen, substituted or unsubstituted alkyl or substituted or unsubstituted heteroalkyl.

Z is —S—, $—S^+R^{13}—$, $—NR^{13}—$, or $—N^+(R^{13})(H)—$.

$R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $—SO_2NH_2$, $—OCCl_3$, $—OCF_3$, $—OCBr_3$, $—OCI_3$, $—OCHCl_2$, $—OCHBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

n1 is an integer from 0 to 50.

z1 and z3 are independently integers from 0 to 100, wherein at least one of z1 or z3 is not 0.

z4 is an integer from 1 to 100.

z2 is an integer from 2 to 100; and z5 is an integer from 1 to 10.

In another aspect, a cell-penetrating complex including a nucleic acid non-covalently bound to a cationic amphipathic polymer is provided, the cationic amphipathic polymer including a pH-sensitive immolation domain and a lipophilic polymer domain, wherein the cationic amphipathic polymer has the formula:

(XIV)

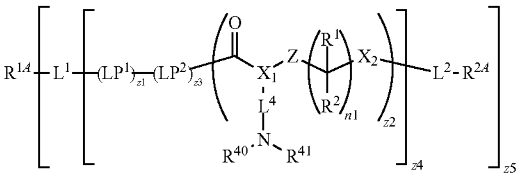

or (XV)

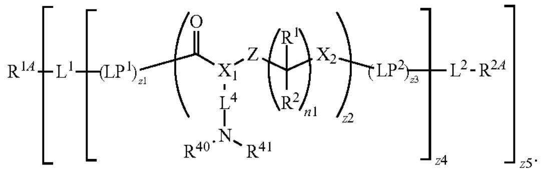

In Formula (XIV) and (XV), $R^{1A}$ is hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ is hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$LP^1$ and $LP^2$ are independently a lipophilic polymer domain.

$X^1$ is a bond, $—C(R^5)(R^6)—$, $—C(R^5)(R^6)—C(R^7)(R^8)—$, $—O—C(R^5)(R^6)—$, or $—O—C(R^5)(R^6)—C(R^7)(R^8)—$.

$X^2$ is —O— or —S—.

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$L^4$ is a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene.

$R^{40}$ and $R^{41}$ are independently hydrogen, substituted or unsubstituted alkyl or substituted or unsubstituted heteroalkyl.

Z is —S—, $—S^+R^{13}—$, $—NR^{13}—$ or $—N^+(R^{13})(H)—$.

$R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $—SO_2NH_2$, $—OCCl_3$, $—OCF_3$, $—OCBr_3$, $—OCI_3$, $—OCHCl_2$, $—OCHBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

n1 is an integer from 0 to 50.

z1 and z3 are independently integers from 0 to 100, wherein at least one of z1 or z3 is not 0.

z4 is an integer from 1 to 100.

z2 is an integer from 2 to 100; and z5 is an integer from 1 to 10.

In one aspect is provided a complex including a nucleic acid non-covalently bound to a cationic amphipathic polymer, wherein the cationic amphipathic polymer has the formula:

(XII)

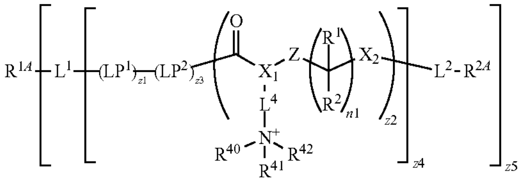

or (XIII)

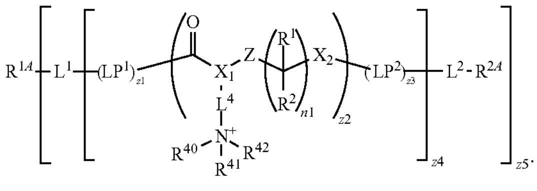

wherein $R^{1A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, independently —COOH, $—CONH_2$, $—NO_2$, —SH, $—SO_3H$, $—SO_4H$, $—SO_2NH_2$, $—NHNH_2$, $—ONH_2$, independently $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, $—C(R^5)(R^6)—$, $—C(R^5)(R^6)—C(R^7)(R^8)—$, $—O—C(R^5)(R^6)—$, or $—O—C(R^5)(R^6)—C(R^7)(R^8)—$;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, $—S^+R^{13}—$, $—NR^{13}—$ or $—N^+(R^{13})(H)—$;

$R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $SO_2NH_2$, $—OCCl_3$, $—OCF_3$, $—OCBr_3$, $—OCI_3$, $—OCHCl_2$, $—OCHBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z1 or z3 is not 0;

z2 is an integer from 2 to 100;

z4 is an integer from 1 to 100; and z5 is an integer from 1 to 10.

In one aspect is provided a cell-penetrating complex including a nucleic acid non-covalently bound to a cationic amphipathic polymer, wherein the cationic amphipathic polymer has the formula:

(XII)

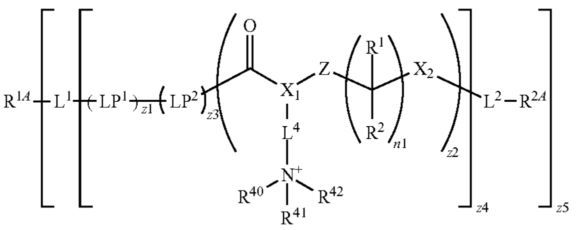

or (XIII)

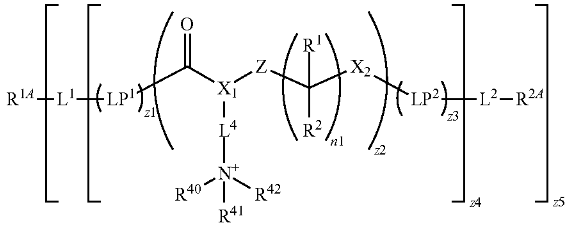

wherein $R^{1A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, independently —COOH, $—CONH_2$, $—NO_2$, —SH, $—SO_3H$, $—SO_4H$, $—SO_2NH_2$, $—NHNH_2$, $—ONH_2$, independently $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain; $X^1$ is a bond, $—C(R^5)(R^6)—$, $—C(R^5)(R^6)—C(R^7)(R^8)—$, $—O—C(R^5)(R^6)—$, or $—O—C(R^5)(R^6)—C(R^7)(R^8)—$;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, $—S^+R^{13}—$, $—NR^{13}—$, or $—N^+(R^{13})(H)—$;

$R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $—SO_2NH_2$, $—OCCl_3$, $—OCF_3$, $—OCBr_3$, $—OCI_3$, $—OCHCl_2$, $—OCHBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z1 or z3 is not 0; z2 is an integer from 2 to 100; z4 is an integer from 1 to 100; and z5 is an integer from 1 to 10.

In one aspect is provided a cell penetrating complex including a nucleic acid non-covalently bound to a first cationic amphipathic polymer and a second amphipathic polymer, wherein the first cationic amphipathic polymer has the formula:

(XII)

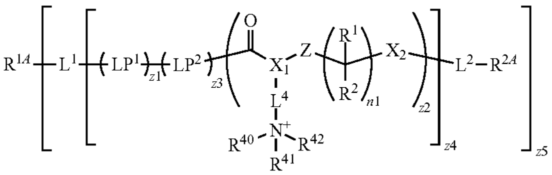

or (XIII)

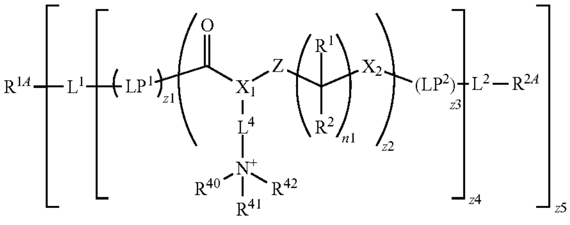

wherein $R^{1A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCH_{12}$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, independently —COOH, $—CONH_2$, $—NO_2$, —SH, $—SO_3H$, $—SO_4H$, $—SO_2NH_2$, $—NHNH_2$, $—ONH_2$, independently $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, $—C(R^5)(R^6)—$, $—C(R^5)(R^6)—C(R^7)(R^8)—$, $—O—C(R^5)(R^6)—$, or $—O—C(R^5)(R^6)—C(R^7)(R^8)—$;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, $—S^+R^{13}—$, $—NR^{13}—$, or $—N^+(R^{13})(H)—$;

$R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $SO_2NH_2$, $—OCCl_3$, $—OCF_3$, $—OCBr_3$, $—OCI_3$, $—OCHCl_2$, $—OCHBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z1 or z3 is not 0;

z2 is an integer from 2 to 100;

z4 is an integer from 1 to 100;

z5 is an integer from 1 to 10; and wherein the first cationic amphipathic polymer and the second amphipathic polymer are different.

In another aspect is provided a nanoparticle composition including a plurality of cell-penetrating complexes as provided herein, including embodiments thereof.

In another aspect is provided a pharmaceutical composition including a cell-penetrating complex as provided herein, including embodiments thereof.

In another aspect a method of transfecting a nucleic acid into a cell is provided. The method includes contacting a cell with a cell-penetrating complex as provided herein, including embodiments thereof.

In another aspect is provided a method of delivering a nucleic acid to the lung of a subject in need thereof, the method including administering to said subject a cell-penetrating complex as provided herein, including embodiments thereof.

In another aspect a method of treating a lung disease in a subject in need thereof is provided. The method includes administering a therapeutically effective amount of a cell-penetrating complex as provided herein, including embodiments thereof.

In another aspect a method of delivering a nucleic acid to a plurality of tissues in a subject in need thereof is provided. The method includes administering a first cell-penetrating complex and a second cell-penetrating complex to the subject, wherein the first cell-penetrating complex is the cell-penetrating complex as provided herein, including embodiments thereof, and wherein the first cell-penetrating complex and the second cell-penetrating complex are chemically different.

In another aspect a method of delivering a nucleic acid to a plurality of tissues in a subject in need thereof is provided. The method includes administering a first amphipathic polymer and a second amphipathic polymer to the subject, wherein the first amphipathic polymer is an amphipathic polymer as provided herein, including embodiments thereof, and wherein the first amphipathic polymer and the second amphipathic polymer are chemically different.

In one aspect is provided a method of transfecting a nucleic acid into a reticulocyte, the method including contacting a cell with a cell-penetrating complex as described herein, including embodiments thereof.

In one aspect is provided a method of transfecting a nucleic acid into a hematopoietic stem cell, the method including contacting a cell with a cell-penetrating complex as described herein, including embodiments.

BRIEF DESCRIPTION OF THE DRAWINGS

(FIG. 1A) Several homo-polymers were dissolved in pH 6.5 buffer and monitored for degradation products using $^1$H NMR. (FIG. 1B-1D) The kinetics of degradation for several homo-polymers is shown.

(FIG. 2A) DLS sizing measurements of mRNA CART NPs (FIG. 2B) mRNA release assay using an intercalating fluorophore (q-Bit) to monitor mRNA encapsulation over time. (FIG. 2C) DLS was used to monitor mRNA-CART-NP size over time when exposed to Media. (FIG. 2D) Zeta potential was used to measure surface charge of mRNA-CART-NPs over time.

(FIG. 4A) 5 ug Flluc mRNA administered IV. At 8 hours BLI was performed. The variable n on left of the structure on the top left of FIG. 4A can be 13 and the variable n on right of the structure on the top left of FIG. 4A can be 11. Therefore, the structure may be:

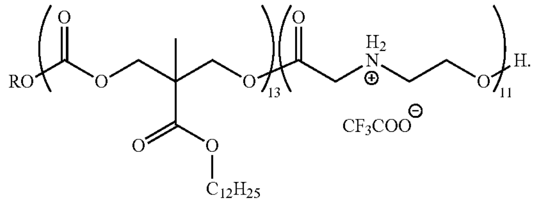

Figure 5A:
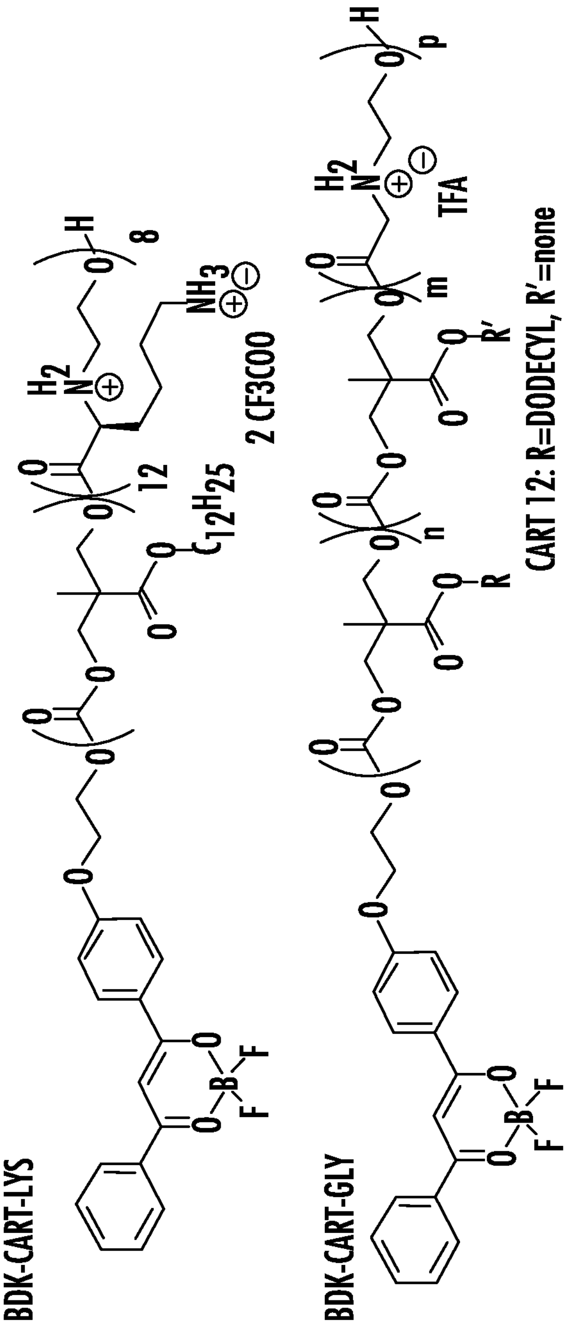
Figure 5B:
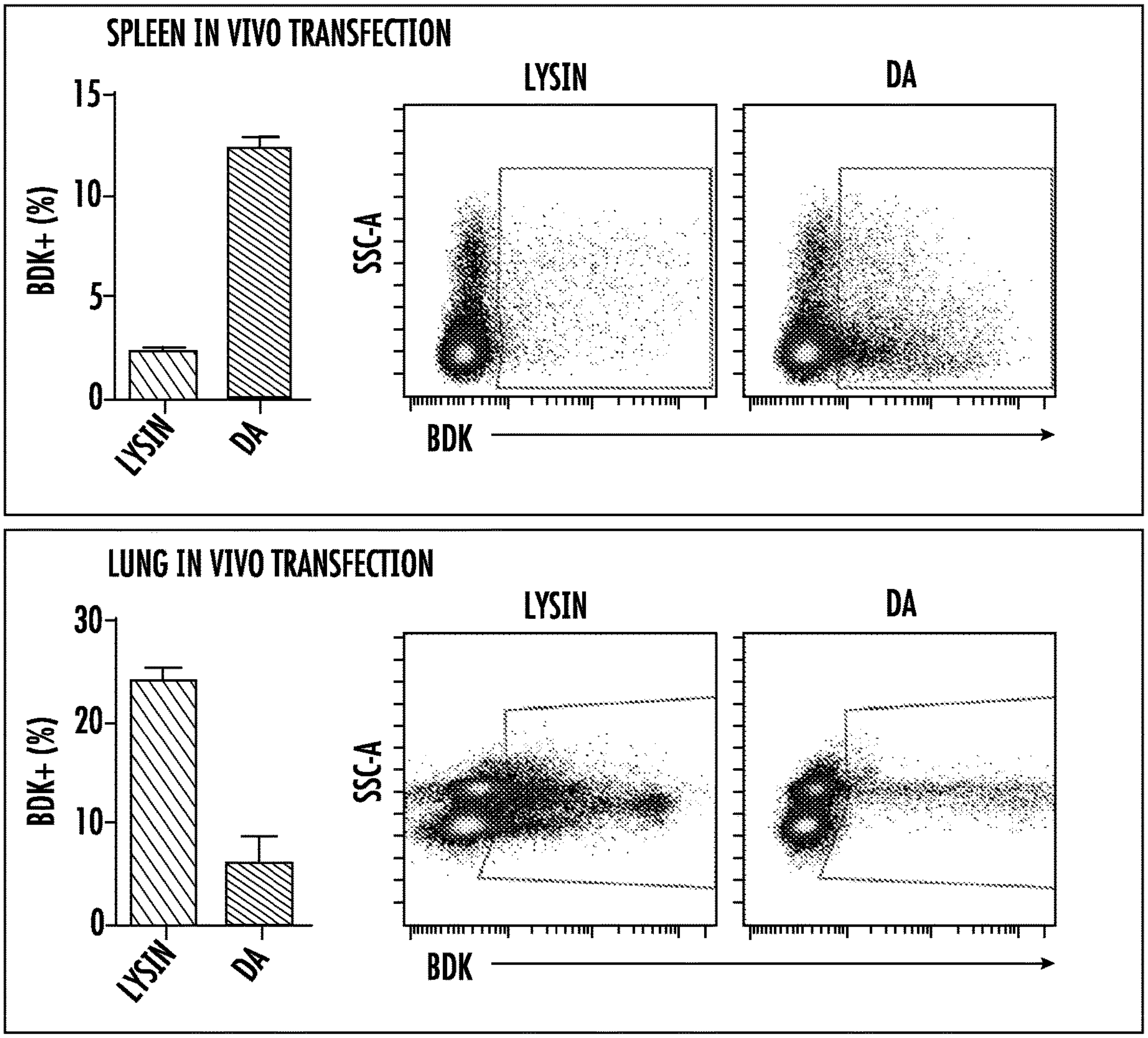

FIGS. 5A-5B show fluorescent CARTs used for phenotyping. (FIG. 5A) Two fluorescent CARTs: BDK-CART-lys (lysine CART functionalized with a difluoroboron-β-diketonate fluorophore) and BDK-CART-gly (glycine CART functionalized with a difluoroboron-β-diketonate fluorophore; n=13, m=0, p=11). (FIG. 5B) Spleen and lung after transfection.

Figure 6A:
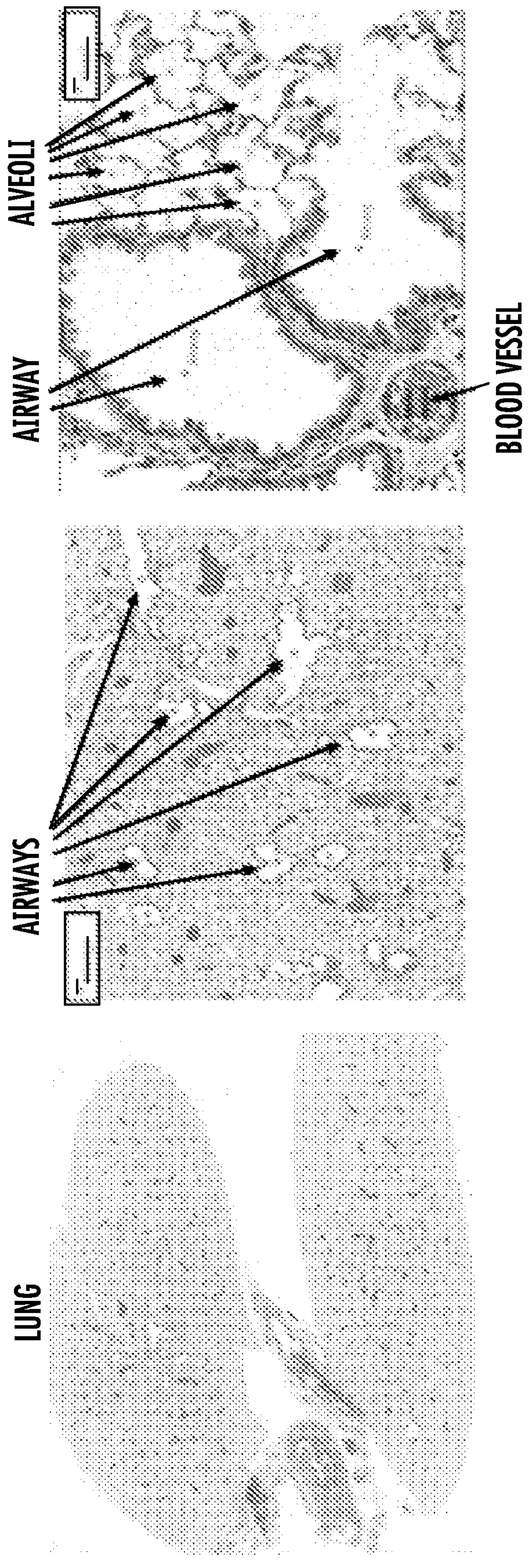
Figure 6B:
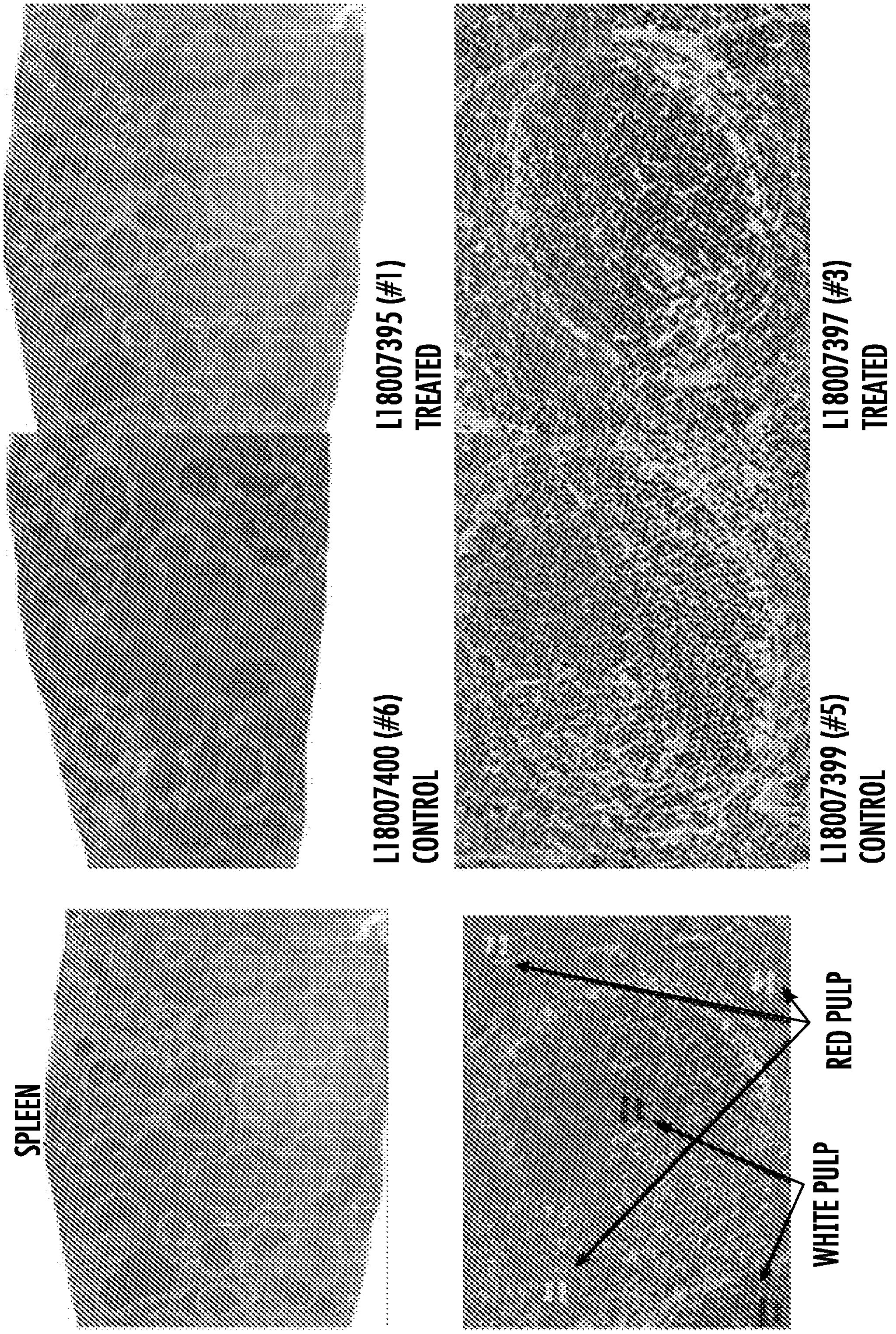

FIGS. 6A-6B show pathological studies. IV treatment with 10 ug mRNA. Mice were sacrificed at 8 hours, then organs were harvested, frozen, and sectioned. Histologic findings: microscopic findings: Examined are sections of heart, lung, liver, spleen, kidney, cerebrum, cerebellum, eyes, reproductive tract, salivary gland, pancreas, tongue, trachea, thyroid gland, esophagus, stomach, small intestine, large intestine, white adipose tissue, brown adipose tissue, thymus, lymph nodes, and haired skin. All tissues examined are histologically within normal limits. There were no obvious changes that could be resolved by light microscopy in H&E-stained slides.

Figure 7:
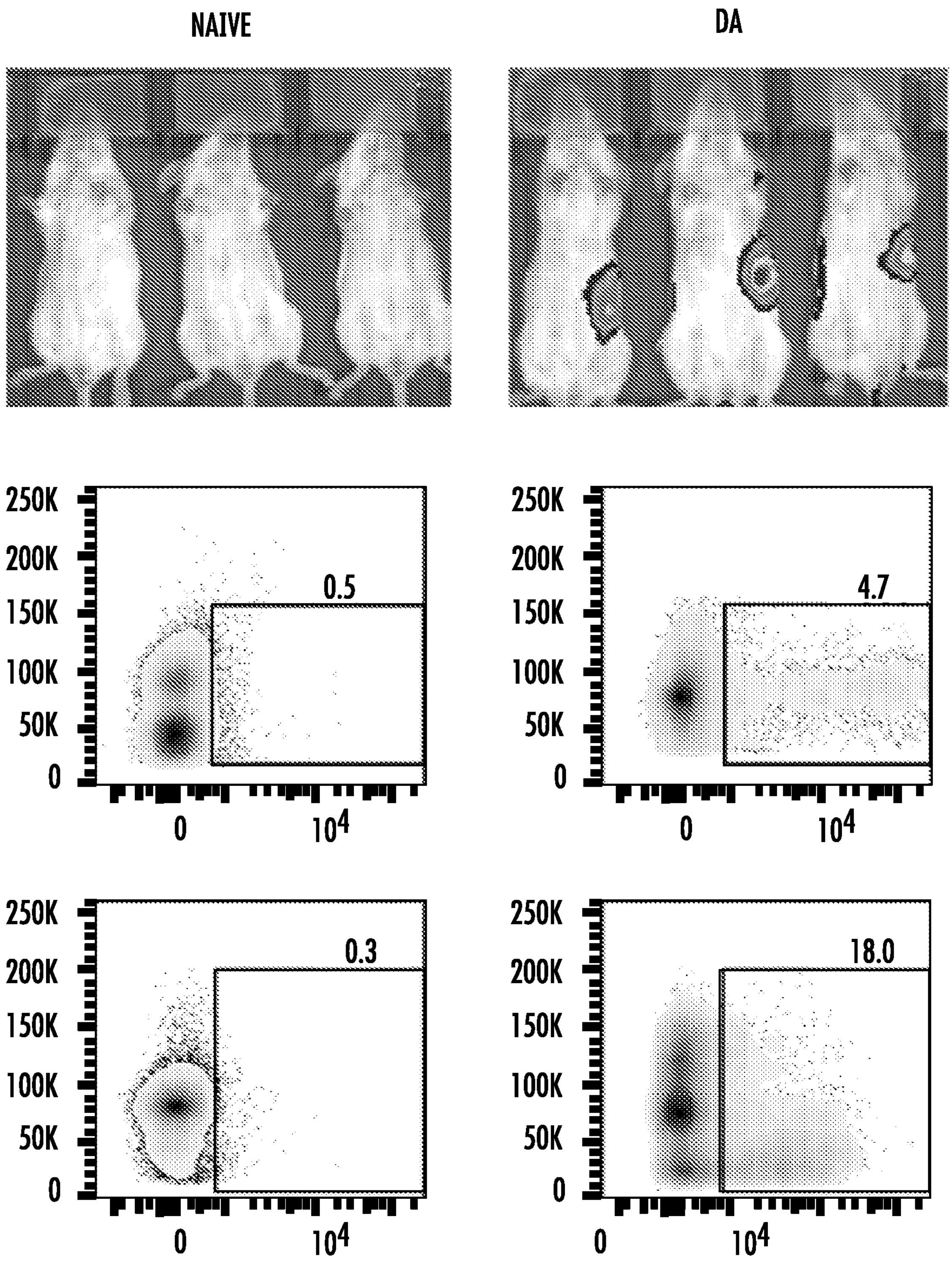
Figure 7:
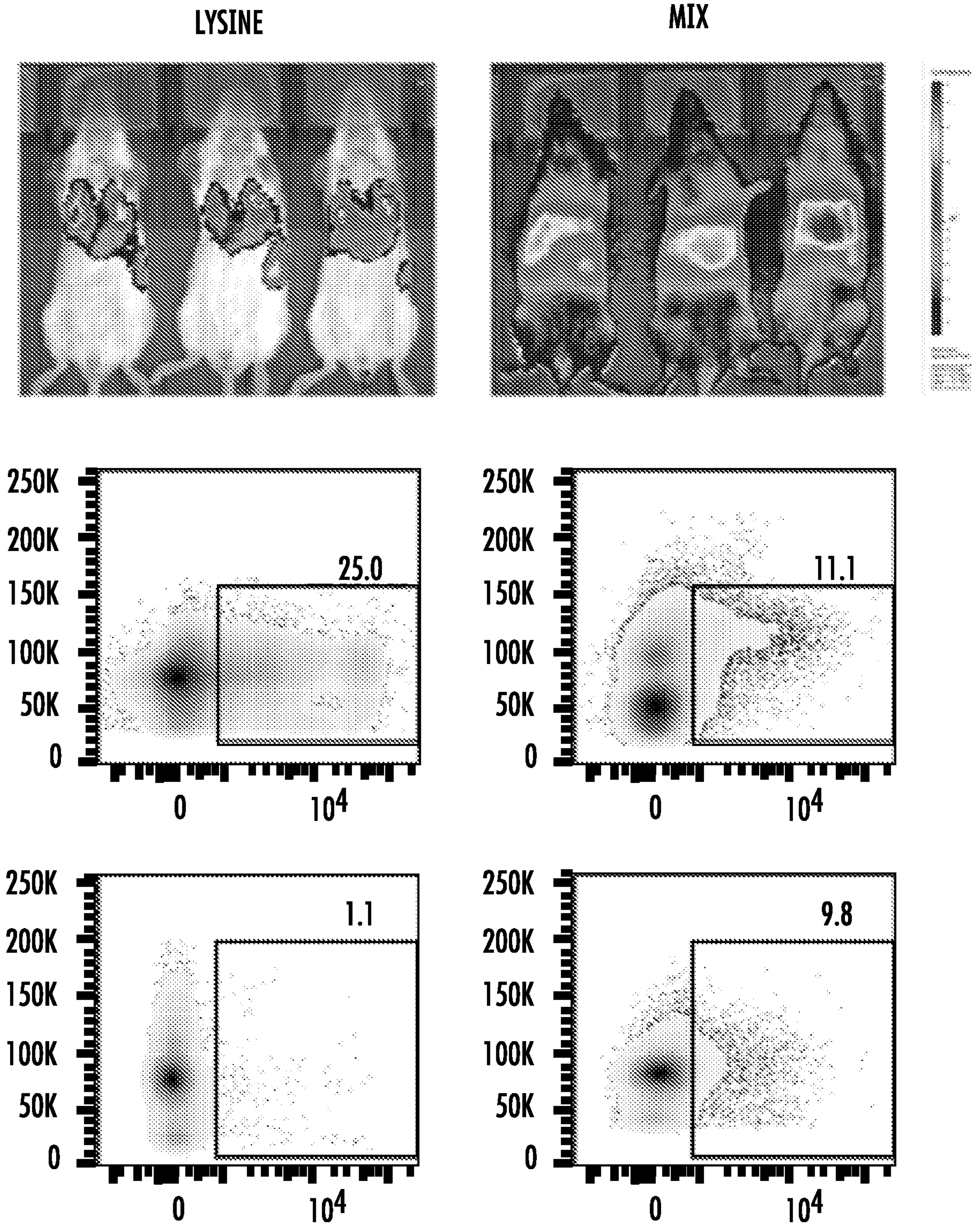
Figure 7:
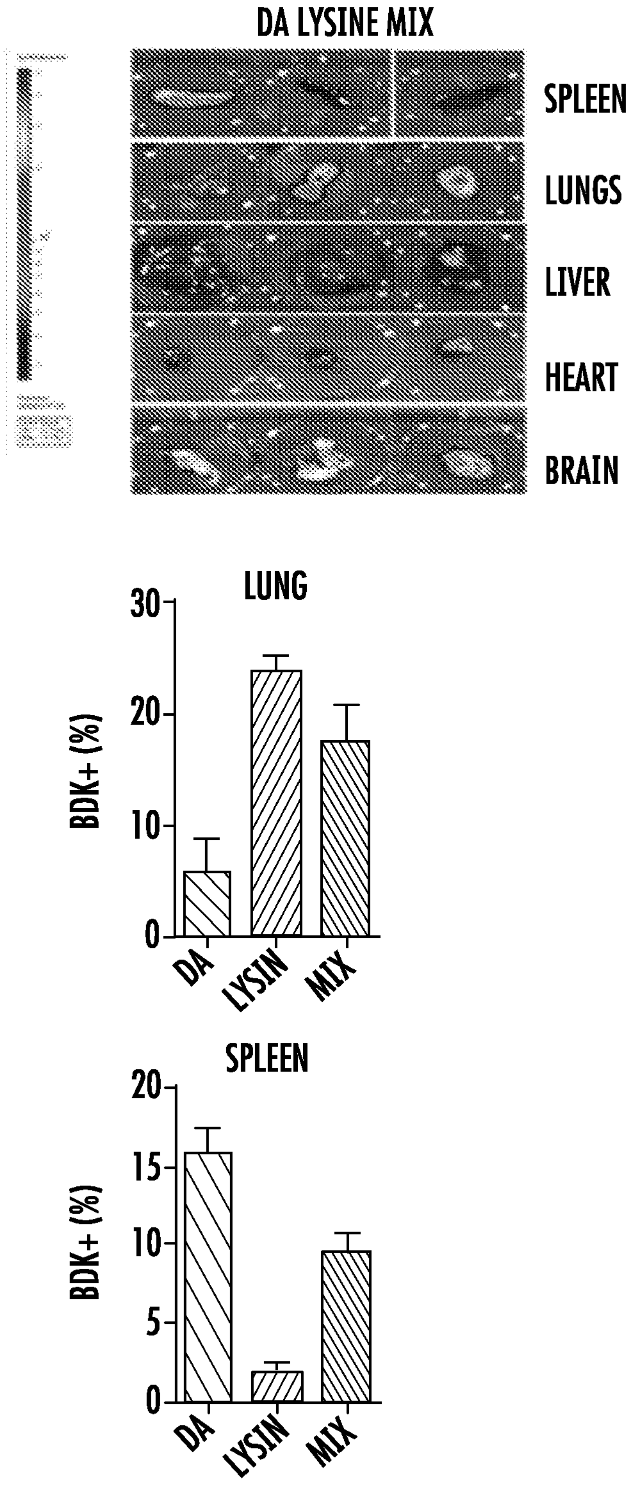

FIG. 7 shows a summary of vivo data. Representative bioluminescence images of whole mice (and selected organs) after mice were i.v. injected with PBS or 5 ug fLUC mRNA formulated in either CART-Gly (DA), CART-Lys (Lysine), or a 1:1 mix of CART-Gly and CART-Lys (MIX). Imaged 8 hrs post treatment. Representative (dot plots) and summarized data (bar graphs) of transfection efficacy of CART-Gly and CART-Lys in lungs and spleen, respectively. Mice were injected with 5 ug control mRNA formulated in BDK labeled CART-Gly or CART-Lys.

Figure 8:
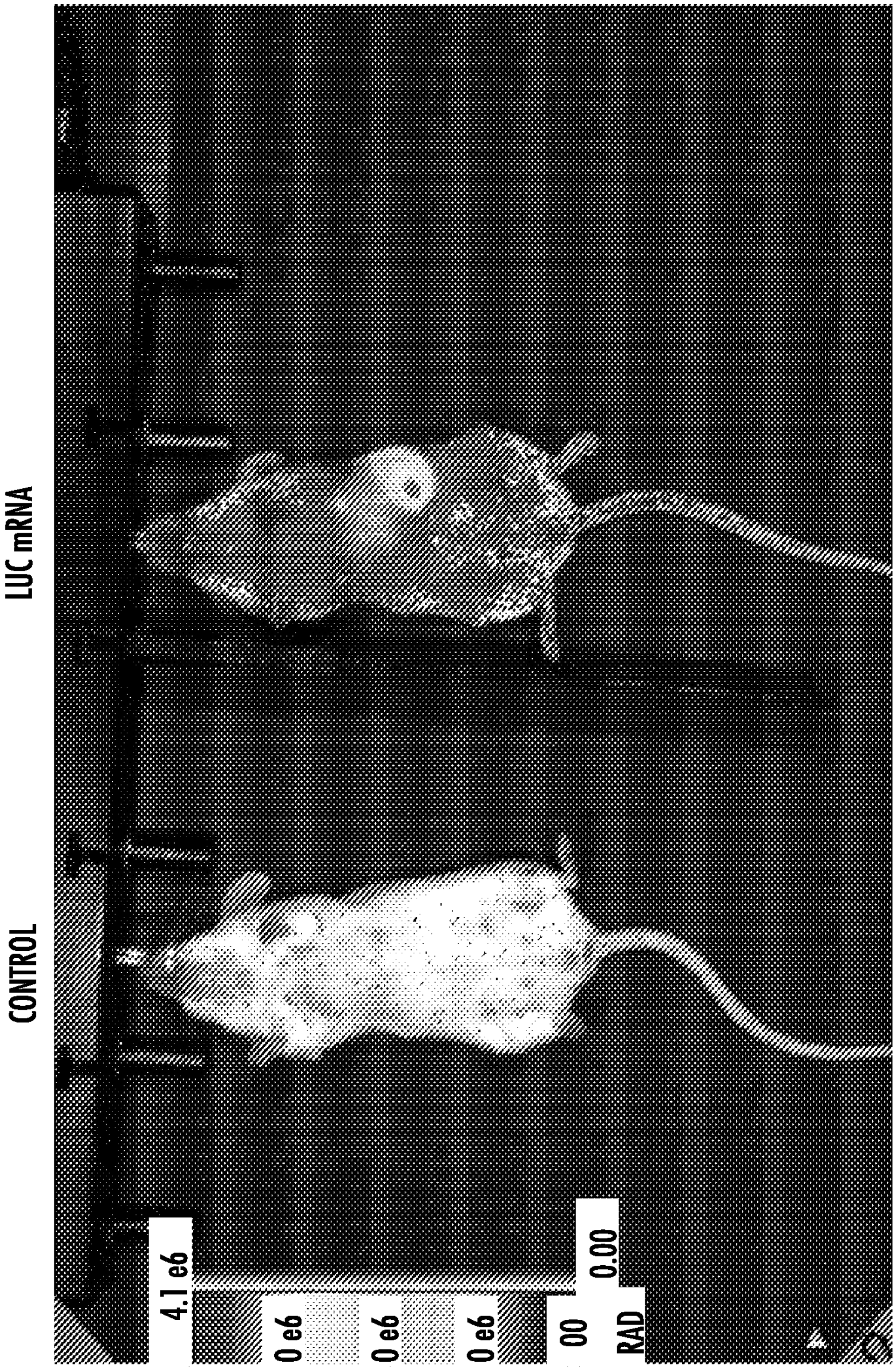

FIG. 8. A mixture of DA and Lysine CART gives a full body signal. Representative illustration of fLuc expression after intraveinous injection of fLuc mRNA formulated with Lysine CART and DA CART (also referred to herein as glycine CART) (mixed 1:1 DA Lysine). Mice were tail vein injected with 5 ug of fLuc mRNA formulated with 1:1 DA:Lysine CART mixture. Eight hours later, mice were injected with 33 g luciferin and bioluminescence signal due to fLuc activity was imaged.

Figure 9:
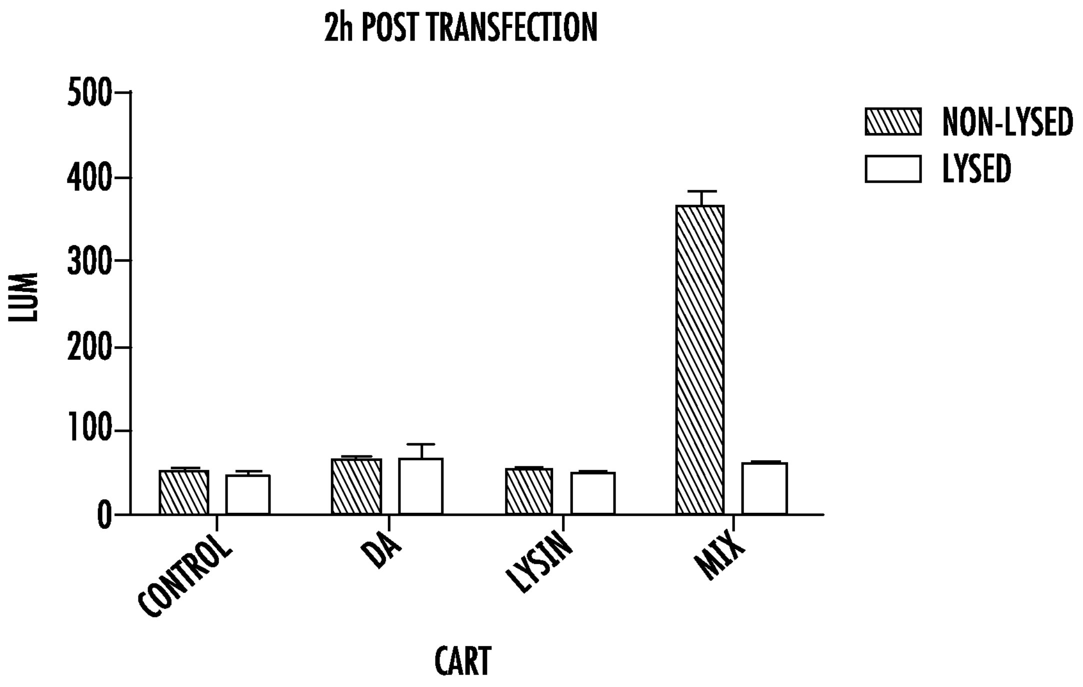

FIG. 9. Bioluminescence is detected in blood before red blood cell lysis but not after red blood cell lysis. This suggests that the bioluminescent signal comes from the red blood cells compartment. Mice were i.v. injected with 5 ug fLuc mRNA formulated with DA CART alone, Lysine CART alone or Lysine and DA CART mixed 1:1. Two hours later, 10 ul of blood was collected and mixed with luciferin to measure bioluminescence (Non-lysed, black bars). After this first measurement, red blood cells were lysed using ACK buffer and bioluminescence was measured again (Lysed, white bars).

Figure 10:
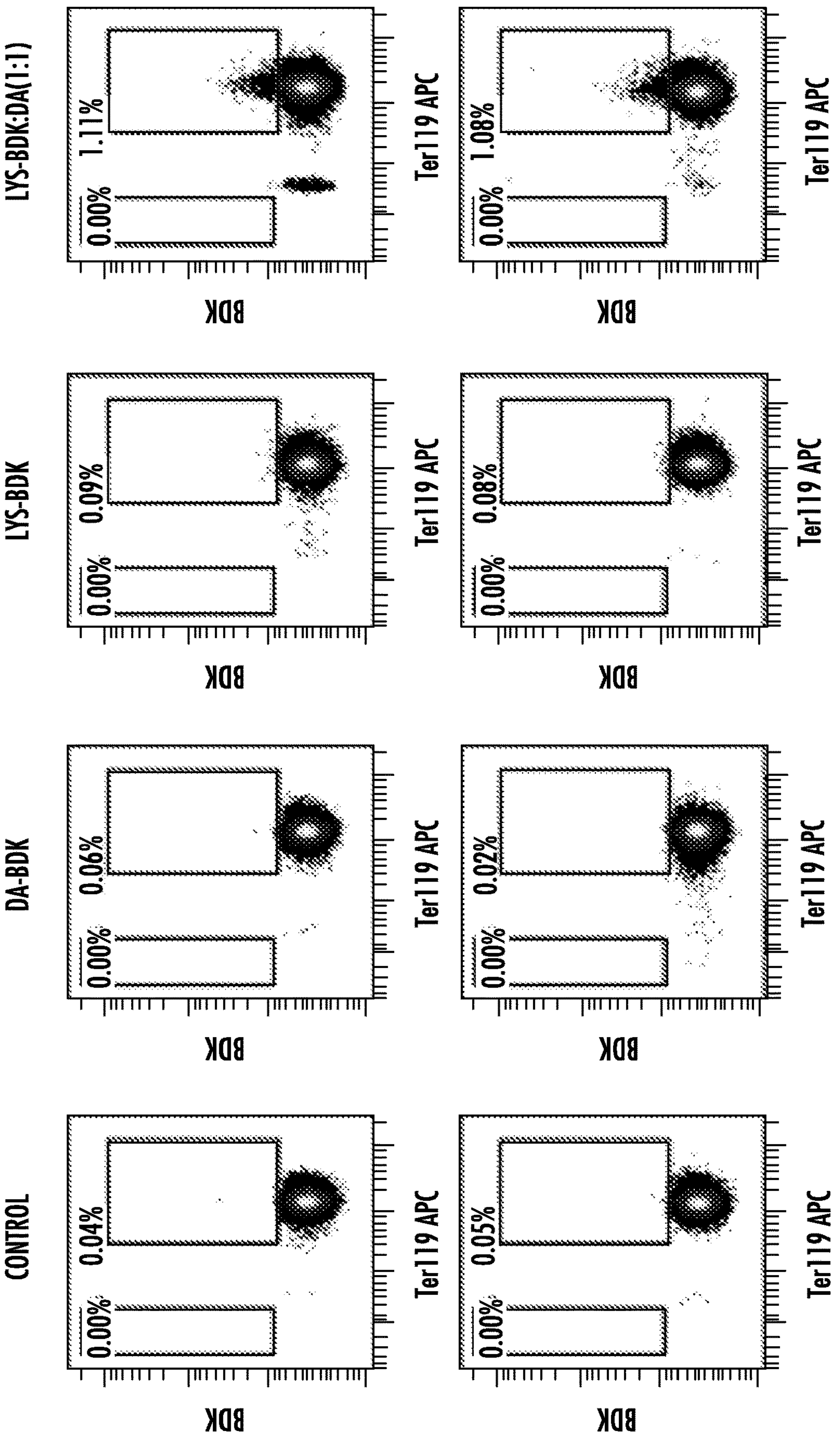

FIG. 10. Using BDK labeled CARTs, BDK signal is detected in the Red Blood Cell population (Ter119+ cells) of mice that were transfected with the mixture of DA and Lysine CART but not with either CART alone. BDK (difluoroboron-β-diketonate fluorophore) is a fluorophore that can be coupled to the CART. Mice were i.v. injected with 5 ug fLuc mRNA formulated with BDK-DA CART alone, BDK-Lysine CART alone or Lysine and BDK-DA CART mixed 1:1. Forty-five minutes later, 10 ul of blood was collected and labeled with anti-Ter119 antibody in order to identify the red blood cell population.

Figure 11:
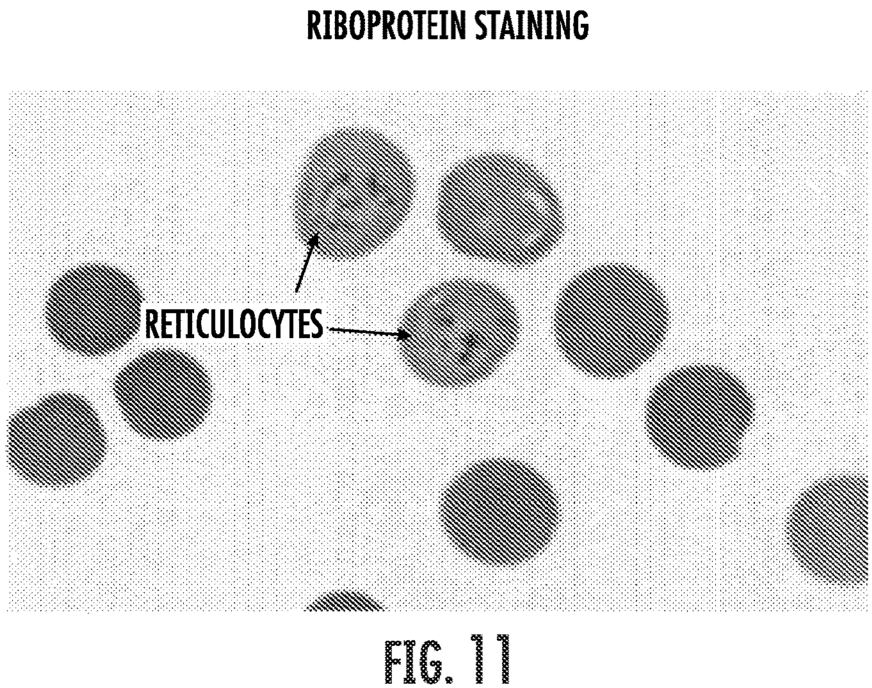

FIG. 11. Mature Red Blood Cells are not able to translate mRNA to protein. Therefore the luciferase signal detected in the blood must come from reticulocytes, which are young red blood cells from which the nucleus has been lost yet contain residual ribosomes. Riboprotein staining identifies reticulocytes in the blood (black arrows).

Figure 12:
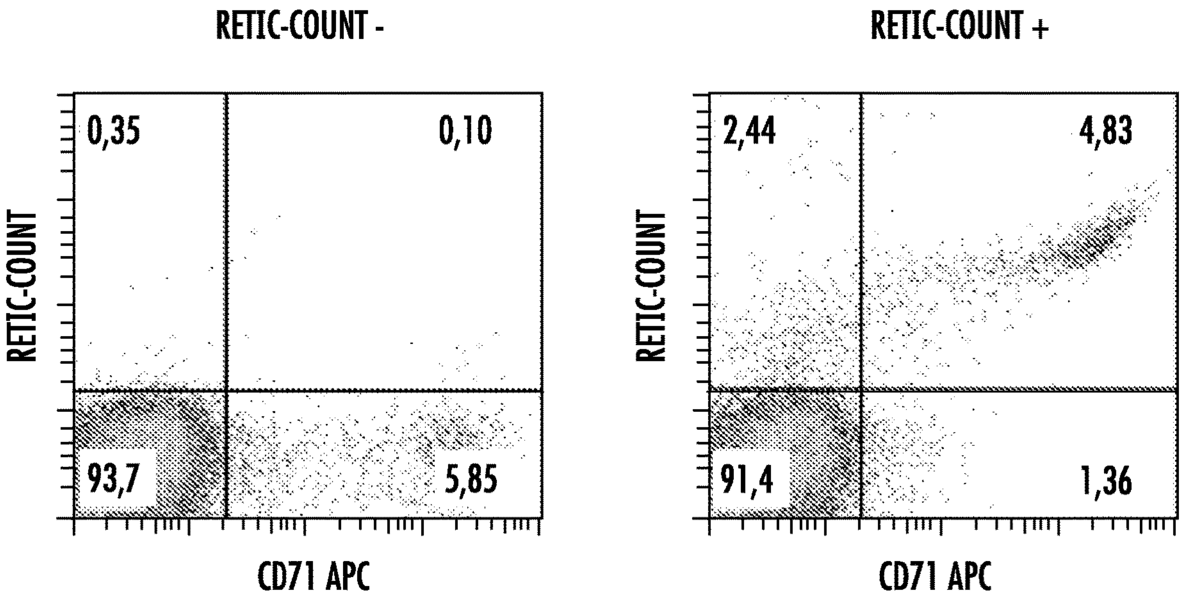
Figure 13:
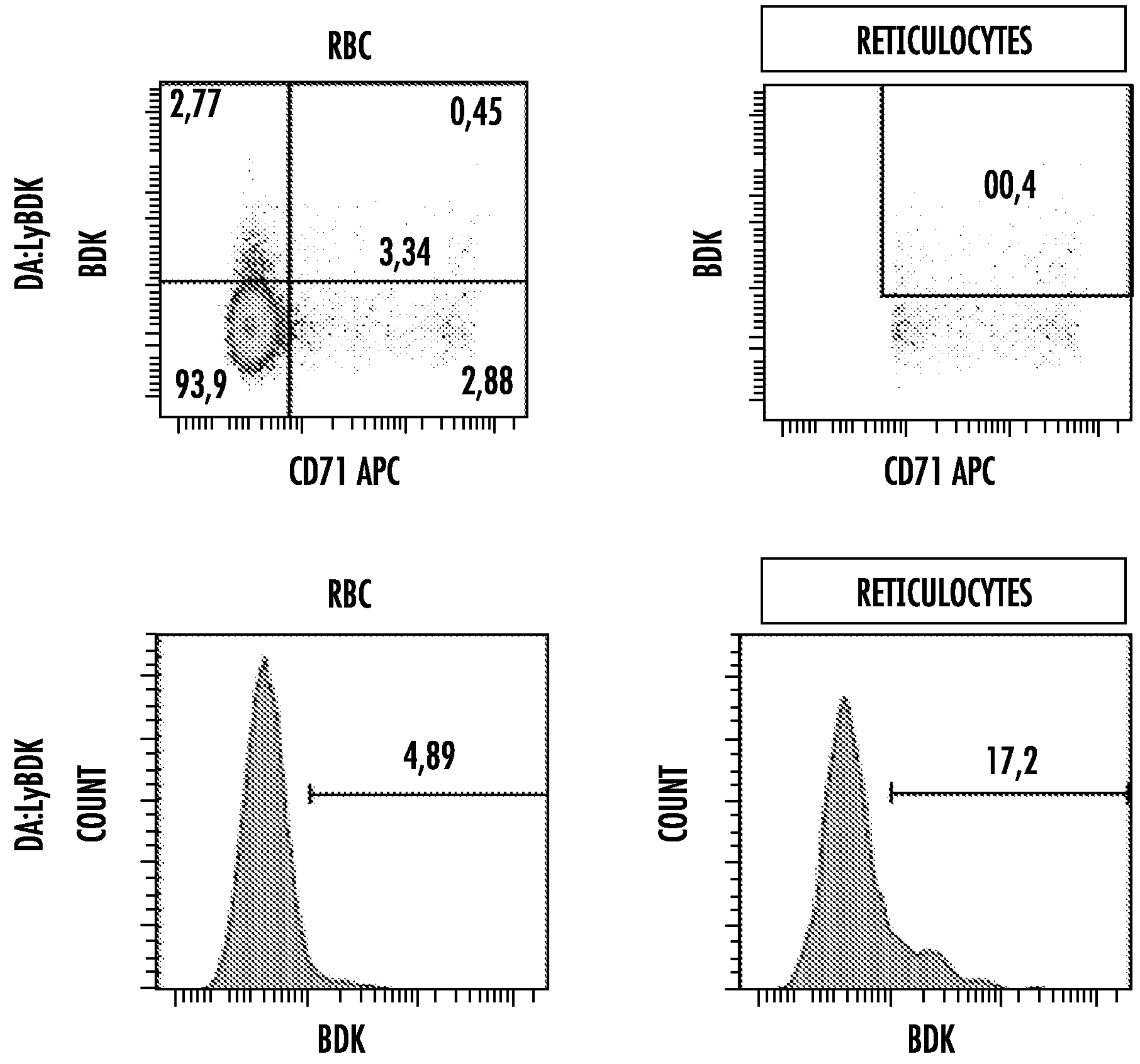
Figure 13:
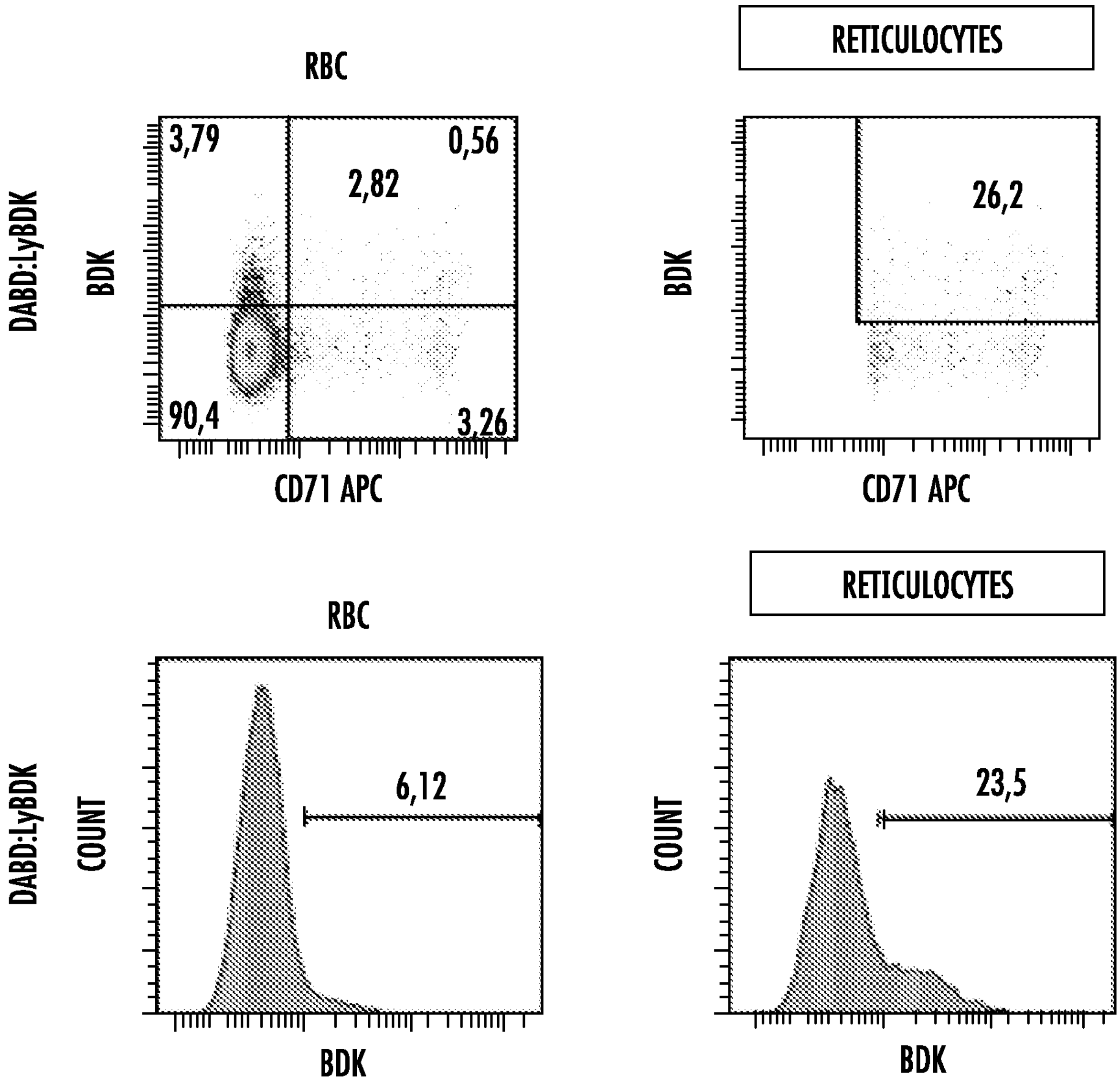
Figure 13:
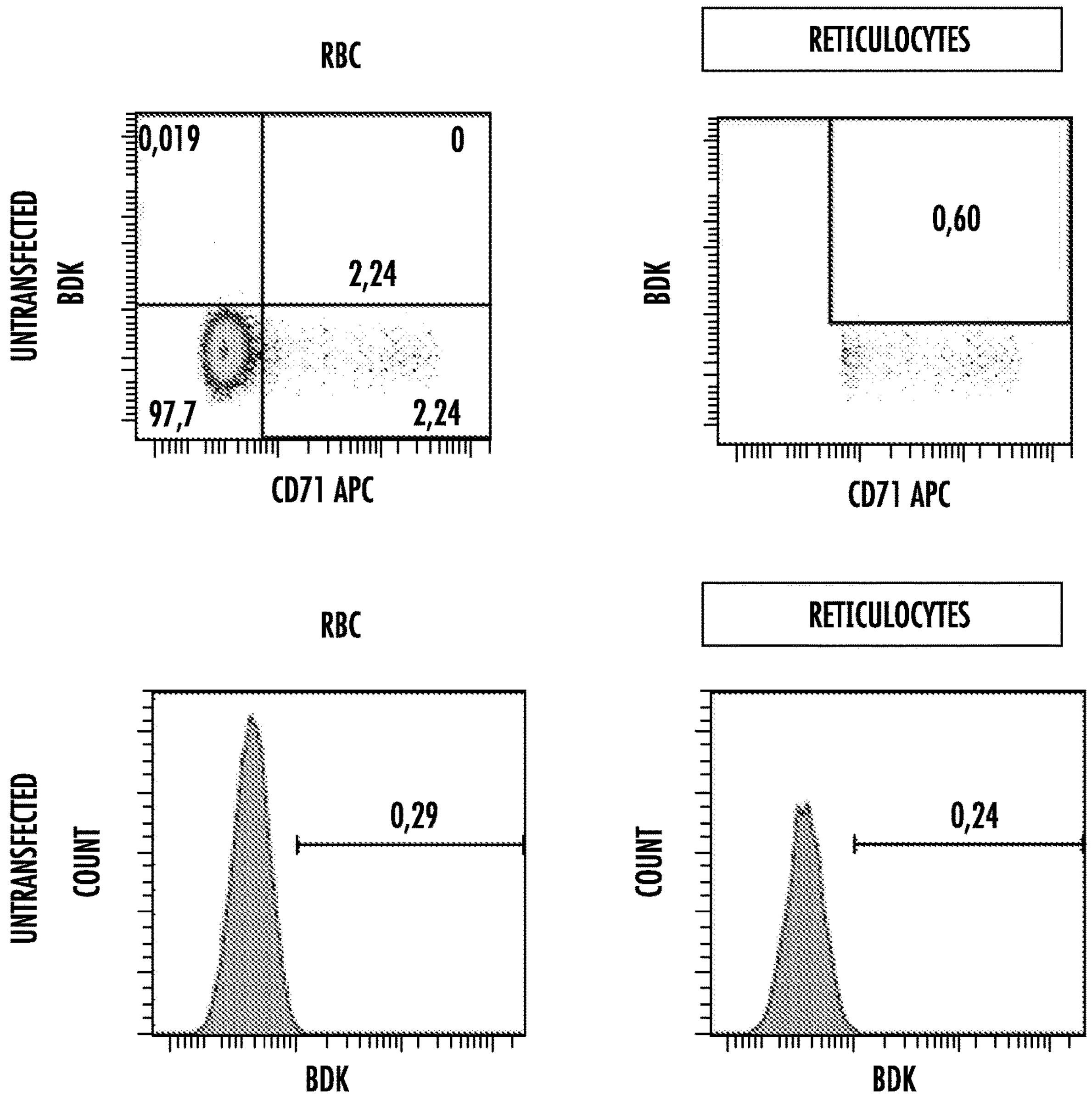
Figure 13:
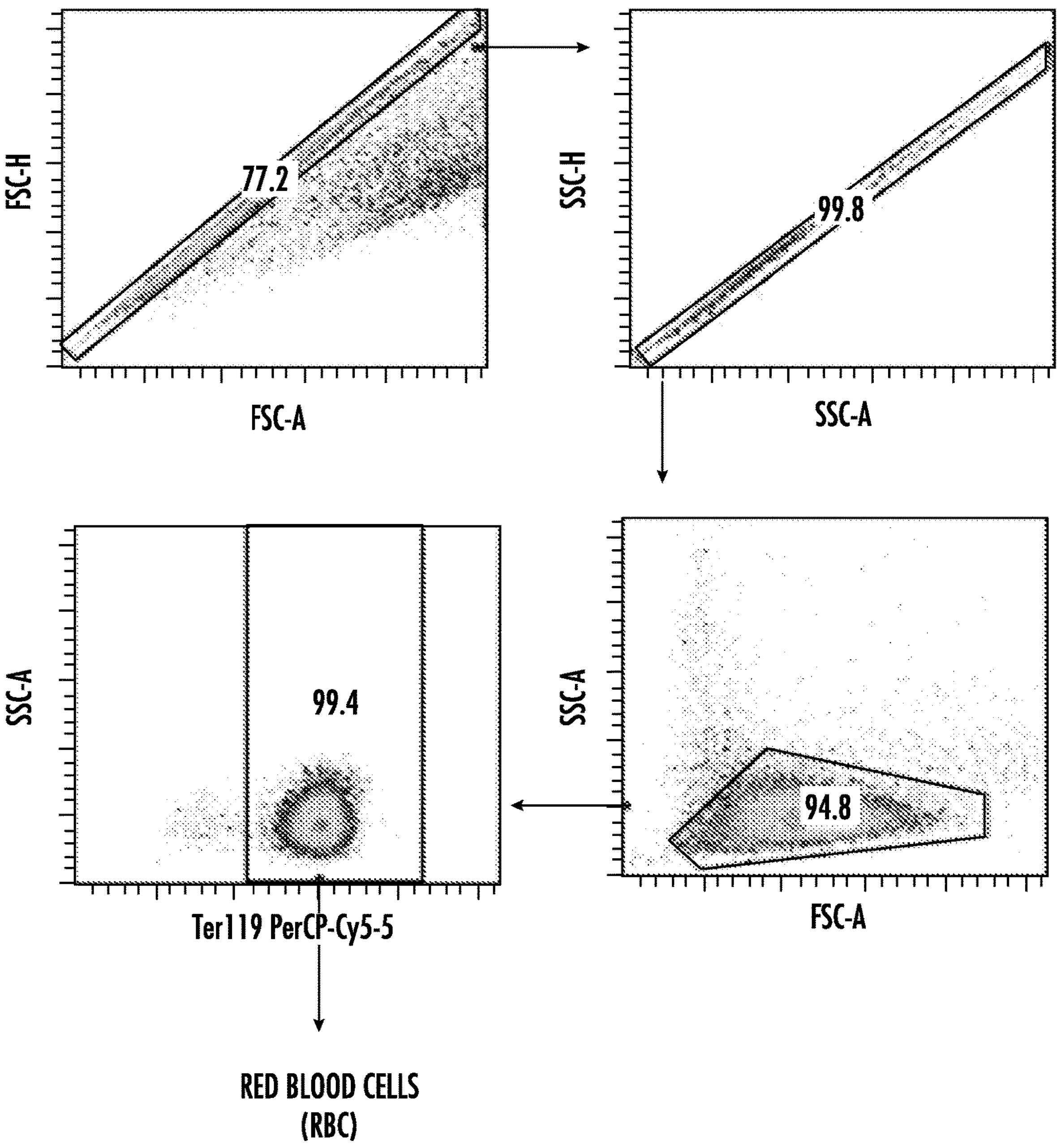

FIG. 12. Retic-count BD (Thiazole Orange) is an intercalating dye that stains for DNA and mRNA and is detectable in the FITC channel. Reticulocytes contain residual ribosomes and mitochondria which contain RNA and DNA, which are absent from mature erythrocytes. Using this dye we confirmed that CD71 can be used to identify reticulocytes FIG. 13. Using BDK labeled CART, 5 ug GFP mRNA was formulated with the mixture of DA and Lysine CART. 45 min post tail vein injection, mice were bled and whole blood was stained with Ter119 and CD71. About 20% of the reticulocytes (CD71+) were BDK positive.

Figure 14:
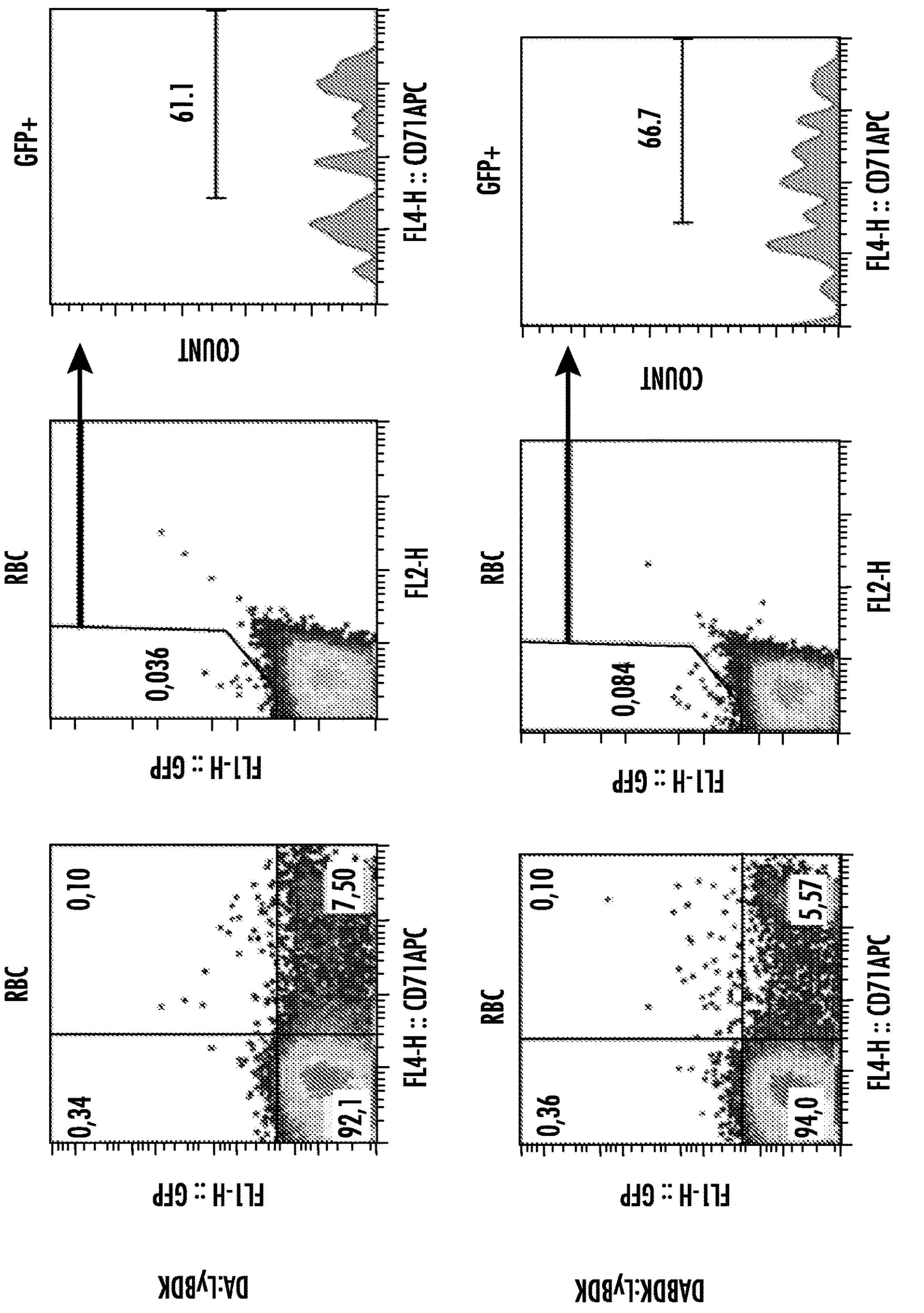
Figure 14:
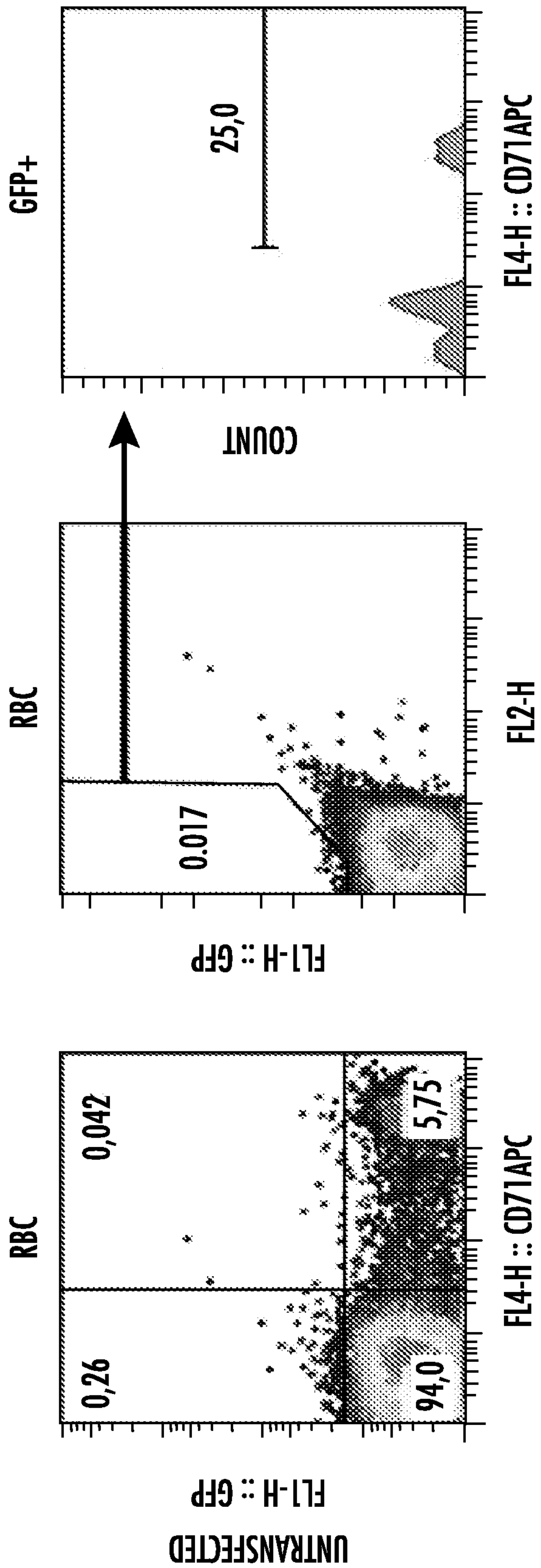
Figure 15:
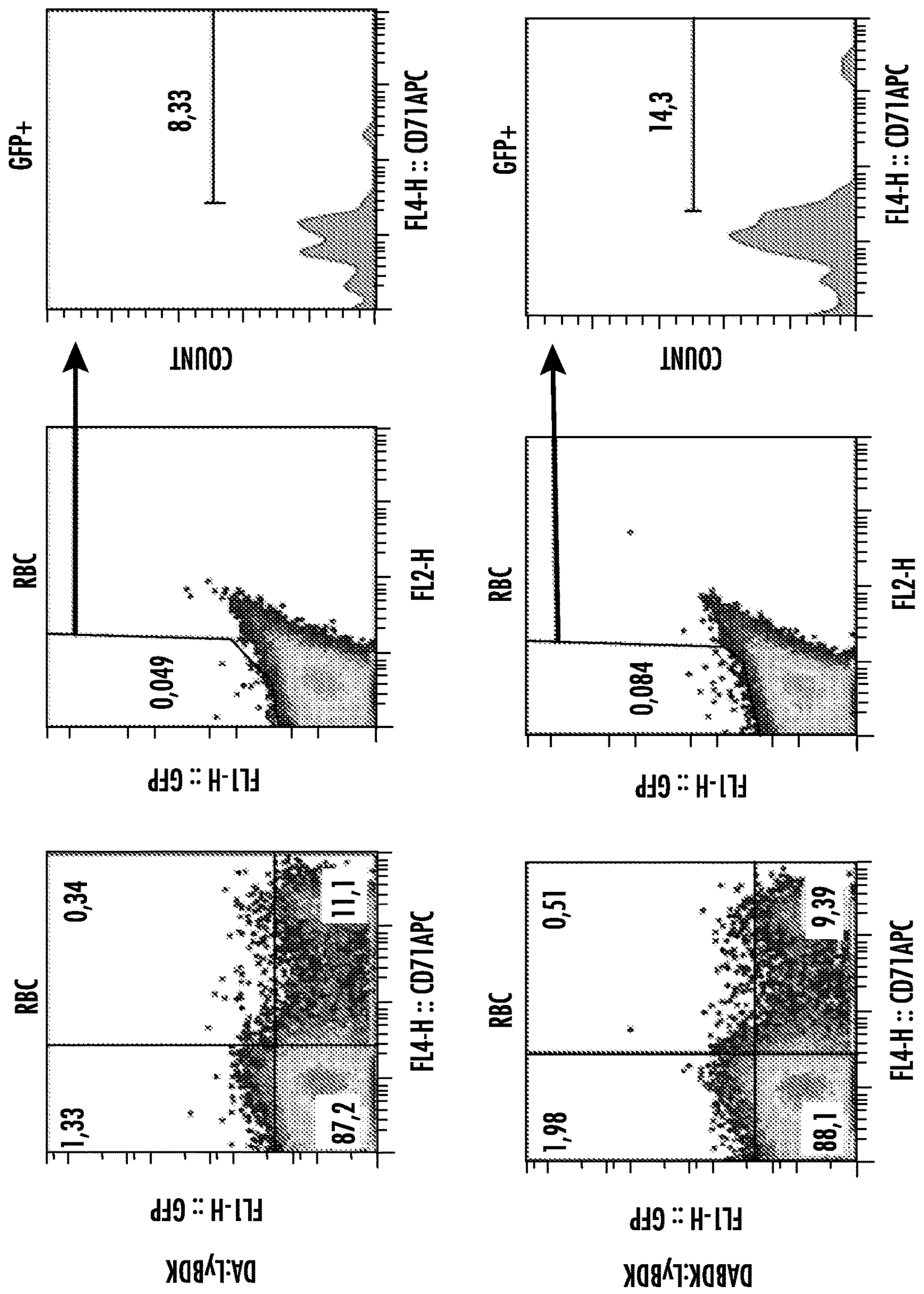
Figure 15:
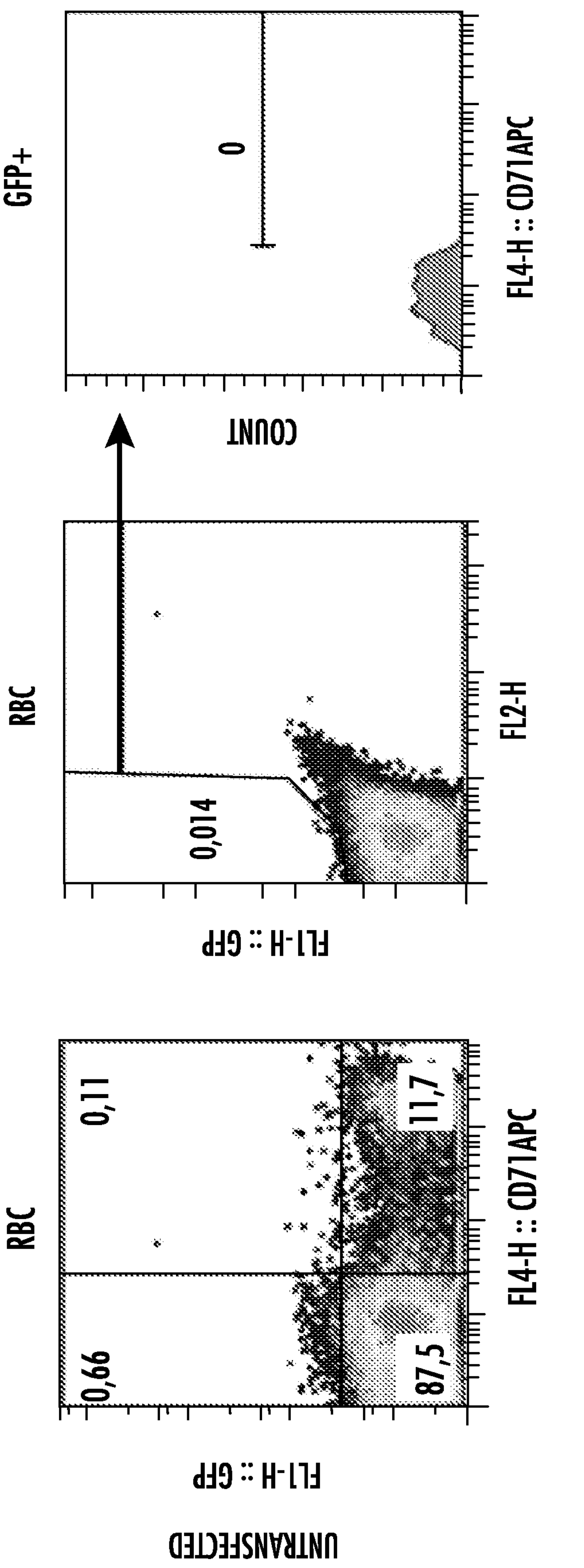

FIG. 14. GFP expression is detected in reticulocytes 1 day post transfection. As opposed to mature red blood cells, reticulocytes have ribosomes and are able to translate the mRNA to GFP protein. Reticulocytes (CD71+) mature to red blood cells (CD71−) after 3 days. Therefore, we expect to detect GFP expression in reticulocytes in the first 3 days post injection. After that GFP should be found in mature red blood cells (CD71−). 1 day post injection GFP positive cells are CD71+ reticulocytes FIG. 15. GFP expression detected in mature RBC day 4 post transfection. On day 4 after injection the GFP+ reticulocytes have matured to mature Red Blood Cells. Now the GFP positive cells are CD71−.

Figure 16:
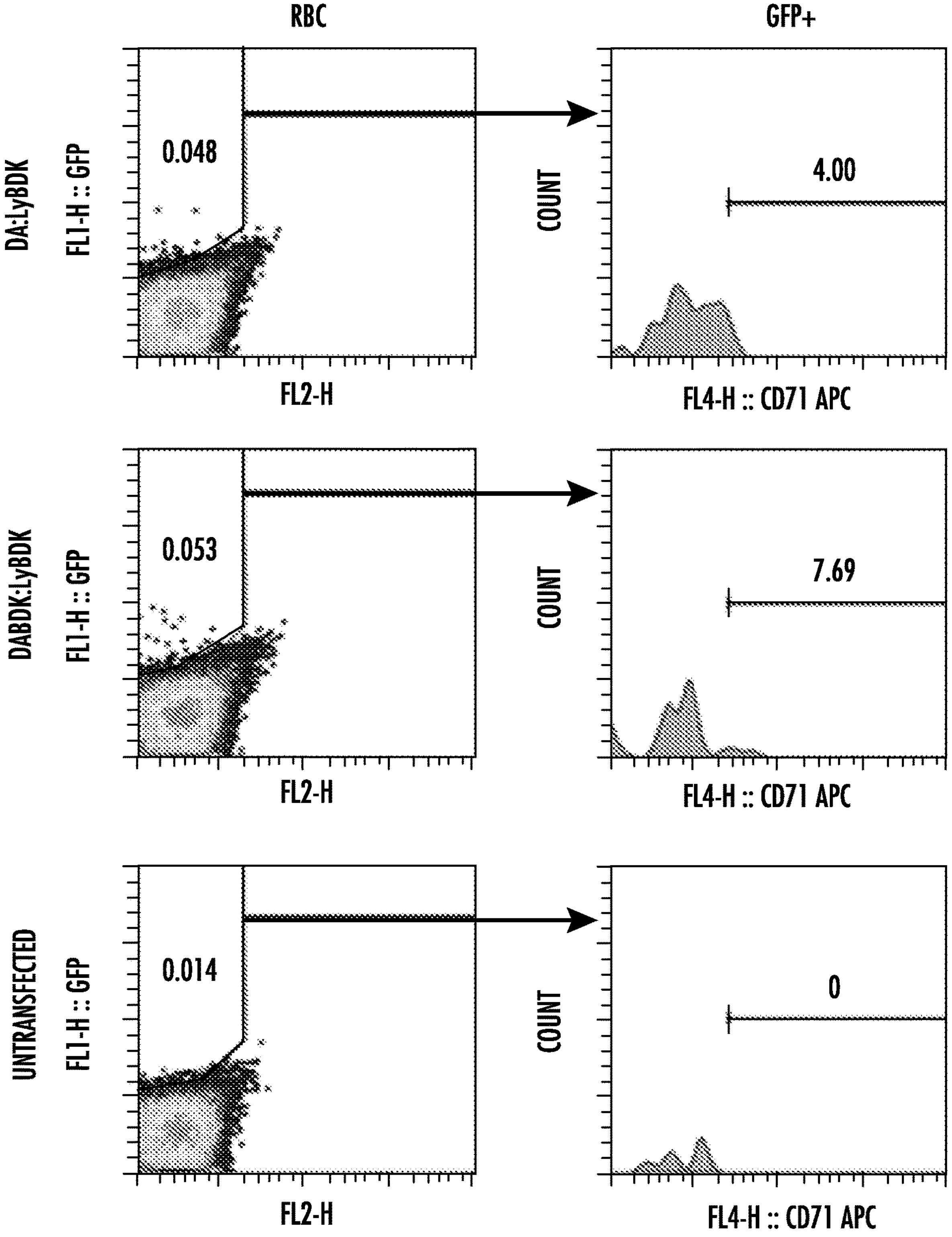

FIG. 16. GFP expression is detected in mature RBC day 14 post transfection. Mature red blood cells are long lived cells. We were able to detect GFP expression 2 weeks post injection.

Figure 17A:
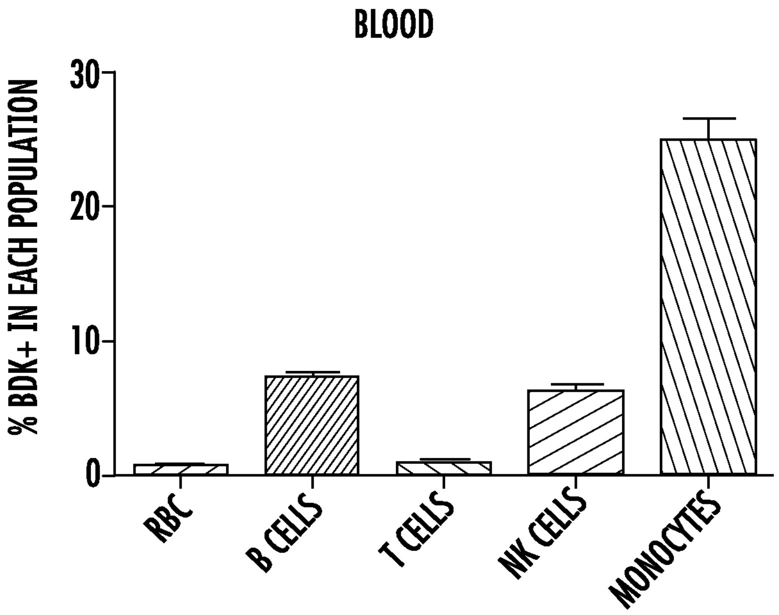
Figure 17B:
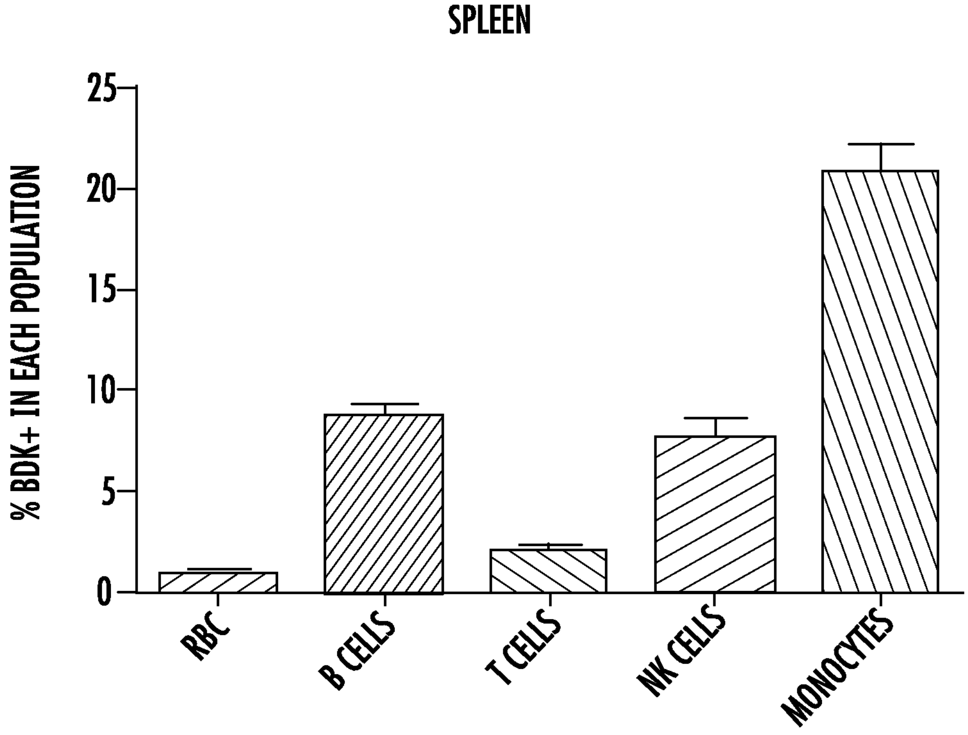
Figure 17C:
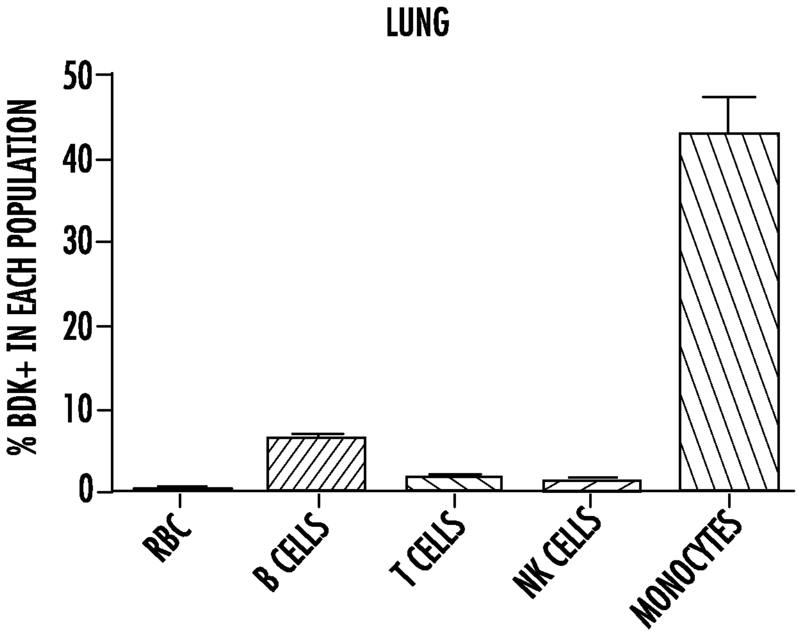

FIG. 17A-17C show distribution of the BDK+ cells across cell types. Reticulocytes are not the only cells that are transfected. Using the BDK CART, 5 mice were injected with 5 ug mRNA formulated with the mixture of Lysine and DA CART. One hour post transfection, blood, spleen and lungs were harvested from each mouse and single cell suspensions were prepared from each organs. Red blood cells were lysed in the blood samples. Cells were stained for cells population specific markers and analyzed by flow cytometry. Graphs show percentage of BDK+ cells in identified cell populations in the Blood (FIG. 17A), Spleen (FIG. 17B) and lung (FIG. 17C).

Figure 18A:
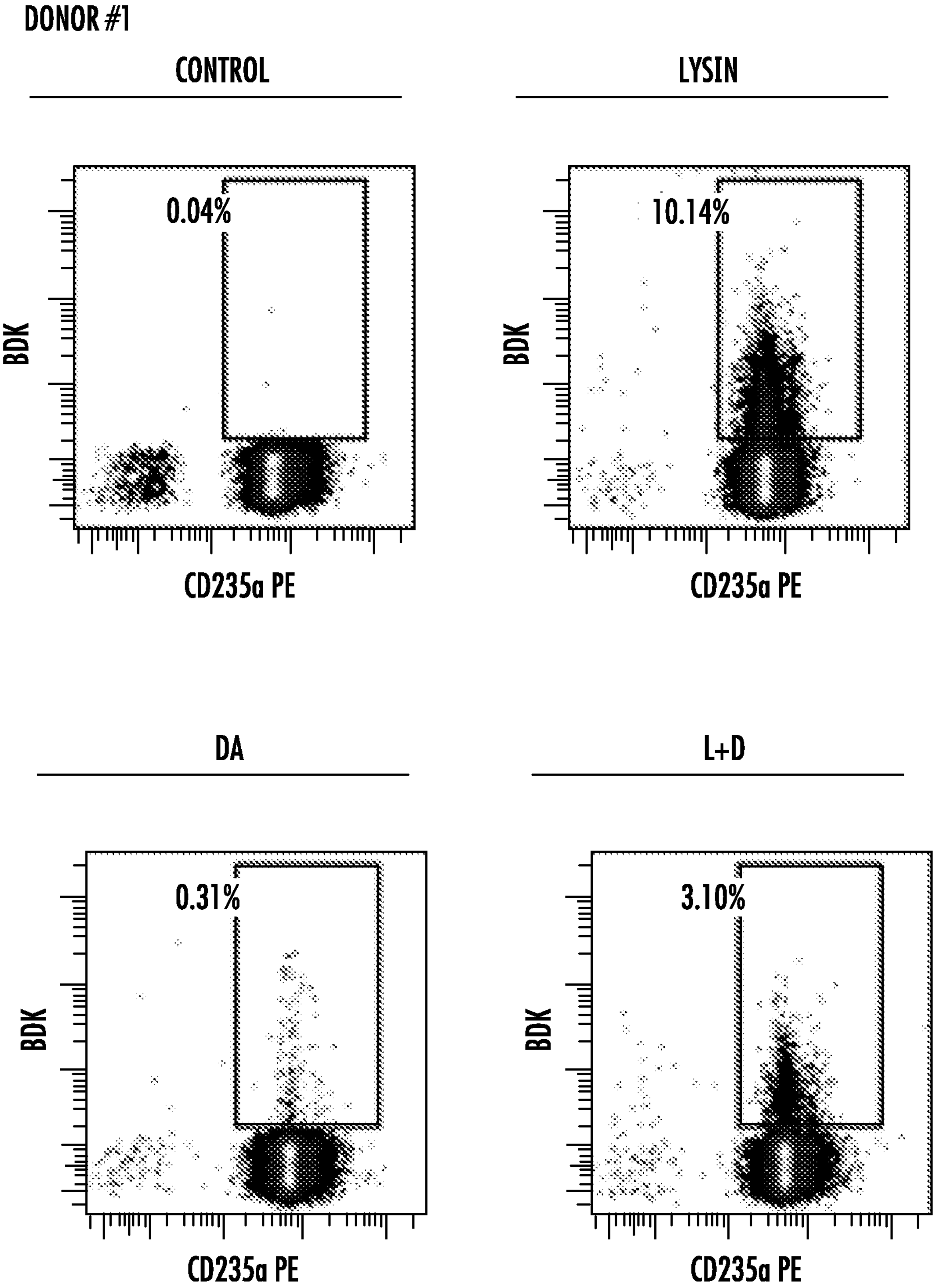
Figure 18B:
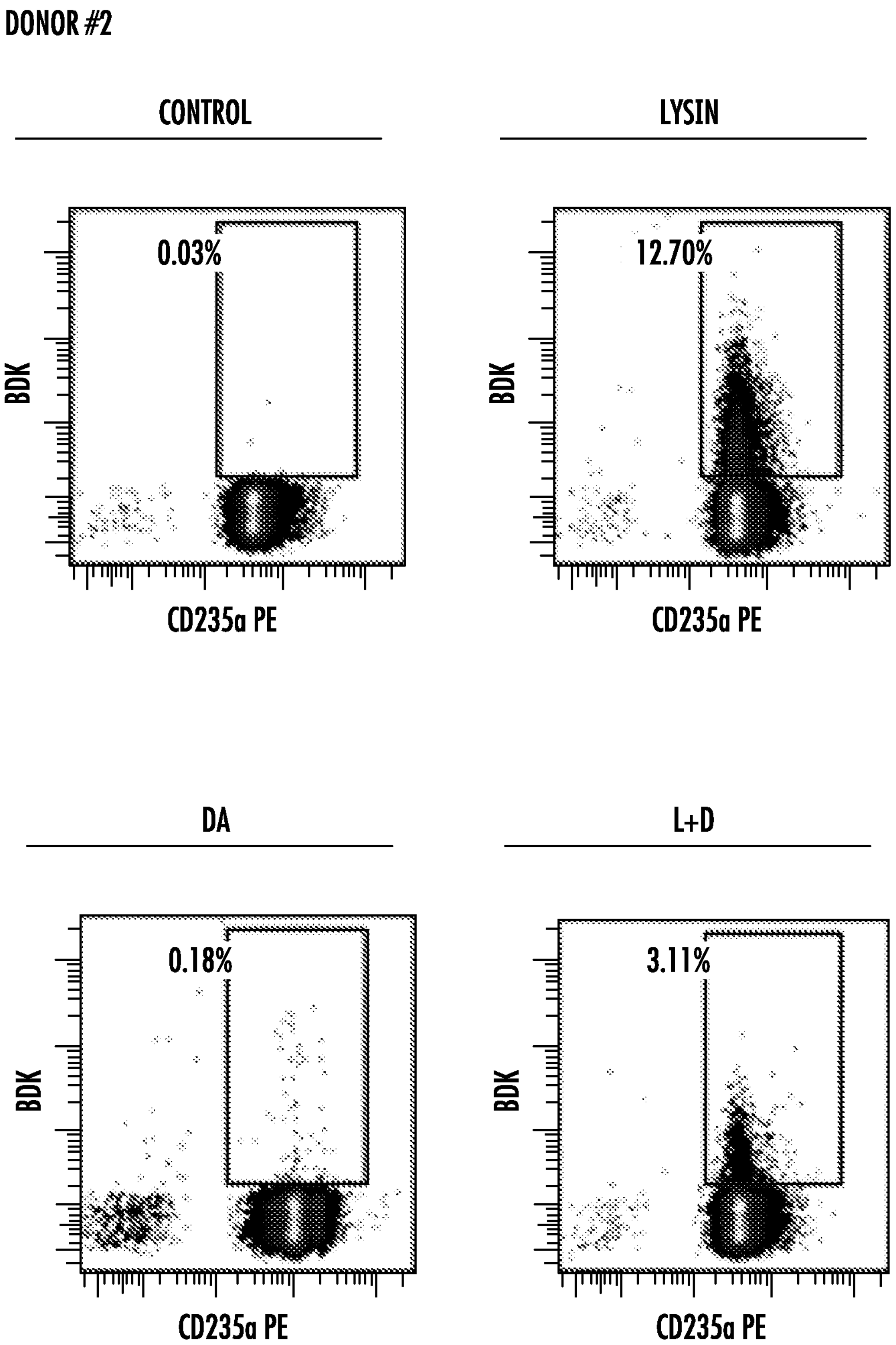
Figure 18C:
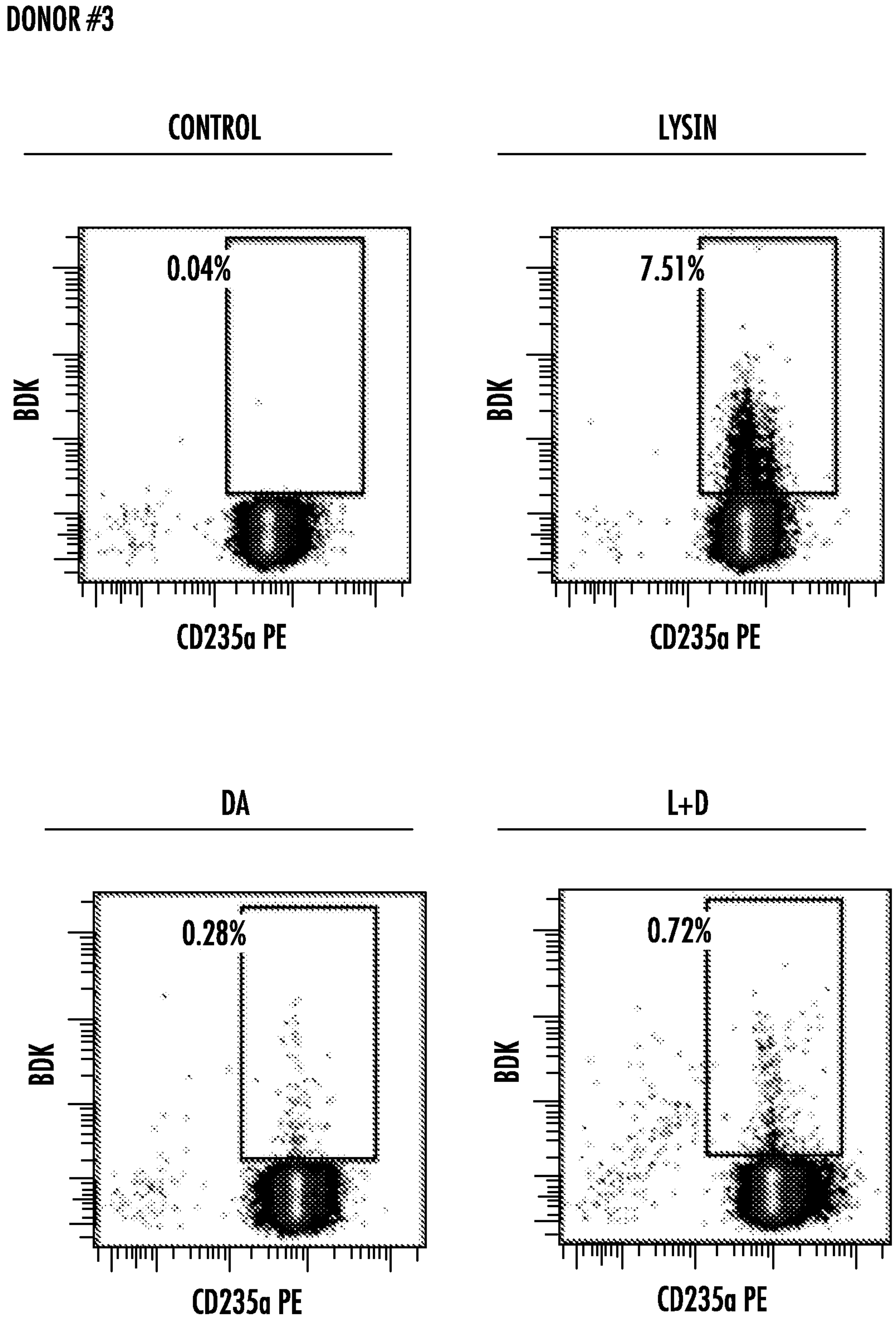

FIG. 18A-C. Human blood was harvested from 3 donors and was transfected ex vivo using BDK-labeled CART. Blood cells were transfected with the Lysine CART, the DA CART or the mixture of Lysine and DA CART. 45 min later cells were stained for the human red blood cell marker CD235a and analyzed by flow cytometry. FIGS. 18A, 18B and 18C correspond to donors 1, 2, and 3, respectively.

Figure 19:
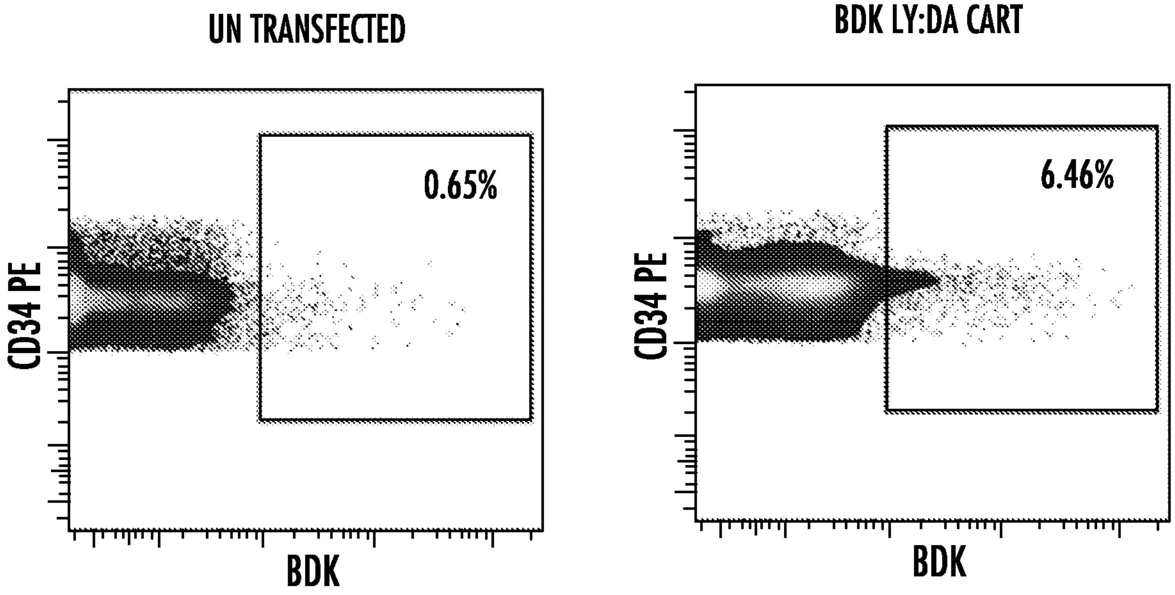
Figure 20A:
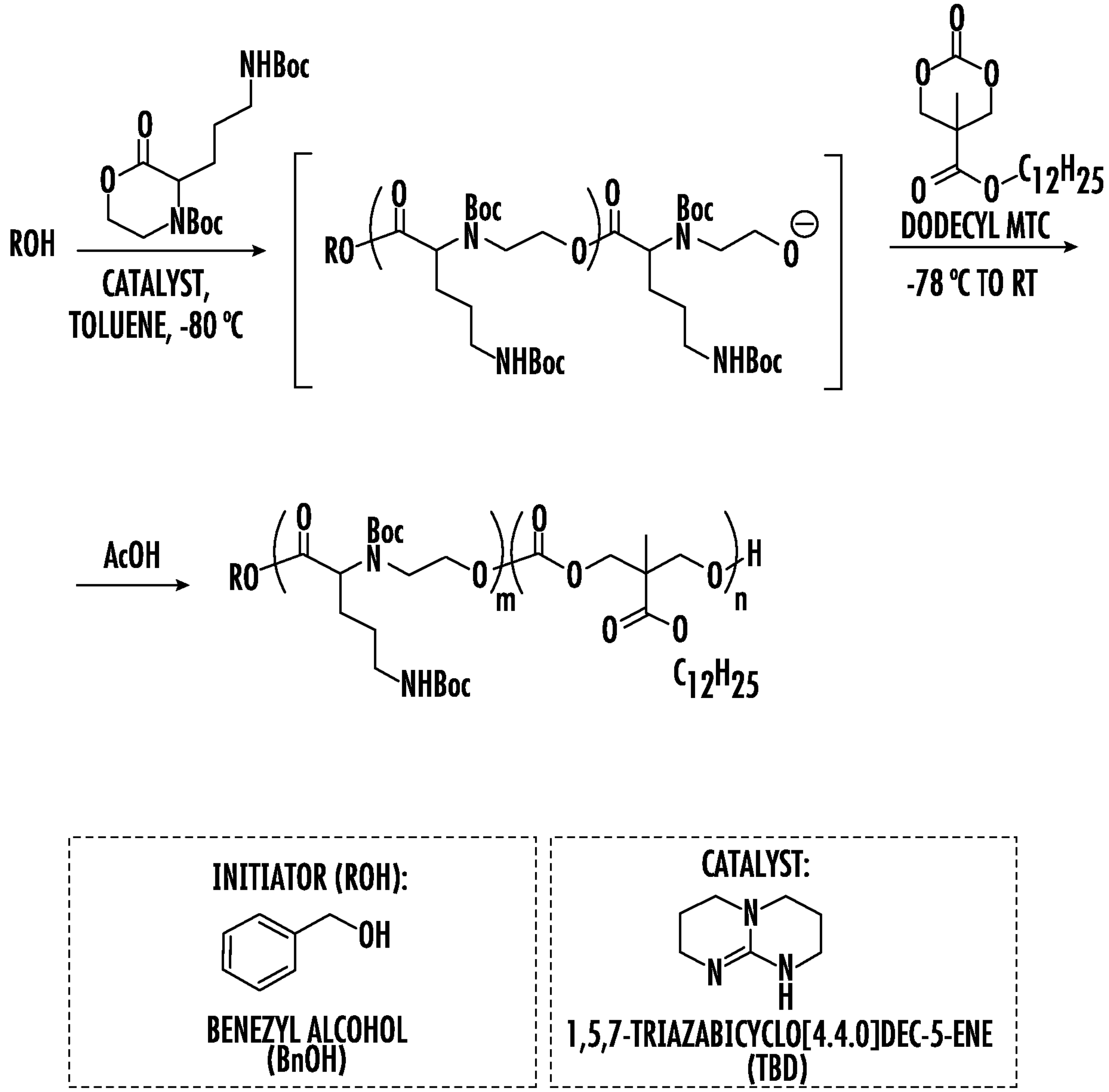
Figure 20B:
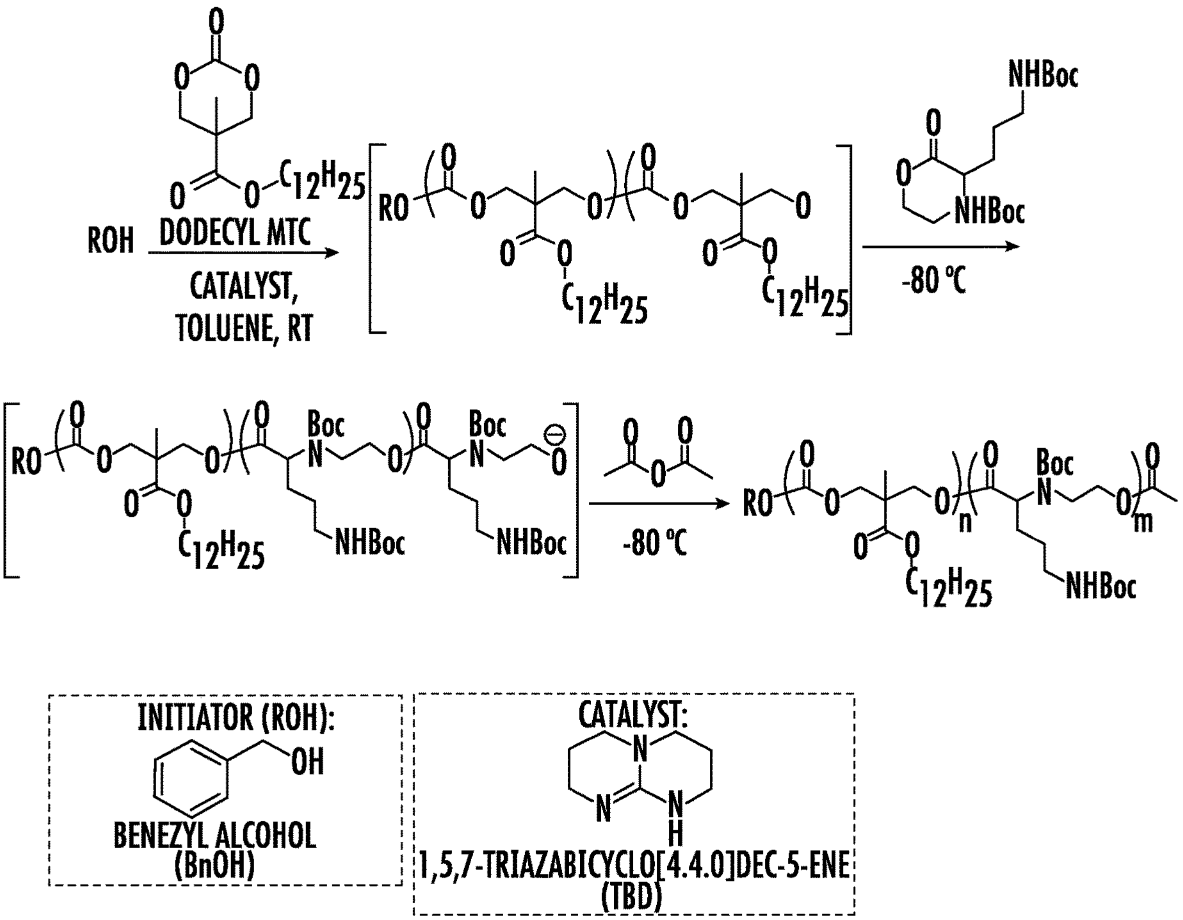

FIG. 19. Red blood cell progenitor cells are transfected in the bone marrow. One mouse was injected in the tail vein with fLuc mRNA formulated with the mixture of DA and Lysine tagged with BDK. 45 min post injection the mouse was sacrificed and bone marrow cell were isolated from the femur. Cells were stained with anti-CD34 which is a marker for hematopoietic stem cells. 6% of the hematopoietic stem cells were BDK positive FIG. 20A-20B. Synthesis of ornithine-derived CARTs: Reverse block strategy: To a solution of the ornithine-derived morpholinone in toluene was added a solution of benzyl alcohol initiator and 1,5,7-triazabicyclo[4.4.0]dec-5-ene in toluene under a nitrogen atmosphere. This solution was cooled to −78° C. After 20 min, a solution of lipid-functionalized monomer in toluene was added. The solution was stirred for 10 minutes at −78° C., and then warmed to room temperature and stirred for an additional 7 minutes. A solution of acetic acid in toluene was added. The solution was stirred for two minutes and then concentrated to dryness. The crude residue was redissolved in dichloromethane and then dialyzed (regenerated cellulose tubing, MWCO 1 kD) against methanol for 18 hours. The product was analyzed by $^1$H NMR analysis to determine the degree of polymerization. The product was subsequently deprotected using 10% p-toluenesulfonic acid in dichloromethane to yield the ornithine-derived CART, which was stored as a 2 mM solution in dimethylsulfoxide. Forward block strategy: To a solution of dodecyl MTC in toluene was added a solution of benzyl alcohol initiator and 1,5,7-triazabicyclo[4.4.0]dec-5-ene in toluene under a nitrogen atmosphere. This solution was stirred at room temperature. After 7 min, the solution of dodecyl MTC, initiator, and catalyst was added to a solution of ornithine-derived morpholinone in toluene. The solution was cooled to −78° C. and stirred for 15 min, after which point a solution of acetic anhydride in toluene was added. This was allowed to warm to room temperature. The crude residue was redissolved in dichloromethane and then dialyzed (regenerated cellulose tubing, MWCO 1 kD) against methanol for 18 hours. The product was analyzed by $^1$H NMR analysis to determine the degree of polymerization. The product was subsequently deprotected using 10% p-toluenesulfonic acid in dichloromethane to yield the ornithine-derived CART, which was stored as a 2 mM solution in dimethylsulfoxide. For values of variables m and n see FIG. 21B.

Figure 21A:
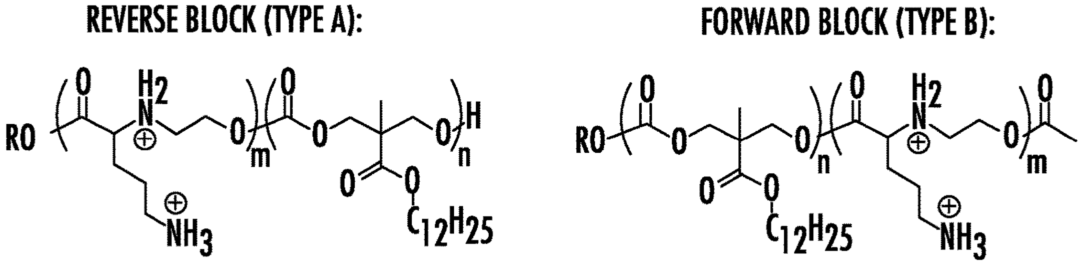
Figures 21B, 21C:
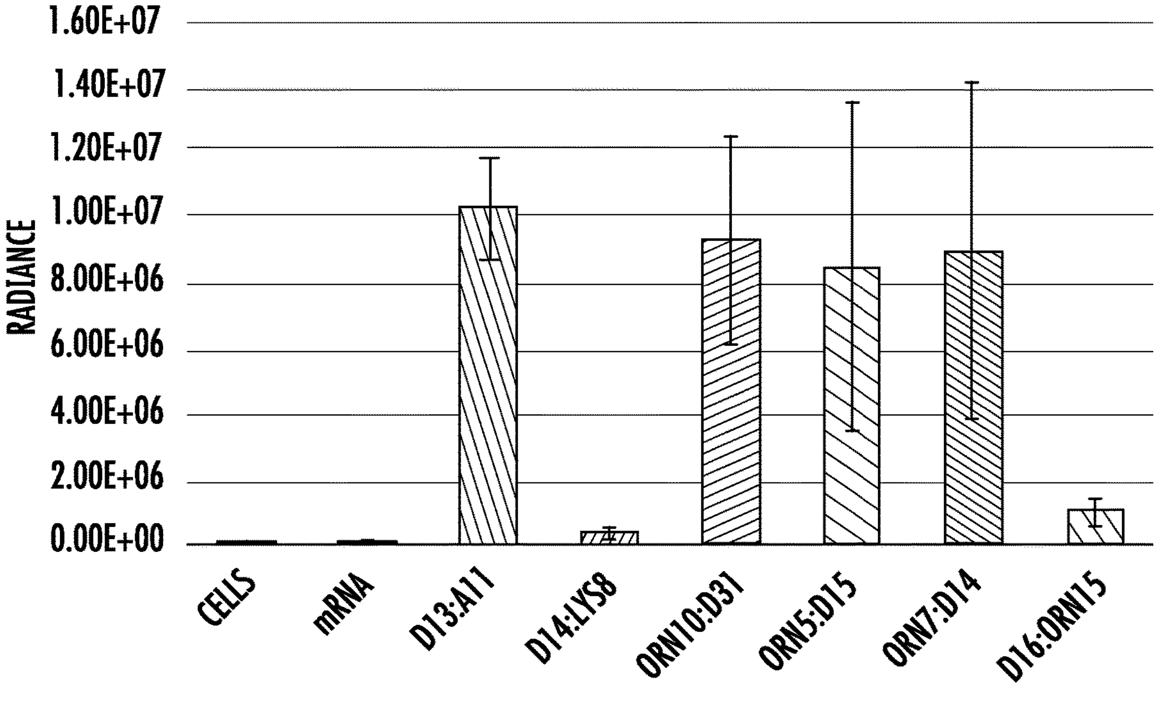
Figure 21D:
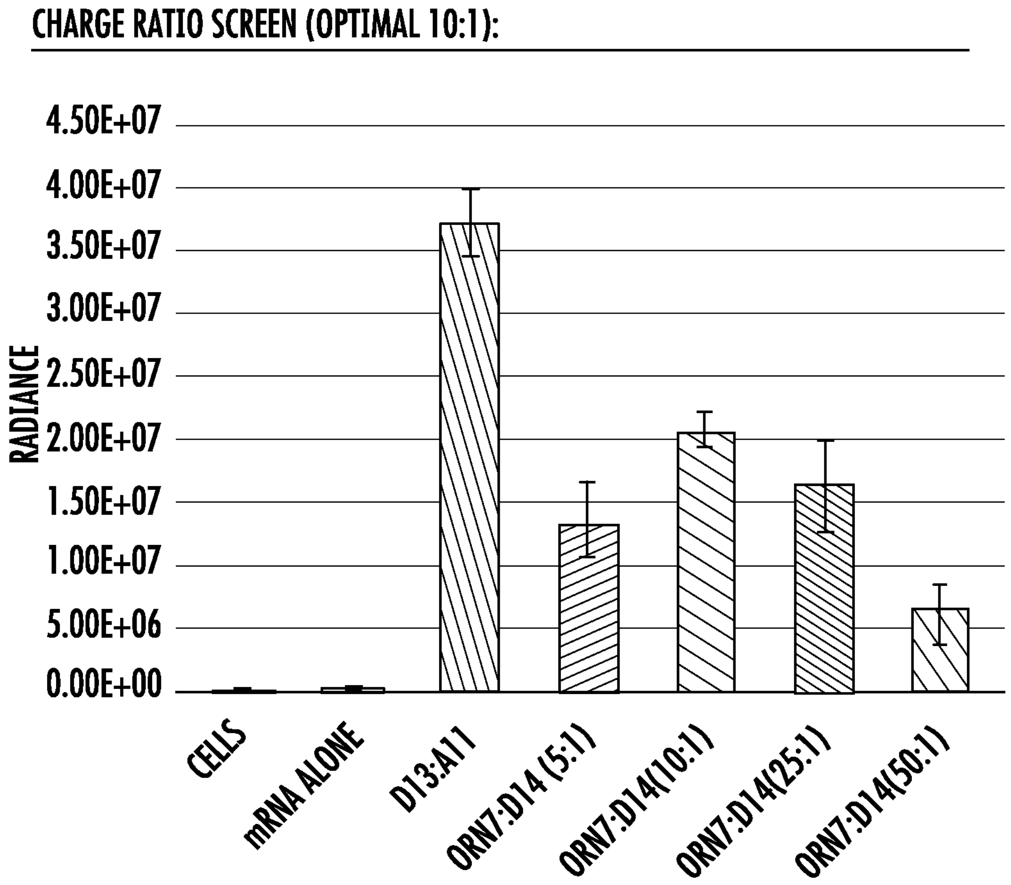

FIG. 21A-21D. In vitro testing of sample library of ornithine-derived CARTs. FIG. 21A: Ornithine CARTs of Type A (reverse block) and Type B (forward block) were isolated. For values of variables m and n see FIG. 21B. FIG. 21B: Four CARTs, three of Type A (entries 1-3) and one of Type B (entry 4) were tested. FIG. 21C: In vitro testing of ornithine-derived CARTs relative to first-generation D13:A11 CART and lysine-derived D14:Lys8. HeLa cells were plated at 15,000 cells/well in serum-containing DMEM in a black-walled 96 well plate. 18 hours after plating, the media was replaced with serum-free DMEM. CARTs were formulated by diluting firefly luciferase-coding mRNA (stored in 0.2 mg/ml solution) in PBS 5.5 and adding the appropriate amount of CART DMSO solution (stored in a 2 mM solution) to obtain a 10:1 (+/−) charge ratio. The solution was mixed for 20 seconds and then pipetted onto cells immediately. Each well was treated with a total of 50 ng fLuc mRNA. 5.5 hours after treatment, to each well was added 15 μg D-luciferin. The cells were incubated for 5 minutes and then imaged on an IVIS 50. D13:A11 is a first-generation CART, and D14:Lys8 is a lysine-derived CART. Each point is the average of 6 wells, and error is expressed as +/−a standard deviation. Radiance in p/sec/$cm^2$/sr. FIG. 22D: Charge ratio screen of ornithine-derived CART. HeLa cells were plated at 15,000 cells/well in serum-containing DMEM in a black-walled 96 well plate. 18 hours after plating, the media was replaced with serum-free DMEM. CARTs were formulated by diluting firefly luciferase-coding mRNA (stored in 0.2 mg/ml solution) in PBS 5.5 and adding the appropriate amount of Orn7:D14 CART DMSO solution (stored in a 2 mM solution) to obtain a 5:1, 10:1, 25:1, or 50:1 (+/−) charge ratio. D13:A11 was used at a 10:1 (+/−) charge ratio. Each well was treated with a total of 50 ng fLuc mRNA. 5.5 hours after treatment, to each well was added 15 μg D-luciferin. The cells were incubated for 5 minutes and then imaged on an IVIS 50. Each point is the average of 6 wells, and error is expressed as +/−a standard deviation. Radiance in p/sec/$cm^2$/sr.

Figure 22:
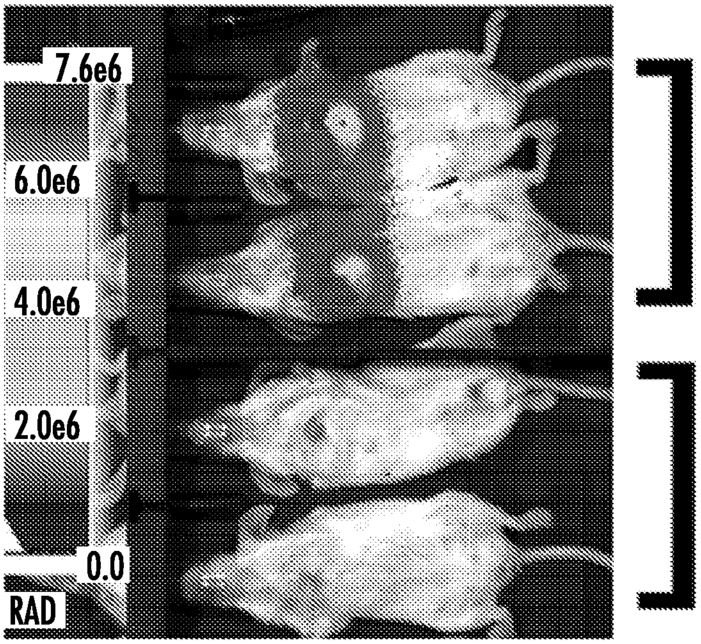

FIG. 22. In vivo testing of ornithine-derived CARTs. Female BALB/c mice were treated with 5 μg of fLuc mRNA either without a transfection agent (bottom) or with ornithine-derived CART Orn7:D14 (top), formulated at a 10:1 (+/−) charge ratio. Mice were injected with mRNA or mRNA/CART intravenously (tail vein). After 6 hours, they were injected intraperitoneally with D-luciferin and imaged on an Ami HT imaging system.

DETAILED DESCRIPTION

While various embodiments and aspects of the present disclosure are shown and described herein, it will be obvious to those skilled in the art that such embodiments and aspects are provided by way of example only. Numerous variations, changes, and substitutions will now occur to those skilled in the art without departing from the disclosure. It should be understood that various alternatives to the embodiments of the disclosure described herein may be employed in practicing the disclosure.

Unless the context indicates otherwise, it is specifically intended that the various features of the disclosure described herein can be used in any combination. Moreover, the disclosure also contemplates that in some embodiments any feature or combination of features set forth herein can be excluded or omitted. To illustrate, if the specification states that a complex has components A, B and C, it is specifically intended that any of A, B or C, or a combination thereof, can be omitted and disclaimed singularly or in any combination.

It must be noted that as used herein and in the appended claims, the singular forms "a", "an", and "the" include plural referents unless the context clearly dictates otherwise. Thus, for example, reference to "a cancer cell" includes a plurality of cancer cells. In other examples, reference to "a nucleic acid" or "nucleic acid" includes a plurality of nucleic acid molecules, i.e. nucleic acids.

The term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

Also as used herein, "and/or" refers to and encompasses any and all possible combinations of one or more of the associated listed items, as well as the lack of combinations when interpreted in the alternative ("or").

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

Definitions

The abbreviations used herein have their conventional meaning within the chemical and biological arts. The chemical structures and formulae set forth herein are constructed according to the standard rules of chemical valency known in the chemical sciences.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

As used herein the terms "oligomer" and "polymer" refer to a compound that has a plurality of repeating subunits, (e.g., polymerized monomers). The terms "co-oligomer" or "co-polymer" refers to an oligomer or polymer that includes 2 or more different residues (monomer units or monomers, which are interchangeably used herein). The number of monomers in oligomers is generally less than the number of monomers in polymers. Therefore, in some examples, oligomers can have 1 to about 10 monomers, 1 to about 20 monomers, 1 to about 30 monomers, 1 to about 40 monomers, 1 to about 50 monomers, 1 to about 100 monomers, 1 to about 150 monomers, 1 to about 200 monomers, 1 to about 250 monomers, 1 to about 300 monomers, 1 to about 350 monomers, 1 to about 400 monomers, 1 to about 450 monomers or 1 to about 500 monomers is in length. In some examples, oligomers can have less than about 500 monomers, less than about 450 monomers, less than about 400 monomers, less than about 350 monomers, less than about 300 monomers, less than about 250 monomers, less than about 200 monomers, less than about 150 monomers, less than about 100 monomers, less than about 50 monomers, less than about 40 monomers, less than about 30 monomers, less than about 20 monomers or less than about 10 monomers in length. In the context of polymers, the number of monomers in polymers is generally more than the number of monomers in oligomers. Therefore, in some examples, polymers can have about 500 to about 1000 monomers, about 500 to about 2000 monomers, about 500 to about 3000 monomers, about 500 to about 4000 monomers, about 500 to about 5000 monomers, about 500 to about 6000 monomers, about 500 to about 7000 monomers, about 500 to about 8000 monomers, about 500 to about 9000 monomers, about 500 to about 10000 monomers, or more than 10000 monomers in length.

The term "polymerizable monomer" is used in accordance with its meaning in the art of polymer chemistry and refers to a compound that may covalently bind chemically to other monomer molecules (such as other polymerizable monomers that are the same or different) to form a polymer.

The term "block copolymer" is used in accordance with its ordinary meaning and refers to two or more portions (e.g., blocks) of polymerized monomers linked by a covalent bond. In embodiments, a block copolymer is a repeating pattern of polymers. In embodiments, the block copolymer includes two or more monomers in a periodic (e.g., repeating pattern) sequence. For example, a diblock copolymer has the formula: -B-B-B-B-B-B-A-A-A-A-A-, where 'B' is a first subunit and 'A' is a second subunit covalently bound together. A triblock copolymer therefore is a copolymer with three distinct blocks, two of which may be the same (e.g., -A-A-A-A-A-B-B-B-B-B-B-A-A-A-A-A-) or all three are different (e.g., -A-A-A-A-A-B-B-B-B-B-B-C-C-C-C-C-) where 'A' is a first subunit, 'B' is a second subunit, and 'C' is a third subunit, covalently bound together.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—S—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The symbol "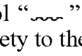" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

The term "alkylarylene" as an arylene moiety covalently bonded to an alkylene moiety (also referred to herein as an alkylene linker). In embodiments, the alkylarylene group has the formula:

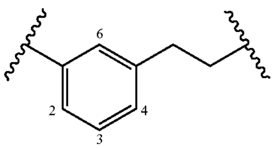

or

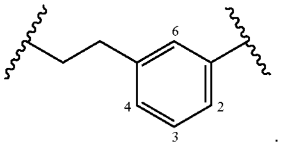

.

An alkylarylene moiety may be substituted (e.g., with a substituent group) on the alkylene moiety or the arylene linker (e.g., at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R"', —OC(O)R', —C(O)R', —$CO_2$R', —CONR'R", —OC(O)NR'R", —NR"C(O)R', —NR'—C(O)NR"R"', —NR"C$(O)_2$R', —NR—C(NR'R"R"')=NR"", —NR—C(NR'R")=NR"', —S(O)R', —S$(O)_2$R', —S$(O)_2$NR'R", —NR$SO_2$R', —NR'NR"R"', —ONR'R", —NR'C(O)NR"NR"'R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")═NR"", —NR—C(NR'R")═NR'", —S(O)R', $—S(O)_2R'$, $—S(O)_2NR'R"$, $—NRSO_2R'$, —NR'NR"R'", —ONR'R", —NR'C(O)NR"NR'"R"", —CN, $—NO_2$, —R', $—N_3$, $—CH(Ph)_2$, fluoro($C_1$-$C_4$)alkoxy, and fluoro($C_1$-$C_4$)alkyl, $—NR'SO_2R"$, —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)—(CRR')_q—U—$, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula $-A-(CH_2)_r—B—$, wherein A and B are independently —CRR'—, —O—, —NR—, —S—, —S(O)—, $—S(O)_2—$, $—S(O)_2NR'—$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $—(CRR')_s—X'— (C"R"R'")_d—$, where s and d are independently integers of from 0 to 3, and X is —O—, —NR'—, —S—, —S(O)—, $—S(O)_2—$, or $—S(O)_2NR'—$. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_5$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_0$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2C$, —$CH_2Br$, —$CH_2F$, —$CH_2I$, —CN, —OH, —$NH_2$, —COOH, —$CONH_2$, —$NO_2$, —SH, —$SO_3H$, —SO 4H, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or"lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth herein.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refer to the resulting association between atoms or molecules of bioconjugate reactive groups or bioconjugate reactive moieties. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to, nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.;

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g., phosphines) to form, for example, phosphate diester bonds;

(n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^3$ and optionally differently.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{201}$ substituents are present, each $R^{201}$ substituent may be distinguished as $R^{201A}$, $R^{201B}$, $R^{201C}$, $R^{201D}$, etc., wherein each of $R^{201A}$, $R^{201B}$, $R^{201C}$, $R^{201D}$, etc. is defined within the scope of the definition of $R^{201}$ and optionally differently.

The term "nucleophilic moiety" refers to a chemical species or functional group that is capable of donating one or more electrons (e.g., 2) to an electrophile. In embodiments, a nucleophilic moiety refers to a chemical species or functional group that can donate an electron to an electrophile in a chemical reaction to form a bond.

The term "electrophilic moiety" refers to a chemical species or functional group that is capable of receiving one or more electrons (e.g., 2). In embodiments, an electrophilic moiety refers to a chemical species or functional group that has a vacant orbital and can thus accept an electron to form a bond in a chemical reaction.

The term "oligoglycol moiety" refers to a chemical entity with the general formula:

$$R^{400}-O-(CH2-CH2-O)_{n300}-$$

where $R^{400}$ is H, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl and n300 is an integer of 1 or more. In some examples, $R^{400}$ is H or alkyl.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Unless defined otherwise, technical and scientific terms used herein have the same meaning as commonly understood by a person of ordinary skill in the art. See, e.g., Singleton et al., Dictionary of Microbiology and Molecular Biology, 2nd ed., J. Wiley & Sons (New York, NY 1994); Sambrook et al., Molecular Cloning, a Laboratory Manual, Cold Springs Harbor Press (Cold Springs Harbor, N Y 1989). Any methods, devices and materials similar or equivalent to those described herein can be used in the practice of this disclosure. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA), and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids has one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: a Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo). In embodiments, the nucleic acid is RNA (e.g. mRNA). In embodiments the nucleic acid is 10 to 100,000 bases in length. In embodiments the nucleic acid is 50 and 10,000 bases in length. In embodiments the nucleic acid is 50 and 5,000 bases in length. In embodiments the nucleic acid is 50 and 1,000 bases in length.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The terms "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. In embodiments, contacting includes, for example, allowing a nucleic acid to interact with an endonuclease.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

The term "stem cell" or "stem cells" refers to a clonal, self-renewing cell population that is multipotent and thus can generate several differentiated cell types.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, Molecular Cloning: A Laboratory Manual, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

A "vector" is a nucleic acid that is capable of transporting another nucleic acid into a cell. A vector is capable of directing expression of a protein or proteins encoded by one or more genes carried by the vector when it is present in the appropriate environment.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism. Given the large number of gene sequences available for a wide variety of animal, plant and microbial species, it is possible to calculate the relative frequencies of codon usage. Codon usage tables are readily available, for example, at the "Codon Usage Database" available at www.kazusa.or.jp/codon/. By utilizing the knowledge on codon usage or codon preference in each organism, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various methods known to those skilled in the art.

A "cell culture" is an in vitro population of cells residing outside of an organism. The cell culture can be established from primary cells isolated from a cell bank or animal, or secondary cells that are derived from one of these sources and immortalized for long-term in vitro cultures.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, having the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relics on attachment of a peptide or protein capable of crossing the cell membrane to the protein of interest. See, e.g., Ford et al. (2001) Gene Therapy 8:1-4 and Prochiantz (2007) Nat. Methods 4:119-20.

As used herein, the terms "specific binding" or "specifically binds" refer to two molecules forming a complex (e.g., a ribonucleoprotein and a transfection peptide) that is relatively stable under physiologic conditions.

Methods for determining whether a ligand binds another species (e.g., a protein or nucleic acid) and/or the affinity of such ligand-species interaction are known in the art. For example, the binding of a ligand to a protein can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), isothermal titration calorimetry (ITC), or enzyme-linked immunosorbent assays (ELISA).

Immunoassays which can be used to analyze immunospecific binding and cross-reactivity of the ligand include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, and fluorescent immunoassays. Such assays are routine and well known in the art.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The terms "antigen" and "epitope" interchangeably refer to the portion of a molecule (e.g., a polypeptide) which is specifically recognized by a component of the immune system, e.g., an antibody, a T cell receptor, or other immune receptor such as a receptor on natural killer (NK) cells. As used herein, the term "antigen" encompasses antigenic epitopes and antigenic fragments thereof.

An exemplary immunoglobulin (antibody) structural unit can have a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, $F(ab)_2'$ and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

As used herein, the terms "immolation," "self-immolation," "self-immolation mechanism," "immolation moiety," "immolation domain" and the like refer herein to the ability of a chemical group to undergo an intramolecular reaction thereby resulting in a chemical rearrangement of the chemical group and release of the rearranged chemical group from the remainder of the compound to which it was attached. A "pH-sensitive" immolation domain refers to a chemical group that undergoes an immolation reaction within a discreet pH range and does not substantially undergo the immolation reaction outside of the discreet pH range (e.g., pH about 1-5, pH about 5-7 or pH about 7-10). In embodiments, the discreet pH range is: pH 1-3, pH 2-4, pH 3-5, pH 4-6, pH 5-7, pH 6-8, pH 7-9, or pH 8-10. In embodiments, the pH-sensitive immolation region includes a cationic alpha amino ester (oligo(α-aminoester)). In embodiments, the cationic component of the cationic alpha amino ester is a positively charged nitrogen atom (e.g. a cationic amine). In embodiments, the cationic component of the cationic alpha amino ester is not a guanidinium group. In embodiments, the cationic component of the cationic alpha amino ester is not a piperidinium group.

The term "cell-penetrating complex" or the like refer, in the usual and customary sense, to a chemical complex (e.g., a complex or composition disclosed herein and embodiments thereof), capable of penetrating into a cell (a biological cell, such as a eukaryotic cell or prokaryotic cell). In embodiments, the cell-penetrating complex includes a nucleic acid ionically bound to a cationic amphipathic polymer. In embodiments, the nucleic acid is unable to substantially penetrate the cell in the absence of the cationic amphipathic polymer. Thus, in embodiments, the cationic amphipathic polymer facilitates the transport of the nucleic acid into the cell. As used herein, the terms "cationic charge altering releasable transporter," "CART" and the like refer to the cell-penetrating complexes disclosed herein. The CART compounds are able to release the nucleic acid component within the cell through the action of a pH-sensitive immolation domain within the cationic amphipathic polymer component, which reacts in response to an intracellular pH thereby releasing the nucleic acid with in the cell. In embodiments, the cationic amphipathic polymer degrades rapidly within the cell (e.g. a T½ of less than 6 hours at pH 7.4). At least in some embodiments, a polyplex, a complex, an electrostatic complex, a CART/mRNA complex, a CART/oligonucleotide complex and nanoparticle can interchangeably be used to refer to a cell-penetrating complex.

The term "amphipathic polymer" as used herein refers to a polymer containing both hydrophilic and hydrophobic portions. In embodiments, the hydrophilic to hydrophobic portions are present in a 1 to 1 mass ratio. In embodiments, the hydrophilic to hydrophobic portions are present in a 1 to 2 mass ratio. In embodiments, the hydrophilic to hydrophobic portions are present in a 1 to 5 mass ratio. In embodiments, the hydrophilic to hydrophobic portions are present in a 2 to 1 mass ratio. In embodiments, the hydrophilic to hydrophobic portions are present in a 5 to 1 mass ratio. An amphipathic polymer may be a diblock or triblock copolymer. In embodiments, the amphiphilic polymer may include two hydrophilic portions (e.g., blocks) and one hydrophobic portion (e.g., block).

The term "lipophilic polymer domain" or the like, often referred to as "lipid block" refers to a region of the cationic amphipathic polymer that is not hydrophilic (e.g. is insoluble in water alone). In embodiments, the lipophilic polymer domain has low solubility in water. For example, low solubility in water refers to the solubility of a lipophilic polymer domain which is about 0.0005 mg/mL to about 10 mg/mL soluble in water.

The term "initiator" refers to a compound that is involved in a reaction synthesizing a cationic amphipathic polymer having the purpose of initiating the polymerization reaction. Thus, the initiator is typically incorporated at the end of a synthesized polymer. For example, a plurality of molecules of one type (or formula) of monomer or more than one type of monomers (e.g. two different types of monomers) can be reacted with an initiator to provide a cationic amphipathic polymer. The initiator can be present on at least one end of the resulting polymer and not constitute a repeating (or polymerized) unit(s) present in the polymer.

The terms "disease" or "condition" refer to a state of being or health status of a subject capable of being treated with a compound, pharmaceutical composition, or method provided herein. The disease can be an autoimmune, inflammatory, cancer, infectious, metabolic, developmental, cardiovascular, liver, intestinal, endocrine, neurological, or other disease. In some examples, the disease is cancer (e.g. breast cancer, ovarian cancer, sarcoma, osteosarcoma, lung cancer, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, neuroblastoma).

The term "infection" or "infectious disease" refers to a disease or condition that can be caused by organisms such as a bacterium, virus, fungi or any other pathogenic microbial agents.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

As defined herein, the term "inhibition", "inhibit", "inhibiting" and the like in reference to an activity and/or functionality of a molecule (e.g. polynucleotide or protein) means negatively affecting (e.g., decreasing or reducing) the activity or function of the molecule relative to the activity or function of the protein in the absence of the inhibition. Thus, inhibition includes, at least in part, partially or totally blocking stimulation, decreasing, preventing, or delaying activation, or inactivating, desensitizing, or down-regulating signal transduction or enzymatic activity or the amount of a protein or polynucleotide. Similarly an "inhibitor" is a compound that inhibits a target bio-molecule (i.e. nucleic acid, peptide, carbohydrate, lipid or any other molecules that can be found from nature), e.g., by binding, partially or totally blocking, decreasing, preventing, delaying, inactivating, desensitizing, or down-regulating activity of the target bio-molecule. In the context of disease prevention treatment, inhibition refers to reduction of a disease or symptoms of disease.

"Treatment," "treating," and "treat" are defined as acting upon a disease, disorder, or condition with an agent to reduce or ameliorate harmful or any other undesired effects of the disease, disorder, or condition and/or its symptoms. "Treating" or "treatment of" a condition or subject in need thereof refers to (1) taking steps to obtain beneficial or desired results, including clinical results such as the reduction of symptoms; (2) inhibiting the disease, for example, arresting or reducing the development of the disease or its clinical symptoms; (3) relieving the disease, for example, causing regression of the disease or its clinical symptoms; or (4) delaying the disease. For example, beneficial or desired clinical results include, but are not limited to, reduction and/or elimination of cancer cells and prevention and/or reduction of metastasis of cancer cells.

The term "prevent," "preventing" or "prevention", in the context of a disease, refers to causing the clinical symptoms of the disease not to develop in a subject that does not yet experience or display symptoms of the disease. In some examples, such prevention can be applied to a subject who can be considered predisposed of the disease, whereas in some other examples, the subject may not be necessarily considered predisposed to the disease.

As used herein, "administering" refers to the physical introduction of a composition to a subject, using any of the various methods and delivery systems known to those skilled in the art. Preferred routes of administration for the composition described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, the composition described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

An "anti-cancer agent" is a therapeutic having an anti-cancer activity that can be used in the treatment or prevention of cancer. An anti-cancer agent can be a large or small molecule. Example anti-cancer agents include antibodies, small molecules, and large molecules or combinations thereof. Examples of "anti-cancer activity" include, but are not limited to, reduction of cancer cell number, reduction of cancer size, killing of cancer cells, reductions and/or inhibition of metastasis and reduction of cancer cell growth and/or proliferation.

The term "associated" or "associated with" in the context of a substance or substance activity or function associated with a disease means that the disease can be caused by (in whole or in part), or a symptom of the disease can be caused by (in whole or in part) the substance or substance activity or function. When the term is used in the context of a symptom, e.g. a symptom being associated with a disease or condition, it means that a symptom can be indicative of the disease or condition present in the subject who shows the symptom.

The term "subject," "individual," "host" or "subject in need thereof" refers to a living organism suffering from a disease or condition or having a possibility to have a disease or condition in the future. A term "patient" refers to a living organism that already has a disease or condition, e.g. a patient who has been diagnosed with a disease or condition or has one or more symptoms associated with a disease or condition. Non-limiting examples include humans, other mammals, bovines, rats, mice, dogs, monkeys, goat, sheep, cows, deer, and other non-mammalian animals. In some embodiments, a patient is human.

The term "vaccine" refers to a composition that can provide active acquired immunity to and/or therapeutic effect (e.g. treatment) of a particular disease or a pathogen. A vaccine typically contains one or more agents that can induce an immune response in a subject against a pathogen or disease, i.e. a target pathogen or disease. The immunogenic agent stimulates the body's immune system to recognize the agent as a threat or indication of the presence of the target pathogen or disease, thereby inducing immunological memory so that the immune system can more easily recognize and destroy any of the pathogen on subsequent exposure. Vaccines can be prophylactic (e.g. preventing or ameliorating the effects of a future infection by any natural or pathogen, or of an anticipated occurrence of cancer in a predisposed subject) or therapeutic (e.g., treating cancer in a subject who has been diagnosed with the cancer). The administration of vaccines is referred to vaccination. In some examples, a vaccine composition can provide nucleic acid, e.g. mRNA that encodes antigenic molecules (e.g. peptides) to a subject. The nucleic acid that is delivered via the vaccine composition in the subject can be expressed into antigenic molecules and allow the subject to acquire immunity against the antigenic molecules. In the context of the vaccination against infection disease, the vaccine composition can provide mRNA encoding antigenic molecules that are associated with a certain pathogen, e.g. one or more peptides that are known to be expressed in the pathogen (e.g. pathogenic bacterium or virus). In the context of cancer vaccine, the vaccine composition can provide mRNA encoding certain peptides that are associated with cancer, e.g. peptides that are substantially exclusively or highly expressed in cancer cells as compared to normal cells. The subject, after vaccination with the cancer vaccine composition, can have immunity against the peptides that are associated with cancer and kill the cancer cells with specificity.

The term "immune response" used herein encompasses, but is not limited to, an "adaptive immune response", also known as an "acquired immune response" in which adaptive immunity elicits immunological memory after an initial response to a specific pathogen or a specific type of cells that is targeted by the immune response, and leads to an enhanced response to that target on subsequent encounters. The induction of immunological memory can provide the basis of vaccination.

The term "immunogenic" or "antigenic" refers to a compound or composition that induces an immune response, e.g., cytotoxic T lymphocyte (CTL) response, a B cell response (for example, production of antibodies that specifically bind the epitope), an NK cell response or any combinations thereof, when administered to an immunocompetent subject. Thus, an immunogenic or antigenic composition is a composition capable of eliciting an immune response in an immunocompetent subject. For example, an immunogenic or antigenic composition can include one or more immunogenic epitopes associated with a pathogen or a specific type of cells that is targeted by the immune response. In addition, an immunogenic composition can include isolated nucleic acid constructs (such as DNA or RNA) that encode one or more immunogenic epitopes of the antigenic polypeptide that can be used to express the epitope (s) (and thus be used to elicit an immune response against this polypeptide or a related polypeptide associated with the targeted pathogen or type of cells).

According to the methods provided herein, the subject can be administered an effective amount of one or more of agents, compositions or complexes, all of which are interchangeably used herein, (e.g. cell-penetrating complex or vaccine composition) provided herein. The terms "effective amount" and "effective dosage" are used interchangeably. The term "effective amount" is defined as any amount necessary to produce a desired effect (e.g., transfection of nucleic acid into cells and exhibiting intended outcome of the transfected nucleic acid). Effective amounts and schedules for administering the agent can be determined empirically by one skilled in the art. The dosage ranges for administration are those large enough to produce the desired effects, e.g. transfection of nucleic acid, modulation in gene expression, gene-edition, induction of stem cells, induction of immune response and more. The dosage should not be so large as to cause substantial adverse side effects, such as unwanted cross-reactions, anaphylactic reactions, and the like. Generally, the dosage can vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount can show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation can depend on the purpose of the treatment, and can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

The term "kill" with respect to a cancer treatment is directed to include any type of manipulation that will lead to the death of that cancer cell or at least of portion of a population of cancer cells.

Cell-Penetrating Complexes

The cell-penetrating complexes provided herein including embodiments thereof, include a nucleic acid non-covalently bound to a cationic amphipathic polymer (e.g., having the formula (XII), (XIII), (XIV), and (XV)). The cationic amphipathic polymer (or a plurality thereof) is capable of delivering the nucleic acid (e.g., RNA or DNA) they are bound to, to a variety of cells in vitro and in vivo. Depending on the chemical composition of the cationic amphipathic polymer, the cell, tissue or organ the nucleic acid is delivered to can be different. For example, in embodiments, the cationic amphipathic polymer delivers the nucleic acid to the lung. In embodiments, the cationic amphipathic polymer delivers the nucleic acid systemically. In yet other embodiments, the cationic amphipathic polymer delivers the nucleic acid to reticulocytes. In yet other embodiments, the cationic amphipathic polymer delivers the nucleic acid to hematopoietic stem cells (HPCs). The cell-penetrating complexes provided herein, including embodiments thereof, may further include a plurality (more than one, e.g., two) of cationic amphipathic polymer types (e.g., a mixture of a first cationic amphipathic polymer and a second amphipathic polymer) wherein each of the cationic amphipathic polymer types is chemically different.

In an aspect, there is provided a complex including a nucleic acid non-covalently bound to a cationic amphipathic polymer of formula (XII) as provided herein including embodiments thereof. In an aspect, there is provided a complex including a nucleic acid non-covalently bound to a cationic amphipathic polymer of formula (XIII) as provided herein including embodiments thereof. In an aspect, there is provided a complex including a nucleic acid non-covalently bound to a cationic amphipathic polymer of formula (XIV) as provided herein including embodiments thereof. In an aspect, there is provided a complex including a nucleic acid non-covalently bound to a cationic amphipathic polymer of formula (XV) as provided herein including embodiments thereof.

In an aspect, there is provided a cell-penetrating complex including a nucleic acid non-covalently bound to a cationic amphipathic polymer of formula (XII) as provided herein including embodiments thereof. In an aspect, there is provided a cell-penetrating complex including a nucleic acid non-covalently bound to a cationic amphipathic polymer of formula (XIII) as provided herein including embodiments thereof. In an aspect, there is provided a cell-penetrating complex including a nucleic acid non-covalently bound to a cationic amphipathic polymer of formula (XIV) as provided herein including embodiments thereof. In an aspect, there is provided a cell-penetrating complex including a nucleic acid non-covalently bound to a cationic amphipathic polymer of formula (XV) as provided herein including embodiments thereof.

In a first aspect, there is provided a cell-penetrating complex including a nucleic acid non-covalently bound to a cationic amphipathic polymer (e.g., having the formula (XII), (XIII), (XIV), and (XV)), the cationic amphipathic polymer including a pH-sensitive immolation domain (e.g., having Formula (XVI), (XVII), (XVIII), (XIX), (XX), and (XXI)). In embodiments, one or more counter ions (e.g., anions) may also be present as countercharges to the positive charges in the cationic amphipathic polymer. In embodiments, the nucleic acid is non-covalently bound to the cationic amphipathic polymer. In embodiments, the nucleic acid is ionically bound to the cationic amphipathic polymer. In embodiments, the cell penetrating complex includes a plurality of optionally different nucleic acids (e.g. 1 to 10 additional nucleic acids, 1 to 5 additional nucleic acids, 1 to 5 additional nucleic acids, 2 additional nucleic acids or 1 additional nucleic acid). In embodiments, the nucleic acid is DNA. In embodiments, the nucleic acid is RNA. In embodiments, the nucleic acid is mRNA.

In embodiments, a ratio between the number of cations in the cationic amphipathic polymer molecules and the number of anions on the nucleic acid molecules present in a cell-penetrating complex can be about 1:1, about 5:1, about 10:1, about 20:1, about 30:1, about 40:1, about 50:1, about 60:1, about 70:1, about 80:1, about 90:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing. In other embodiments, a ratio between the number of anions on the nucleic acid molecules and the number of cations on the cationic amphipathic polymer molecules present in a cell-penetrating complex can be about 1:1, about 5:1, about 10:1, about 20:1, about 30:1, about 40:1, about 50:1, about 60:1, about 70:1, about 80:1, about 90:1, about 10:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing. In some preferred embodiments, this ratio is approximately 10 cationic charges on the amphipathic polymer molecule to 1 negative charge on the nucleic acid. Other embodiments can have 5 cationic charges on the amphipathic polymer molecule to 1 negative charge on the nucleic acid or 20 cationic charges on the amphipathic polymer molecule to 1 negative charge on the nucleic acid.

In embodiments, a ratio between the number of cations in the cationic amphipathic polymer molecules and the number of anions on the nucleic acid molecules present in a cell-penetrating complex can be 1:1, 5:1, 10:1, 20:1, 30:1, 40:1, 50:1, 60:1, 70:1, 80:1, 90:1, $10^2$:1, $10^3$:1, $10^4$:1, $10^5$:1, $10^6$:1, $10^7$:1, $10^8$:1, $10^9$:1, $10^{10}$:1, or more or any intervening ranges of the foregoing. In other embodiments, a ratio between the number of anions on the nucleic acid molecules and the number of cations on the cationic amphipathic polymer molecules present in a cell-penetrating complex can be 1:1, 5:1, 10:1, 20:1, 30:1, 40:1, 50:1, 60:1, 70:1, 80:1, 90:1, 10:1, $10^2$:1, $10^3$:1, $10^4$:1, $10^5$:1, 106:1, $10^7$:1, 10':1, $10^9$:1, $10^{10}$:1, or more or any intervening ranges of the foregoing. In some preferred embodiments, this ratio is approximately 10 cationic charges on the amphipathic polymer molecule to 1 negative charge on the nucleic acid. Other embodiments can have 5 cationic charges on the amphipathic polymer molecule to 1 negative charge on the nucleic acid or 20 cationic charges on the amphipathic polymer molecule to 1 negative charge on the nucleic acid.

In embodiments, a ratio between the number of nucleic acid molecules and the number of cationic amphipathic polymer molecules present in a cell-penetrating complex can be about 1:1, about 10:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing. In other embodiments, a ratio between the number of cationic amphipathic polymer molecules and the number of nucleic acid molecules present in a cell-penetrating complex can be about 1:1, about 10:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing.

In embodiments, a ratio between the number of nucleic acid molecules and the number of cationic amphipathic polymer molecules present in a cell-penetrating complex can be 1:1, 10:1, $10^2$:1, $10^1$:1, $10^4$:1, $10^5$:1, 106:1, $10^7$:1, $10^8$:1, $10^9$:1, $10^{10}$:1, or more or any intervening ranges of the foregoing. In other embodiments, a ratio between the number of cationic amphipathic polymer molecules and the number of nucleic acid molecules present in a cell-penetrating complex can be 1:1, 10:1, $10^2$:1, $10^3$:1, $10^4$:1, $10^5$:1, $10^6$:1, $10^7$:1, $10^2$:1, $10^9$:1, $10^{10}$:1, or more or any intervening ranges of the foregoing.

In embodiments, the cationic amphipathic polymer may be a cationic charge altering releasable transporter (CART). In embodiments, the CART may include an oligomeric chain containing a series of cationic sequences that undergo a pH-sensitive change in charge from cationic to neutral or cationic to anionic.

In embodiments, the cationic amphipathic polymer has a pH-sensitive immolation domain (e.g. of Formula (XVI), (XVII), (XVIII), (XIX), (XX), and (XXI)) and a lipophilic polymer domain (e.g., $LP^1$, $LP^2$, $LP^3$). In embodiments, the lipophilic polymer domain may facilitate cell permeation, cell delivery and/or transport across cell membrane. In embodiments, the lipophilic polymer domain may be substantially insoluble in water (e.g., less than about 0.0005 mg/mL to about 10 mg/mL soluble in water). In embodiments, the lipophilic polymer domain may facilitate aggregation of the cationic amphipathic polymers into nanoparticles. In embodiments, such nanoparticles may have an average longest dimension of about 50 nm to about 500 nm. In embodiments, the lipophilic polymer domain may facilitate endosome fusion of the remnants of the cationic amphipathic polymer subsequent to entry and immolation within the endosome. In embodiments, the cell-penetrating complexes of the present disclosure protect the nucleic acid cargo from degradation. The term "nucleic acid cargo" or the like refers, in the usual and customary sense, to a species desired for transport into a cell by the cell-penetrating complex disclosed herein, and embodiments thereof.

In embodiments, the cationic amphipathic polymer has the formula:

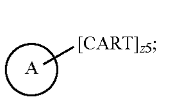

wherein Ring A is a substituted or unsubstituted cycloalkyl, substituted or unsubstituted heterocycloalkyl, substituted or unsubstituted aryl, or substituted or unsubstituted heteroaryl;

CART has the formula: $-L^1-[(LP^1)_{z1}-(LP^2)_{z3}-(IM)_{z2}]_{z4}-L^2-R^{2A}$;

wherein, $R^{2A}$ is hydrogen, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ and $L^2$ are independently a bond, $-C(O)O-$, $-O-$, $-S-$, $-NH-$, $-C(O)NH-$, $-NHC(O)-$, $-S(O)_2-$, $-S(O)NH-$, $-NHC(O)NH-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $LP^1$ and $LP^2$ are independently a lipophilic polymer domain, wherein at least one of $LP^1$ or $LP^2$ is a lipophilic polymer domain; IM has the formula:

(XVI)

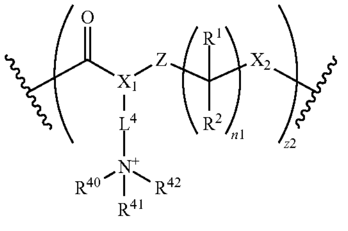

or

-continued (XVII)

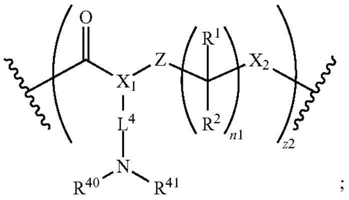

;

z5 are an integer from 1 to 10; z1 and z3 are independently integers from 0 to 100, wherein at least one of z1 or z3 is not 0; z4 is an integer from 1 to 100; and z2 is an integer from 2 to 100.

In formula (XVI) and (XVII) $X^1$ may be a bond, —$C(R^5)(R^6)$—, —$C(R^5)(R^6)$—$C(R^7)(R^8)$—, —O—$C(R^5)(R^6)$—, or —O—$C(R^5)(R^6)$—$C(R^7)(R^8)$—. $X^2$ is —O— or —S—. $R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^4$ is a bond, —C(O)O—, —O—, —S—, —NH—, —C(O)NH—, —NHC(O)—, —$S(O)_2$—, —S(O)NH—, —NHC(O)NH—, substituted or unsubstituted alkylene, or substituted or unsubstituted heteroalkylene. $R^{40}$, $R^{41}$, and $R^{42}$ are independently hydrogen, substituted or unsubstituted alkyl or substituted or unsubstituted heteroalkyl. Z is —S—, —$S^+R^{13}$—, —$NR^{13}$— or —$N^+(R^{13})(H)$—. $R^{13}$ is hydrogen, —$CCl_3$, —$CBr_3$, —$CF_3$, —$CI_3$, —CN, —OH, =O, —$NH_2$, —COOH, —$CONH_2$, —SH, —$SO_3H$, —$SO_2NH_2$, —$OCCl_3$, —$OCF_3$, —$OCBr_3$, —$OCI_3$, —$OCHCl_2$, —$OCHBr_2$, —$OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. n1 is an integer from 0 to 50. z2 is an integer from 2 to 100; and z5 is an integer from 1 to 10.

In embodiments, Ring A is a substituted or unsubstituted aryl. In embodiments, Ring A is a substituted or unsubstituted phenyl. In embodiments, Ring A is a substituted or unsubstituted aryl. In embodiments, Ring A is a substituted or unsubstituted phenyl or naphthalenyl.

In embodiments, the cationic amphipathic polymer has the formula:

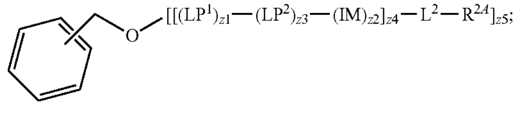

wherein IM has the formula:

(XVI)

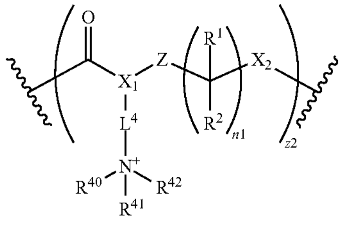

or

-continued (XVII)

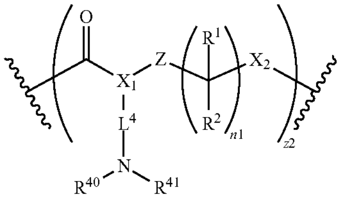

and wherein the substituents and variables are defined as described herein.

In embodiments, the cationic amphipathic polymer has the formula:

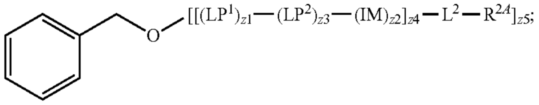

wherein IM has the formula:

(XVI)

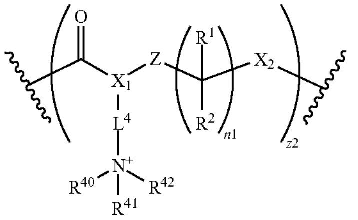

or (XVII)

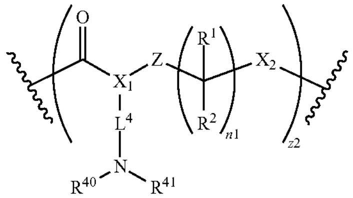

wherein the substituents and variables are defined as described herein.

In embodiments, the cationic amphipathic polymer has the formula:

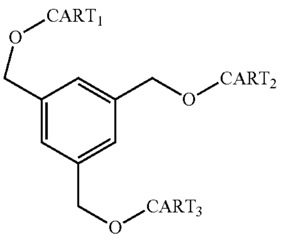

wherein $CART_1$, $CART_2$ and $CART_3$ are independently CART as defined herein.

In embodiments, z5 is an integer from 1 to 3. In embodiments, z5 is 1 or 3. In embodiments, z5 is 1. In embodiments, z5 is 3. In embodiments, $R^{2A}$ is hydrogen. In embodiments, $L^2$ is a bond.

In embodiments, the cationic amphipathic polymer has the formula:

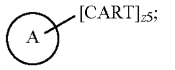

wherein Ring A is a substituted or unsubstituted cycloalkyl, substituted or unsubstituted heterocycloalkyl, substituted or unsubstituted aryl, or substituted or unsubstituted heteroaryl; CART has the formula: $-L^1-[(LP^1)_{z1}-(IM)_{z2}-(LP^2)_{z3}]_{z4}-L^2-R^{2A}$;

wherein, $R^{2A}$ is hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHC(O)NHNH$_2$, —NHC(O)NH$_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $LP^1$ and $LP^2$ are independently a bond or a lipophilic polymer domain, wherein at least one of $LP^1$ or $LP^2$ is a lipophilic polymer domain; IM has the formula:

(XVI)

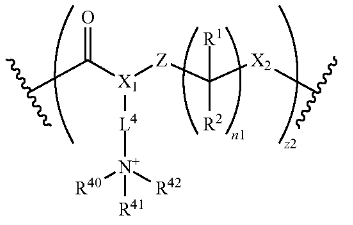

or (XVII)

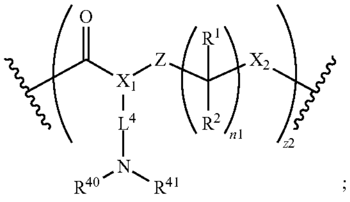

;

z5 are an integer from 1 to 10; z1 and z3 are independently integers from 0 to 100, wherein at least one of z1 or z3 is not 0; z4 is an integer from 1 to 100; and z2 is an integer from 2 to 100.

In formula (XVI) and (XVII) $X_1$ may be a bond, $—C(R^5)(R^6)—$, $—C(R^5)(R^6)—C(R^7)(R^8)—O—C(R^5)(R^6)—$, or $—O—C(R^5)(R^6)—C(R^7)(R^8)—$. $X^2$ is —O— or —S—. $R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^4$ is a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene. $R^{40}$, $R^{41}$, and $R^{42}$ are independently hydrogen, substituted or unsubstituted alkyl or substituted or unsubstituted heteroalkyl. Z is —S—, $—S^+R^{13}—$, $—NR^{13}—$, or $—N^+(R^{13})(H)—$. $R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $—SO_2NH_2$, $—OCCl_3$, $—OCF_3$, $—OCBr_3$, $—OCI_3$, $—OCHCl_2$, $—OCBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. n1 is an integer from 0 to 50. z2 is an integer from 2 to 100; and z5 is an integer from 1 to 10.

In embodiments, Ring A is a substituted or unsubstituted aryl. In embodiments, Ring A is a substituted or unsubstituted phenyl. In embodiments, Ring A is a substituted or unsubstituted aryl. In embodiments, Ring A is a substituted or unsubstituted phenyl or naphthalenyl.

In embodiments, the cationic amphipathic polymer has the formula:

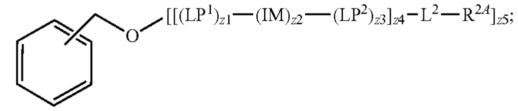

wherein IM has the formula:

(XVI)

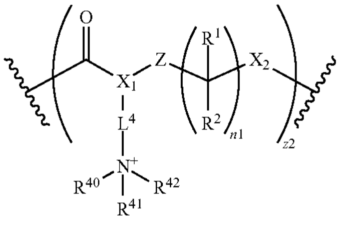

or (XVII)

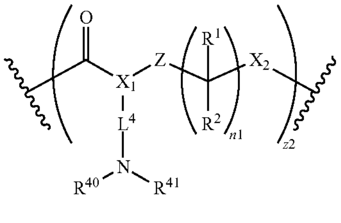

.

In embodiments, the cationic amphipathic polymer has the formula:

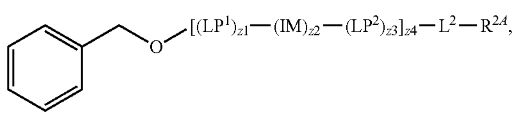

wherein IM has the formula:

(XVI)

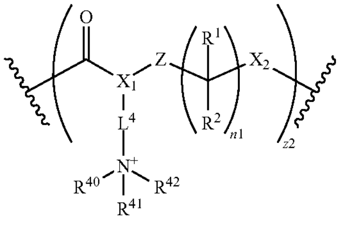

or (XVII)

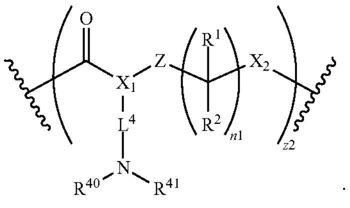

.

In embodiments, the cationic amphipathic polymer has the formula

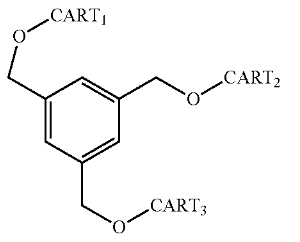

wherein $CART_1$, $CART_2$ and $CART_3$ are independently CART as defined herein.

In embodiments, Ring A is a substituted or unsubstituted aryl. In some other embodiments, Ring A is a substituted or unsubstituted phenyl. In still some other embodiments, Ring A is a substituted or unsubstituted aryl. In still some other embodiments, Ring A is a substituted or unsubstituted phenyl or naphthalenyl.

In embodiments, Ring A is an unsubstituted aryl (i.e. unsubstituted beyond the CART moiety). In embodiments, Ring A is an unsubstituted phenyl (i.e. unsubstituted beyond the CART moiety). In embodiments, Ring A is an unsubstituted phenyl or naphthalenyl (i.e. unsubstituted beyond the CART moiety). In embodiments, Ring A is a substituted aryl (i.e. substituted in addition to the CART moiety). In embodiments, Ring A is a substituted phenyl (i.e. substituted in addition to the CART moiety). In embodiments, Ring A is a substituted phenyl or naphthalenyl (i.e. substituted in addition to the CART moiety).

In embodiments, the cell-penetrating complex has a detectable agent (e.g., fluorophore).

In embodiments, $R^{1A}$ is an aryl substituted with a methoxy linker. In embodiments, $R^{1A}$ is an aryl substituted with a linker (e.g., $—CH_2—O—$). A non-limiting example wherein $R^{1A}$ is an aryl substituted with a methoxy linker has the formula:

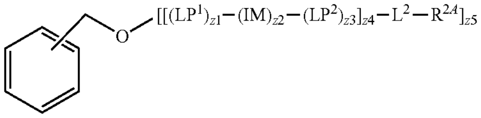

wherein $LP^1$, $LP^2$, IM, $L^2$, $R^{2A}$, z1, z2, z3, z4, and z5 are defined as herein.

In embodiments, the cationic amphipathic polymer has the formula (IX):

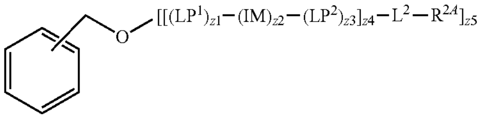

wherein $LP^1$, $LP^2$, IM, $L^2$, $R^{2A}$, z1, z2, z3, z4, and z5 are defined as herein.

In embodiments, the cationic amphipathic polymer has the formula (X):

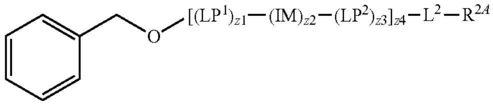

wherein $LP^1$, $LP^2$, IM, $L^2$, $R^{2A}$, z1, z2, z3, z4, and z5 are defined as herein.

In some embodiments, the cationic amphipathic polymer has the formula (XI):

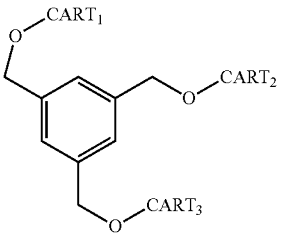

wherein $CART_1$, $CART_2$ and $CART_3$ are independently a CART moiety as defined in formula (VIII) (e.g., $-L^1-[(LP^1)_{z1}-(IM)_{z2}-(LP^2)_{z3}]_{z4}-L^2-R^{2A}$). In embodiments each CART moiety is optionally different.

In embodiments, the $L^1$ is $—CH_2—O—$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In one aspect, a cell-penetrating complex including a nucleic acid non-covalently bound to a cationic amphipathic polymer is provided, the cationic amphipathic polymer including a pH-sensitive immolation domain and a lipophilic polymer domain, wherein the cationic amphipathic polymer has the formula:

(XII)

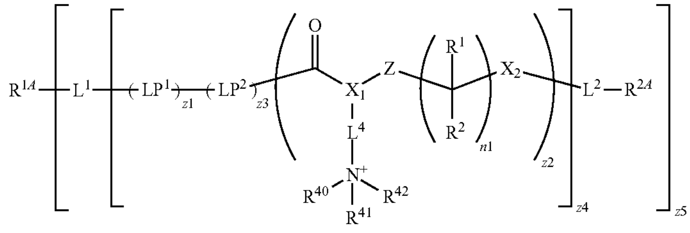

or (XIII)

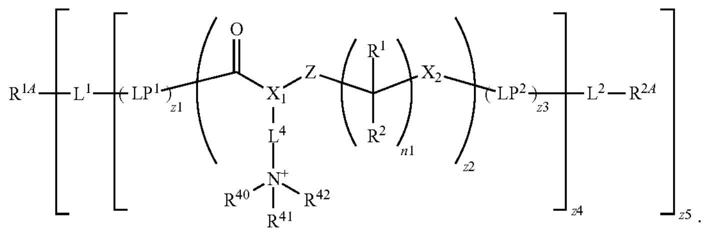

In Formula (XII) and (XIII), $R^{1A}$ is hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ is hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$LP^1$ and $LP^2$ are independently a lipophilic polymer domain.

$X^1$ is a bond, $—C(R^5)(R^6)—$, $—C(R^5)(R^6)—C(R^7)(R^8)—$, $—O—C(R^5)(R^6)—$, or $—O—C(R^5)(R^6)—C(R^7)(R^8)—$.

$X^2$ is —O— or —S—.

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$L^4$ is a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene.

$R^{40}$, $R^{41}$, and $R^{42}$ are independently hydrogen, substituted or unsubstituted alkyl or substituted or unsubstituted heteroalkyl.

Z is —S—, $—S^+R^{13}—$, $—NR^{13}—$, or $—N^+(R^{13})(H)—$.

$R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $—SO_2NH_2$, $—OCCl_3$, $—OCF_3$, $—OCBr_3$, $—OCI_3$, $—OCHCl_2$, $—OCHBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

n1 is an integer from 0 to 50.

z1 and z3 are independently integers from 0 to 100, wherein at least one of z1 or z3 is not 0.

z4 is an integer from 1 to 100.

z2 is an integer from 2 to 100; and z5 is an integer from 1 to 10.

In one aspect, a cell-penetrating complex including a nucleic acid non-covalently bound to a cationic amphipathic polymer is provided, the cationic amphipathic polymer including a pH-sensitive immolation domain and a lipophilic polymer domain, wherein the cationic amphipathic polymer has the formula:

(XIV)

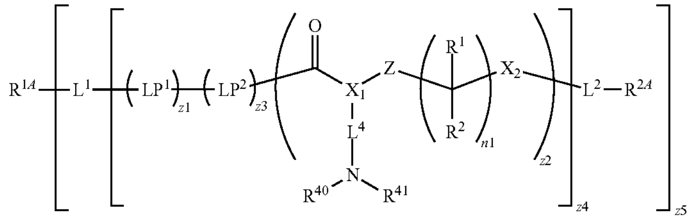

or (XV)

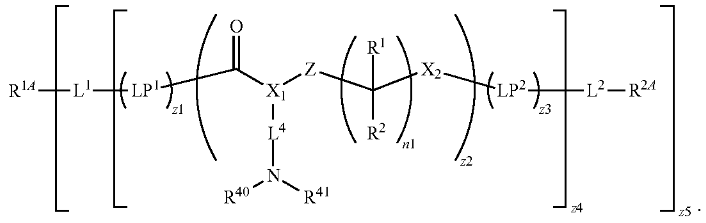

In Formula (XIV) and (XV), $R^{1A}$ is hydrogen, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ is hydrogen, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ and $L^2$ are independently a bond, $-C(O)O-$, $-O-$, $-S-$, $-NH-$, $-C(O)NH-$, $-NHC(O)-$, $-S(O)_2-$, $-S(O)NH-$, $-NHC(O)NH-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$LP^1$ and $LP^2$ are independently a lipophilic polymer domain;

$X^1$ is a bond, $-C(R^5)(R^6)-$, $-C(R^5)(R^6)-C(R^7)(R^8)-$, $-O-C(R^5)(R^6)-$, or $-O-C(R^5)(R^6)-C(R^7)(R^8)-$.

$X^2$ is $-O-$ or $-S-$.

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

$L^4$ is a bond, $-C(O)O-$, $-O-$, $-S-$, $-NH-$, $-C(O)NH-$, $-NHC(O)-$, $-S(O)_2-$, $-S(O)NH-$, $-NHC(O)NH-$, substituted or unsubstituted alkylene, or substituted or unsubstituted heteroalkylene.

$R^{40}$ and $R^{41}$ are independently hydrogen, substituted or unsubstituted alkyl or substituted or unsubstituted heteroalkyl.

Z is $-S-$, $-S^+R^{13}-$, $-NR^{13}-$ or $-N^+(R^{13})(H)-$.

$R^{13}$ is hydrogen, $-CCl_3$, $-CBr_3$, $-CF_3$, $-CI_3$, $-CN$, $-OH$, $=O$, $-NH_2$, $-COOH$, $-CONH_2$, $-SH$, $-SO_3H$, $-SO_2NH_2$, $-OCCl_3$, $-OCF_3$, $-OCBr_3$, $-OCI_3$, $-OCHCl_2$, $-OCHBr_2$, $-OCHI_2$, $-OCHF$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

n1 is an integer from 0 to 50.

z1 and z3 are independently integers from 0 to 100, wherein at least one of z1 or z3 is not 0. z4 is an integer from 1 to 100. z2 is an integer from 2 to 100; and z5 is an integer from 1 to 10.

In one aspect is provided a complex including a nucleic acid non-covalently bound to a cationic amphipathic polymer, wherein the cationic amphipathic polymer has the formula:

(XII)

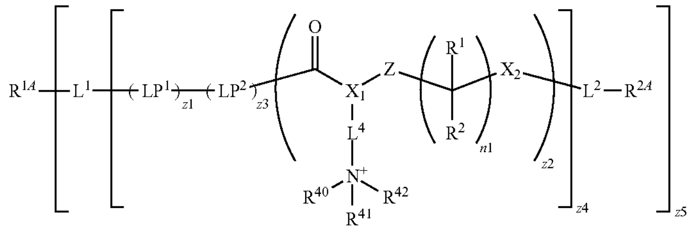

or (XIII)

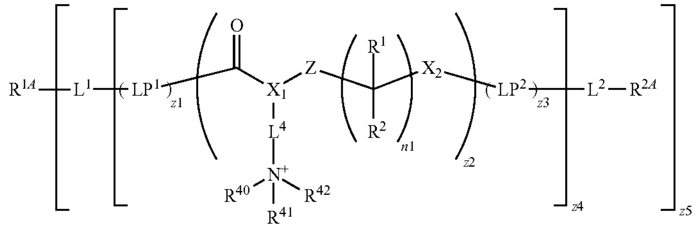

wherein $R^{1A}$ is independently hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —CHF, —$CH_2I$, —CN, —OH, —$NH_2$, independently —COOH, —$CONH_2$, —$NO_2$, —SH, —$SO_3H$, —$SO_4H$, —$SO_2NH_2$, —$NHNH_2$, —$ONH_2$, independently —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —$S(O)_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, —$C(R^5)(R^6)$—, —$C(R^5)(R^6)$—$C(R^7)$(R")—, —O—$C(R^5)(R^6)$—, or —O—$C(R^5)(R^6)$—$C(R^7)(R^8)$—.

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, —C(O)O—, —O—, —S—, —NH—, —C(O)NH—, —NHC(O)—, —$S(O)_2$—, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, —$S^+R^{13}$—, —$NR^{13}$—, or —$N^+(R^{13})(H)$—;

$R^{13}$ is hydrogen, —$CCl_3$, —$CBr_3$, —$CF_3$, —$CI_3$, —CN, —OH, =O, —$NH_2$, —COOH, —$CONH_2$, —SH, —$SO_3H$, $SO_2NH_2$, —$OCCl_3$, —$OCF_3$, —$OCBr_3$, —$OCI_3$, —$OCHCl_2$, —$OCHBr_2$, —$OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z1 or z3 is not 0;

z2 is an integer from 2 to 100;

z4 is an integer from 1 to 100; and z5 is an integer from 1 to 10.

In one aspect is provided a cell-penetrating complex including a nucleic acid non-covalently bound to a cationic amphipathic polymer, wherein the cationic amphipathic polymer has the formula:

(XII)

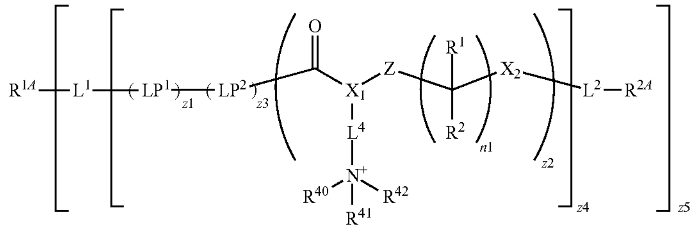

or (XIII)

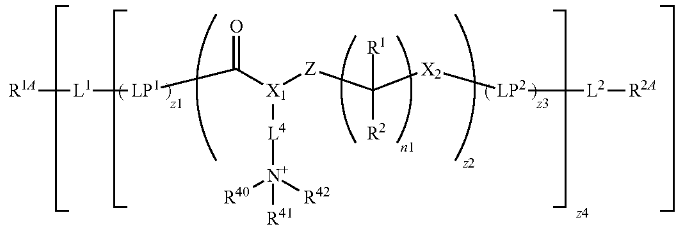

wherein $R^{1A}$ is independently hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, independently —COOH, —$CONH_2$, —$NO_2$, —SH, —$SO_3H$, —$SO_4H$, —$SO_2NH_2$, —$NHNH_2$, —$ONH_2$, independently —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —$S(O)_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, —C($R^5$)($R^6$)—, —C($R^5$)($R^6$)—C($R^7$)($R^8$)—, —O—C($R^5$)($R^6$)—, or —O—C($R^5$)($R^6$)—C($R^7$)($R^8$)—;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, —C(O)O—, —O—, —S—, —NH—, —C(O)NH—, —NHC(O)—, —$S(O)_2$—, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, —$S^+R^{13}$—, —$NR^{13}$— or —$N^+(R^{13})(H)$—;

$R^{13}$ is hydrogen, —$CCl_3$, —$CBr_3$, —$CF_3$, —$CI_3$, —CN, —OH, =O, —$NH_2$, —COOH, —$CONH_2$, —SH, —$SO_3H$, $SO_2NH_2$, —$OCCl_3$, —$OCF_3$, —$OCBr_3$, —$OCI_3$, —$OCHCl_2$, —$OCHBr_2$, —$OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z or z3 is not 0; z2 is an integer from 2 to 100; z4 is an integer from 1 to 100; and z5 is an integer from 1 to 10.

In embodiments, $X_1$ is $CH_2$.

In embodiments, $L^4$ is substituted or unsubstituted $C_2$-$C_8$ alkylene. In embodiments, $L^4$ is substituted or unsubstituted $C_8$ alkylene. In embodiments, $L^4$ is substituted or unsubstituted $C_7$ alkylene. In embodiments, $L^4$ is substituted or unsubstituted $C_6$ alkylene. In embodiments, $L^4$ is substituted or unsubstituted $C_8$ alkylene. In embodiments, $L^4$ is substituted or unsubstituted $C_4$ alkylene. In embodiments, $L^4$ is substituted or unsubstituted $C_3$ alkylene. In embodiments, $L^4$ is substituted or unsubstituted $C_2$ alkylene. In embodiments, $L^4$ is unsubstituted $C_2$-$C_8$ alkylene. In embodiments, $L^4$ is unsubstituted $C_8$ alkylene. In embodiments, $L^4$ is unsubstituted $C_7$ alkylene. In embodiments, $L^4$ is unsubstituted $C_6$ alkylene. In embodiments, $L^4$ is unsubstituted $C_5$ alkylene. In embodiments, $L^4$ is unsubstituted $C_4$ alkylene.

In embodiments, $L^4$ is unsubstituted $C_3$ alkylene. In embodiments, $L^4$ is unsubstituted $C_2$ alkylene. In embodiments, $L^4$ is unsubstituted $C_2$ alkylene, unsubstituted $C_3$ alkylene or unsubstituted $C_4$ alkylene.

In embodiments, $L^4$ is substituted (e.g., substituted with at least one substituent group, size-limited substituent group, or lower substituent group) or unsubstituted $C_2$-$C_8$ alkylene (e.g., $C_2$-$C_8$, $C_2$-$C_6$, $C_2$-$C_4$, or $C_2$). In embodiments, $L^4$ is unsubstituted $C_2$-$C_8$ alkylene (e.g., $C_2$-$C_8$, $C_2$-$C_6$, $C_2$-$C_4$, or $C_2$). In embodiments, $L^4$ is unsubstituted $C_2$ alkylene, unsubstituted $C_3$ alkylene or unsubstituted $C_4$ alkylene.

In embodiments, a substituted $L^4$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^4$ is substituted with a plurality of groups selected from substituent groups, size-limited substituent groups, and lower substituent groups, each substituent group, size-limited substituent group, and/or lower substituent group may optionally be different. In embodiments, when $L^4$ is substituted, it is substituted with at least one substituent group. In embodiments, when $L^4$ is substituted, it is substituted with at least one size-limited substituent group. In embodiments, when $L^4$ is substituted, it is substituted with at least one lower substituent group.

In embodiments, $R^{40}$ is independently hydrogen, substituted or unsubstituted alkyl or substituted or unsubstituted heteroalkyl. In embodiments, $R^{40}$ is independently hydrogen, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$) or substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered).

In embodiments, a substituted $R^{40}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{40}$ is substituted with a plurality of groups selected from substituent groups, size-limited substituent groups, and lower substituent groups; each substituent group, size-limited substituent group, and/or lower substituent group may optionally be different. In embodiments, when $R^{40}$ is substituted, it is substituted with at least one substituent group. In embodiments, when $R^{40}$ is substituted, it is substituted with at least one size-limited substituent group. In embodiments, when $R^{40}$ is substituted, it is substituted with at least one lower substituent group.

In embodiments, $R^{41}$ is independently hydrogen, substituted or unsubstituted alkyl or substituted or unsubstituted heteroalkyl. In embodiments, $R^{41}$ is independently hydrogen, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$) or substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered).

In embodiments, a substituted $R^{41}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{41}$ is substituted with a plurality of groups selected from substituent groups, size-limited substituent groups, and lower substituent groups; each substituent group, size-limited substituent group, and/or lower substituent group may optionally be different. In embodiments, when $R^{41}$ is substituted, it is substituted with at least one substituent group. In embodiments, when $R^{41}$ is substituted, it is substituted with at least one size-limited substituent group. In embodiments, when $R^{41}$ is substituted, it is substituted with at least one lower substituent group.

In embodiments, $R^{42}$ is independently hydrogen, substituted or unsubstituted alkyl or substituted or unsubstituted heteroalkyl. In embodiments, $R^{42}$ is independently hydrogen, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$) or substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered).

In embodiments, a substituted $R^{42}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{42}$ is substituted with a plurality of groups selected from substituent groups, size-limited substituent groups, and lower substituent groups; each substituent group, size-limited substituent group, and/or lower substituent group may optionally be different. In embodiments, when $R^{42}$ is substituted, it is substituted with at least one substituent group. In embodiments, when $R^{42}$ is substituted, it is substituted with at least one size-limited substituent group. In embodiments, when $R^{42}$ is substituted, it is substituted with at least one lower substituent group.

In embodiments, $R^{40}$, $R^{41}$, and $R^{42}$ are independently hydrogen or substituted heteroalkyl. In embodiments, $R^{40}$, $R^{41}$, and $R^{42}$ are independently hydrogen or —C(NH)$NH_2$. n embodiments, at least two of $R^{40}$, $R^{41}$, and $R^{42}$ are hydrogen and one is —C(NH)$NH_2$.

In embodiments, $R^{1A}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{1A}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{1A}$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{1A}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^{1A}$ is substituted or unsubstituted alkyl (e.g., $C_1$-$C_8$ alkyl, $C_1$-$C_6$ alkyl, or $C_1$-$C_4$ alkyl). In embodiments, $R^{\prime A}$ is substituted alkyl (e.g., $C_1$-$C_8$ alkyl, $C_1$-$C_6$ alkyl, or $C_1$-$C_4$ alkyl). In embodiments, $R^{1A}$ is an unsubstituted alkyl (e.g., $C_1$-$C_8$ alkyl, $C_1$-$C_6$ alkyl, or $C_1$-$C_4$ alkyl). In embodiments, $R^{1A}$ is substituted or unsubstituted heteroalkyl (e.g., 2 to 8 membered heteroalkyl, 2 to 6 membered heteroalkyl, or 2 to 4 membered heteroalkyl). In embodiments, $R^{1A}$ is substituted heteroalkyl (e.g., 2 to 8 membered heteroalkyl, 2 to 6 membered heteroalkyl, or 2 to 4 membered heteroalkyl). In embodiments, RIA is an unsubstituted heteroalkyl (e.g., 2 to 8 membered heteroalkyl, 2 to 6 membered heteroalkyl, or 2 to 4 membered heteroalkyl). In embodiments, $R^{1A}$ is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is substituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is substituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is substituted or unsubstituted aryl (e.g., $C_6$-$C_{10}$ aryl, $C_{10}$ aryl, or phenyl). In embodiments, $R^{1A}$ is substituted aryl (e.g., $C_6$-$C_{10}$ aryl, $C_{10}$ aryl, or phenyl). In embodiments, $R^{1A}$ is an unsubstituted aryl (e.g., $C_6$-$C_{10}$ aryl, $C_{10}$ aryl, or phenyl). In embodiments, $R^{1A}$ is substituted or unsubstituted heteroaryl (e.g., 5 to 10 membered heteroaryl, 5 to 9 membered heteroaryl, or 5 to 6 membered heteroaryl). In embodiments, $R^{1A}$ is substituted heteroaryl (e.g., 5 to 10 membered heteroaryl, 5 to 9 membered heteroaryl, or 5 to 6 membered heteroaryl). In embodiments, $R^{1A}$ is an unsubstituted heteroaryl (e.g., 5 to 10 membered heteroaryl, 5 to 9 membered heteroaryl, or 5 to 6 membered heteroaryl).

In embodiments, $R^{1A}$ is a substituted or unsubstituted aryl. In some other embodiments, $R^{1A}$ is a substituted or unsubstituted phenyl. In still some other embodiments, $R^{1A}$ is a substituted or unsubstituted aryl. In still some other embodiments, $R^{\prime A}$ is a substituted or unsubstituted phenyl or naphthalenyl.

In embodiments, $R^{2A}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{2A}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{2A}$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{2A}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^{2A}$ is substituted or unsubstituted alkyl (e.g., $C_1$-$C_8$ alkyl, $C_1$-$C_6$ alkyl, or $C_1$-$C_4$ alkyl). In embodiments, $R^{2A}$ is substituted alkyl (e.g., $C_1$-$C_8$ alkyl, $C_1$-$C_6$ alkyl, or $C_1$-$C_4$ alkyl). In embodiments, $R^{2A}$ is an unsubstituted alkyl (e.g., $C_1$-$C_8$ alkyl, $C_1$-$C_6$ alkyl, or $C_1$-$C_4$ alkyl). In embodiments, $R^{2A}$ is substituted or unsubstituted heteroalkyl (e.g., 2 to 8 membered heteroalkyl, 2 to 6 membered heteroalkyl, or 2 to 4 membered heteroalkyl). In embodiments, $R^{2A}$ is substituted heteroalkyl (e.g., 2 to 8 membered heteroalkyl, 2 to 6 membered heteroalkyl, or 2 to 4 membered heteroalkyl). In embodiments, $R^{2A}$ is an unsubstituted heteroalkyl (e.g., 2 to 8 membered heteroalkyl, 2 to 6 membered heteroalkyl, or 2 to 4 membered heteroalkyl). In embodiments, $R^{2A}$ is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is substituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is substituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is substituted or unsubstituted aryl (e.g., $C_6$-$C_{10}$ aryl, $C_{10}$ aryl, or phenyl). In embodiments, $R^{2A}$ is substituted aryl (e.g., $C_6$-$C_{10}$ aryl, $C_{10}$ aryl, or phenyl). In embodiments, $R^{2A}$ is an unsubstituted aryl (e.g., $C_6$-$C_{10}$ aryl, $C_{10}$ aryl, or phenyl). In embodiments, $R^{2A}$ is substituted or unsubstituted heteroaryl (e.g., 5 to 10 membered heteroaryl, 5 to 9 membered heteroaryl, or 5 to 6 membered heteroaryl). In embodiments, $R^{2A}$ is substituted heteroaryl (e.g., 5 to 10 membered heteroaryl, 5 to 9 membered heteroaryl, or 5 to 6 membered heteroaryl). In embodiments, $R^{2A}$ is an unsubstituted heteroaryl (e.g., 5 to 10 membered heteroaryl, 5 to 9 membered heteroaryl, or 5 to 6 membered heteroaryl).

In embodiments, $R^{3A}$ is independently hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3A}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{3A}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{3A}$ is unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{A}$ is hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^{3A}$ is a substituted or unsubstituted aryl. In some other embodiments, $R^{3A}$ is a substituted or unsubstituted phenyl. In still some other embodiments, $R^{3A}$ is a substituted or unsubstituted aryl. In still some other embodiments, $R^{3A}$ is a substituted or unsubstituted phenyl or naphthalenyl.

In embodiments, $R^{3A}$ is substituted or unsubstituted alkyl (e.g., $C_1$-$C_8$ alkyl, $C_1$-$C_6$ alkyl, or $C_1$-$C_4$ alkyl). In embodiments, $R^{3A}$ is substituted alkyl (e.g., $C_1$-$C_8$ alkyl, $C_1$-$C_6$ alkyl, or $C_1$-$C_4$ alkyl). In embodiments, $R^{3A}$ is an unsubstituted alkyl (e.g., $C_1$-$C_8$ alkyl, $C_1$-$C_6$ alkyl, or $C_1$-$C_4$ alkyl). In embodiments, $R^{3A}$ is substituted or unsubstituted heteroalkyl (e.g., 2 to 8 membered heteroalkyl, 2 to 6 membered heteroalkyl, or 2 to 4 membered heteroalkyl). In embodiments, $R^{3A}$ is substituted heteroalkyl (e.g., 2 to 8 membered heteroalkyl, 2 to 6 membered heteroalkyl, or 2 to 4 membered heteroalkyl). In embodiments, $R^{3A}$ is an unsubstituted heteroalkyl (e.g., 2 to 8 membered heteroalkyl, 2 to 6 membered heteroalkyl, or 2 to 4 membered heteroalkyl). In embodiments, $R^{3A}$ is substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is substituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3A}$ is substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is substituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{3A}$ is substituted or unsubstituted aryl (e.g., $C_6$-$C_{10}$ aryl, $C_{10}$ aryl, or phenyl). In embodiments, $R^{3A}$ is substituted aryl (e.g., $C_6$-$C_{10}$ aryl, $C_{10}$ aryl, or phenyl). In embodiments, $R^{3A}$ is an unsubstituted aryl (e.g., $C_6$-$C_{10}$ aryl, $C_{10}$ aryl, or phenyl). In embodiments, $R^{3A}$ is substituted or unsubstituted heteroaryl (e.g., 5 to 10 membered heteroaryl, 5 to 9 membered heteroaryl, or 5 to 6 membered heteroaryl). In embodiments, $R^{3A}$ is substituted heteroaryl (e.g., 5 to 10 membered heteroaryl, 5 to 9 membered heteroaryl, or 5 to 6 membered heteroaryl). In embodiments, $R^{3A}$ is an unsubstituted heteroaryl (e.g., 5 to 10 membered heteroaryl, 5 to 9 membered heteroaryl, or 5 to 6 membered heteroaryl).

In Formula XII, XIII, XIV, and XV as provided herein, including embodiments thereof, $L^1$ may be substituted or unsubstituted $C_1$-$C_3$ alkylene. In embodiments, $L^1$ is substituted or unsubstituted methylene. In embodiments, $L^r$ is substituted or unsubstituted $C_1$-$C_6$ alkylene, or substituted or unsubstituted 2 to 6 membered heteroalkylene. In embodiments, $L^1$ is substituted or unsubstituted $C_1$-$C_3$ alkylene, or substituted or unsubstituted 2 to 3 membered heteroalkylene.

In embodiments, $L^1$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_5$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered). In embodiments, $L^1$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted aryl ene, or substituted (e.g., substituted with a substituent group, a size-limited substituent group, or lower substituent group) or unsubstituted heteroarylene. In embodiments, $L^1$ is unsubstituted alkylene, unsubstituted heteroalkylene, unsubstituted cycloalkylene, unsubstituted heterocycloalkylene, unsubstituted arylene, or unsubstituted heteroarylene. In embodiments, $L^1$ is unsubstituted alkyl ene (e.g., $C_1$-$C_6$ alkylene). In embodiments, $L^1$ is a bond.

In embodiments, the $L^1$ is —$CH_2$—O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is —$CH_2$—O—.

In embodiments, $L^1$ is —$CH_2$—O—,

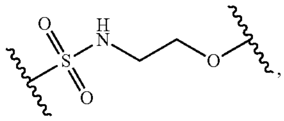, 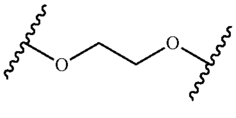, or

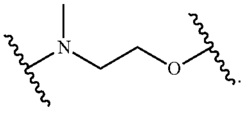.

In embodiments, $L^1$ is —$CH_2$—O—. In embodiments, $L^1$ is

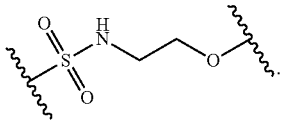 [SMILES: *OCCNS(*)(=O)=O].

In embodiments, $L^1$ is

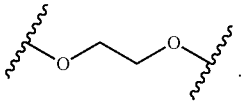 [SMILES: *OCCO*].

In embodiments, $L^1$ is

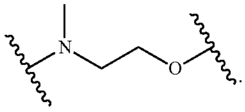 [SMILES: *OCCN(*)C].

In Formula XII, XIII, XIV, and XV, as provided herein, including embodiments thereof, $L^2$ may be substituted or unsubstituted $C_1$-$C_3$ alkylene. In embodiments, $L^2$ is substituted or unsubstituted methylene. In embodiments, $L^2$ is substituted or unsubstituted $C_1$-$C_6$ alkylene, or substituted or unsubstituted 2 to 6 membered heteroalkylene. In embodiments, $L^2$ is substituted or unsubstituted $C_1$-$C_3$ alkylene, or substituted or unsubstituted 2 to 3 membered heteroalkylene In embodiments, $L^2$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered). In embodiments, $L^2$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, $L^2$ is unsubstituted alkylene, unsubstituted heteroalkylene, unsubstituted cycloalkylene, unsubstituted heterocycloalkylene, unsubstituted arylene, or unsubstituted heteroarylene. In embodiments, $L^2$ is unsubstituted alkylene (e.g., $C_1$-$C_6$ alkylene). In embodiments, $L^2$ is a bond.

In Formula XII, XIII, XIV, and XV, as provided herein, including embodiments thereof, $L^4$ may be substituted or unsubstituted $C_1$-$C_3$ alkylene. In embodiments, $L^4$ is substituted or unsubstituted methylene. In embodiments, $L^4$ is substituted or unsubstituted $C_1$-$C_6$ alkylene, or substituted or unsubstituted 2 to 6 membered heteroalkylene. In embodiments, $L^4$ is substituted or unsubstituted $C_1$-$C_3$ alkylene, or substituted or unsubstituted 2 to 3 membered heteroalkylene.

$L^4$ as provided herein may be an aliphatic linker, a peptide linker or a pegylated linker. In embodiments, $L^4$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered). In embodiments, $L^4$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, $L^4$ is unsubstituted alkylene, unsubstituted heteroalkylene, unsubstituted cycloalkylene, unsubstituted heterocycloalkylene, unsubstituted arylene, or unsubstituted heteroarylene. In embodiments, $L^4$ is unsubstituted alkylene (e.g., $C_1$-$C_6$ alkylene). In embodiments, $L^4$ is a bond.

In Formula XII, XIII, XIV, and XV, as provided herein, including embodiments thereof, z2 may be an integer from 2 to 90 (e.g. 5 to 90, 10 to 90 or 20 to 90), 2 to 80 (e.g. 5 to 80, 10 to 80 or 20 to 80), 2 to 70 (e.g. 5 to 70, 10 to 70 or 20 to 70), 2 to 50 (e.g. 5 to 50, 10 to 50 or 20 to 50) or 2 to 25. In embodiments, z1 and z3 are independently integers from 0 to 90 (e.g. 5 to 90, 10 to 90 or 20 to 90), 0 to 80 (e.g. 5 to 80, 10 to 80 or 20 to 80), 0 to 70 (e.g. 5 to 70, 10 to 70 or 20 to 70), 0 to 50 (e.g. 5 to 50, 10 to 50 or 20 to 50) or 2 to 25. In embodiments, z1 and A are independently integers from 2 to 90 (e.g. 5 to 90, 10 to 90 or 20 to 90), 2 to 80 (e.g. 5 to 80, 10 to 80 or 20 to 80), 2 to 70 (e.g. 5 to 70, 10 to 70 or 20 to 70), 2 to 50 (e.g. 5 to 50, 10 to 50 or 20 to 50) or 2 to 25. In embodiments, z4 is independently an integer from 1 to 90 (e.g. 5 to 90, 10 to 90 or 20 to 90), 1 to 80 (e.g. 5 to 80, 10 to 80 or 20 to 80), 1 to 70 (e.g. 5 to 70, 10 to 70 or 20 to 70), 1 to 50 (e.g. 5 to 50, 10 to 50 or 20 to 50) or 2 to 25. In embodiments, z4 is independently an integer from 2 to 90 (e.g. 5 to 90, 10 to 90 or 20 to 90), 2 to 80 (e.g. 5 to 80, 10 to 80 or 20 to 80), 2 to 70 (e.g. 5 to 70, 10 to 70 or 20 to 70), 2 to 50 (e.g. 5 to 50, 10 to 50 or 20 to 50) or 2 to 25.

In embodiments of the cell-penetrating complex, the pH-sensitive immolation domain includes a first nucleophilic moiety (e.g. Z) and a first electrophilic moiety, wherein the first nucleophilic moiety is reactive with the first electrophilic moiety within a pH range and is not substantially reactive with the electrophilic moiety outside that pH range (e.g., pH about 1-5, pH about 5-7 or pH about 7-10). In embodiments, the pH range within which the first nucleophilic moiety is most reactive with the first electrophilic moiety is: pH 1-3, pH 2-4, pH 3-5, pH 4-6, pH 5-7, pH 6-8, pH 7-9, or pH 8-10. A nucleophilic moiety is used in accordance with its plain ordinary meaning in chemistry and refers to a moiety (e.g., functional group) capable of donating electrons.

In embodiments, the pH range within which the first nucleophilic moiety is most reactive with the first electrophilic moiety is pH 1-3. In embodiments, the pH range within which the first nucleophilic moiety is most reactive with the first electrophilic moiety is pH 2-4. In embodiments, the pH range within which the first nucleophilic moiety is most reactive with the first electrophilic moiety is pH 3-5. In embodiments, the pH range within which the first nucleophilic moiety is most reactive with the first electrophilic moiety is pH 4-6. In embodiments, the pH range within which the first nucleophilic moiety is most reactive with the first electrophilic moiety is pH 5-7. In embodiments, the pH range within which the first nucleophilic moiety is most reactive with the first electrophilic moiety is pH 6-8. In embodiments, the pH range within which the first nucleophilic moiety is most reactive with the first electrophilic moiety is pH 7-9. In embodiments, the pH range within which the first nucleophilic moiety is most reactive with the first electrophilic moiety is pH 8-10. In embodiments, the pH is 1. In embodiments, the pH is 2. In embodiments, the pH is 3. In embodiments, the pH is 4. In embodiments, the pH is 5. In embodiments, the pH is 6. In embodiments, the pH is 7. In embodiments, the pH is 8. In embodiments, the pH is 9. In embodiments, the pH is 10. In embodiments, the pH is about 1. In embodiments, the pH is about 2. In embodiments, the pH is about 3. In embodiments, the pH is about 4. In embodiments, the pH is about 5. In embodiments, the pH is about 6. In embodiments, the pH is about 7. In embodiments, the pH is about 8. In embodiments, the pH is about 9. In embodiments, the pH is about 10.

In embodiments, the first nucleophilic moiety is substantially protonated at low pH (e.g., pH about 1 to about 5). In embodiments, the first nucleophilic moiety is substantially protonated in the range pH 5-7. In embodiments, the first nucleophilic moiety is cationic. In embodiments, the first nucleophilic moiety includes a cationic nitrogen (e.g. a cationic amine).

In embodiments, the first nucleophilic moiety can be attached to a pH-labile protecting group. The term "pH-labile protecting group" or the like refers, in the usual and customary sense, to a chemical moiety capable of protecting another functionality to which it is attached, and which protecting group can be cleaved or otherwise inactivated as a protecting group under certain pH conditions (e.g., such as decreasing the pH). In one embodiment, the pH-labile protecting group is —$CO_2$-t-Bu, a group removed under acidic conditions (e.g., pH below 7). Additional nucleophile protecting groups could also include those that are cleaved by light, heat, nucleophile, and bases.

In embodiments, the pH-sensitive immolation domain has the formula:

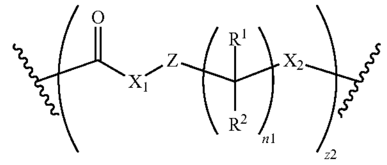

wherein z2 is an integer of 2 or more;

n1 is an integer from 0 to 50;

Z is a nucleophilic moiety;

$X^1$ is a bond, —$C(R^5)(R^6)$—, —$C(R^5)(R^6)$—$C(R^7)(R^8)$—, —O—$C(R^5)(R^6)$—, or —O—$C(R^5)(R^6)$—$C(R^7)(R^8)$—;

$X^2$ is —O— or —S—; and $R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, the pH-sensitive immolation domain has the formula:

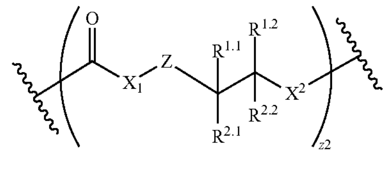

wherein z2 is an integer of 2 or more;

Z is a nucleophilic moiety;

$X^1$ is a bond, —$C(R^5)(R^6)$—, —$C(R^5)(R^6)$—$C(R^7)(R^8)$—, —O—$C(R^5)(R^6)$—, or —O—$C(R^5)(R^6)$—$C(R^7)(R^8)$—;

$X^2$ is —O— or —S—; and $R^{1.1}$, $R^{1.2}$, $R^{2.1}$, $R^{2.2}$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments the pH-sensitive immolation domain has the structure of Formula:

(XVI)

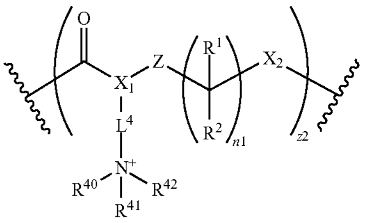

or (XVII)

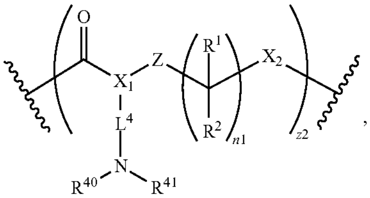

,

In formula (XVI) or (XVII) $X^1$ is a bond, —C(R')($R^6$)—, —C($R^5$)($R^6$)—C(R')(R')—, —O—C(R')($R^6$)—, or —O—C($R^5$)($R^6$)—C($R^7$)($R^8$)—. $X^2$ is —O— or —S—; $R^1$ and $R^2$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $L^4$ is a bond, —C(O)O—, —O—, —S—, —NH—, —C(O)NH—, —NHC(O)—, —$S(O)_2$—, —S(O)NH—, —NHC(O)NH—, substituted or unsubstituted alkylene, or substituted or unsubstituted heteroalkylene. $R^{40}$, $R^{41}$, and $R^{42}$ are independently hydrogen, substituted or unsubstituted alkyl or substituted or unsubstituted heteroalkyl; Z is —S—, —$S^+R^{13}$—, —$NR^{13}$—, or —$N^+(R^{13})(H)$—; $R^{13}$ is hydrogen, —$CCl_3$, —$CBr_3$, —$CF_3$, —$CI_3$, —CN, —OH, =O, —$NH_2$, —COOH, —$CONH_2$, —SH, —$SO_3H$, —$SO_2NH_2$, —$OCCl_3$, —$OCF_3$, —$OCBr_3$, —$OCI_3$, —$OCHCI_2$, —$OCHBr_2$, —$OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; n1 is an integer from 0 to 50; z2 is an integer from 2 to 100; and z5 is an integer from 1 to 10.

In Formula (XII), (XIII), (XIV), (XV), (XVI) and (XVII), $R^1$, $R^2$, $R^5$, $R^6$, $R^7$, and $R^8$ may independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$, $R^2$, $R^5$, $R^6$, $R^7$, and $R^8$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^1$, $R^2$, $R^5$, $R^6$, $R^7$, and $R^8$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$, $R^2$, $R^5$, $R^6$, $R^7$, and $R^8$ are independently hydrogen or unsubstituted alkyl (e.g., $C_1$-$C_6$ alkyl). In embodiments, $R^1$, $R^2$, $R^5$, $R^6$, $R^7$, and $R^8$ are hydrogen.

In embodiments, the pH-sensitive immolation domain has the formula:

(XVIII)

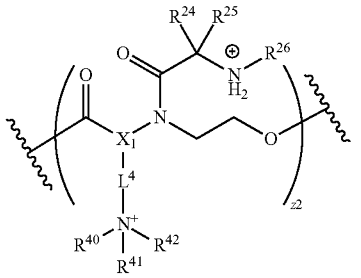

or (XIX)

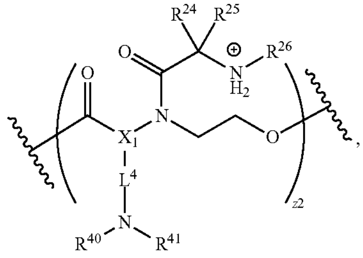

, wherein $R^{24}$, $R^{25}$ and $R^{26}$ are hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, and z2 is an integer from 1 to 50.

In embodiments, $R^{24}$, $R^{25}$ and $R^{26}$ are independently substituted or unsubstituted alkyl (e.g., $C_1$-$C_8$, $C_1$-$C_8$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{24}$, $R^{25}$ and $R^{26}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{1.1}$, $R^{24}$, $R^{25}$ and $R^{26}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{24}$, $R^{25}$ and $R^{26}$ are independently hydrogen or unsubstituted alkyl (e.g., $C_1$-$C_6$ alkyl). In embodiments, $R^{24}$, $R^{25}$ and $R^{26}$ are independently hydrogen.

In Formula (XII), (XIII), (XIV), (XV), (XVI), (XVII), (XVIII), and (XIX) provided herein, including embodiments thereof, $R^1$, $R^{1A}$, $R^{2A}$, $R^{3A}$, $R^5$, $R^6$, $R^8$, $R^{13}$, $R^{14}$, $R^{15}$, $R^{16}$, $R^{17}$, $R^{18}$, $R^{19}$, $R^{24}$, $R^{25}$, $R^{26}$, $R^{40}$, $R^{41}$, $R^{42}$, $R^{201}$, $R^{202}$ and $R^{203}$ may be independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$, $R^{1A}$, $R^{2A}$, $R^{3A}$, $R^5$, $R^6$, $R^7$, $R^8$, $R^{13}$, $R^{14}$, $R^{15}$, $R^{16}$, $R^{17}$, $R^{18}$, $R^{19}$, $R^{24}$, $R^{25}$, $R^{26}$, $R^{40}$, $R^{41}$, $R^{42}$, $R^{201}$, $R^{202}$ and $R^{203}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^1$, $R^{1A}$, $R^{2A}$, $R^{3A}$, $R^5$, $R^6$, $R^7$, $R^8$, $R^{13}$, $R^{14}$, $R^{15}$, $R^{16}$, $R^{17}$, $R^{18}$, $R^{19}$, $R^{24}$, $R^{25}$, $R^{26}$, $R^{40}$, $R^{41}$, $R^{42}$, $R^{201}$, $R^{202}$ and $R^{203}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$, $R^{1A}$, $R^{2A}$, $R^{3A}$, $R^5$, $R^6$, $R^7$, $R^8$, $R^{13}$, $R^{14}$, $R^{15}$, $R^{16}$, $R^{17}$, $R^{18}$, $R^{19}$, $R^{24}$, $R^2$, $R^{26}$, $R^{40}$, $R^{41}$, $R^{42}$, $R^{201}$, $R^{202}$ and $R^{203}$ are independently hydrogen or unsubstituted alkyl (e.g., $C_1$-$C_8$ alkyl). In embodiments, $R^1$, $R^{1A}$, $R^{2A}$, $R^{3A}$, $R^5$, $R^6$, $R^7$, $R^8$, $R^{13}$, $R^{14}$, $R^{15}$, $R^{16}$, $R^{17}$, $R^{18}$, $R^{19}$, $R^{40}$, $R^{41}$, $R^{42}$, $R^{201}$, $R^{202}$ and $R^{203}$ are hydrogen.

In Formula (XII), (XIII), (XIV), (XV), (XVI), (XVII), (XVIII), and (XIX) provided herein, including embodiments thereof, $R^{40}$, $R^{41}$, and $R^{42}$ may be independently substituted or unsubstituted alkyl (e.g., $C_1$-$C_8$, $C_1$-$C_6$, $C_1$-$C_4$, or $C_1$-$C_2$) or substituted or unsubstituted heteroalkyl (e.g., 2 to 8 membered, 2 to 6 membered, 4 to 6 membered, 2 to 3 membered, or 4 to 5 membered). In embodiments, $R^{40}$, $R^{41}$, and $R^{42}$, are independently substituted (e.g., substituted with a substituent group, a size-limited substituent group, or lower substituent group) or unsubstituted alkyl or substituted (e.g., substituted with a substituent group, a size-limited substituent group, or lower substituent group) or unsubstituted heteroalkyl. In embodiments, $R^{40}$, $R^{41}$, and $R^{42}$ are independently unsubstituted alkyl or unsubstituted heteroalkyl. In embodiments, $R^{40}$, $R^{41}$, and $R^{42}$ are independently hydrogen or unsubstituted alkyl (e.g., $C_1$-$C_6$ alkyl). In embodiments, $R^{40}$, $R^{41}$, and $R^{42}$ are hydrogen.

In embodiments, Z is a nucleophilic moiety. In embodiments, Z is —S—, —$OR^{13}$—, —$S^+R^{13}$—, —$NR^3$—, or —$N^+(R^{13})(H)$—, wherein $R^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments Z is —S—. In embodiments, Z is —$S^+R^{13}$— In embodiments, Z is —$NR^{13}$— In embodiments, Z is —$N^+(R^{13})(H)$—. In embodiments, Z is —$S^+H$. In embodiments, Z is —NH—. In embodiments, Z is —$N^+H_2$—. In embodiments, Z is —OH—. In embodiments, Z is —$N^+(R^{13})(H)$— and $R^{13}$ is hydrogen.

In embodiments, $R^{13}$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{13}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{13}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{13}$ are independently hydrogen or unsubstituted alkyl (e.g., $C_1$-$C_6$ alkyl). In embodiments, $R^{13}$ is hydrogen. In embodiments, $R^{13}$ is —$NH_3^+$. In embodiments, $R^{13}$ is —$NH_2$.

In embodiments, $R^{3A}$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{13A}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{3A}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{1A3}$ are independently hydrogen or unsubstituted alkyl (e.g., $C_1$-$C_6$ alkyl). In embodiments, $R^{13A}$ is hydrogen. In embodiments, $R^{13A}$ is —$NH_3^+$. In embodiments, $R^{13A}$ is —$NH_2$.

In embodiments, Z is

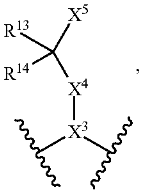
, wherein $X^3$ is —$C(R^{15})$— or —N—; $X^4$ is a bond, —C(O)—, —$P(O)(OR^{16})_2$—, —$S(O)(OR^{17})_2$—, —$C(R^{16})(R^{17})$— or —$C(R^{16})(R^{17})$—$C(R^{18})(R^{19})$—; $X^5$ is a nucleophilic moiety; and $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $X^3$ is —CH.

In embodiments, $R^{13}$, $R^{14}$, R', $R^{16}$, $R^{17}$, $R^{18}$ and $R^{19}$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$, $R^{14}$, $R^{515}$, $R^{16}$, $R^{17}$, $R^{18}$ and $R^{19}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments $R^{13}$, $R^{14}$, $R^{15}$, $R^{16}$, $R^{17}$, $R^{18}$ and $R^{19}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{13}$, $R^{14}$, $R^{15}$, $R^1$, $R^{17}$, $R^{18}$ and $R^{19}$ are independently hydrogen or unsubstituted alkyl (e.g., $C_1$-$C_6$ alkyl).

In embodiments, $X^5$ is —$N(R^{13})(H)$, wherein $R^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, the pH-sensitive immolation domain has the formula (XX):

(XX)

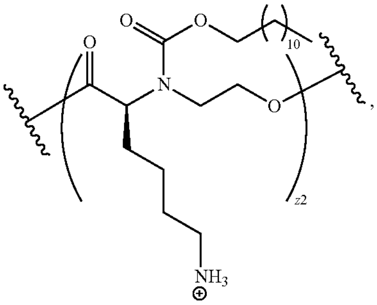
, wherein z2 is as defined herein.

In embodiments, the pH-sensitive immolation domain has the formula (XXb):

(XXb)

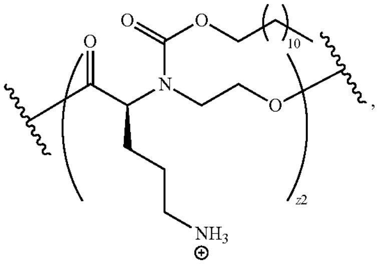
, wherein z2 is as defined herein.

In embodiments, the pH-sensitive immolation domain has the formula (XXI):

(XXI)

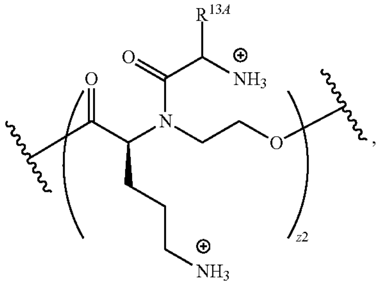
, wherein z2 and $R^{13A}$ are as defined herein.

In embodiments, the pH-sensitive immolation domain has the formula (XXIa):

(XXIa)

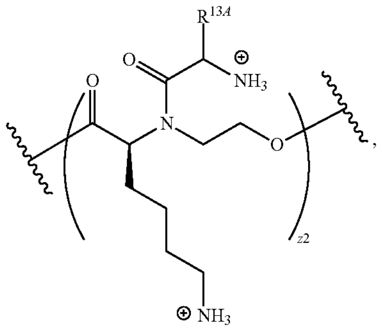

wherein z2 and $R^{13A}$ are as defined herein.

In embodiments, the lipophilic polymer domain ($LP^1$ or $LP^2$) has the formula:

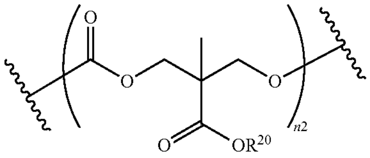

wherein, n2 is an integer from 1 to 100; $R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{20}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{20}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{20}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{20}$ is hydrogen or unsubstituted alkyl (e.g., $C_1$-$C_6$ alkyl).

In embodiments, $R^{20}$ is an unsubstituted $C_1$-$C_{30}$ alkyl. In embodiments, $R^{20}$ is an unsubstituted $C_1$-$C_{20}$ alkyl. In embodiments, $R^{20}$ is an unsubstituted $C_5$-$C_{30}$ alkyl. In embodiments, $R^{20}$ is an unsubstituted $C_8$-$C_{20}$ alkyl. In embodiments, $R^{20}$ is an unsubstituted $C_9$-$C_{20}$ alkyl. In embodiments, $R^{20}$ is an unsubstituted $C_9$-$C_{18}$ alkyl. In embodiments, $R^{20}$ is an unsubstituted $C_{18}$ alkyl. In embodiments, $R^{20}$ is an unsubstituted $C_{17}$ alkyl. In embodiments, $R^{20}$ is an unsubstituted $C_{16}$ alkyl. In embodiments, $R^{20}$ is an unsubstituted $C_{15}$ alkyl. In embodiments, $R^{20}$ is an unsubstituted $C_{14}$ alkyl. In embodiments, $R^{20}$ is an unsubstituted Cu alkyl. In embodiments, $R^{20}$ is an unsubstituted $C_{12}$ alkyl. In embodiments, $R^{20}$ is an unsubstituted $C_{11}$ alkyl. In embodiments, $R^{20}$ is an unsubstituted $C_{10}$ alkyl. In embodiments, $R^{20}$ is an unsubstituted $C_9$ alkyl. In embodiments, $R^{20}$ is an unsubstituted $C_8$ alkyl. In embodiments, $R^{20}$ is an unsubstituted $C_7$ alkyl. In embodiments, $R^{20}$ is an unsubstituted $C_6$ alkyl. In embodiments, $R^{20}$ is an unsubstituted $C_5$ alkyl. In embodiments, $R^{20}$ is an unsubstituted $C_4$ alkyl. In embodiments, $R^{20}$ is an unsubstituted $C_3$ alkyl. In embodiments, $R^{20}$ is an unsubstituted $C_2$ alkyl.

In embodiments, $R^{20}$ is an unsubstituted $C_1$-$C_{30}$ alkenyl. In embodiments, $R^{20}$ is an unsubstituted $C_1$-$C_{20}$ alkenyl. In embodiments, $R^{20}$ is an unsubstituted $C_5$-$C_{30}$ alkenyl. In embodiments, $R^{20}$ is an unsubstituted $C_5$-$C_{20}$ alkenyl. In embodiments, $R^{20}$ is an unsubstituted $C_9$-$C_{20}$ alkenyl. In embodiments, $R^{20}$ is an unsubstituted $C_9$-$C_{18}$ alkenyl. In embodiments, $R^{20}$ is an unsubstituted $C_{18}$ alkenyl. In embodiments, $R^{20}$ is an unsubstituted $C_{17}$ alkenyl. In embodiments, $R^{20}$ is an unsubstituted $C_{16}$ alkenyl. In embodiments, $R^{20}$ is an unsubstituted $C_{18}$ alkenyl. In embodiments, $R^{20}$ is an unsubstituted $C_{14}$ alkenyl. In embodiments, $R^{20}$ is an unsubstituted $C_{13}$ alkenyl. In embodiments, $R^{20}$ is an unsubstituted $C_{12}$ alkenyl. In embodiments, $R^{20}$ is an unsubstituted Cu alkenyl. In embodiments, $R^{20}$ is an unsubstituted $C_{10}$ alkenyl. In embodiments, $R^{20}$ is an unsubstituted $C_9$ alkenyl. In embodiments, $R^{20}$ is an unsubstituted $C_8$ alkenyl. In embodiments, $R^{20}$ is an unsubstituted $C_7$ alkenyl. In embodiments, $R^{20}$ is an unsubstituted $C_6$ alkenyl. In embodiments, $R^{20}$ is an unsubstituted $C_8$ alkenyl. In embodiments, $R^{20}$ is an unsubstituted $C_4$ alkenyl. In embodiments, $R^{20}$ is an unsubstituted $C_3$ alkenyl. In embodiments, $R^{20}$ is an unsubstituted $C_2$ alkenyl.

In embodiments, $R^{20}$ is a stearyl moiety (e.g., an unsubstituted $C_{18}$ alkyl). In embodiments, $R^{20}$ is an oleyl moiety (e.g., an unsubstituted $C_{18}$ alkenyl). In embodiments, $R^{20}$ is an linoleyl moiety (e.g., an unsubstituted $C_{18}$ alkenyl). In embodiments, $R^{20}$ is an dodecyl moiety (e.g., an unsubstituted $C_{12}$ alkyl). In embodiments, $R^{20}$ is an nonenyl moiety (e.g., an unsubstituted $C_9$ alkenyl). In embodiments, $R^{20}$ is

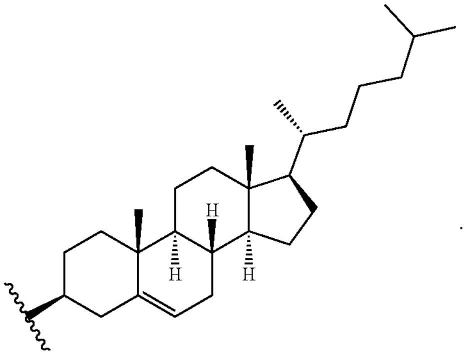

In embodiments, $R^1$ and $R^2$ are independently hydrogen or substituted or unsubstituted alkyl.

In embodiments, n1 is 2.

In embodiments, $X_2$ is —O—.

In embodiments, z1 or z3 are independently integers from 10-40.

In embodiments, z2 is independently an integer from 3-20.

In embodiments, $LP^1$ has the formula:

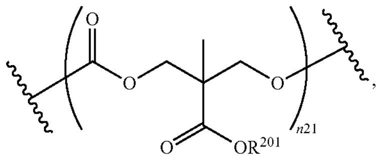

wherein n21 is an integer from 1 to 100;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, n21 is 10-40. In embodiments, $R^{201}$ is unsubstituted $C_{12}$ alkyl.

In embodiments, $R^{201}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_8$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{201}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{201}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{201}$ is hydrogen or unsubstituted alkyl (e.g., $C_1$-$C_6$ alkyl).

In embodiments, $R^{201}$ is an unsubstituted $C_1$-$C_{30}$ alkyl. In embodiments, $R^{201}$ is an unsubstituted $C_1$-$C_{20}$ alkyl. In embodiments, $R^{201}$ is an unsubstituted $C_8$-$C_{30}$ alkyl. In embodiments, $R^{201}$ is an unsubstituted $C_5$-$C_{20}$ alkyl. In embodiments, $R^{201}$ is an unsubstituted $C_9$-$C_{20}$ alkyl. In embodiments, $R^{201}$ is an unsubstituted $C_9$-$C_{18}$ alkyl. In embodiments, $R^{201}$ is an unsubstituted $C_{18}$ alkyl. In embodiments, $R^{201}$ is an unsubstituted $C_{17}$ alkyl. In embodiments, $R^{201}$ is an unsubstituted $C_{16}$ alkyl. In embodiments, $R^{201}$ is an unsubstituted $C_{15}$ alkyl. In embodiments, $R^{201}$ is an unsubstituted $C_{14}$ alkyl. In embodiments, $R^{201}$ is an unsubstituted $C_{13}$ alkyl. In embodiments, $R^{201}$ is an unsubstituted $C_{12}$ alkyl. In embodiments, $R^{201}$ is an unsubstituted Cn alkyl. In embodiments, $R^{201}$ is an unsubstituted $C_{10}$ alkyl. In embodiments, $R^{201}$ is an unsubstituted $C_9$ alkyl. In embodiments, $R^{201}$ is an unsubstituted $C_8$ alkyl. In embodiments, $R^{201}$ is an unsubstituted $C_7$ alkyl. In embodiments, $R^{201}$ is an unsubstituted $C_6$ alkyl. In embodiments, $R^{201}$ is an unsubstituted $C_8$ alkyl. In embodiments, $R^{201}$ is an unsubstituted $C_4$ alkyl. In embodiments, $R^{201}$ is an unsubstituted $C_3$ alkyl. In embodiments, $R^{201}$ is an unsubstituted $C_2$ alkyl.

In embodiments, $R^{201}$ is an unsubstituted $C_1$-$C_{30}$ alkenyl. In embodiments, $R^{201}$ is an unsubstituted $C_1$-$C_{20}$ alkenyl. In embodiments, $R^{201}$ is an unsubstituted $C_5$-$C_{30}$ alkenyl. In embodiments, $R^{201}$ is an unsubstituted $C_5$-$C_{20}$ alkenyl. In embodiments, $R^{201}$ is an unsubstituted $C_9$-$C_{20}$ alkenyl. In embodiments, $R^{201}$ is an unsubstituted $C_9$-$C_{18}$ alkenyl. In embodiments, $R^{201}$ is an unsubstituted $C_{18}$ alkenyl. In embodiments, $R^{20'}$ is an unsubstituted $C_{12}$ alkenyl. In embodiments, $R^{201}$ is an unsubstituted $C_{16}$ alkenyl. In embodiments, $R^{201}$ is an unsubstituted $C_{18}$ alkenyl. In embodiments, $R^{201}$ is an unsubstituted $C_{14}$ alkenyl. In embodiments, $R^{201}$ is an unsubstituted $C_{13}$ alkenyl. In embodiments, $R^{201}$ is an unsubstituted $C_{12}$ alkenyl. In embodiments, $R^{201}$ is an unsubstituted $C_{11}$ alkenyl. In embodiments, $R^{20}$ is an unsubstituted $C_{10}$ alkenyl. In embodiments, $R^{201}$ is an unsubstituted $C_9$ alkenyl. In embodiments, $R^{201}$ is an unsubstituted $C_5$ alkenyl. In embodiments, $R^{201}$ is an unsubstituted $C_7$ alkenyl. In embodiments, $R^{201}$ is an unsubstituted $C_6$ alkenyl. In embodiments, $R^{201}$ is an unsubstituted $C_5$ alkenyl. In embodiments, $R^{201}$ is an unsubstituted $C_4$ alkenyl. In embodiments, $R^{201}$ is an unsubstituted $C_3$ alkenyl. In embodiments, $R^{20}$ is an unsubstituted $C_2$ alkenyl.

In embodiments, $R^{201}$ is a stearyl moiety (e.g., an unsubstituted $C_{18}$ alkyl). In embodiments, $R^{201}$ is an oleyl moiety (e.g., an unsubstituted $C_{18}$ alkenyl). In embodiments, $R^{201}$ is an linoleyl moiety (e.g., an unsubstituted $C_{18}$ alkenyl). In embodiments, $R^{201}$ is an dodecyl moiety (e.g., an unsubstituted $C_{12}$ alkyl). In embodiments, $R^{201}$ is an nonenyl moiety (e.g., an unsubstituted $C_9$ alkenyl). In embodiments, $R^{201}$ is

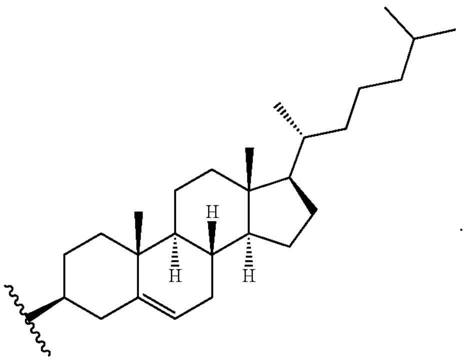

.

In embodiments, n21 is 5 and $R^{201}$ is unsubstituted $C_{18}$ alkenyl. In embodiments, the unsubstituted $C_{18}$ alkenyl is oleyl.

In embodiments, $LP^2$ has the formula:

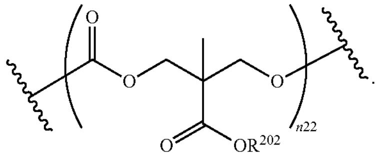

.

n22 is an integer from 1 to 100. $R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^{202}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{202}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{202}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{202}$ is hydrogen or unsubstituted alkyl (e.g., $C_1$-$C_6$ alkyl).

In embodiments, $R^{202}$ is an unsubstituted $C_1$-$C_{30}$ alkyl. In embodiments, $R^{202}$ is an unsubstituted $C_1$-$C_{20}$ alkyl. In embodiments, $R^{202}$ is an unsubstituted $C_5$-$C_{30}$ alkyl. In embodiments, $R^{202}$ is an unsubstituted $C_5$-$C_{20}$ alkyl. In embodiments, $R^{202}$ is an unsubstituted $C_9$-$C_{20}$ alkyl. In embodiments, $R^{202}$ is an unsubstituted $C_9$-$C_{18}$ alkyl. In embodiments, $R^{202}$ is an unsubstituted $C_{18}$ alkyl. In embodiments, $R^{202}$ is an unsubstituted $C_{17}$ alkyl. In embodiments, $R^{202}$ is an unsubstituted $C_{16}$ alkyl. In embodiments, $R^{202}$ is an unsubstituted $C_{15}$ alkyl. In embodiments, $R^{202}$ is an unsubstituted $C_{14}$ alkyl. In embodiments, $R^{202}$ is an unsubstituted $C_{13}$ alkyl. In embodiments, $R^{202}$ is an unsubstituted $C_{12}$ alkyl. In embodiments, $R^{202}$ is an unsubstituted $C_1n$ alkyl. In embodiments, $R^{202}$ is an unsubstituted $C_{10}$ alkyl. In embodiments, $R^{202}$ is an unsubstituted $C_9$ alkyl. In embodiments, $R^{202}$ is an unsubstituted $C_8$ alkyl. In embodiments, $R^{202}$ is an unsubstituted $C_7$ alkyl. In embodiments, $R^{202}$ is an unsubstituted $C_6$ alkyl. In embodiments, $R^{202}$ is an unsubstituted $C_8$ alkyl. In embodiments, $R^{202}$ is an unsubstituted $C_4$ alkyl. In embodiments, $R^{202}$ is an unsubstituted $C_3$ alkyl. In embodiments, $R^{202}$ is an unsubstituted $C_2$ alkyl.

In embodiments, $R^{202}$ is an unsubstituted $C_1$-$C_{30}$ alkenyl. In embodiments, $R^{202}$ is an unsubstituted $C_1$-$C_{20}$ alkenyl. In embodiments, $R^{202}$ is an unsubstituted $C_5$-$C_{30}$ alkenyl. In embodiments, $R^{202}$ is an unsubstituted $C_5$-$C_{20}$ alkenyl. In embodiments, $R^{202}$ is an unsubstituted $C_9$-$C_{20}$ alkenyl. In embodiments, $R^{202}$ is an unsubstituted $C_9$-$C_{18}$alkenyl. In embodiments, $R^{202}$ is an unsubstituted $C_{18}$ alkenyl. In embodiments, $R^{202}$ is an unsubstituted $C_{17}$ alkenyl. In embodiments, $R^{202}$ is an unsubstituted $C_{16}$ alkenyl. In embodiments, $R^{202}$ is an unsubstituted $C_{15}$ alkenyl. In embodiments, $R^{202}$ is an unsubstituted $C_{14}$ alkenyl. In embodiments, $R^{202}$ is an unsubstituted $C_{13}$ alkenyl. In embodiments, $R^{202}$ is an unsubstituted $C_{12}$ alkenyl. In embodiments, $R^{202}$ is an unsubstituted $C_{11}$ alkenyl. In embodiments, $R^{202}$ is an unsubstituted $C_{10}$ alkenyl. In embodiments, $R^{202}$ is an unsubstituted $C_9$ alkenyl. In embodiments, $R^{202}$ is an unsubstituted $C_8$ alkenyl. In embodiments, $R^{202}$ is an unsubstituted $C_7$ alkenyl. In embodiments, $R^{202}$ is an unsubstituted $C_6$ alkenyl. In embodiments, $R^{202}$ is an unsubstituted $C_8$ alkenyl. In embodiments, $R^{202}$ is an unsubstituted $C_4$ alkenyl. In embodiments, $R^{202}$ is an unsubstituted $C_3$ alkenyl. In embodiments, $R^{202}$ is an unsubstituted $C_2$ alkenyl.

In embodiments, $R^{202}$ is a stearyl moiety (e.g., an unsubstituted $C_{18}$ alkyl). In embodiments, $R^{202}$ is an oleyl moiety (e.g., an unsubstituted $C_{18}$ alkenyl). In embodiments, $R^{202}$ is an linoleyl moiety (e.g., an unsubstituted $C_{18}$ alkenyl). In embodiments, $R^{202}$ is an dodecyl moiety (e.g., an unsubstituted $C_{12}$ alkyl). In embodiments, $R^{202}$ is an nonenyl moiety (e.g., an unsubstituted $C_9$ alkenyl). In embodiments, $R^{202}$ is

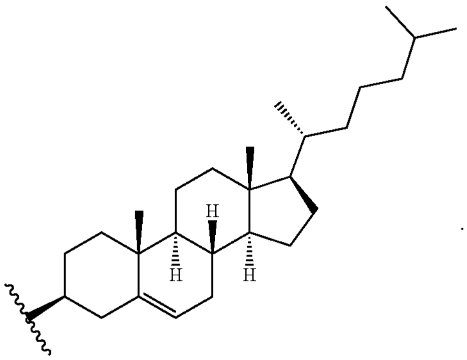

.

In embodiments, n22 is 10-35. In embodiments, $R^{202}$ is unsubstituted $C_{12}$ alkenyl.

In embodiments, n22 is 5 and $R^{202}$ is unsubstituted $C_9$ alkenyl. In embodiments, the unsubstituted $C_9$ alkenyl is nonenyl.

In embodiments, the lipophilic polymer domain is a compound of Formula (Ia) following:

(Ia)

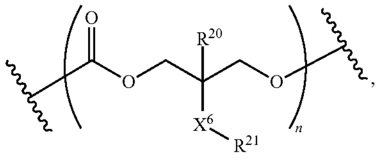

wherein $X^6$ may be —O—, —NH—, —$CO_2$—, —CONH—, —$O_2C$—, or —NHCO—, $R^{21}$ is hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, $R^{21}$ is hydrogen, substituted or unsubstituted alkyl, and n is an integer from 1 to 100. In embodiments, $R^{20}$ is an oligoglycol moiety.

In embodiments, $R^{20}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{20}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{20}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{20}$ is hydrogen or unsubstituted alkyl (e.g., $C_1$-$C_6$ alkyl).

In embodiments, $R^{21}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{21}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{21}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{21}$ is hydrogen or unsubstituted alkyl (e.g., $C_1$-$C_6$ alkyl).

In embodiments, the lipophilic polymer has the structure:

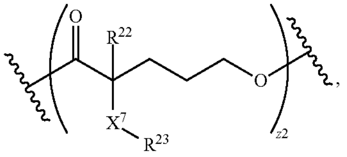

wherein $X^7$ is —O—, —NH—, —$CO_2$—, —CONH—, —$O_2C$—, or —NHCO—; $R^{22}$ is hydrogen, or substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, and $R^{23}$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^{22}$ is an oligoglycol moiety.

In embodiments, $R^{22}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{22}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{22}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$ is hydrogen or unsubstituted alkyl (e.g., $C_1$-$C_6$ alkyl).

In embodiments, the lipophilic polymer domain (e.g., $LP^1$, $LP^2$) has the Formula:

(Ib)

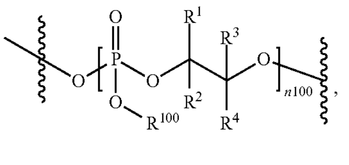

wherein $R^{100}$ is hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $R^1$, $R^2$, $R^3$, $R^4$ are hydrogen, substituted or unsubstituted heteroalkyl, substituted or unsubstituted heterocycloalkyl, substituted or unsubstituted aryl, or substituted or unsubstituted heteroaryl, and n100 is an integer of 2 or more is as defined herein.

In embodiments, $R^1$, $R^2$, $R^3$, $R^4$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$, $R^2$, $R^3$, $R^4$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^1$, $R^2$, $R^3$, $R^4$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$, $R^2$, $R^3$, $R^4$ are independently hydrogen or unsubstituted alkyl (e.g., $C_1$-$C_6$ alkyl). In embodiments, $R^1$, $R^2$, $R^3$, $R^4$ are hydrogen.

In embodiments, the lipophilic polymer domain has the Formula (Ic):

(Ic)

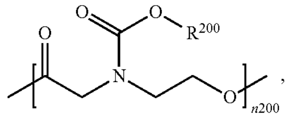

wherein $R^{200}$ is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, and n200 is an integer of 2 or more. In embodiments $R^{200}$ is an oligoglycol moiety. In embodiments, $R^{200}$ is an amine-terminated oligoglycol moiety. The term "oligoglycol moiety" refers to

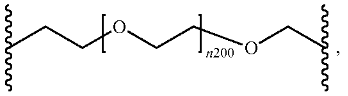

and "amine-terminated oligoglycol moiety" refers to

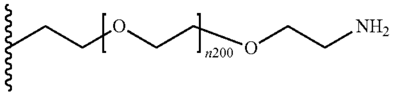

wherein n200 is an integer of 2 or more.

In embodiments, $R^{200}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_8$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{200}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{200}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{200}$ is hydrogen or unsubstituted alkyl (e.g., $C_1$-$C_6$ alkyl). In embodiments, $R^{200}$ is hydrogen.

In embodiments, the lipophilic polymer domain has the formula:

(Id)

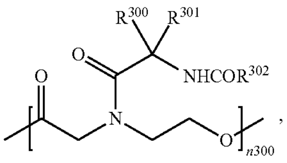

wherein R is substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, $R^{300}$ and $R^{301}$ are independently hydrogen or substituted or unsubstituted alkyl, and n300 is as defined herein. In embodiments $R^{302}$ is an oligoglycol moiety. In embodiments, R is an amine-terminated an oligoglycol moiety. In embodiments $R^{300}$, $R^{301}$, and $R^{302}$ are hydrogen.

In embodiments, $R^{300}$, $R^{301}$, and $R^{302}$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{300}$, $R^{301}$, and $R^{302}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{300}$, $R^{301}$, and $R^{302}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{300}$, $R^{301}$, and $R^{302}$ are independently hydrogen or unsubstituted alkyl (e.g., $C_1$-$C_6$ alkyl).

In embodiments, the lipophilic polymer domain, has the below formula, wherein R is defined therein as stearyl, oleyl, linoleyl, dodecyl, noneyl and cholesterol:

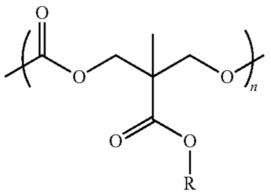

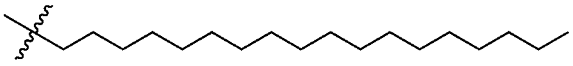

Stearyl (S)

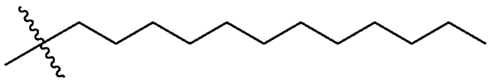

Dodecyl (D)

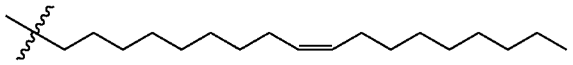

Oleyl (O)

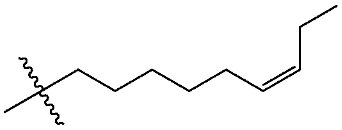

Nonenyl (N)

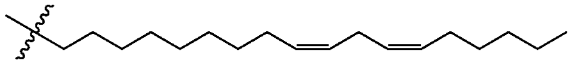

Linoleyl (Lin)

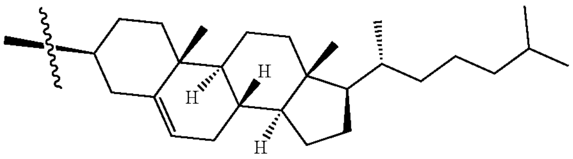

Cholesterol (Chol)

In embodiments, the cationic amphipathic polymer has the formula:

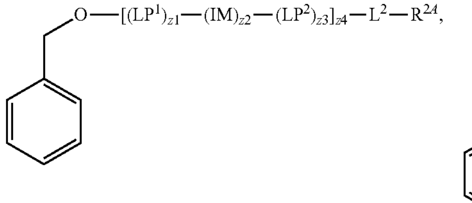

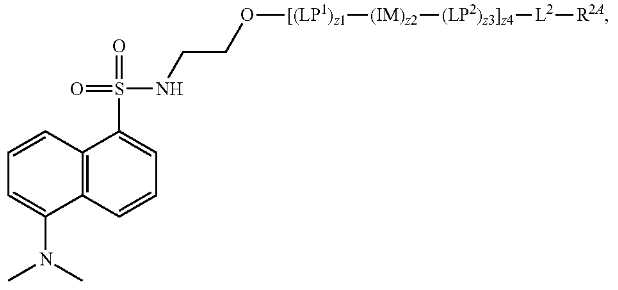

-continued

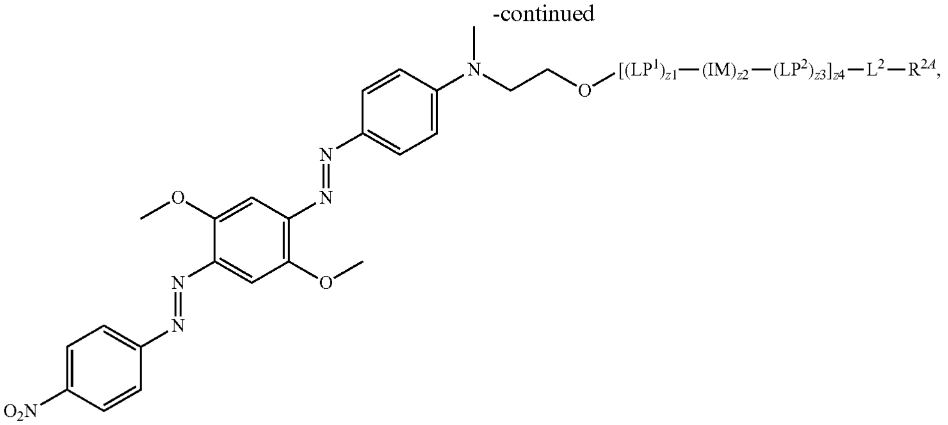

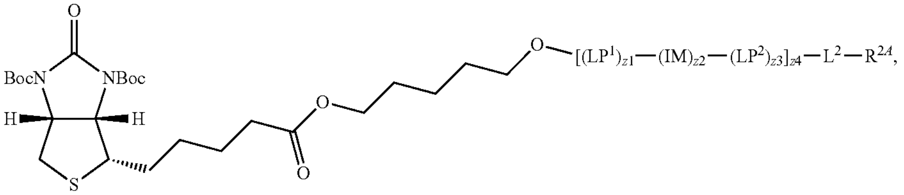

or

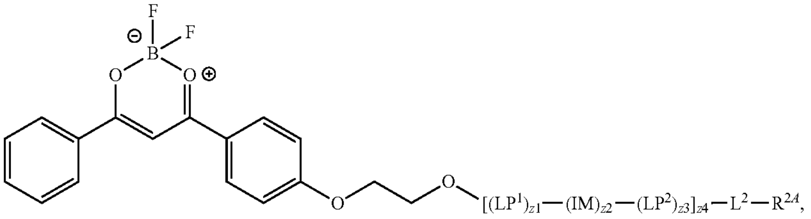

wherein $LP^1$, $LP^2$, IM, $L^2$, $R^{2A}$, z1, z2, z3, and z4 are defined as herein.

In embodiments, the cationic amphipathic polymer has the formula:

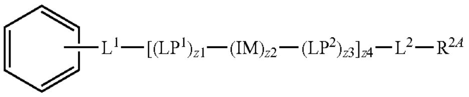

wherein $LP^1$, $LP^2$, IM, $L^1$, $L^2$, $R^{2A}$, z1, z2, z3, and z4 are defined as herein. In embodiments, the cationic amphipathic polymer has the formula

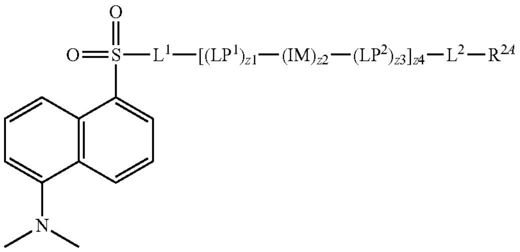

wherein $LP^1$, $LP^2$, IM, $L^1$, $L^2$, $R^{2A}$, z1, z2, z3, and z4 are defined as herein. In embodiments, the cationic amphipathic polymer has the formula:

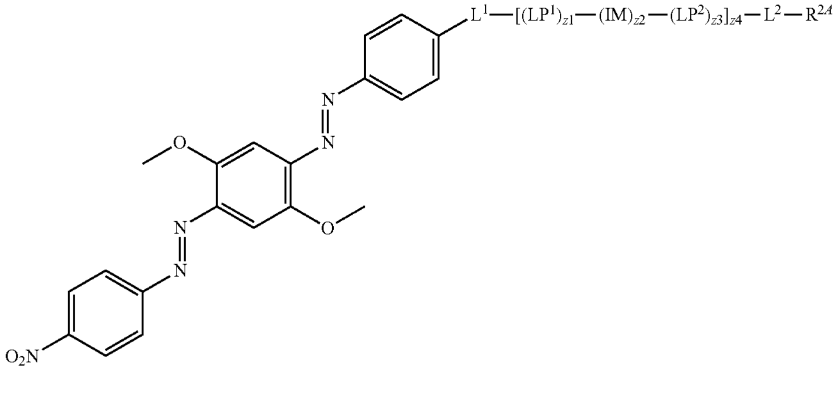

wherein $LP^1$, $LP^2$, IM, $L^1$, $L^2$, $R^{2A}$, z1, z2, z3, and z4 are defined as herein. In embodiments, the cationic amphipathic polymer has the formula:

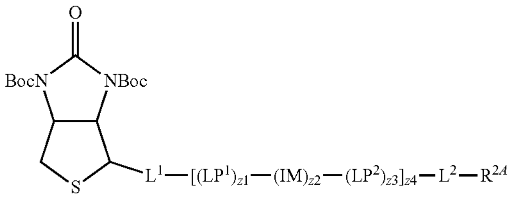

wherein $LP^1$, $LP^2$, IM, $L^1$, $L^2$, $R^{2A}$, z1, z2, z3, and z4 are defined as herein. In embodiments, the cationic amphipathic polymer has the formula:

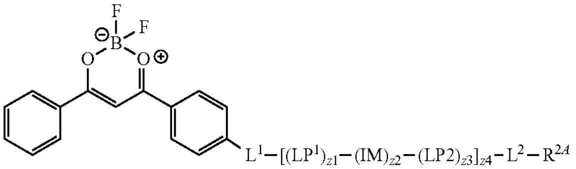

wherein $LP^1$, $LP^2$, IM, $L^1$, $L^2$, $R^{2A}$, z1, z2, z3, and z4 are defined as herein.

In embodiments, z1, z3 and z4 can be independently integers in the range 2-100, 2-90, 2-80, 2-70, 2-60, 2-50, 2-40, 2-30, 2-2, or 2-10, wherein at least one of z1 or z3 is not 0.

In embodiments, z1, z3 and z4 can be independently integers in the range 2-100 or 2-50, wherein at least one of z1 or z3 is not 0.

In embodiments, z1 is 0. In embodiments, z1 is 1. In embodiments, z1 is 2. In embodiments, z1 is 3. In embodiments, z1 is 4. In embodiments, z1 is 5. In embodiments, z1 is 6. In embodiments, z1 is 7. In embodiments, z1 is 8. In embodiments, z1 is 9. In embodiments, z1 is 10. In embodiments, z1 is 11. In embodiments, z1 is 12. In embodiments, z1 is 13. In embodiments, z1 is 14. In embodiments, z1 is 15. In embodiments, z1 is 16. In embodiments, z1 is 17. In embodiments, z1 is 18. In embodiments, z1 is 19. In embodiments, z1 is 20. In embodiments, z1 is 21. In embodiments, z1 is 22. In embodiments, z1 is 23. In embodiments, z1 is 24. In embodiments, z1 is 25. In embodiments, z1 is 26. In embodiments, z1 is 27. In embodiments, z1 is 28. In embodiments, z1 is 29. In embodiments, z1 is 30. In embodiments, z1 is 31. In embodiments, z1 is 32. In embodiments, z1 is 33. In embodiments, z1 is 34. In embodiments, z1 is 35. In embodiments, z1 is 36. In embodiments, z1 is 37. In embodiments, z1 is 38. In embodiments, z1 is 39. In embodiments, z1 is 40. In embodiments, z1 is 41. In embodiments, z1 is 42. In embodiments, z1 is 43. In embodiments, z1 is 44. In embodiments, z1 is 45. In embodiments, z1 is 46. In embodiments, z1 is 47. In embodiments, z1 is 48. In embodiments, z1 is 49. In embodiments, z1 is 50. In embodiments, z1 is 51. In embodiments, z1 is 52. In embodiments, z1 is 53. In embodiments, z1 is 54. In embodiments, z1 is 55. In embodiments, z1 is 56. In embodiments, z1 is 57. In embodiments, z1 is 58. In embodiments, z1 is 59. In embodiments, z1 is 60. In embodiments, z1 is 61. In embodiments, z1 is 62. In embodiments, z1 is 63. In embodiments, z1 is 64. In embodiments, z1 is 65. In embodiments, z1 is 66. In embodiments, z1 is 67. In embodiments, z1 is 68. In embodiments, z1 is 69. In embodiments, z1 is 70. In embodiments, z1 is 71. In embodiments, z1 is 72. In embodiments, z1 is 73. In embodiments, z1 is 74. In embodiments, z1 is 75. In embodiments, z1 is 76. In embodiments, z1 is 77. In embodiments, z1 is 78. In embodiments, z1 is 79. In embodiments, z1 is 80. In embodiments, z1 is 81. In embodiments, z1 is 82. In embodiments, z1 is 83. In embodiments, z1 is 84. In embodiments, z1 is 85. In embodiments, z1 is 86. In embodiments, z1 is 87. In embodiments, z1 is 88. In embodiments, z1 is 89. In embodiments, z1 is 90. In embodiments, z1 is 91. In embodiments, z1 is 92. In embodiments, z1 is 93. In embodiments, z1 is 94. In embodiments, z1 is 95. In embodiments, z1 is 96. In embodiments, z1 is 97. In embodiments, z1 is 98. In embodiments, z1 is 99. In embodiments, z1 is 100.

In embodiments, z3 is 0. In embodiments, z3 is 1. In embodiments, z3 is 2. In embodiments, z3 is 3. In embodiments, z3 is 4. In embodiments, z3 is 5. In embodiments, z3 is 6. In embodiments, z3 is 7. In embodiments, z3 is 8. In embodiments, z3 is 9. In embodiments, z3 is 10. In embodiments, z3 is 11. In embodiments, z3 is 12. In embodiments, z3 is 13. In embodiments, z3 is 14. In embodiments, z3 is 15. In embodiments, z3 is 16. In embodiments, z3 is 17. In embodiments, z3 is 18. In embodiments, z3 is 19. In embodiments, z3 is 20. In embodiments, z3 is 21. In embodiments, z3 is 22. In embodiments, z3 is 23. In embodiments, z3 is 24. In embodiments, z3 is 25. In embodiments, z3 is 26. In embodiments, z3 is 27. In embodiments, z3 is 28. In embodiments, z3 is 29. In embodiments, z3 is 30. In embodiments, z3 is 31. In embodiments, z3 is 32. In embodiments, z3 is 33. In embodiments, z3 is 34. In embodiments, z3 is 35. In embodiments, z3 is 36. In embodiments, z3 is 37. In embodiments, z3 is 38. In embodiments, z3 is 39. In embodiments, z3 is 40. In embodiments, z3 is 41. In embodiments, z3 is 42. In embodiments, z3 is 43. In embodiments, z3 is 44. In embodiments, z3 is 45. In embodiments, z3 is 46. In embodiments, z3 is 47. In embodiments, z3 is 48. In embodiments, z3 is 49. In embodiments, z3 is 50. In embodiments, z3 is 51. In embodiments, z3 is 52. In embodiments, z3 is 53. In embodiments, z3 is 54. In embodiments, z3 is 55. In embodiments, z3 is 56. In embodiments, z3 is 57. In embodiments, z3 is 58. In embodiments, z3 is 59. In embodiments, z3 is 60. In embodiments, z3 is 61. In embodiments, z3 is 62. In embodiments, z3 is 63. In embodiments, z3 is 64. In embodiments, z3 is 65. In embodiments, z3 is 66. In embodiments, z3 is 67. In embodiments, z3 is 68. In embodiments, z3 is 69. In embodiments, z3 is 70. In embodiments, z3 is 71. In embodiments, z3 is 72. In embodiments, z3 is 73. In embodiments, z3 is 74. In embodiments, z3 is 75. In embodiments, z3 is 76. In embodiments, z3 is 77. In embodiments, z3 is 78. In embodiments, z3 is 79. In embodiments, z3 is 80. In embodiments, z3 is 81. In embodiments, z3 is 82. In embodiments, z3 is 83. In embodiments, z3 is 84. In embodiments, z3 is 85. In embodiments, z3 is 86. In embodiments, z3 is 87. In embodiments, z3 is 88. In embodiments, z3 is 89. In embodiments, z3 is 90. In embodiments, z3 is 91. In embodiments, z3 is 92. In embodiments, z3 is 93. In embodiments, z3 is 94. In embodiments, z3 is 95. In embodiments, z3 is 96. In embodiments, z3 is 97. In embodiments, z3 is 98. In embodiments, z3 is 99. In embodiments, z3 is 100.

In embodiments, z4 is 1. In embodiments, z4 is 2. In embodiments, z4 is 3. In embodiments, z4 is 4. In embodiments, z4 is 5. In embodiments, z4 is 6. In embodiments, z4 is 7. In embodiments, z4 is 8. In embodiments, z4 is 9. In embodiments, z4 is 10. In embodiments, z4 is 11. In embodiments, z4 is 12. In embodiments, z4 is 13. In embodiments, z4 is 14. In embodiments, z4 is 15. In embodiments, z4 is 16. In embodiments, z4 is 17. In embodiments, z4 is 18. In embodiments, z4 is 19. In embodiments, z4 is 20. In embodiments, z4 is 21. In embodiments, z4 is 22. In embodiments, z4 is 23. In embodiments, z4 is 24. In embodiments, z4 is 25. In embodiments, z4 is 26. In embodiments, z4 is 27. In embodiments, z4 is 28. In embodiments, z4 is 29. In embodiments, z4 is 30. In embodiments, z4 is 31. In embodiments, z4 is 32. In embodiments, z4 is 33. In embodiments, z4 is 34. In embodiments, z4 is 35. In embodiments, z4 is 36. In embodiments, z4 is 37. In embodiments, z4 is 38. In embodiments, z4 is 39. In embodiments, z4 is 40. In embodiments, z4 is 41. In embodiments, z4 is 42. In embodiments, z4 is 43. In embodiments, z4 is 44. In embodiments, z4 is 45. In embodiments, z4 is 46. In embodiments, z4 is 47. In embodiments, z4 is 48. In embodiments, z4 is 49. In embodiments, z4 is 50. In embodiments, z4 is 51. In embodiments, z4 is 52. In embodiments, z4 is 53. In embodiments, z4 is 54. In embodiments, z4 is 55. In embodiments, z4 is 56. In embodiments, z4 is 57. In embodiments, z4 is 58. In embodiments, z4 is 59. In embodiments, z4 is 60. In embodiments, z4 is 61. In embodiments, z4 is 62. In embodiments, z4 is 63. In embodiments, z4 is 64. In embodiments, z4 is 65. In embodiments, z4 is 66. In embodiments, z4 is 67. In embodiments, z4 is 68. In embodiments, z4 is 69. In embodiments, z4 is 70. In embodiments, z4 is 71. In embodiments, z4 is 72. In embodiments, z4 is 73. In embodiments, z4 is 74. In embodiments, z4 is 75. In embodiments, z4 is 76. In embodiments, z4 is 77. In embodiments, z4 is 78. In embodiments, z4 is 79. In embodiments, z4 is 80. In embodiments, z4 is 81. In embodiments, z4 is 82. In embodiments, z4 is 83. In embodiments, z4 is 84. In embodiments, z4 is 85. In embodiments, z4 is 86. In embodiments, z4 is 87. In embodiments, z4 is 88. In embodiments, z4 is 89. In embodiments, z4 is 90. In embodiments, z4 is 91. In embodiments, z4 is 92. In embodiments, z4 is 93. In embodiments, z4 is 94. In embodiments, z4 is 95. In embodiments, z4 is 96. In embodiments, z4 is 97. In embodiments, z4 is 98. In embodiments, z4 is 99. In embodiments, z4 is 100.

In embodiments, n is 2. In embodiments, n is 3. In embodiments, n is 4. In embodiments, n is 5. In embodiments, n is 6. In embodiments, n is 7. In embodiments, n is 8. In embodiments, n is 9. In embodiments, n is 10. In embodiments, n is 11. In embodiments, n is 12. In embodiments, n is 13. In embodiments, n is 14. In embodiments, n is 15. In embodiments, n is 16. In embodiments, n is 17. In embodiments, n is 18. In embodiments, n is 19. In embodiments, n is 20. In embodiments, n is 21. In embodiments, n is 22. In embodiments, n is 23. In embodiments, n is 24. In embodiments, n is 25. In embodiments, n is 26. In embodiments, n is 27. In embodiments, n is 28. In embodiments, n is 29. In embodiments, n is 30. In embodiments, n is 31. In embodiments, n is 32. In embodiments, n is 33. In embodiments, n is 34. In embodiments, n is 35. In embodiments, n is 36. In embodiments, n is 37. In embodiments, n is 38. In embodiments, n is 39. In embodiments, n is 40. In embodiments, n is 41. In embodiments, n is 42. In embodiments, n is 43. In embodiments, n is 44. In embodiments, n is 45. In embodiments, n is 46. In embodiments, n is 47. In embodiments, n is 48. In embodiments, n is 49. In embodiments, n is 50. In embodiments, n is 51. In embodiments, n is 52. In embodiments, n is 53. In embodiments, n is 54. In embodiments, n is 55. In embodiments, n is 56. In embodiments, n is 57. In embodiments, n is 58. In embodiments, n is 59. In embodiments, n is 60. In embodiments, n is 61. In embodiments, n is 62. In embodiments, n is 63. In embodiments, n is 64. In embodiments, n is 65. In embodiments, n is 66. In embodiments, n is 67. In embodiments, n is 68. In embodiments, n is 69. In embodiments, n is 70. In embodiments, n is 71. In embodiments, n is 72. In embodiments, n is 73. In embodiments, n is 74. In embodiments, n is 75. In embodiments, n is 76. In embodiments, n is 77. In embodiments, n is 78. In embodiments, n is 79. In embodiments, n is 80. In embodiments, n is 81. In embodiments, n is 82. In embodiments, n is 83. In embodiments, n is 84. In embodiments, n is 85. In embodiments, n is 86. In embodiments, n is 87. In embodiments, n is 88. In embodiments, n is 89. In embodiments, n is 90. In embodiments, n is 91. In embodiments, n is 92. In embodiments, n is 93. In embodiments, n is 94. In embodiments, n is 95. In embodiments, n is 96. In embodiments, n is 97. In embodiments, n is 98. In embodiments, n is 99. In embodiments, n is 100.

In embodiments, n1 is 0. In embodiments, n1 is 1. In embodiments, n1 is 2. In embodiments, n1 is 3. In embodiments, n1 is 4. In embodiments, n1 is 5. In embodiments, n1 is 6. In embodiments, n1 is 7. In embodiments, n1 is 8. In embodiments, n1 is 9. In embodiments, n1 is 10. In embodiments, n1 is 11. In embodiments, n1 is 12. In embodiments, n1 is 13. In embodiments, n1 is 14. In embodiments, n1 is 15. In embodiments, n1 is 16. In embodiments, n1 is 17. In embodiments, n1 is 18. In embodiments, n1 is 19. In embodiments, n1 is 20. In embodiments, n1 is 21. In embodiments, n1 is 22. In embodiments, n1 is 23. In embodiments, n1 is 24. In embodiments, n1 is 25. In embodiments, n1 is 26. In embodiments, n1 is 27. In embodiments, n1 is 28. In embodiments, n1 is 29. In embodiments, n1 is 30. In embodiments, n1 is 31. In embodiments, n1 is 32. In embodiments, n1 is 33. In embodiments, n1 is 34. In embodiments, n1 is 35. In embodiments, n1 is 36. In embodiments, n1 is 37. In embodiments, n1 is 38. In embodiments, n1 is 39. In embodiments, n1 is 40. In embodiments, n1 is 41. In embodiments, n1 is 42. In embodiments, n1 is 43. In embodiments, n1 is 44. In embodiments, n1 is 45. In embodiments, n1 is 46. In embodiments, n1 is 47. In embodiments, n1 is 48. In embodiments, n1 is 49. In embodiments, n1 is 50.

In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12. In embodiments, n2 is 13. In embodiments, n2 is 14. In embodiments, n2 is 15. In embodiments, n2 is 16. In embodiments, n2 is 17. In embodiments, n2 is 18. In embodiments, n2 is 19. In embodiments, n2 is 20. In embodiments, n2 is 21. In embodiments, n2 is 22. In embodiments, n2 is 23. In embodiments, n2 is 24. In embodiments, n2 is 25. In embodiments, n2 is 26. In embodiments, n2 is 27. In embodiments, n2 is 28. In embodiments, n2 is 29. In embodiments, n2 is 30. In embodiments, n2 is 31. In embodiments, n2 is 32. In embodiments, n2 is 33. In embodiments, n2 is 34. In embodiments, n2 is 35. In embodiments, n2 is 36. In embodiments, n2 is 37. In embodiments, n2 is 38. In embodiments, n2 is 39. In embodiments, n2 is 40. In embodiments, n2 is 41. In embodiments, n2 is 42. In embodiments, n2 is 43. In embodiments, n2 is 44. In embodiments, n2 is 45. In embodiments, n2 is 46. In embodiments, n2 is 47. In embodiments, n2 is 48. In embodiments, n2 is 49. In embodiments, n2 is 50. In embodiments, n2 is 51. In embodiments, n2 is 52. In embodiments, n2 is 53. In embodiments, n2 is 54. In embodiments, n2 is 55. In embodiments, n2 is 56. In embodiments, n2 is 57. In embodiments, n2 is 58. In embodiments, n2 is 59. In embodiments, n2 is 60. In embodiments, n2 is 61. In embodiments, n2 is 62. In embodiments, n2 is 63. In embodiments, n2 is 64. In embodiments, n2 is 65. In embodiments, n2 is 66. In embodiments, n2 is 67. In embodiments, n2 is 68. In embodiments, n2 is 69. In embodiments, n2 is 70. In embodiments, n2 is 71. In embodiments, n2 is 72. In embodiments, n2 is 73. In embodiments, n2 is 74. In embodiments, n2 is 75. In embodiments, n2 is 76. In embodiments, n2 is 77. In embodiments, n2 is 78. In embodiments, n2 is 79. In embodiments, n2 is 80. In embodiments, n2 is 81. In embodiments, n2 is 82. In embodiments, n2 is 83. In embodiments, n2 is 84. In embodiments, n2 is 85. In embodiments, n2 is 86. In embodiments, n2 is 87. In embodiments, n2 is 88. In embodiments, n2 is 89. In embodiments, n2 is 90. In embodiments, n2 is 91. In embodiments, n2 is 92. In embodiments, n2 is 93. In embodiments, n2 is 94. In embodiments, n2 is 95. In embodiments, n2 is 96. In embodiments, n2 is 97. In embodiments, n2 is 98. In embodiments, n2 is 99. In embodiments, n2 is 100.

In embodiments, z2 is 2. In embodiments, z2 is 3. In embodiments, z2 is 4. In embodiments, z2 is 5. In embodiments, z2 is 6. In embodiments, z2 is 7. In embodiments, z2 is 8. In embodiments, z2 is 9. In embodiments, z2 is 10. In embodiments, z2 is 11. In embodiments, z2 is 12. In embodiments, z2 is 13. In embodiments, z2 is 14. In embodiments, z2 is 15. In embodiments, z2 is 16. In embodiments, z2 is 17. In embodiments, z2 is 18. In embodiments, z2 is 19. In embodiments, z2 is 20. In embodiments, z2 is 21. In embodiments, z2 is 22. In embodiments, z2 is 23. In embodiments, z2 is 24. In embodiments, z2 is 25. In embodiments, z2 is 26. In embodiments, z2 is 27. In embodiments, z2 is 28. In embodiments, z2 is 29. In embodiments, z2 is 30. In embodiments, z2 is 31. In embodiments, z2 is 32. In embodiments, z2 is 33. In embodiments, z2 is 34. In embodiments, z2 is 35. In embodiments, z2 is 36. In embodiments, z2 is 37. In embodiments, z2 is 38. In embodiments, z2 is 39. In embodiments, z2 is 40. In embodiments, z2 is 41. In embodiments, z2 is 42. In embodiments, z2 is 43. In embodiments, z2 is 44. In embodiments, z2 is 45. In embodiments, z2 is 46. In embodiments, z2 is 47. In embodiments, z2 is 48. In embodiments, z2 is 49. In embodiments, z2 is 50. In embodiments, z2 is 51. In embodiments, z2 is 52. In embodiments, z2 is 53. In embodiments, z2 is 54. In embodiments, z2 is 55. In embodiments, z2 is 56. In embodiments, z2 is 57. In embodiments, z2 is 58. In embodiments, z2 is 59. In embodiments, z2 is 60. In embodiments, z2 is 61. In embodiments, z2 is 62. In embodiments, z2 is 63. In embodiments, z2 is 64. In embodiments, z2 is 65. In embodiments, z2 is 66. In embodiments, z2 is 67. In embodiments, z2 is 68. In embodiments, z2 is 69. In embodiments, z2 is 70. In embodiments, z2 is 71. In embodiments, z2 is 72. In embodiments, z2 is 73. In embodiments, z2 is 74. In embodiments, z2 is 75. In embodiments, z2 is 76. In embodiments, z2 is 77. In embodiments, z2 is 78. In embodiments, z2 is 79. In embodiments, z2 is 80. In embodiments, z2 is 81. In embodiments, z2 is 82. In embodiments, z2 is 83. In embodiments, z2 is 84. In embodiments, z2 is 85. In embodiments, z2 is 86. In embodiments, z2 is 87. In embodiments, z2 is 88. In embodiments, z2 is 89. In embodiments, z2 is 90. In embodiments, z2 is 91. In embodiments, z2 is 92. In embodiments, z2 is 93. In embodiments, z2 is 94. In embodiments, z2 is 95. In embodiments, z2 is 96. In embodiments, z2 is 97. In embodiments, z2 is 98. In embodiments, z2 is 99. In embodiments, z2 is 100.

In embodiments, z5 is 1. In embodiments, z5 is 2. In embodiments, z5 is 3. In embodiments, z5 is 4. In embodiments, z5 is 5. In embodiments, z5 is 6. In embodiments, z5 is 7. In embodiments, z5 is 8. In embodiments, z5 is 9. In embodiments, z5 is 10.

In embodiments, the cationic amphipathic polymer has any of the foregoing formula wherein z2 is an integer from 2 to 100. In embodiments, z2 can be an integer in the range 2-100, 2-90, 2-80, 2-70, 2-60, 2-50, 2-40, 2-30, 2-2, or 2-10. In embodiments, z2 is an integer from 2-100 or 2-50.

In embodiments, the cationic amphipathic polymer has any of the foregoing formula wherein z5 is an integer from 1 to 3. In other embodiments, z5 is 1 or 3. In still some other embodiments, z5 is 1. In some other embodiments, z5 is 3.

In embodiments, the cationic amphipathic polymer has any of the foregoing formula wherein $R^2$ is hydrogen.

In embodiments, the cationic amphipathic polymer has any of the foregoing formula wherein $L^2$ is a bond.

In embodiments, the cationic amphipathic polymer has the formula:

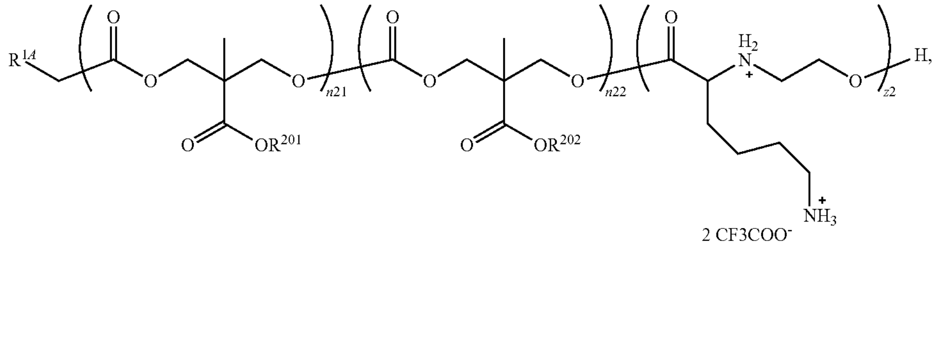

wherein n21 is 5, $R^{201}$ is oleyl, n22 is 5, $R^{202}$ is nonenyl and z2 is 7.

In embodiments, the cationic amphipathic polymer has the formula:

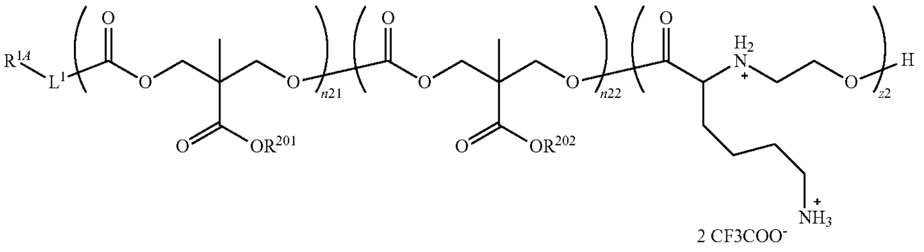

wherein n21 is 5 $R^{201}$ is oleyl, $L^1$ is —O—, n22 is 5, $R^{202}$ is nonenyl and z2 is 7.

In embodiments, the cationic amphipathic polymer has the formula:

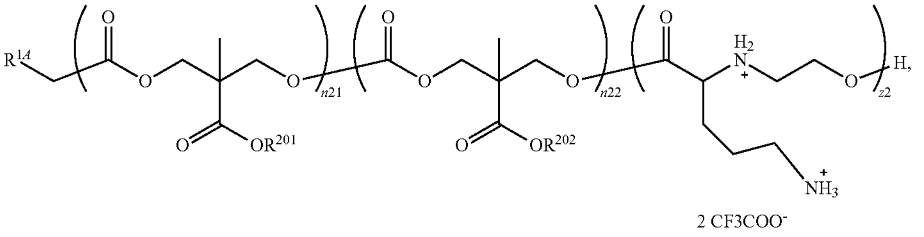

wherein n21 is 5, $R^{201}$ is oleyl, n22 is 5, $R^{202}$ is nonenyl and z2 is 7.

In embodiments, the cationic amphipathic polymer has the formula:

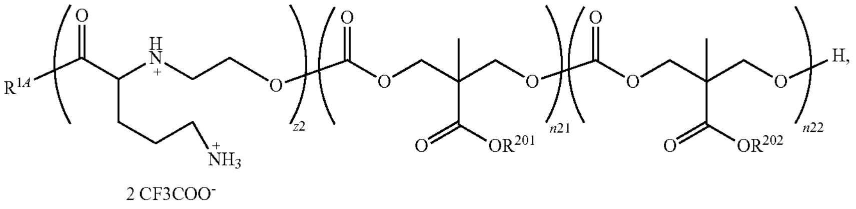

wherein n21 is 5, $R^{201}$ is oleyl, n22 is 5, $R^{202}$ is nonenyl and z2 is 7.

In embodiments, the cationic amphipathic polymer has the formula:

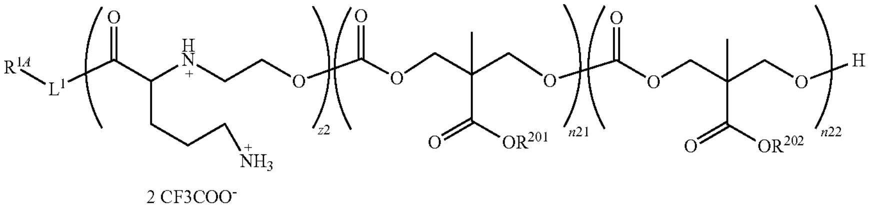

wherein n21 is 5, $R^{201}$ is oleyl, $L^1$ is —O—, n22 is 5, $R^{202}$ is nonenyl and z2 is 7.

In embodiments, the cationic amphipathic polymer has the formula:

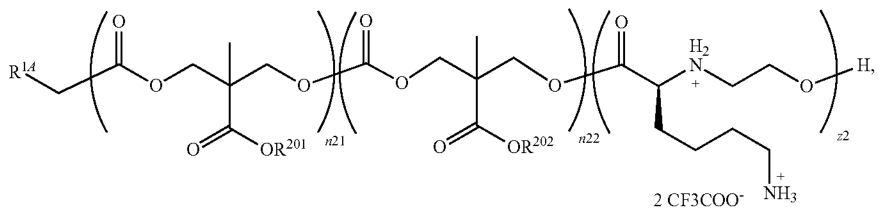

wherein n21 is 5, $R^{201}$ is oleyl, n22 is 5, $R^{202}$ is nonenyl and z2 is 7.

In embodiments, the cationic amphipathic polymer has the formula:

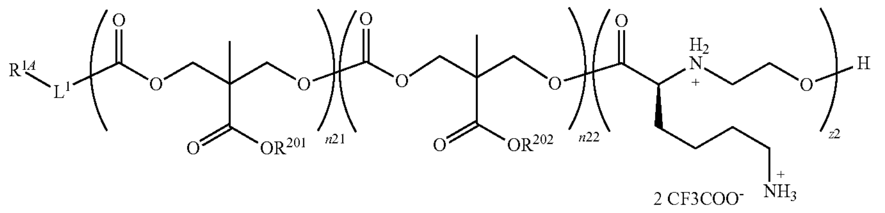

wherein n21 is 5, $R^{201}$ is oleyl, $L^1$ is —O—, n22 is 5, $R^{202}$ is nonenyl and z2 is 7.

In embodiments, the cationic amphipathic polymer has the formula:

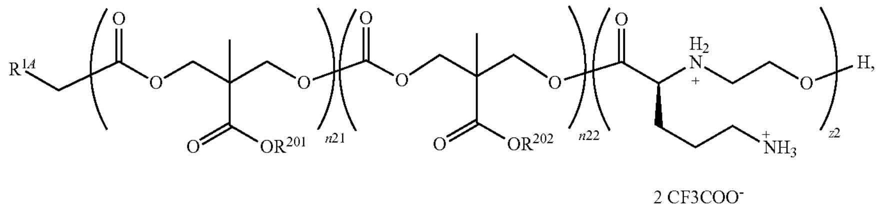

wherein n21 is 5, $R^{201}$ is oleyl, n22 is 5, $R^{202}$ is nonenyl and z2 is 7.

In embodiments, the cationic amphipathic polymer has the formula:

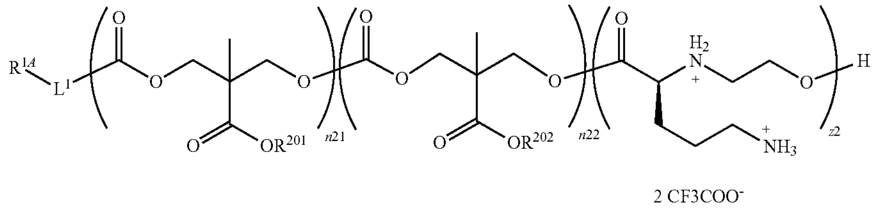

wherein n21 is 5, $R^{201}$ is oleyl, $L^1$ is —O—, n22 is 5, $R^{202}$ is nonenyl and z2 is 7.

In embodiments, the cationic amphipathic polymer has the formula:

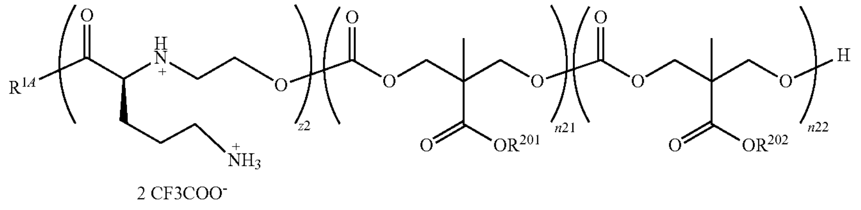

wherein n21 is 5, $R^{201}$ is oleyl, n22 is 5, $R^{202}$ is nonenyl and z2 is 7.

In embodiments, the cationic amphipathic polymer has the formula:

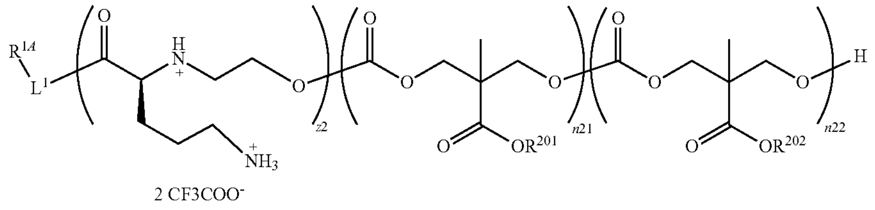

wherein n21 is 5, $R^{201}$ is oleyl, $L^1$ is —O—, n22 is 5, $R^{202}$ is nonenyl and z2 is 7.

In embodiments, the cationic amphipathic polymer has the formula:

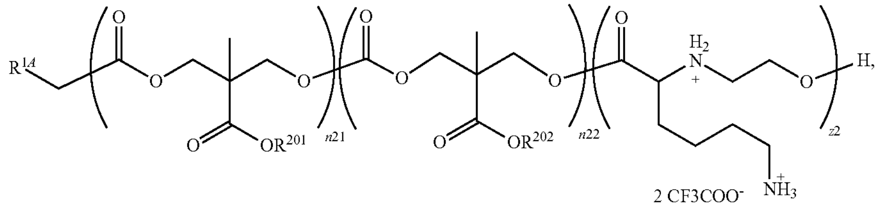

wherein n21 is 4, n22 is 4, and z2 is 8.

In embodiments, the cationic amphipathic polymer has the formula:

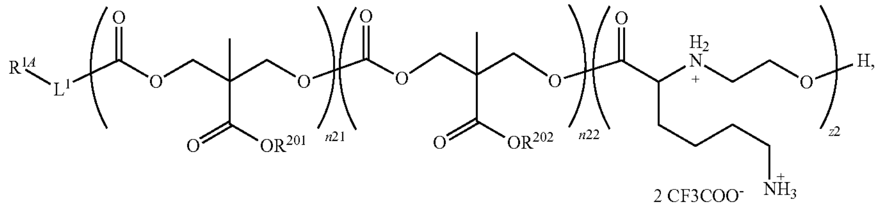

wherein n21 is 4, n22 is 4, and z2 is 8.

In embodiments, the cationic amphipathic polymer has the formula:

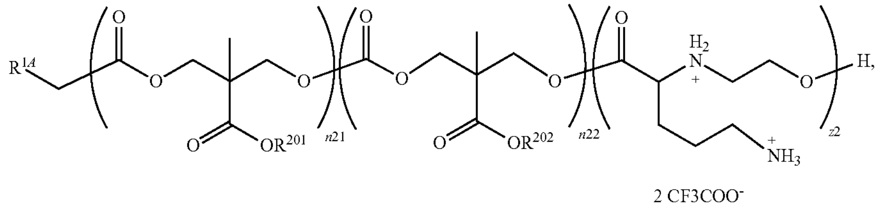

wherein n21 is 4, n22 is 4, and z2 is 8.

In embodiments, the cationic amphipathic polymer has the formula:

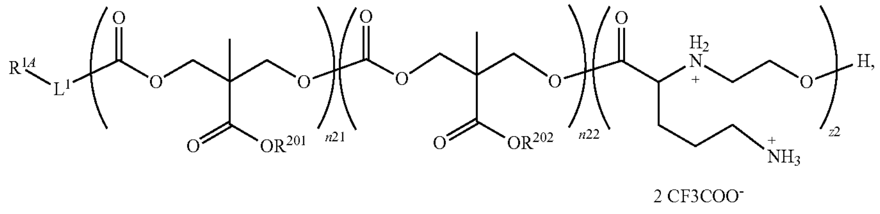

wherein n21 is 4, $L^1$ is —O—, n22 is 4, and z2 is 8.

In embodiments, the cationic amphipathic polymer has the formula:

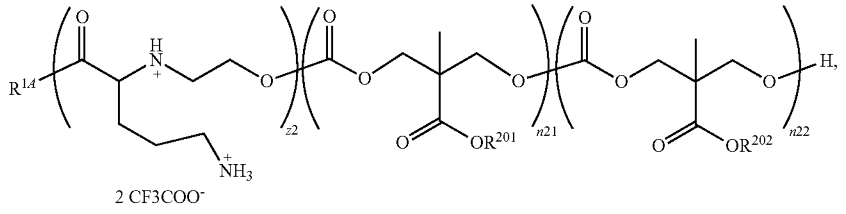

wherein n21 is 4, n22 is 4, and z2 is 8.

In embodiments, the cationic amphipathic polymer has the formula:

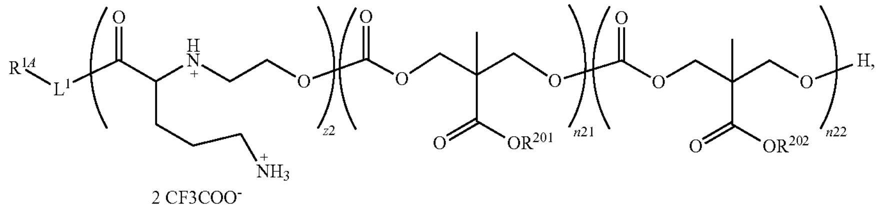

wherein n21 is 4, $L^1$ is —O—, n22 is 4, and z2 is 8.

In embodiments, the cationic amphipathic polymer has the formula:

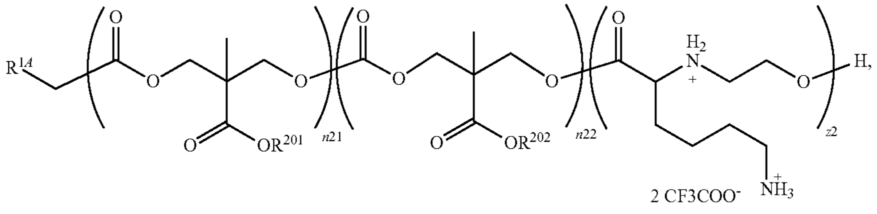

wherein n21 is 5, n22 is 6, and z2 is 10.

In embodiments, the cationic amphipathic polymer has the formula:

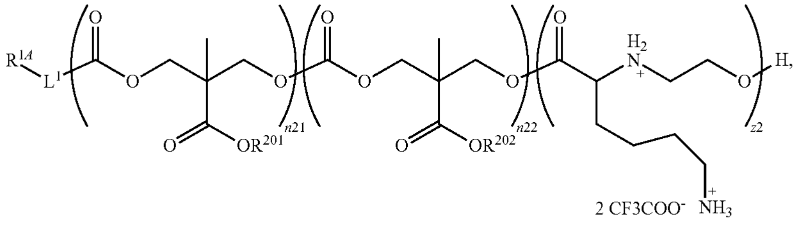

wherein n21 is 5, $L^1$ is —O—, n22 is 6, and z2 is 10.

In embodiments, the cationic amphipathic polymer has the formula:

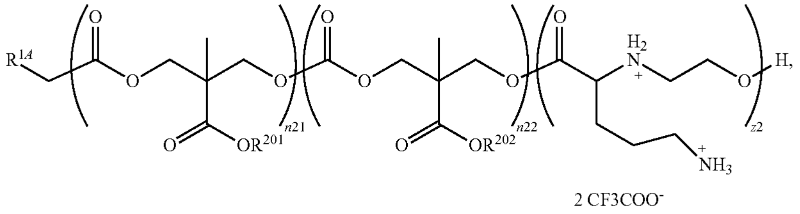

wherein n21 is 5, n22 is 6, and z2 is 10.

In embodiments, the cationic amphipathic polymer has the formula:

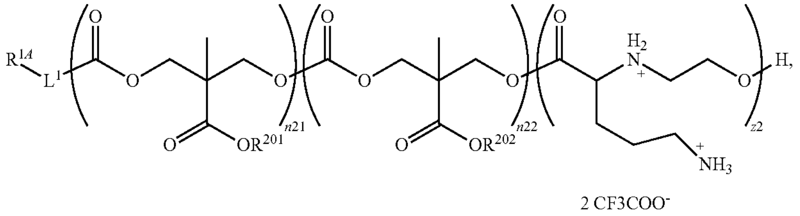

wherein n21 is 5, $L^1$ is —O—, n22 is 6, and z2 is 10.

In embodiments, the cationic amphipathic polymer has the formula:

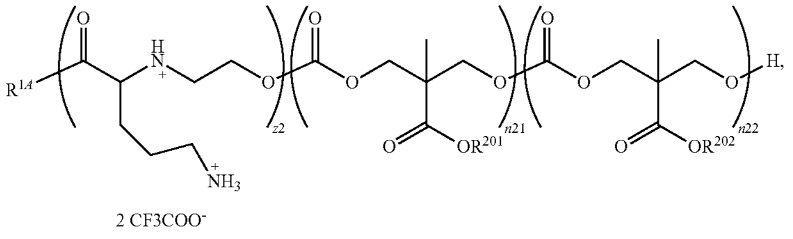

wherein n21 is 5, n22 is 6, and z2 is 10.

In embodiments, the cationic amphipathic polymer has the formula:

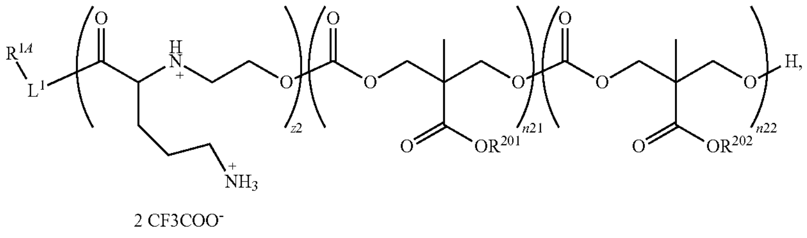

wherein n21 is 5, $L^1$ is —O—, n22 is 6, and z2 is 10.

In embodiments, the cationic amphipathic polymer has the formula:

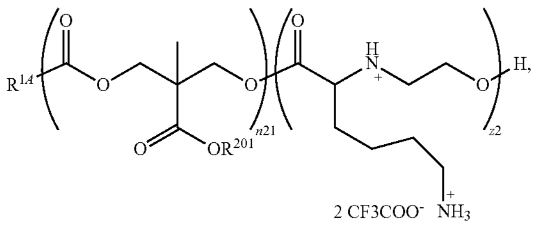

wherein n21 is 14, $R^{201}$ is dodecyl and z2 is 8.

In embodiments, the cationic amphipathic polymer has the formula:

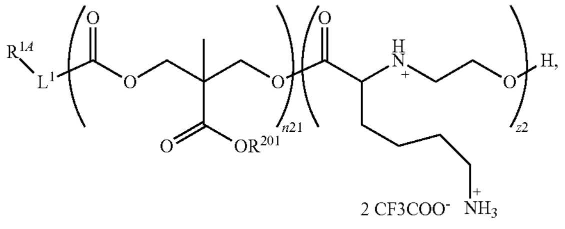

wherein n21 is 14, $L^1$ is —O—, $R^{201}$ is dodecyl and z2 is 8.

In embodiments, the cationic amphipathic polymer has the formula:

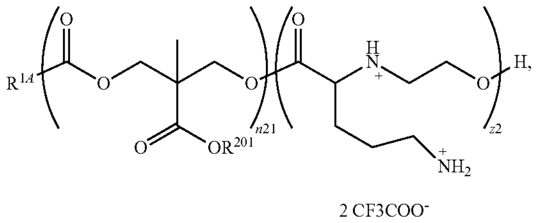

wherein n21 is 14, $R^{201}$ is dodecyl and z2 is 8.

In embodiments, the cationic amphipathic polymer has the formula:

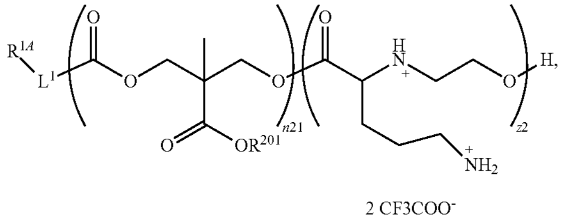

wherein n21 is 14, $L^1$ is —O—, $R^{201}$ is dodecyl and z2 is 8.

In embodiments, the cationic amphipathic polymer has the formula:

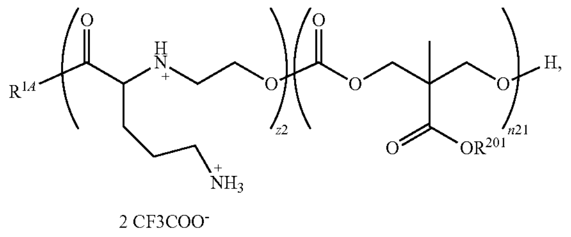

wherein n21 is 14, $R^{201}$ is dodecyl and z2 is 8.

In embodiments, the cationic amphipathic polymer has the formula:

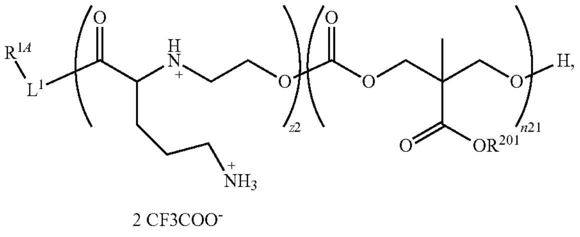

wherein n21 is 14, $L^1$ is —O—, $R^{201}$ is dodecyl and z2 is 8.

In embodiments, the cationic amphipathic polymer has the formula:

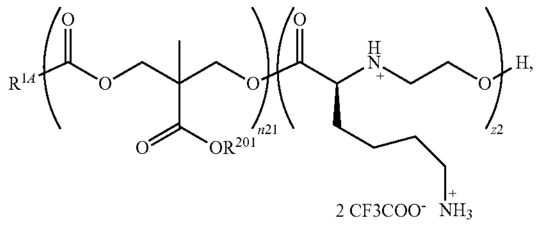

wherein n21 is 14, $R^{201}$ is dodecyl and z2 is 8.

In embodiments, the cationic amphipathic polymer has the formula:

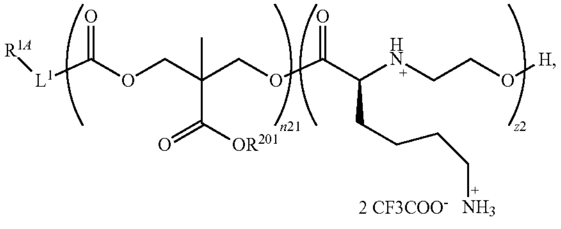

wherein n21 is 14, $L^1$ is —O—, $R^{201}$ is dodecyl and z2 is 8.

In embodiments, the cationic amphipathic polymer has the formula:

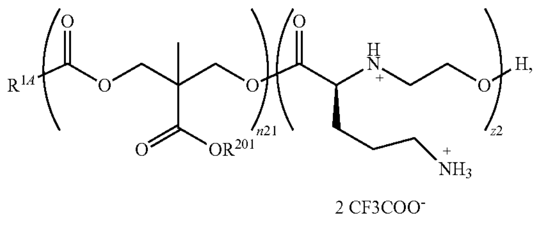

wherein n21 is 14, $R^{201}$ is dodecyl and z2 is 8.

In embodiments, the cationic amphipathic polymer has the formula:

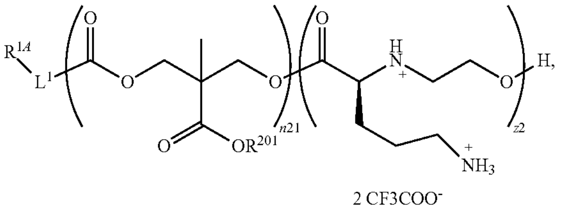

wherein n21 is 14, $L^1$ is —O—, $R^{201}$ is dodecyl and z2 is 8.

In embodiments, the cationic amphipathic polymer has the formula:

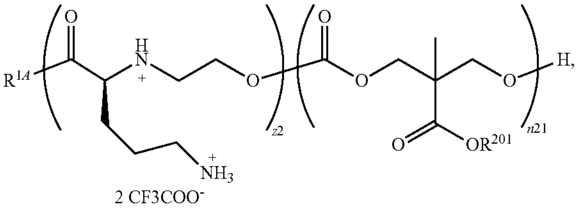

wherein n21 is 14, $R^{201}$ is dodecyl and z2 is 8.

In embodiments, the cationic amphipathic polymer has the formula:

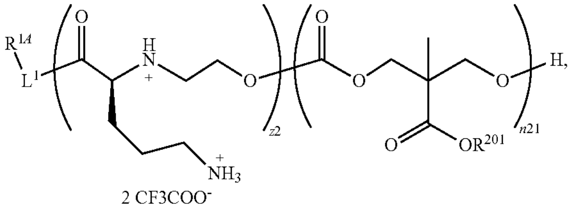

wherein n21 is 14, $L^1$ is —O—, $R^{201}$ is dodecyl and z2 is 8.

In embodiments, the cationic amphipathic polymer has the formula:

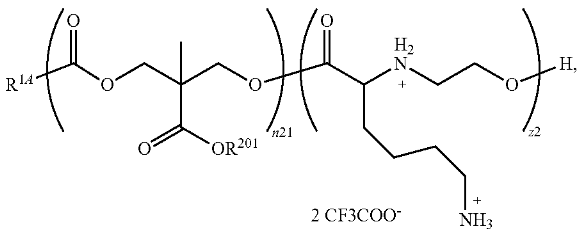

wherein n21 is an integer from 10 to 20;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 3-10.

In embodiments, n21 is 14, $R^{201}$ is dodecyl and z2 is 8.

In embodiments, the cationic amphipathic polymer has the formula:

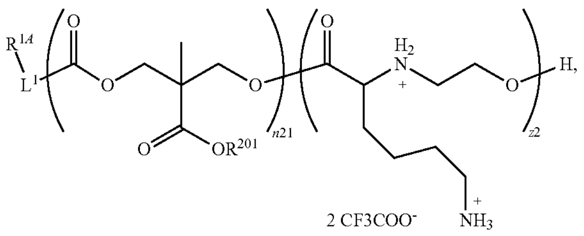

wherein $R^{1A}$ is as described herein, n21 is an integer from 10 to 20 and $L^1$ is as described herein;

In embodiments, the cationic amphipathic polymer has the formula:

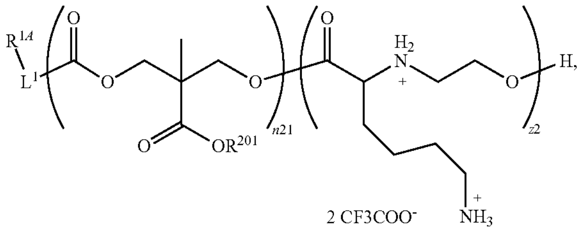

wherein $R^{1A}$ is as described herein, n21 is 14; $L^1$ is —O—, $R^{201}$ is $C_{12}H_{25}$ and z2 is 8.

In embodiments, the cationic amphipathic polymer has the formula:

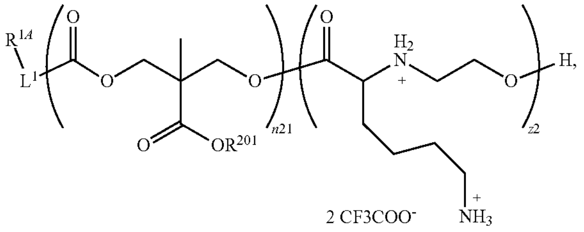

wherein $R^{1A}$ is as described herein, n21 is 12; $L^1$ is —O—, $R^{201}$ is $C_{12}H_{25}$ and z2 is 6.

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 3-10.

In embodiments, n21 is 14, $R^{201}$ is dodecyl and z2 is 8.

In embodiments, the cationic amphipathic polymer has the formula:

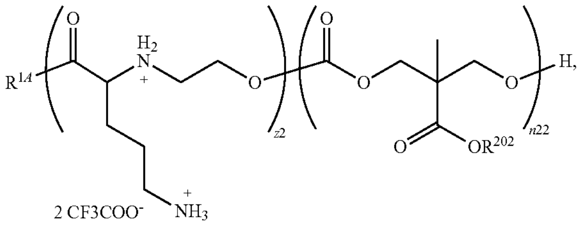

wherein n22 is an integer from 10 to 35;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 5-20.

In embodiments, n22 is 14, $R^{202}$ is dodecyl and z2 is 7.

In embodiments, the cationic amphipathic polymer has the formula:

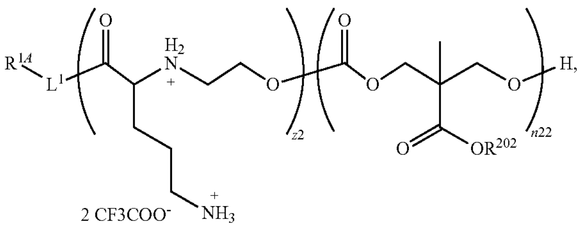

wherein n22 is an integer from 10 to 35; $L^1$ is defined as herein;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 5-20.

In embodiments, n22 is 14, $R^{202}$ is dodecyl and z2 is 7.

In embodiments, the cationic amphipathic polymer has the formula:

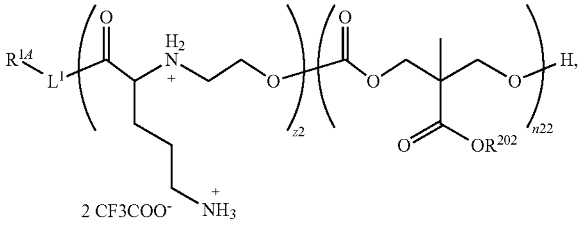

wherein $R^{1A}$ is as described herein, n22 is 31; $L^1$-O—, $R^{202}$ is $C_{12}H_{25}$ and z2 is 10.

In embodiments, the cationic amphipathic polymer has the formula:

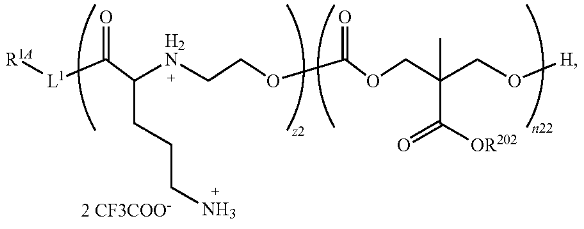

wherein $R^{1A}$ is as described herein, n22 is 15; $L^1$-O—, $R^{202}$ is $C_{12}H_{25}$ and z2 is 5.

In embodiments, the cationic amphipathic polymer has the formula:

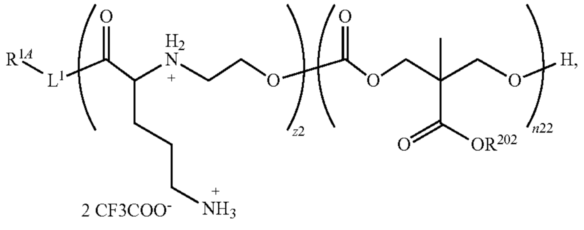

wherein $R^{1A}$ is as described herein, n22 is 14; $L^1$-O—, $R^{202}$ is $C_{12}H_{25}$ and z2 is 7.

In embodiments, the cationic amphipathic polymer has the formula:

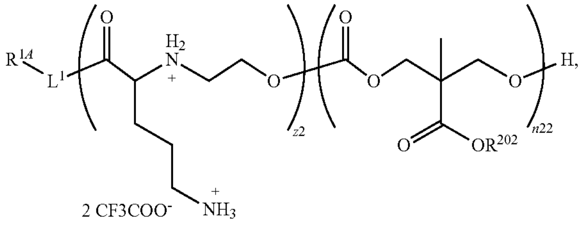

wherein $R^{1A}$ is as described herein, n22 is 16; $L^1$-O—, $R^{202}$ is $C_{12}H_{25}$ and z2 is 15.

In embodiments, the cell penetrating complex further includes a second cationic amphipathic polymer, wherein the second cationic amphipathic polymer is different from the cationic amphipathic polymer.

In embodiments, the second cationic amphipathic polymer has the formula:

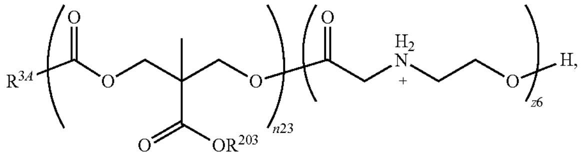

n23 is an integer from 1 to 100;

z6 is an integer from 5-15;

$R^{3A}$ is independently hydrogen, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_{21}$, —CN, —OH, $-NH_2$, —COOH, $-CONH_2$, $-NO_2$, —SH, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{203}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, the second cationic amphipathic polymer has the formula:

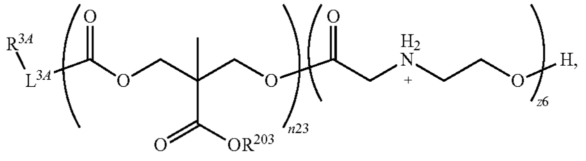

n23 is an integer from 1 to 100;

z6 is an integer from 5-15;

$L^{3A}$ is a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{3A}$ is independently hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{203}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^{203}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{203}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{203}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{203}$ is hydrogen or unsubstituted alkyl (e.g., $C_1$-$C_6$ alkyl).

In embodiments, $R^{203}$ is an unsubstituted $C_1$-$C_{30}$ alkyl. In embodiments, $R^{203}$ is an unsubstituted $C_1$-$C_{20}$ alkyl. In embodiments, $R^{203}$ is an unsubstituted $C_8$-$C_{30}$ alkyl. In embodiments, $R^{203}$ is an unsubstituted $C_5$-$C_{20}$ alkyl. In embodiments, $R^{203}$ is an unsubstituted $C_9$-$C_{20}$ alkyl. In embodiments, $R^{203}$ is an unsubstituted $C_9$-$C_{18}$ alkyl. In embodiments, $R^{203}$ is an unsubstituted $C_{18}$ alkyl. In embodiments, $R^{203}$ is an unsubstituted $C_{17}$ alkyl. In embodiments, $R^{203}$ is an unsubstituted $C_{16}$ alkyl. In embodiments, $R^{203}$ is an unsubstituted $C_{15}$ alkyl. In embodiments, $R^{203}$ is an unsubstituted $C_{14}$ alkyl. In embodiments, $R^{203}$ is an unsubstituted $C_{13}$ alkyl. In embodiments, $R^{203}$ is an unsubstituted $C_{12}$ alkyl. In embodiments, $R^{203}$ is an unsubstituted $C_{11}$ alkyl. In embodiments, $R^{203}$ is an unsubstituted $C_{10}$ alkyl. In embodiments, $R^{203}$ is an unsubstituted $C_9$ alkyl. In embodiments, $R^{203}$ is an unsubstituted $C_8$ alkyl. In embodiments, $R^{20}$ is an unsubstituted $C_7$ alkyl. In embodiments, $R^{203}$ is an unsubstituted $C_6$ alkyl. In embodiments, $R^{203}$ is an unsubstituted $C_5$ alkyl. In embodiments, $R^{203}$ is an unsubstituted $C_4$ alkyl. In embodiments, $R^{203}$ is an unsubstituted $C_3$ alkyl. In embodiments, $R^{203}$ is an unsubstituted $C_2$ alkyl.

In embodiments, $R^{203}$ is an unsubstituted $C_1$-$C_{30}$ alkenyl. In embodiments, $R^{203}$ is an unsubstituted $C_1$-$C_{20}$ alkenyl. In embodiments, $R^{203}$ is an unsubstituted $C_8$-$C_{30}$ alkenyl. In embodiments, $R^{203}$ is an unsubstituted $C_5$-$C_{20}$ alkenyl. In embodiments, $R^{203}$ is an unsubstituted $C_9$-$C_{20}$ alkenyl. In embodiments, $R^{203}$ is an unsubstituted $C_9$-$C_{18}$ alkenyl. In embodiments, $R^{203}$ is an unsubstituted $C_{18}$ alkenyl. In embodiments, $R^{203}$ is an unsubstituted $C_{17}$ alkenyl. In embodiments, $R^{203}$ is an unsubstituted $C_{16}$ alkenyl. In embodiments, $R^{203}$ is an unsubstituted $C_{15}$ alkenyl. In embodiments, $R^{203}$ is an unsubstituted $C_4$ alkenyl. In embodiments, $R^{203}$ is an unsubstituted $C_{13}$ alkenyl. In embodiments, $R^{203}$ is an unsubstituted $C_{12}$ alkenyl. In embodiments, $R^{203}$ is an unsubstituted $C_{11}$ alkenyl. In embodiments, $R^{203}$ is an unsubstituted $C_{10}$ alkenyl. In embodiments, $R^{203}$ is an unsubstituted $C_9$ alkenyl. In embodiments, $R^{203}$ is an unsubstituted $C_8$ alkenyl. In embodiments, $R^{203}$ is an unsubstituted $C_7$ alkenyl. In embodiments, $R^{203}$ is an unsubstituted $C_6$ alkenyl. In embodiments, $R^{203}$ is an unsubstituted $C_5$ alkenyl. In embodiments, $R^{203}$ is an unsubstituted $C_4$ alkenyl. In embodiments, $R^{203}$ is an unsubstituted $C_3$ alkenyl. In embodiments, $R^{203}$ is an unsubstituted $C_2$ alkenyl.

In embodiments, the second cationic amphipathic polymer has the formula:

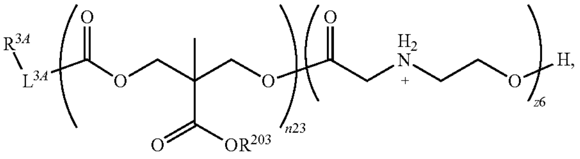

wherein $R^{3A}$ is as described herein, $L^{3A}$ is —O—, z6 is 16, $R^{203}$ is $C_2H_{25}$ and n23 is 15.

In embodiments, the second cationic amphipathic polymer has the formula:

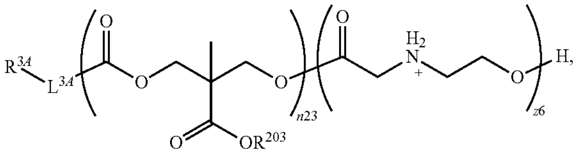

wherein $R^{3A}$ is as described herein, $L^{3A}$ is —O—, z6 is 11, $R^{203}$ is $C_{12}H_{25}$ and n23 is 13.

In embodiments, $R^{203}$ is a stearyl moiety (e.g., an unsubstituted $C_{18}$ alkyl). In embodiments, $R^{203}$ is an oleyl moiety (e.g., an unsubstituted $C_{18}$ alkenyl). In embodiments, $R^{203}$ is an linoleyl moiety (e.g., an unsubstituted $C_{18}$ alkenyl). In embodiments, $R^{203}$ is an dodecyl moiety (e.g., an unsubstituted $C_{12}$ alkyl). In embodiments, $R^{203}$ is an nonenyl moiety (e.g., an unsubstituted $C_9$ alkenyl). In embodiments, $R^{203}$ is
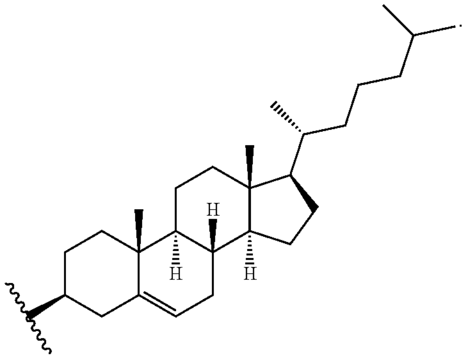
In embodiments, n23 is 13, z6 is 11 and $R^{203}$ is dodecyl. In embodiments, CART has the formula:
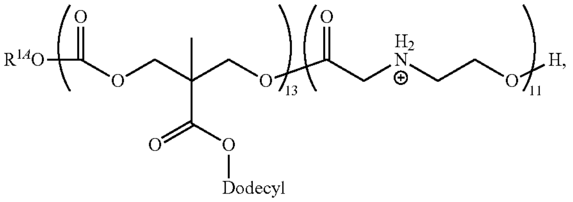
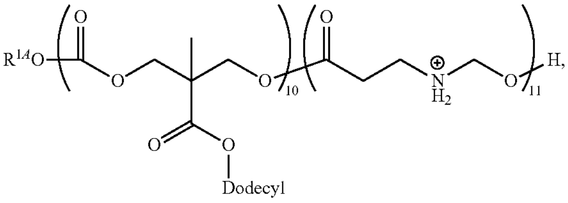
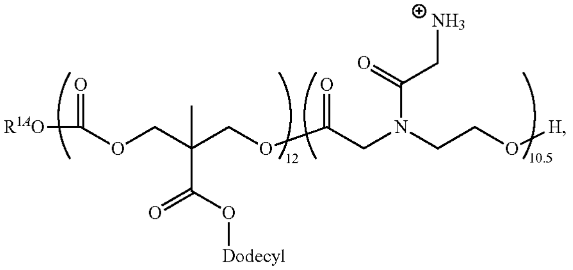
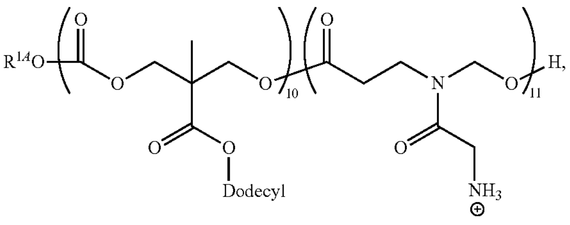
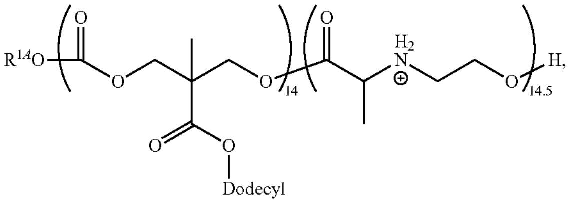
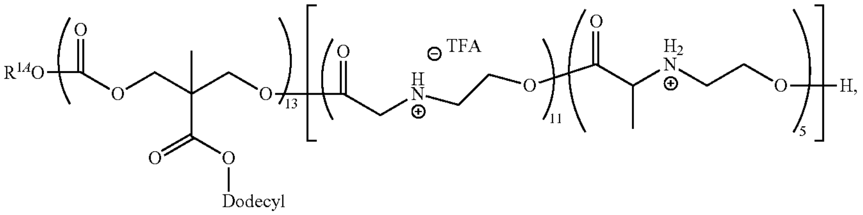
"Random" block
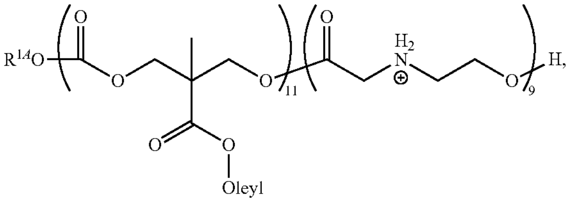
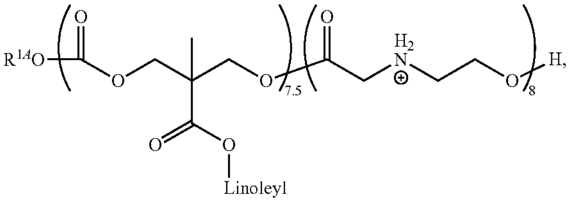

-continued

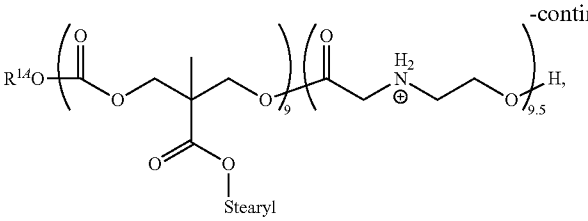

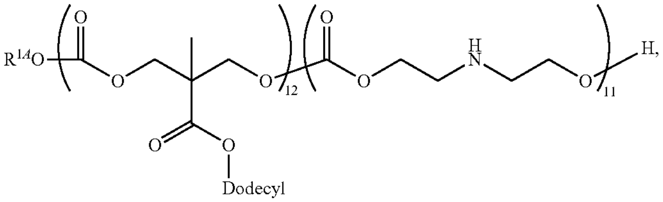

or

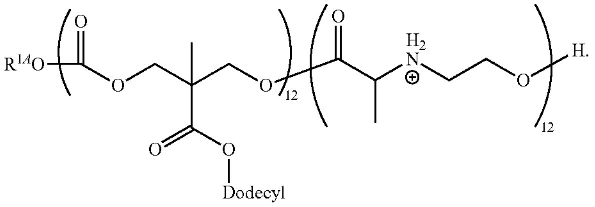

In one aspect is a provided a cell penetrating complex including a nucleic acid non-covalently bound to a first cationic amphipathic polymer and a second amphipathic polymer, wherein the first cationic amphipathic polymer has the formula:

(XII)

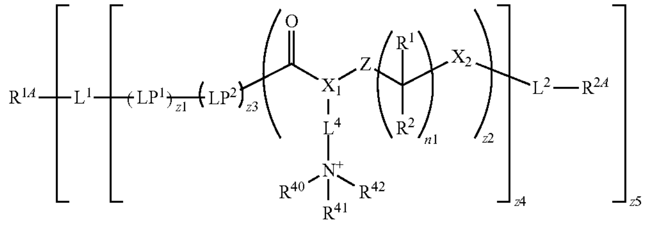

or (XIII)

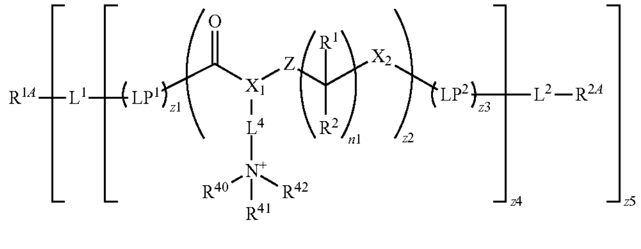

wherein $R^{1A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCH_{12}$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, independently —COOH, $—CONH_2$, $—NO_2$, —SH, $—SO_3H$, $—SO_4H$, $—SO_2NH_2$, $—NHNH_2$, $—ONH_2$, independently $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S$(O)_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, —$C(R^5)(R^6)$—, —$C(R^5)(R^6)$—$C(R^7)(R'')$—, —O—$C(R^5)(R^6)$—, or —O—$C(R^5)(R^6)$—$C(R^7)(R^8)$—;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, —C(O)O—, —O—, —S—, —NH—, —C(O)NH—, —NHC(O)—, —$S(O)_2$—, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, —$S^*R^{13}$—, —$NR^3$—, or —$N^+(R^{13})(H)$—;

$R^{13}$ is hydrogen, —$CCl_3$, —$CBr_3$, —$CF_3$, —$CI_3$, —CN, —OH, =O, —$NH_2$, —COOH, —$CONH_2$, —SH, —$SO_3H$, $SO_2NH_2$, —$OCCl_3$, —$OCF_3$, —$OCBr_3$, —$OCI_3$, —$OCHCl_2$, —$OCHBr_2$, —$OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z1 or z3 is not 0;

z2 is an integer from 2 to 100;

z4 is an integer from 1 to 100;

z5 is an integer from 1 to 10; and wherein the first cationic amphipathic polymer and the second amphipathic polymer are different.

The first cationic amphipathic polymer may be any of the cationic amphipathic polymers provided herein including embodiments thereof. The second cationic amphipathic polymer may be any of the cationic amphipathic polymers provided herein including embodiments thereof or it may be any other cationic amphipathic polymer useful for the complexes provided herein. In embodiments, the second cationic amphipathic polymer is any of the cationic amphipathic polymers described in PCT application serial number PCT/US17/44238 published as WO 2018/022930, which is hereby incorporated by reference in its entirety and for all purposes.

In embodiments, the first cationic amphipathic polymer has the formula:

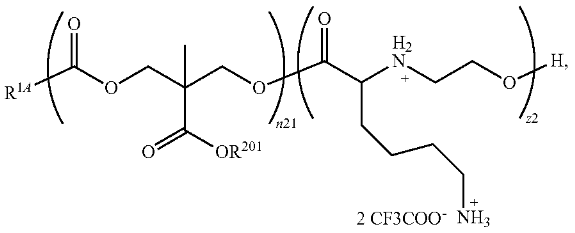

wherein n21 is an integer from 10 to 20;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 3-10.

In embodiments, n21 is 14, $R^{201}$ is dodecyl and z2 is 8.

In embodiments, the first cationic amphipathic polymer has the formula:

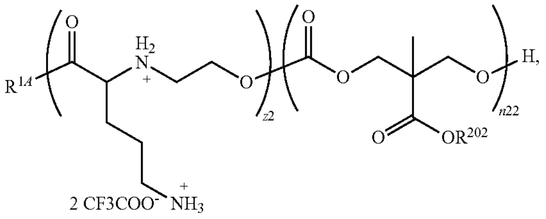

or

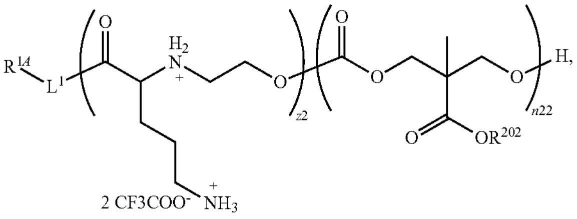

wherein n22 is an integer from 10 to 35;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, and z2 is independently an integer from 5-20.

In embodiments, n22 is 14, $R^{202}$ is dodecyl and z2 is 7.

In embodiments, the second cationic amphipathic polymer has the formula:

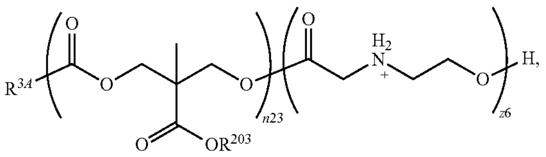

or

-continued

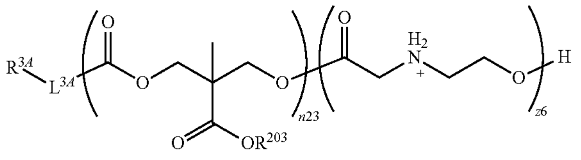

wherein n23 is an integer from 1 to 100;

z6 is an integer from 5-15; and $R^{3A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_{21}$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^A$ is a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{203}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, n23 is 13, z6 is 11 and $R^{203}$ is dodecyl.

In embodiments, the first cationic amphipathic polymer has the formula:

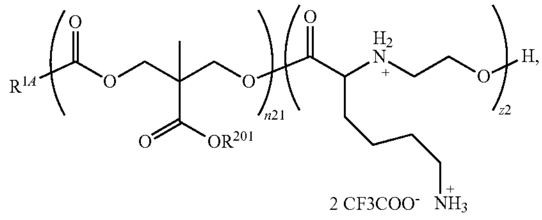

or

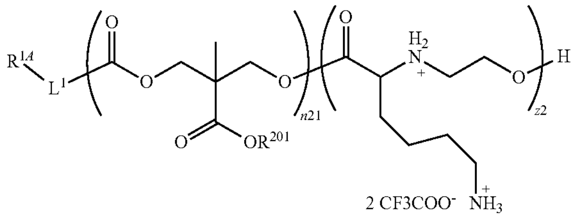

wherein n21 is 14, $R^{201}$ is dodecyl and z2 is 8; and wherein the second cationic amphipathic polymer has the formula:

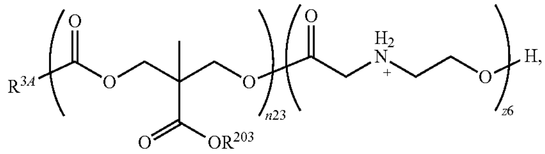

or

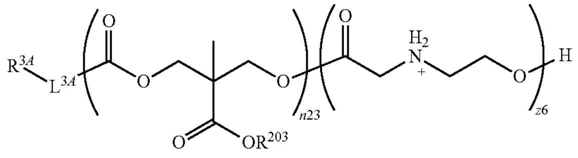

wherein n23 is 13, $R^{203}$ is dodecyl and z6 is 11.

In embodiments, the first cationic amphipathic polymer has the formula:

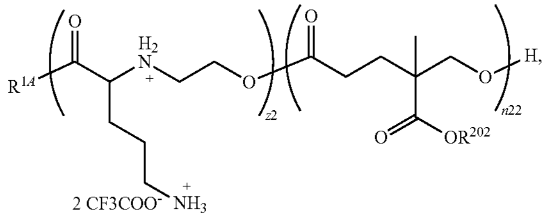

or

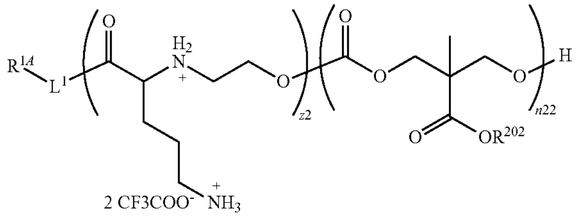

wherein n22 is an integer from 10-35, $R^{202}$ is dodecyl and z2 is 3-15; and wherein the second cationic amphipathic polymer has the formula:

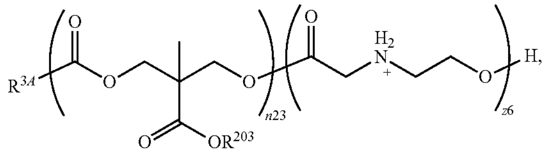

or

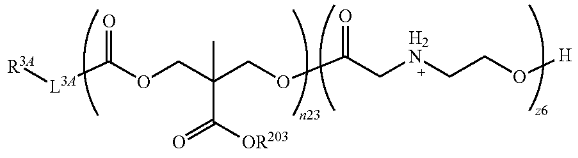

wherein n23 is 13, $R^{203}$ is dodecyl and z6 is 11.

In one aspect is provided a nanoparticle composition including a plurality of cell-penetrating complexes as described herein, including embodiments.

In one aspect is provided a pharmaceutical composition including a cell-penetrating complex as described herein, including embodiments, and a pharmaceutical excipient.

In embodiments, the nucleic acid is DNA or RNA, such as messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA). The cell-penetration complex may further include a protein or peptide.

In embodiments, the nucleic acid is a messenger RNA (mRNA), a small interference RNA (siRNA), a short hairpin RNA (shRNA), a micro RNA (miRNA), a guide RNA (gRNA), a CRISPR RNA (crRNA), a transactivating RNA (tracrRNA), a plasmid DNA (pDNA), a minicircle DNA, or a genomic DNA (gNDA).

Further to the cell-penetration complex disclosed herein and embodiments thereof, in embodiments the cell-penetrating complex further includes a plurality of lipophilic moieties.

Further to the cell-penetration complex disclosed herein and embodiments thereof, in embodiments the cell-penetrating complex further includes a plurality of immolation domains.

Further to the cell-penetration complex disclosed herein and embodiments thereof, in embodiments, the counteranion to the above cationic sequences can include common counterions known in the art, such as for example acetate, trifluoroacetate, triflate, chloride, bromide, sulfate, phosphate, succinate, or citrate. In embodiments, the counteranion is acetate, trifluoroacetate, triflate, chloride, bromide, sulfate, phosphate, succinate, or citrate.

In one aspect is provided a nanoparticle composition including a plurality of cell-penetrating complexes as provided herein, including embodiments thereof.

In one aspect is provided a pharmaceutical composition including a cell-penetrating complex as provided herein, including embodiments thereof.

Transfection

In another aspect, there is provided a method of transfecting a nucleic acid into a cell, the method including contacting a cell with a cell-penetrating complex as disclosed herein, or embodiment thereof. The compositions provided herein including embodiments thereof are, inter alia, useful for the targeted delivery of nucleic acids to the lung.

In embodiments, the method further includes allowing the cationic amphipathic polymer to degrade within the cell thereby forming a degradation product. In embodiments, the degradation product is a substituted or unsubstituted diketopiperazine.

Further to any embodiment of the method of transfecting a nucleic acid into a cell, in embodiments the nucleic acid is an mRNA. In embodiments, the method further includes allowing the mRNA to be expressed in the cell. In embodiments, the cell forms part of an organism. In embodiments, the organism is a human.

Provided herein, inter alia, are novel materials and strategies that enable or enhance the complexation, protection, delivery and release of oligonucleotides and polyanionic cargos, e.g., messenger RNA (mRNA), into target cells, tissues, and organs both in vitro and in vivo.

For example, one strategy disclosed herein for mRNA delivery is accomplished using biodegradable poly(carbonate-co-aminoester)s oligomers and variations thereof which were discovered to electrostatically complex polyanions such as mRNA, producing noncovalent macromolecular particles that protect the mRNA cargo, readily enter cells and uniquely release oligonucleotide cargos. The mRNA released in the cell is then converted by cellular processes into peptides and proteins whose sequence and thus activity is determined by the mRNA sequence.

Thus, there is provided, for example, greatly increased improved cellular transfection efficiency over the use of nucleic acids themselves and known gene delivery vectors. The materials and strategy used for the delivery of mRNA can also be used to deliver other oligonucleotides such as siRNA, pDNA, shRNA, and gDNA. They can additionally be utilized to deliver other anionic biomolecules such as heparin, inorganic polyphosphate, and inositol polyphosphates (e.g., IP3, IP7, IP8). This delivery can be achieved with a variety of human and non-human cell lines, as well as through multiple modes of administration in vivo including but not limited to intramuscular, intravenous, intraperitoneal, intraocular, intranasal, subcutaneous, buccal and topical. The poly(carbonate-co-aminoester)s disclosed herein can be utilized, for example, as customizable, biodegradable, biocompatible materials for applications in biomedical therapies, imaging and devices. The copolymerization with biodegradable, non-toxic compounds materials such as valerolactone, caprolactone, lactide, and cyclic carbonates allows for tuning physical and biological properties including cargo release rates, hydrophobicity, incorporation of targeting ligands, biodistribution, and toxicity.

Accordingly, in some embodiments, the agents provided herein include oligomers, polymers, co-oligomers, and copolymers which may be derived from cyclic amino-ester and cyclic methyl trimethylene carbonate (MTC) monomers. Cyclic amino-esters have the base structure of morpholin-2-one and homologs thereof, with multiple substitution patterns possible including the following.

(1) N-acylation with a variety of hydrophobic groups (e.g., R=alkyl, alkenyl, aryl, polycycles including steroids, heterocycles), cationic groups (e.g., ammonium, phosphonium, sulfonium, guanidinium, including acylation with amino acids such as glycine, lysine, ornithine, arginine), anionic groups (e.g., carboxylate, sulfate, phosphate), or hydrophilic (e.g., PEG) carbamates. Protection of the morpholine nitrogen with N-Boc or N-Cbz groups followed by organocatalytic ring opening oligomerization or polymerization can afford upon deprotection cationic polymer or oligomer backbones.

(2) Alpha-alkylation or functionalization next to the ester carbonyl with the aforementioned possible functionalities selected to allow for cargo complexation and subsequent cargo release by biodegradation.

(3) Alkylation proximal to the morpholine nitrogen with the aforementioned functionalities.

(4) A combination of the above modifications.

Additionally, copolymers or co-oligomers (block or statistical) can be made by mixing two or more morpholin-2-one monomers, or by the copolymerization (or co-oligomerization) of one or multiple morpholin-2-one monomers with one or multiple cyclic carbonate monomers described herein. These carbonate monomers can incorporate a similar variety of side chain functionality, notably lipophilic groups or cationic groups to modulate oligonucleotide stability, delivery, and release properties. Furthermore, a variety of other commercially available cyclic ester monomers can be used including but not limited to lactide, glycolide, valerolactone, and/or caprolactone to incorporate lipophilic functionality.

The synthesis of polyaminoesters and poly(carbonate-co-aminoester)s is achieved through the ring-opening polymerization and/or copolymerization of morpholine-2-one and cyclic carbonate monomers. The N-Boc protected morpholinone (MBoc) polymerizes to high conversion (>85%), tunable Mn (1 kDa-20 kDa), and low molecular weight distributions (Mw/Mn—1.1-1.3) using an organocatalytic system. Post-polymerization deprotection of the Boc groups affords a cationic (diprotic, secondary amine) water-soluble polymer (~0.5M in D20, stable for >3 days). Furthermore, copolymerization of MBoc with MTC-dodecyl carbonate monomers followed by deprotection give rise to moderately charged cationic materials in high yield (>60%) with narrow polydispersity<1.4 PDI) and tunable block length. Block length is controlled by the ratio of initiator to monomer.

The polyaminoesters and poly(carbonate-co-aminoester)s are biocompatible and biodegradable. The cationic polyaminoesters rapidly degrade through a novel pH- and buffer-dependent immolation mechanism to generate in one embodiment bis-N-hydroxyethy-2,5-piperizinedionebis-hydroxyethyl glycine. This unforeseen degradation produces a product that is nontoxic at treatment concentrations, and the monomeric form (the expected product of further hydrolysis) is a natural biomarker for phospholipid modification in the Maillard reaction. The carbonate segment of the aminoester/carbonate copolymers degrades through hydrolysis and decarboxylation, and its byproducts have previously been shown to be non-toxic. The new poly- and oligo (carbonate-co-aminoester)s exhibit unanticipated performance as gene delivery agents due to their unique degradation mechanism. These new materials non-covalently complex, protect, deliver, and release mRNA at moderate theoretical charge ratios (e.g., about 10:1) resulting in exceptional transfection efficiencies (in some cases >99%) and robust induction of gene expression in vitro and in vivo. This strategy is effective for the delivery of mRNA molecules of different lengths (1000 and 2000 nucleotide transcripts tested). In one embodiment, gene delivery is achieved through formulation of cationic poly(carbonate-co-aminoester)s with anionic cargos to form self-assembled particles 200-400 nm in size. These particles are stable on the timescales necessary for intracellular gene delivery, and then they release the oligonucleotide cargo once inside the cell. While not bound to any particular theory, these materials degrade to the bis-N-hydroxyethyl-2,5-piperizinedione product bis-hydroxyethyl glycine. Treatment of a variety of human and non-human cell lines (e.g., HeLa, HaCaT, J774, HEK293) with the mRNA/amphiphile complex results in the induction of protein expression (e.g., GFP, luciferase) in vitro and in vivo through multiple modes of administration (intramuscular and intravenous tested).

Protein expression has been measured using mRNA encoding fluorescent reporter genes by flow cytometry and fluorescence microscopy (GFP), as well as bioluminescence (firefly luciferase). The poly(carbonate-co-aminoester)s have been shown to be more efficient transfection agents than the commercial standard Lipofectamine 2000, as well as many other lead compounds previously described for siRNA delivery.

In embodiments, gene delivery is achieved by formulation of the mixed amphipathic oligomer with an mRNA cargo in the presence of third components selected to tune stability and size of the resulting complex, increase cellular uptake, tune rate of mRNA release from the complex, and enhance expression of the cargo mRNA. Tertiary components include but are not limited to coordinating metal such as $Zn^{+2}$, $Mg^{+2}$, $Ca^{+2}$, etc; dynamic non-covalent cross linkers such as carbohydrates, counterions such as $Cl^-$, $AcO^-$, succinate, and citrate; and solubility modulators such as lipids and PEGs.

Applications of this technology may include: Clinical Applications: (1a) Nucleic acid transfection vectors: While utilizing DNA and RNA has been proposed to treat genetic disease for many years, the greatest obstacle to clinical use of gene therapy remains the effective delivery of the oligonucleotide cargos (1b) RNA Vaccination to prevent infectious diseases: mRNA-based vaccines display strong safety advantages over DNA vaccines, however they are clinically currently limited by mRNA delivery into cells. This application is currently being investigated clinically, but the most advanced technologies require removal of primary cells from patients for in vitro transfection with electroporation, followed by subsequent reintroduction of the transformed cells into the patient. This method can be significantly improved using our delivery technology to directly induce mRNA expression in vivo. (1c) Stem cell induction: pluripotency can be induced in undifferentiated stem cells by using our technology to induce the expression of 4 known transcription factors. The modular nature of the poly(carbonate-co-aminoester) delivery vehicles enables facile delivery of all four necessary mRNA transcripts simultaneously. (1) Basic research applications including, but not limited to: in vitro transfection of cultured cells, gene editing using CRISPR/Cas9, pathway validation using combination gene expression (mRNA translation) and gene knockdown (RNAi). Cancer immunotherapy, allergy tolerance, protein replacement therapy, gene editing, diagnostics, Advantages of the presently disclosed complexes, compositions and methods may include, for example:

(1) Higher mRNA transfection efficiency in vitro than commercially available transfection agents such as Lipofectamine 2000, even in difficult-to-transfect cell lines such as J774 macrophages, thereby improving efficacy while increasingly tolerability.
(2) Robust gene expression in vivo (BALB/c mice), demonstrating the clinical applicability of this technology, thereby avoiding toxicities of cationic carriers such as lipofectamine and providing a clinical alternative to ex-vivo methods of gene delivery and expression.
(3) Differential in vivo gene expression can be achieved using distinct routes of administration, with liver and spleen expression dominating upon intravenous injection, while local expression is sustained at the site of administration with an intramuscular (for example) delivery. Nasal delivery provides a route to mucosal membrane and/or lung uptake.
(4) Rapid degradation to known metabolites (bis-hydroxyethylglycine) which enables efficient gene expression
(5) Release of mRNA in a pH-dependent manner, such as with oligonucleotide-bearing particles displaying stability in low pH environments (such as the skin or intestinal tract), but degrading in higher pH environments.
(6) Materials are easily accessed through metal-free synthesis to make oligomers, polymers, or block/statistical copolymers or co-oligomers with targeted molecular weight and a high degree of control over dispersity.
(7) Materials are amenable to targeting through addition of targeting ligands such as folate or biotin to the surface of the formed particle or through attachment to monoclonal antibodies.
(8) The specific immolation mechanism of the cationic polyaminoester domain to an isolable neutral small molecule results in the formation of the biocompatible/biodegradable product, bis-N-hydroxyethyl-2,5-piperizinedione, a cyclic dimer of hydroxyethylglycine.

Features of the complexes, compositions and methods include the following. In embodiments, the poly(carbonate-co-aminoester)s poly(aminoester)s and the cationic materials derived thereof that can exhibit at least one of the following properties and functions:

(1) A specific, pH-responsive immolation mechanism of the cationic polyaminoesters that results in bio-compatible/biodegradable hydroxyethylglycine dimers; domain of these materials that leads to the release of the oligonucleotide cargo is unique even among other responsive biomaterials in that it occurs via an unanticipated intramolecular bond-forming event that results in irreversible neutralization of the cationic ammonium to rapidly trigger the release of the anionic cargo.

(2) An isolable product of intramolecular degradation, such as bis-N-hydroxyethyl-2,5-pipericla-7-inedione, which further degrades to hydroxyethyl glycine.

(3) Providing a temporal window of activity, such that the anionic cargo is electrostatically packaged into particles for delivery, then rapidly released following cellular internalization.

(4) Enablement of copolymerization of multiple lactone monomers with control over macromolecular architecture. Functionalized monomers may be polymerized in block or statistical architectures, and this further allows the combination of multiple monomer types such as cyclic carbonates or phosphates.

(5) The use of these materials in vivo may occur without acute toxicity, even when administered locally or systemically, indicative of high tolerability at concentrations necessary for a therapeutic response.

(6) Use as gene delivery vehicles, poly(carbonate-co-aminoester)s enable the efficient delivery and release of oligonucleotides including messenger RNA. Amphipathic block co-oligomers of MTC-dodecyl carbonate and N-Boc morpholine-2-one monomers can be formulated with large anionic cargos such as mRNA, to form stable, sub-400 nm particles. These resulting particles may effectively be taken up by cells and release their mRNA cargo, resulting in robust gene expression. This concept has been demonstrated in vitro in multiple cell lines as well as in vivo in mouse studies. The efficacy of these materials has been shown to be due to the pH-responsive rearrangement of the cationic aminoester block to form the neutral small molecule bis-N-hydroxyethyl-2,5-piperidinedione bis-hydroxyethylglycine. While other cationic gene delivery vehicles have been previously reported, these oligo (carbonate-co-aminoester)s are unique and among the top performers, due to their unique ability to release the mRNA (or other oligonucleotide) cargo on a time scale appropriate for cellular uptake and their tolerability.

(7) The empirically determined optimal length for mRNA delivery teaches away from our prior art in that diblocks of average DP 12 for both MTC-dodecyl carbonate and N-Boc morpholine-2-one domains perform optimally. This length is much shorter than commercially available cationic polyamine vectors such as PEI; it is also longer than our previously discovered siRNA delivery vectors (Reference WO2013036532 A1 and PNAS 2012, 109 (33), 13171-13176).

In one aspect, provided herewith is a method of transfecting a nucleic acid into a cell (e.g., a lung cell). The method includes contacting a cell with a cell-penetrating complex described herein including embodiments thereof. In embodiments, the method causes gene-edition in the cell. In embodiments, the gene-edition can encompass genome-edition or genome editing which is a type of genetic engineering in which DNA is inserted, deleted or replaced in the genome of a living organism using an isolated or engineered nuclease system. In certain embodiments, the method disclosed herein can be used to deliver a genetic tool or system that can cause gene-edition in the transfected cells. Some non-limiting examples of a genetic tool or system for gene-edition include a CRISPR-Cas system and transposon system.

In one aspect, a nucleic acid (i.e. the cargo nucleic acid) transfected by the transfection method according to some embodiments can have one or more vectors having a first nucleotide sequence encoding a CRISPR-Cas system guide RNA that hybridizes with a target sequence in the genome of the cell and a second nucleotide sequence encoding a Cas9 protein. In certain embodiments, the first and second nucleotide sequence can be located on the same or different vectors.

In general, a system adopting CRISPR/Cas9 offers a high degree of fidelity and relatively simple construction for gene edition. The system can depend on two factors for its specificity: a target sequence and a protospacer adjacent motifs (PAM). The target sequence can be, e.g. 20 bases long as part of each CRISPR locus in a crRNA array. A crRNA array can have multiple unique target sequences. Cas9 proteins can select a correct location on the host's genome by utilizing the sequence to bind with base pairs on the host DNA. The PAM sequence on the host genome can be recognized by Cas9. Once the elements are assembled, e.g. into one or more plasmids and transfected into cells, the Cas9 protein with the help of the crRNA can find the correct sequence in the host cell's DNA and—depending on the Cas9 variant—creates a single or double strand break in the DNA. Properly spaced breaks in the host DNA can trigger homology directed repair. Providing a DNA repair template can allow for the insertion of a specific DNA sequence at an intended location within the genome. Once incorporated, the new sequence is now part of the cell's genetic material and can pass into its daughter cells. Many online tools are available in the art to aid in designing effective sgRNA sequences. According to some embodiments, the method and composition according to certain embodiments herewith can deliver or transfect a nucleotide sequence encoding CRISPR-Cas system guide RNA and a nucleotide sequence encoding a Cas9 protein to induce gene-edition in the transfected cells.

In some embodiments, a cargo nucleic acid transfected by the transfection method according to certain embodiments can have a CRISPR RNA (crRNA). In some embodiments, this crRNA can be in the same vector of the first nucleotide sequence encoding a CRISPR-Cas system guide RNA.

In some embodiments, a cargo nucleic acid transfected by the transfection method according to certain embodiments can have a transactivating RNA (tracrRNA). In some embodiments, this tracrRNA can be in the same vector of the second nucleotide sequence encoding a Cas9 protein.

In some embodiments, the Cas9 protein utilized in the transfection method according to some embodiments can be codon optimized for expression in the transfected cell.

In another aspect, a nucleic acid (i.e. the cargo nucleic acid) transfected by the transfection method according to some embodiments can have one or more vectors having a first nucleotide sequence encoding a transposase and a second nucleotide sequence having a nucleic acid sequence of a gene of interest flanked by a transposase recognition site. In some embodiments, the first and second nucleotide sequences can be located on the same or different vectors.

A transposable element (or transposon) generally refers to a DNA sequence that can change its position within a genome, sometimes creating or reversing mutations and altering the cell's genetic composition and genome size.

Transposase generally refers to an enzyme that can bind to a transposon and catalyze the movement of the transposon to another part of the genome by, e.g. a cut and paste mechanism or a replicative transposition mechanism. Introduction of transposase and a gene of interest flanked by a transposase recognition site in cells can induce insertion of the gene of interest into a cellular genome. According to some embodiments, the method and composition according to certain embodiments herewith can deliver or transfect a nucleic acid encoding a transposase and a gene of interest to induce gene-edition in the transfected cells.

In embodiments, the transposase used in the transfection method according to some embodiments can recognize and excise a genomic sequence. In some other embodiments, the nucleic acid sequence of the gene of interest that is transfected via the transfection method can be integrated into a genome of the transfected cell.

In embodiments, the gene-editing done via the transfection method according to some embodiments can cause one or more of the following: a DNA deletion, a gene disruption, a DNA insertion, a DNA inversion, a point mutation, a DNA replacement, a knock-in, and a knock-down.

In one aspect a method of transfecting a nucleic acid into a cell is provided. The method includes contacting a cell with a cell-penetrating complex as provided herein, including embodiments thereof. In embodiments, the cell is a lung cell.

Methods and Compositions for Lung Delivery

In another aspect, provided herein are methods of delivering a nucleic acid to a lung cell (e.g, in vitro or in vivo in a subject in need thereof). In embodiments, the methods can treat and/or prevent a disease or condition using the cell-penetrating complex provided herein including embodiments thereof. The methods generally involve administering to a subject in need thereof a therapeutically effective amount of the cell-penetrating complex provided herein including embodiments thereof or a pharmaceutical composition including the cell-penetrating complex described herein, alone (e.g., in monotherapy) or in combination (e.g., in combination therapy) with one or more additional ingredients, e.g., a pharmaceutically acceptable excipient and/or additional therapeutic agent.

Thus, in one aspect is provided a method of delivering a nucleic acid to the lung of a subject in need thereof, the method including administering to said subject a cell-penetrating complex as provided herein, including embodiments thereof.

In embodiments, the cell-penetrating complex is not directly administered to the lung.

In embodiments, the cell-penetrating complex is administered intravenously. In embodiments, the cell-penetrating complex is administered intramuscularly, intraperitoneally, intranasally, topically, per gavage, or ocularly.

In one aspect a method of treating a lung disease in a subject in need thereof is provided. The method includes administering a therapeutically effective amount of a cell-penetrating complex as provided herein, including embodiments thereof. The terms "lung disease," "pulmonary disease," "pulmonary disorder," etc. are used interchangeably herein. The term is used to broadly refer to lung disorders characterized by difficulty breathing, coughing, airway discomfort and inflammation, increased mucus, and/or pulmonary fibrosis. Non-limiting examples of lung diseases include lung cancer, cystic fibrosis, asthma, Chronic Obstructive Pulmonary Disease (COPD), bronchitis, emphysema, bronchiectasis, pulmonary edema, pulmonary fibrosis, sarcoidosis, pulmonary hypertension, pneumonia, tuberculosis, Interstitial Pulmonary Fibrosis (IPF), Interstitial Lung Disease (ILD), Acute Interstitial Pneumonia (AIP), Respiratory Bronchiolitis-associated Interstitial Lung Disease (RBILD), Desquamative Interstitial Pneumonia (DIP), Non-Specific Interstitial Pneumonia (NSIP), Idiopathic Interstitial Pneumonia (IIP), Bronchiolitis obliterans, with Organizing Pneumonia (BOOP), restrictive lung disease, or pleurisy.

In one aspect a method of delivering a nucleic acid to a plurality of tissues in a subject in need thereof is provided. The method includes administering a first cell-penetrating complex and a second cell-penetrating complex to the subject, wherein the first cell-penetrating complex is the cell-penetrating complex as provided herein, including embodiments thereof, and wherein the first cell-penetrating complex and the second cell-penetrating complex are chemically different. Where the first cell-penetrating complex and the second cell-penetrating complex are chemically different the first cell-penetrating complex does not fall within the genus of the second cell-penetrating complex. In embodiments, the second cell-penetrating complex is any cell penetrating complex described in published PCT application WO 2018/022930, which is hereby incorporated by reference in its entirety and for all purposes.

In embodiments, the plurality of tissues includes at least two of spleen, liver, lung, kidney, heart, thymus, muscle, brain, ovaries, gut associated lymphoid tissue (GALT), pancrease, bone marrow, lymphnodes, circulating cells of hematopoietic origin and adrenal glands.

In one aspect is provided a method of transfecting a nucleic acid into a cell, the method including contacting a cell with a cell-penetrating complex as described herein, including embodiments. In embodiments, the cell is a lung cell. In embodiments, the cell is a reticulocyte. In embodiments, the cell is a hematopoietic stem cell.

In one aspect is provided a method of transfecting a nucleic acid into a reticulocyte, the method including contacting a cell with a cell-penetrating complex as described herein, including embodiments.

In one aspect is provided a method of transfecting a nucleic acid into a hematopoietic stem cell, the method including contacting a cell with a cell-penetrating complex as described herein, including embodiments.

In one aspect is provided a method of delivering a nucleic acid to the lung of a subject in need thereof, the method including administering to the subject a cell-penetrating complex as described herein, including embodiments. In embodiments, the cell-penetrating complex is not directly administered to the lung. In embodiments, the cell-penetrating complex is administered intravenously.

In one aspect is provided a method of delivering a nucleic acid to a plurality of tissues in a subject in need thereof, the method including administering a cell-penetrating complex as described herein, including embodiments.

In embodiments, the plurality of tissues include at least one of spleen, liver, lungs, kidney, heart, thymus, muscle, brain, ovaries, gut associated lymphoid tissue (GALT), pancreas, bone marrow, lymph nodes, circulating cells of hematopoietic origin or adrenal glands.

The cell-penetrating complex provided herein including embodiments thereof or a pharmaceutical composition including the cell-penetrating complex provided herein may be used as a vaccine that can induce an immune response in a subject who was administered with the cell-penetrating complex or a pharmaceutical composition thereof.

In some embodiments, the vaccine can have a prophylactic activity such that the vaccine can prevent or reduce a likelihood of the occurrence of a disease or condition in a subject. In some examples where the vaccine is used for a prophylactic purpose, a subject can be an animal who does not have the disease or condition, e.g. a human who was not diagnosed with the disease or condition or who does not have a noticeable symptom associated with the disease or condition. In some other embodiments, the vaccine has a therapeutic effect such that the vaccine can be used to treat a disease or condition. Some examples of therapeutic vaccines can include, but are not limited to, cancer vaccines that can be administered to a patient who already suffers from cancer. The cancer vaccines can exhibit one or more anticancer activity, e.g. reduction of cancer cell number, reduction of cancer size, killing of cancer cells, reductions and/or inhibition of metastasis and reduction of cancer cell growth and/or proliferation. In some other embodiments, cancer vaccines can also be used for a prophylactic purpose, especially in a subject who is considered predisposed of cancer but presently does not have the cancer. The prophylactic vaccine can be administered to the predisposed subject with a certain cancer and prevents or reduce a likelihood of the occurrence of the cancer in the subject.

In one aspect, the disclosures herewith provide a method of inducing an immune response against a disease in a subject in need thereof. The method can contain administering an effective amount of a cell-penetrating complex to a subject.

In some embodiments, a cell-penetrating complex can be used as a vaccine that can induce an immune response in a subject who is administrated with the complex. The complex can contain a nucleic acid non-covalently bound to a cationic amphipathic polymer and the cationic amphipathic polymer can have a pH-sensitive immolation domain.

In some embodiments, a disease or condition that is targeted by the vaccine or vaccine composition can include, but not limited to, an autoimmune, inflammatory, cancer, infectious, metabolic, developmental, cardiovascular, liver, intestinal, endocrine, neurological, or other disease.

In some embodiments, the nucleic acid that is contained in the vaccine or composition thereof can be a nucleic acid sequence encoding an antigenic or immunogenic epitope. For example, when an infectious disease is concerned, the nucleic acid contained in the vaccine can encode one or more peptides that are known to be expressed in the pathogen (e.g. pathogenic bacterium or virus) of the infectious disease and can induce an immune response when administered in a subject. In another example where the disease is a specific type of cancer, the nucleic acid administered to a subject using the vaccine composition can encode one or more peptides associated with the cancer, e.g. a peptide that is substantially exclusively expressed in the type of cancer or its expression level is notably higher in the cancer cells as compared to non-cancer cells. When the nucleic acid encoding antigenic or immunogenic peptide(s) is administered to a subject and delivered (i.e. transfected) into certain cells of the subject, the transfected nucleic acid can be eventually translated and expressed into the antigenic peptide(s). Since the expressed peptide(s) is antigenic or immunogenic, an immune response against the expressed peptide can be induced in the subject. The induced immune response can function to treat the target disease, e.g. by reducing the population of affected cells with specificity if the subject already suffers from the disease, exhibiting a therapeutic effect. Alternatively, the subject can have an acquired immune response via this vaccination in which adaptive immunity can elicit immunological memory after an initial response to the immunogenic peptides that is targeted by the immune response, and leads to an enhanced response to that target on subsequent encounters, exhibiting a prophylactic effect.

In some embodiments, vaccination can provide dual activities of therapeutic and prophylactic effects by delivering two separate types (or sequences) of nucleic acids in a single vaccine composition. The two separate nucleic acids can encode two different immunogenic peptides. Therefore, in some embodiments, the vaccine composition can transfect (1) a first nucleic acid encoding a first immunogenic peptide that can induce more immediate treatment effect to an existing disease or condition and (2) a second nucleic acid encoding a different, second immunogenic peptide that is aimed to induce adaptive immunity in the subject for future occurrence of a different disease or condition. In some embodiments, the vaccine can deliver two or more different nucleic acids to a subject and each nucleic acid independently exhibits a therapeutic or prophylactic effect, respectively.

In embodiments a vaccine composition can have two or more different types (or different formulas) of cationic amphipathic polymer. Alternatively, a vaccine composition can have only a single type (or single formula) of cationic amphipathic polymer. In some embodiments, a single type of cationic amphipathic polymer can be non-covalently bound to one type (sequence) of nucleic acid. Alternatively, a single type of cationic amphipathic polymer can be non-covalently bound to two or more types (sequences) of nucleic acid. Therefore in some examples, a mixture of different types of cationic amphipathic polymers, each of which is bound to a different sequence of nucleic acid, can be administered together to a subject in order to deliver two or more sequences (or types) of nucleic acids. Alternatively, a single type (or formula) of cationic amphipathic polymer that is bound to multiple types (or sequences) of nucleic acid can be administered to a subject in order to deliver two or more sequences (or types) of nucleic acid. Still alternatively, a single type (or formula) of cationic amphipathic polymer that is bound to a single sequence (or type) of nucleic acid can be administered to a subject.

In some embodiments, the nucleic acid that is contained the vaccine or composition thereof can be messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA). In alternative embodiments, the nucleic acid that is contained the vaccine or composition thereof can be mRNA. In some embodiments, nucleic acid is transfected into one or more cells in the subject via vaccination. In some embodiments, one or more than one nucleic acid sequences can be transfected via a vaccine composition. Therefore, in some embodiments, a vaccine composition contains two different nucleic acids, each of which encodes different antigenic peptides, respectively. Accordingly, when the vaccine is administered into a subject in need of the vaccination, two or more types of antigenic epitopes can be expressed and induce immune responses in the subject. In alternative embodiments, one type of nucleic acid can be transfected via vaccination such that one type of epitope can be expressed and induce an immune response in the subject.

In some embodiments, a method of inducing an immune response in a subject in need thereof can have administering one or more additional pharmaceutical composition in an effective amount to the subject, in addition to administering an effective amount of a cell-penetrating complex to the subject. In some embodiments, the additional pharmaceutical composition can contain an anti-cancer agent and optionally a pharmaceutically acceptable carrier. The additional anti-cancer agents can be, for example, antibodies, small molecules, and large molecules or combinations thereof. Examples of anti-cancer activity include, but are not limited to, reduction of cancer cell number, reduction of cancer size, killing of cancer cells, reductions and/or inhibition of metastasis and reduction of cancer cell growth and/or proliferation. In some examples, the administration of the cell-penetrating complex and additional pharmaceutical composition can exhibit a synergistic effect that is more than a sum of individual administration.

Pharmaceutical Compositions

In embodiments, the compositions provided herein are used for a therapeutic purpose. In some embodiments, a therapeutic purpose encompasses a prophylactic purpose (a purpose of preventing a disease or condition from occurring) and a treatment purpose (a purpose of treating an existing disease or condition). When the composition has a cationic amphipathic polymer but not a cargo nucleic acid, the cargo nucleic acid, which can exhibit a therapeutic effect, can be non-covalently bound to the cationic amphipathic polymer, before administration to a subject.

In some embodiments, a composition can be a vaccine or a composition thereof, i.e. a composition that contains the vaccine and optionally a pharmaceutically acceptable carrier. The vaccine or vaccine composition can be used to prevent and/or treat a disease or condition or a pathogen associated with the disease or condition. In some embodiments, the vaccine or vaccine composition contains a cell-penetrating complex which has a cationic amphipathic polymer and a cargo nucleic acid. In some embodiments, the cell-penetrating complex, when administered to a subject, can induce an immune response, i.e. immunogenic. This immunogenicity can be induced, at least in part, when one or more antigenic peptides encoded by the cargo nucleic acid are expressed in the transfected cells.

In one aspect, a cationic amphipathic polymer or a cell-penetrating complex disclosed herein can be formulated in a pharmaceutical composition. The cationic amphipathic polymer can have a pH-sensitive immolation domain. In one embodiment, the pharmaceutical composition can further contain a pharmaceutically acceptable excipient and/or a pharmaceutically acceptable carrier.

In some embodiments, pharmaceutical compositions can have a cell-penetrating complex, which has a nucleic acid non-covalently bound to a cationic amphipathic polymer, as an active ingredient and further contain pharmaceutically acceptable excipients or additives depending on the route of administration. Examples of such excipients or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used can be chosen from, but not limited to, the above or combinations thereof, as appropriate, depending on the dosage form of the present disclosure.

In some embodiments, the pharmaceutically acceptable carrier is an immunological adjuvant. In some examples, the immunological adjuvant can include, but is not limited to, agonists of Toll-like Receptors (TLRs), agonists of the STING pathway, agonistic antibodies against CD40, OX40, CTLA4, PD1, or PD1-L, Freund's adjuvant, bryostatins and ligands for CD40, OX40, CD137, PD1, CTLA4 and any combinations thereof. In some embodiments, the adjuvant can increase immunogenicity that is induced when a cell-penetrating complex by co-administered with the complex to a subject.

Formulation of the pharmaceutical compositions of the present disclosure can vary according to the route of administration selected (e.g., solution, emulsion). Routes of administration can be, for example, intramuscular, subcutaneous, intravenous, intralymphatic, subcutaneous, intramuscular, intraocular, topical skin, topical conjunctival, oral, intravesical (bladder), intraanal and intravaginal.

In some embodiments, the composition can include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In some embodiments, the formulation is a controlled release formulation. The term "controlled release formulation" includes sustained release and time-release formulations. Controlled release formulations are well-known in the art. These include excipients that allow for sustained, periodic, pulse, or delayed release of the composition. Controlled release formulations include, without limitation, embedding of the composition into a matrix; enteric coatings; micro-encapsulation; gels and hydrogels; implants; and any other formulation that allows for controlled release of a composition.

In one aspect is provided a kit of parts having a cell-penetrating complex or composition thereof. In another aspect is provided a kit of parts having a cationic amphipathic polymer that is not bound to a nucleic acid or composition thereof. The kit can further contain a document or an instruction that describes a protocol for making a cell-penetrating complex using a cationic amphipathic polymer and a cargo nucleic acid. The document or instruction of the kit can also describe a protocol for administering the composition to a subject in need thereof.

Therapeutic formulations described herein can be prepared for storage by mixing the active ingredients, i.e., immunogenic agent(s) having the desired degree of purity with optional physiologically acceptable carriers, excipients or stabilizers. Acceptable carriers, excipients, or stabilizers can be nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound (e.g., a second active agent in addition to the immunogenic agent(s) that has a cell-penetrating complex), which may be selected for complementary activities that do not adversely affect each other. Such molecules can be suitably present in combination in amounts that can be effective for the purpose intended.

Administration

In aspects provided are methods for delivering the compositions provided herein including embodiments thereof to cells or a subject so as to provide a desired activity into the cells or subject. In some embodiments, the composition contains a cell-penetrating complex having a cargo nucleic acid that is non-covalently bound to a cationic amphipathic polymer. The cargo nucleic acid, when transfected into the cells or administered to the subject, can provide a variety of intended effects, depending on the nature of the nucleic acid sequence. Some non-limiting examples of intended effects include modulation on gene expression, modulation of cellular pathways, genome-edition and induction of an immune response. In some embodiments, the composition can be administered to a subject in an effective amount that is sufficient to achieve at least part of the intended effects in the subject.

"Administration," "administering" and the like, when used in connection with a composition refer both to direct administration, which may be administration to cells in vitro, administration to cells in vivo, administration to a subject by a medical professional or by self-administration by the subject and/or to indirect administration, which may be the act of prescribing a composition of the disclosure. When used herein in reference to a cell, refers to introducing a composition to the cell. Typically, an effective amount is administered, which amount can be determined by one of skill in the art. Any method of administration may be used. Compounds (e.g., drugs and antibodies) may be administered to the cells by, for example, addition of the compounds to the cell culture media or injection in vivo. Administration to a subject can be achieved by, for example, intravascular injection, direct intratumoral delivery, and the like.

Administering may mean oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the disclosure can be administered alone or can be co-administered to the patient. Co-administration is meant to include simultaneous or sequential administration of the compounds individually or in combination (more than one compound).

The dosage and frequency (single or multiple doses) administered to a subject can vary depending upon a variety of factors, for example, whether the subject suffers from another disease, its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In some embodiments, the subject is a mammal, for example a human, a non-human primate, a murine (i.e., mouse and rat), a canine, a feline, or an equine. In one embodiment, the subject is a human.

In some embodiments, a composition can be administered in a dose (or an amount) of about 1 ng/kg of subject body weight, about 10 ng/kg of subject body weight, about 50 ng/kg of subject body weight, about 100 ng/kg of subject body weight, about 500 ng/kg of subject body weight, about 1 ug/kg of subject body weight, about 10 μg/kg of subject body weight, about 50 ug/kg of subject body weight, about 100 μg/kg of subject body weight, about 150 μg/kg of subject body weight, about 200 μg/kg of subject body weight, about 250 μg/kg of subject body weight, about 300 μg/kg of subject body weight, about 350 μg/kg of subject body weight, about 375 μg/kg of subject body weight, about 400 μg/kg of subject body weight, about 450 g/kg of subject body weight, about 500 μg/kg of subject body weight, about 550 μg/kg of subject body weight, about 600 μg/kg of subject body weight, about 650 μg/kg of subject body weight, about 700 μg/kg of subject body weight, about 750 μg/kg of subject body weight, about 800 μg/kg of subject body weight, about 850 μg/kg of subject body weight, about 900 μg/kg of subject body weight, about 1 mg/kg of subject body weight, about 10 mg/kg of subject body weight, about 50 mg/kg of subject body weight, about 100 mg/kg of subject body weight, about 500 mg/kg of subject body weight, about 1 g/kg of subject body weight or more or any intervening ranges of the of the foregoing. In some embodiments, a composition can be administered in a dose (or an amount) of about 0.5 μg, about 1.0 μg, about 1.5 μg, about 2.0 μg, about 2.5 μg, about 3.0 μg, about 3.5 μg, about 4.0 μg, about 4.5 μg about 5.0 g, about 5.5 μg, about 6.0 μg, about 6.5 μg, about 7.0 μg, about 7.5 μg, about 8.0 μg, about 8.5 μg, about 9.0 μg, about 9.5 μg, about 1.0 mg, about 1.5 mg, about 2.0 mg, about 2.5 mg, about 3.0 mg, about 3.5 mg, about 4.0 mg, about 4.5 mg about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 1 g or more or any intervening ranges of the foregoing. In some embodiments, a composition can be administered in a dose (or an amount) of about 7.5 μg or about 0.375 mg/kg of subject body weight. Administration can be repeated over a desired period, e.g., repeated over a period of about 1 day to about 5 days or once every several days, for example, about five days, over about 1 month, about 2 months, etc. The weight herein can be a weight of a cell-penetrating complex or a weight of a composition or pharmaceutical formulation thereof. In some embodiments, In one embodiment, a composition can be administered systemically or locally (e.g. intratumoral injection, intravenous injection) at intervals of 6 hours, 12 hours, daily or every other day or on a weekly or monthly basis to elicit the desired benefit or otherwise provide a therapeutic effect.

In one embodiment, a response rate to a composition, in particular a cancer vaccine, can be reduced as compared to baseline reference or control reference. The term "response rate" is used herein in its customary sense to indicate the percentage of patients who respond with cancer recession following treatment. Response rates include, for example, partial or complete recession. A partial response includes an about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, or about 99% recession of cancer cells. In some embodiments, the control reference is obtained from a healthy subject, a cancer subject (e.g., the cancer subject being treated or another cancer subject), or any population thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

In embodiments, the cationic amphipathic polymer is allowed to degrade within the cell thereby forming a degradation product. In embodiments, the degradation product is a substituted or unsubstituted diketopiperazine.

In embodiments, the nucleic acid includes a CAR encoding messenger RNA (mRNA).

In embodiments, the methods further include allowing the mRNA to be expressed in the cell. In embodiments, the cell is an eukaryotic cell. In embodiments, the cell is a mammalian or human cell. In embodiments, the cell forms part of an organism. In embodiments, the organism is a human. In embodiments, the cell is a lymphoid cell or a myeloid cell. In embodiments, the cell is a T cell. In embodiments, the cell is a myeloid cell.

In an aspect is provided, a method of inducing an immune response in a subject in need thereof, the method including administering an effective amount of the complex as provided herein including embodiments thereof. In embodiments, the immune response is an anti-cancer immune response.

In an aspect, a method of treating cancer in a subject in need thereof is provided. The method includes administering an effective amount of the complex as provided herein including embodiments thereof. In embodiments, the administering includes intravenous injection or subcutaneous injection.

EMBODIMENTS

Embodiment P1. A cell-penetrating complex comprising a nucleic acid non-covalently bound to a cationic amphipathic polymer, said cationic amphipathic polymer comprising a pH-sensitive immolation domain and a lipophilic polymer domain, wherein said cationic amphipathic polymer has the formula:

(XII)

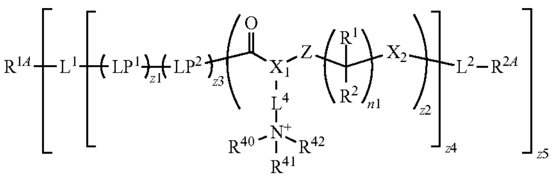

or (XIII)

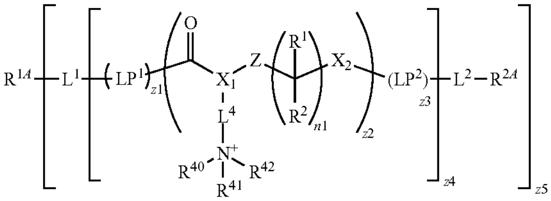

wherein $R^{1A}$ is hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —$S(O)_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, —$C(R^5)(R^6)$—, —$C(R^5)(R^6)$—$C(R^7)(R^8)$—, —O—$C(R^5)(R^6)$—, or —O—$C(R^5)(R^6)$—$C(R^7)(R^8)$—;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is a bond, —C(O)O—, —O—, —S—, —NH—, —C(O)NH—, —NHC(O)—, —$S(O)_2$—, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, —$S^+R^{13}$—, —$NR^{13}$—, or —$N^+(R^{13})(H)$—;

$R^{13}$ is hydrogen, —$CCl_3$, —$CBr_3$, —$CF_3$, —$CI_3$, —CN, —OH, =O, —$NH_2$, —COOH, —$CONH_2$, —SH, —$SO_3H$, $SO_2NH_2$, —$OCCl_3$, —$OCF_3$, —$OCBr_3$, —$OCI_3$, —$OCHCl_2$, —$OCHBr_2$, —$OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1, z3 and z4 are independently integers from 0 to 100, wherein at least one of z1 or z3 is not 0;

z2 is an integer from 2 to 100; and z5 is an integer from 1 to 10.

Embodiment P2. The cell-penetrating complex of embodiment P1, wherein $X_1$ is $CH_2$.

Embodiment P3. The cell-penetrating complex of embodiment P1 or P2, wherein $L^4$ is substituted or unsubstituted $C_2$-$C_8$ alkylene.

Embodiment P4. The cell-penetrating complex of any one of embodiments P1-P3, wherein $L^4$ is unsubstituted $C_2$-$C_8$ alkylene.

Embodiment P5. The cell-penetrating complex of any one of embodiments P1-P4, wherein $L^4$ is unsubstituted $C_2$ alkylene, unsubstituted $C_3$ alkylene or unsubstituted $C_4$ alkylene.

Embodiment P6. The cell-penetrating complex of any one of embodiments P1-P5, wherein $R^{40}$, $R^{41}$, and $R^{42}$ are independently hydrogen or substituted heteroalkyl.

Embodiment P7. The cell-penetrating complex of any one of embodiments P1-P6, wherein $R^{40}$, $R^{41}$, and $R^{42}$ are independently hydrogen or —$C(NH)NH_2$.

Embodiment P8. The cell-penetrating complex of any one of embodiments P1-P7, wherein at least two of $R^{40}$, $R^{41}$, and $R^{42}$ are hydrogen and one is —$C(NH)NH_2$.

Embodiment P9. The cell-penetrating complex of any one of embodiments P1-P8, wherein $LP^1$ has the formula:

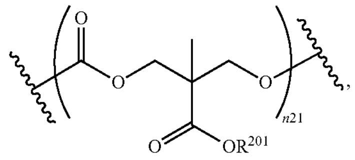

wherein n21 is an integer from 1 to 100;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment P10. The cell-penetrating complex of embodiment P9, wherein n21 is 5 and $R^{201}$ is unsubstituted $C_{18}$ alkenyl.

Embodiment P11. The cell-penetrating complex of embodiment P10, wherein said unsubstituted $C_{18}$ alkenyl is oleyl.

Embodiment P12. The cell-penetrating complex of any one of embodiments P1-P11, wherein $LP^2$ has the formula:

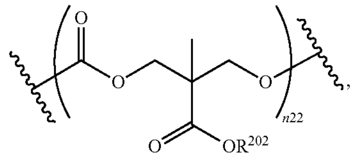

wherein n22 is an integer from 1 to 100;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment P13. The cell-penetrating complex of embodiment P12, wherein n22 is 5 and $R^{202}$ is unsubstituted $C_9$ alkenyl.

Embodiment P14. The cell-penetrating complex of embodiment P13, wherein said unsubstituted $C_9$ alkenyl is nonenyl.

Embodiment P15. The cell-penetrating complex of embodiment P1, wherein said cationic amphipathic polymer has the formula:

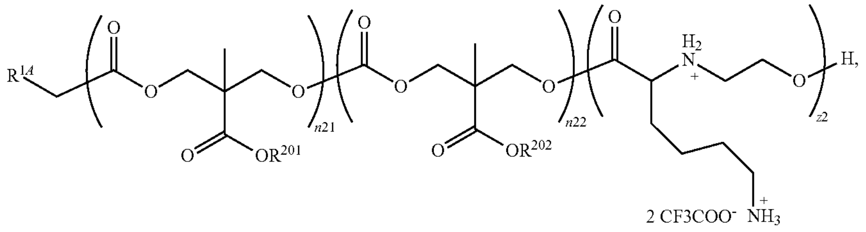

wherein n21 is 5, $R^{201}$ is oleyl, n22 is 5, $R^{202}$ is nonenyl and z2 is 7.

Embodiment P16. The cell-penetrating complex of embodiment P6, wherein said cationic amphipathic polymer has the formula:

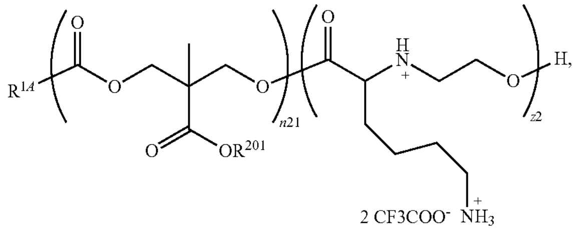

wherein n21 is 14, $R^{201}$ is dodecyl and z2 is 8.

Embodiment P17. The cell-penetrating complex of any one of embodiments P1-P16, wherein said nucleic acid is a messenger RNA (mRNA), a small interference RNA (siRNA), a short hairpin RNA (shRNA), a micro RNA (miRNA), a guide RNA (gRNA), a CRISPR RNA (crRNA), a transactivating RNA (tracrRNA), a plasmid DNA (pDNA), a minicircle DNA, or a genomic DNA (gNDA).

Embodiment P18. A nanoparticle composition comprising a plurality of cell-penetrating complexes according to any one of embodiments P1-P17.

Embodiment P19. A pharmaceutical composition comprising a cell-penetrating complex of any one of embodiments P1-P17.

Embodiment P25. A method of treating a lung disease in a subject in need thereof, the method comprising administering a therapeutically effective amount of a cell-penetrating complex of any one of embodiments P1-P17.

Embodiment P26. A method of delivering a nucleic acid to a plurality of tissues in a subject in need thereof, said method comprising administering a first cell-penetrating complex and a second cell-penetrating complex to said subject, wherein said first cell-penetrating complex is the cell-penetrating complex of any one of embodiments P1-P17 and wherein said first cell-penetrating complex and said second cell-penetrating complex are chemically different.

Embodiment P27. The method of embodiment P26, wherein said plurality of tissues include at least one of spleen, liver, lungs, kidney, heart, thymus, muscle, brain, ovaries, gut associated lymphoid tissue (GALT), pancreas, bone marrow, lymph nodes, circulating cells of hematopoietic origin or adrenal glands.

Additional Embodiments

Embodiment 1. A cell-penetrating complex comprising a nucleic acid non-covalently bound to a cationic amphipathic polymer, said cationic amphipathic polymer comprising a pH-sensitive immolation domain and a lipophilic polymer domain, wherein said cationic amphipathic polymer has the formula:

(XII)

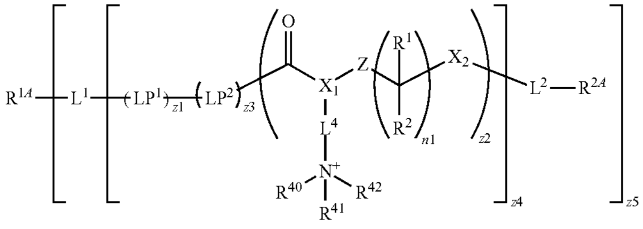

or (XIII)

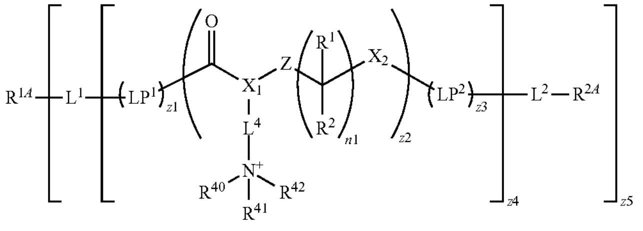

Embodiment P20. A method of transfecting a nucleic acid into a cell, the method comprising contacting a cell with a cell-penetrating complex of any one of embodiments P1-P17.

Embodiment P21. The method of embodiment P20, wherein said cell is a lung cell.

Embodiment P22. A method of delivering a nucleic acid to the lung of a subject in need thereof, said method comprising administering to said subject a cell-penetrating complex of any one of embodiments P1-P17.

Embodiment P23. The method of embodiment P22, wherein said cell-penetrating complex is not directly administered to the lung.

Embodiment P24. The method of embodiment P22 or P23, wherein said cell-penetrating complex is administered intravenously.

wherein $R^{1A}$ is hydrogen, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —$S(O)_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, —$C(R^5)(R^6)$—, —$C(R^5)(R^6)$—$C(R^7)(R^8)$—, —O—$C(R^5)(R^6)$—, or —O—$C(R^5)(R^6)$—$C(R^7)(R^8)$—;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is a bond, —C(O)O—, —O—, —S—, —NH—, —C(O)NH—, —NHC(O)—, —$S(O)_2$—, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, —$S^+R^{13}$—, —$NR^{13}$—, or —$N^+(R^{13})(H)$—;

$R^{13}$ is hydrogen, —$CCl_3$, —$CBr_3$, —$CF_3$, —$CI_3$, —CN, —OH, =O, —$NH_2$, —COOH, —$CONH_2$, —SH, —$SO_3H$, $SO_2NH_2$, —$OCCl_3$, —$OCF_3$, —$OCBr_3$, —$OCI_3$, —$OCHCl_2$, —$OCHBr_2$, —$OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; n1 is an integer from 0 to 50;

z1, z3 and z4 are independently integers from 0 to 100, wherein at least one of z1 or z3 is not 0;

z2 is an integer from 2 to 100; and z5 is an integer from 1 to 10.

Embodiment 2. The cell-penetrating complex of embodiment 1, wherein $X_1$ is $CH_2$.

Embodiment 3. The cell-penetrating complex of embodiment 1 or 2, wherein $L^4$ is substituted or unsubstituted $C_2$-$C_8$ alkylene.

Embodiment 4. The cell-penetrating complex of any one of embodiments 1-3, wherein $L^4$ is unsubstituted $C_2$-$C_8$ alkylene.

Embodiment 5. The cell-penetrating complex of any one of embodiments 1-4, wherein $L^4$ is unsubstituted $C_2$ alkylene, unsubstituted $C_3$ alkylene or unsubstituted $C_4$ alkylene.

Embodiment 6. The cell-penetrating complex of any one of embodiments 1-5, wherein $R^{40}$, $R^{41}$, and $R^{42}$ are independently hydrogen or substituted heteroalkyl.

Embodiment 7. The cell-penetrating complex of any one of embodiments 1-6, wherein $R^{40}$, $R^{41}$, and $R^{42}$ are independently hydrogen or —$C(NH)NH_2$.

Embodiment 8. The cell-penetrating complex of any one of embodiments 1-7, wherein at least two of $R^{40}$, $R^{41}$, and $R^{42}$ are hydrogen and one is —$C(NH)NH_2$.

Embodiment 9. The cell-penetrating complex of any one of embodiments 1-8, wherein $LP^1$ has the formula:

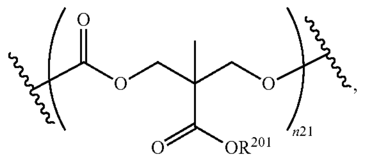

wherein n21 is an integer from 1 to 100;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 10. The cell-penetrating complex of embodiment 9, wherein n21 is 5 and $R^{201}$ is unsubstituted $C_{18}$ alkenyl.

Embodiment 11. The cell-penetrating complex of embodiment 10, wherein said unsubstituted $C_{18}$ alkenyl is oleyl.

Embodiment 12. The cell-penetrating complex of any one of embodiments 1-11, wherein $LP^2$ has the formula:

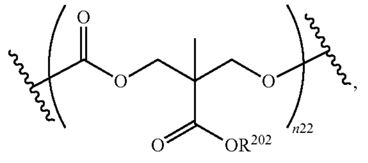

wherein n22 is an integer from 1 to 100;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 13. The cell-penetrating complex of embodiment 12, wherein n22 is 5 and $R^{202}$ is unsubstituted $C_9$ alkenyl.

Embodiment 14. The cell-penetrating complex of embodiment 13, wherein said unsubstituted $C_9$ alkenyl is nonenyl.

Embodiment 15. The cell-penetrating complex of embodiment 1, wherein said cationic amphipathic polymer has the formula:

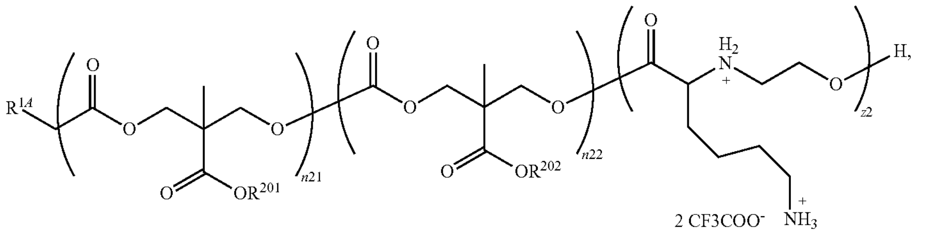

wherein n21 is 5, $R^{201}$ is oleyl, n22 is 5, $R^{202}$ is nonenyl and z2 is 7.

Embodiment P16. The cell-penetrating complex of embodiment 1, wherein said cationic amphipathic polymer has the formula:

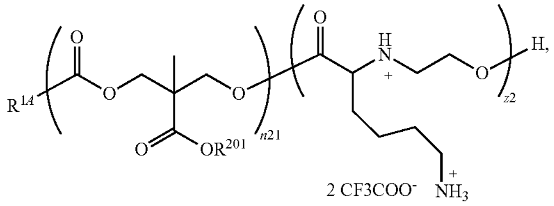

wherein n21 is 14, $R^{201}$ is dodecyl and z2 is 8.

Embodiment 17. The cell-penetrating complex of any one of embodiments 1-16, wherein said nucleic acid is a messenger RNA (mRNA), a small interference RNA (siRNA), a short hairpin RNA (shRNA), a micro RNA (miRNA), a guide RNA (gRNA), a CRISPR RNA (crRNA), a transactivating RNA (tracrRNA), a plasmid DNA (pDNA), a minicircle DNA, or a genomic DNA (gNDA).

Embodiment 18. A nanoparticle composition comprising a plurality of cell-penetrating complexes according to any one of embodiments 1-17.

Embodiment 19. A pharmaceutical composition comprising a cell-penetrating complex of any one of embodiments 1-17.

Embodiment 20. A method of transfecting a nucleic acid into a cell, the method comprising contacting a cell with a cell-penetrating complex of any one of embodiments 1-17.

Embodiment 21. The method of embodiment 20, wherein said cell is a lung cell.

Embodiment 22. A method of delivering a nucleic acid to the lung of a subject in need thereof, said method comprising administering to said subject a cell-penetrating complex of any one of embodiments 1-17.

Embodiment 23. The method of embodiment 22, wherein said cell-penetrating complex is not directly administered to the lung.

Embodiment 24. The method of embodiment 22 or 23, wherein said cell-penetrating complex is administered intravenously.

Embodiment 25. A method of treating a lung disease in a subject in need thereof, the method comprising administering a therapeutically effective amount of a cell-penetrating complex of any one of embodiments 1-17.

Embodiment 26. A method of delivering a nucleic acid to a plurality of tissues in a subject in need thereof, said method comprising administering a first cell-penetrating complex and a second cell-penetrating complex to said subject, wherein said first cell-penetrating complex is the cell-penetrating complex of any one of embodiments 1-17 and wherein said first cell-penetrating complex and said second cell-penetrating complex are chemically different.

Embodiment 27. The method of embodiment 26, wherein said plurality of tissues include at least one of spleen, liver, lungs, kidney, heart, thymus, muscle, brain, ovaries, gut associated lymphoid tissue (GALT), pancreas, bone marrow, lymph nodes, circulating cells of hematopoietic origin or adrenal glands.

Embodiment 28. A cell penetrating complex comprising a nucleic acid non-covalently bound to a cationic amphipathic polymer, wherein said cationic amphipathic polymer has the formula:

(XII)

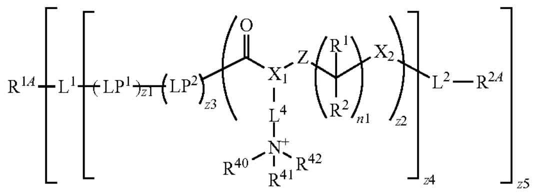

or (XIII)

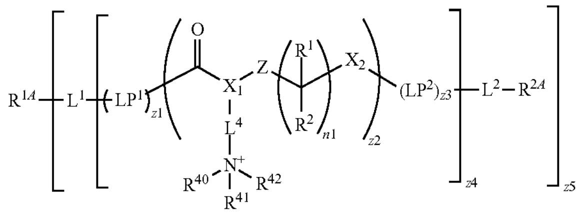

wherein $R^{1A}$ is independently hydrogen, halogen, $-CCl_3$, $-CBr_3$, $-CF_3$, $-CI_3$, $CHCl_2$, $-CHBr_2$, $-CHF_2$, $-CH_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, independently $-COOH$, $-CONH_2$, $-NO_2$, $-SH$, $-SO_3H$, $-SO_4H$, $-SO_2NH_2$, $-NHNH_2$, $-ONH_2$, independently $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, $-C(O)O-$, $-O-$, $-S-$, $-NH-$, $-C(O)NH-$, $-NHC(O)-$, $-S(O)_2-$, $-S(O)NH-$, $-NHC(O)NH-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain; $X^1$ is a bond, $-C(R^5)(R^6)-$, $-C(R^5)(R^6)-C(R^7)(R^8)-$, $-O-C(R^5)(R^6)-$, or $-O-C(R^5)(R^6)-C(R^7)(R^8)-$;

$X^2$ is $-O-$ or $-S-$;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, $-C(O)O-$, $-O-$, $-S-$, $-NH-$, $-C(O)NH-$, $-NHC(O)-$, $-S(O)_2-$, $-S(O)NH-$, $-NHC(O)NH-$, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is $-S-$, $-S^+R^{13}-$, $-NR^{13}-$, or $-N^+(R^{13})(H)-$;

$R^{13}$ is hydrogen, $-CCl_3$, $-CBr_3$, $-CF_3$, $-CI_3$, $-CN$, $-OH$, $=O$, $-NH_2$, $-COOH$, $-CONH_2$, $-SH$, $-SO_3H$, $SO_2NH_2$, $-OCCl_3$, $-OCF_3$, $-OCBr_3$, $-OCI_3$, $-OCHCl_2$, $-OCHBr_2$, $-OCHI_2$, $-OCHF$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z1 or z3 is not 0;

z2 is an integer from 2 to 100;

z4 is an integer from 1 to 100;

and z5 is an integer from 1 to 10.

Embodiment 29. The cell penetrating complex of embodiment 28, wherein $X_1$ is $CH_2$.

Embodiment 30. The cell penetrating complex of embodiments 28 or 29, wherein $L^4$ is independently substituted or unsubstituted $C_2$-$C_8$ alkylene.

Embodiment 31. The cell penetrating complex of any one of embodiments 28-30, wherein $L^4$ is independently unsubstituted $C_2$-$C_8$ alkylene.

Embodiment 32. The cell penetrating complex of any one of embodiments 28-31, wherein $L^4$ is independently unsubstituted $C_2$ alkylene, unsubstituted $C_3$ alkylene or unsubstituted $C_4$ alkylene.

Embodiment 33. The cell penetrating complex of any one of embodiments 28-32, wherein $L^4$ is independently unsubstituted $C_3$ alkylene or unsubstituted $C_4$ alkylene.

Embodiment 34. The cell penetrating complex of any one of embodiments 28-34, wherein $R^{40}$, $R^{41}$, and $R^{42}$ are independently hydrogen or substituted heteroalkyl.

Embodiment 35. The cell penetrating complex of any one of embodiments 28-34, wherein $R^{40}$, $R^{41}$, and $R^{42}$ are independently hydrogen or $-C(NH)NH_2$.

Embodiment 36. The cell penetrating complex of any one of embodiments 28-35, wherein at least two of $R^{40}$, $R^{41}$, and $R^{42}$ are hydrogen and one is $-C(NH)NH_2$.

Embodiment 37. The cell penetrating complex of any one of embodiments 28-36, wherein Z is $-N^+(R^{13})(II)$- and $R^{13}$ is hydrogen.

Embodiment 38. The cell penetrating complex of any one of embodiments 28-37, wherein $R^1$ and $R^2$ are independently hydrogen or substituted or unsubstituted alkyl.

Embodiment 39. The cell penetrating complex of any one of embodiments 28-38, wherein n1 is 2.

Embodiment 40. The cell penetrating complex of any one of embodiments 28-39, wherein $X_2$ is $-O-$.

Embodiment 41. The cell penetrating complex of any one of embodiments 28-40, wherein z1 or z3 are independently integers from 10-40.

Embodiment 42. The cell penetrating complex of any one of embodiments 28-41, wherein z2 is independently an integer from 3-20.

Embodiment 43. The cell penetrating complex of any one of embodiments 28-42, wherein $LP^1$ has the formula:

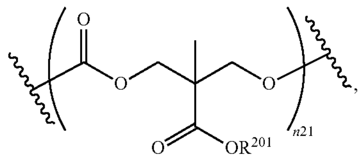

wherein n21 is an integer from 1 to 100;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 44. The cell penetrating complex of embodiment 43, wherein n21 is 10-40.

Embodiment 45. The cell penetrating complex of any one of embodiments 43-44, wherein $R^{201}$ is unsubstituted $C_{12}$ alkyl.

Embodiment 46. The cell penetrating complex of any one of embodiments 43-45, wherein $LP^2$ has the formula:

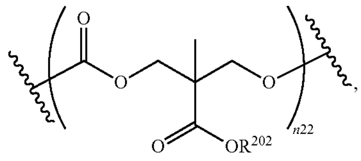

wherein n22 is an integer from 1 to 100;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 47. The cell penetrating complex of embodiment 46, wherein n22 is 10-35.

Embodiment 48. The cell penetrating complex of embodiments 46 or 47, wherein $R^{202}$ is unsubstituted $C_{12}$ alkenyl.

Embodiment 49. The cell penetrating complex of any one of embodiments 28-45, wherein said cationic amphipathic polymer has the formula:

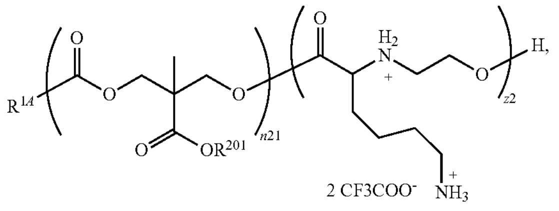

wherein n21 is an integer from 10 to 20;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 3-10.

Embodiment 50. The cell penetrating complex of embodiment 49, wherein n21 is 14, $R^{201}$ is dodecyl and z2 is 8.

Embodiment 51. The cell penetrating complex of any one of embodiments 28-45, wherein said cationic amphipathic polymer has the formula:

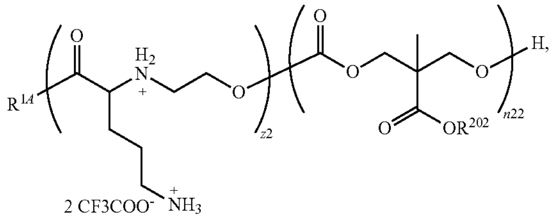

wherein n22 is an integer from 10 to 35;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 5-20.

Embodiment 52. The cell penetrating complex of embodiment 53, wherein n22 is 14, $R^{202}$ is dodecyl and z2 is 7.

Embodiment 53. The cell penetrating complex of any one of embodiments 1-52, further comprising a second cationic amphipathic polymer, wherein said second cationic amphipathic polymer is different from said cationic amphipathic polymer.

Embodiment 54. The cell penetrating complex of embodiment 53, wherein said second cationic amphipathic polymer has the formula:

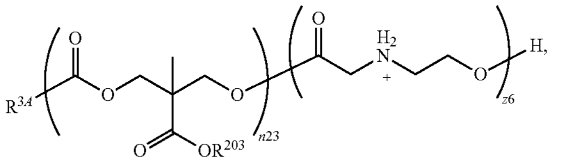

n23 is an integer from 1 to 100;

z6 is an integer from 5-15;

$R^{3A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{203}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 55. The cell penetrating complex of embodiment 54, wherein n23 is 13, z6 is 11 and $R^{203}$ is dodecyl.

Embodiment 56. A cell penetrating complex comprising a nucleic acid non-covalently bound to a first cationic amphipathic polymer and a second amphipathic polymer, wherein said first cationic amphipathic polymer has the formula:

(XII)

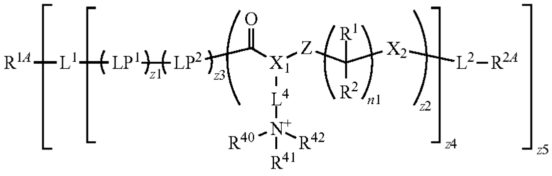

or (XIII)

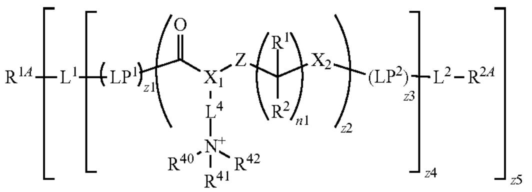

wherein $R^{1A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, independently —COOH, $—CONH_2$, $—NO_2$, —SH, $—SO_3H$, $—SO_4H$, $—SO_2NH_2$, $—NHNH_2$, $—ONH_2$, independently $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

$X^1$ is a bond, $—C(R^5)(R^6)—$, $—C(R^5)(R^6)—C(R^7)(R^8)—$, $—O—C(R^5)(R^6)—$, or $—O—C(R^5)(R^6)—C(R^7)(R^8)—$;

$X^2$ is —O— or —S—;

$R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$L^4$ is independently a bond, —C(O)O—, —O—, —S—, —NH—, —C(O)NH—, —NHC(O)—, $—S(O)_2—$, —S(O)NH—, —NHC(O)NH—, substituted or unsubstituted alkylene, or substituted or unsubstituted heteroalkylene;

$R^{40}$, $R^{41}$, and $R^{42}$ are independently hydrogen, substituted or unsubstituted alkyl or substituted or unsubstituted heteroalkyl;

Z is —S—, $—S^+R^{13}—$, $—NR^{13}—$, or $—N^+(R^{13})(H)—$;

$R^{13}$ is hydrogen, $—CCl_3$, $—CBr_3$, $—CF_3$, $—CI_3$, —CN, —OH, =O, $—NH_2$, —COOH, $—CONH_2$, —SH, $—SO_3H$, $SO_2NH_2$, $—OCCl_3$, $—OCF_3$, $—OCBr_3$, $—OCI_3$, $—OCHCl_2$, $—OCHBr_2$, $—OCHI_2$, —OCHF, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

n1 is an integer from 0 to 50;

z1 and z3 are independently integers from 0 to 100, wherein at least one of z1 or z3 is not 0;

z2 is an integer from 2 to 100;

z4 is an integer from 1 to 100;

z5 is an integer from 1 to 10; and wherein said first cationic amphipathic polymer and said second amphipathic polymer are different.

Embodiment 57. The cell penetrating complex of embodiment 56, wherein said first cationic amphipathic polymer has the formula:

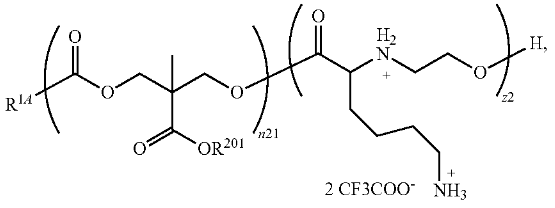

wherein n21 is an integer from 10 to 20;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 3-10.

Embodiment 58. The cell penetrating complex of embodiment 57, wherein n21 is 14, $R^{201}$ is dodecyl and z2 is 8.

Embodiment 59. The cell penetrating complex of embodiment 56, wherein said first cationic amphipathic polymer has the formula:

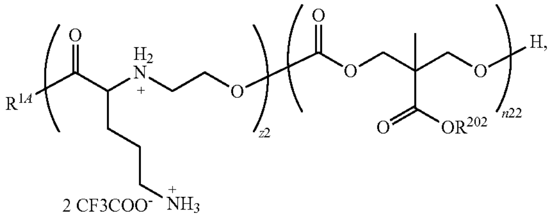

wherein n22 is an integer from 10 to 35;

$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and z2 is independently an integer from 5-20.

Embodiment 60. The cell penetrating complex of embodiment 59, wherein n22 is 14, $R^{202}$ is dodecyl and z2 is 7.

Embodiment 61. The cell penetrating complex of any one of embodiments 56-60, wherein said second cationic amphipathic polymer has the formula:

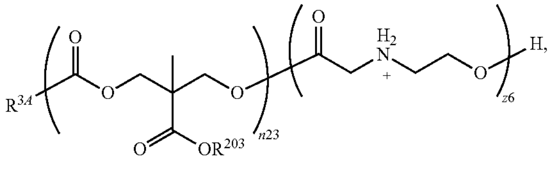

wherein n23 is an integer from 1 to 100;

z6 is an integer from 5-15; and $R^{3A}$ is independently hydrogen, halogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_{21}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $NHC(O)NH_2$, —$NHSO_2H$, —NHC(O)H, —NHC(O)OH, —NHOH, —$OCCl_3$, —$OCF_3$, —$OCBr_3$, —$OCI_3$—$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{203}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 62. The cell penetrating complex of embodiment 61, wherein n23 is 13, z6 is 11 and $R^{203}$ is dodecyl.

Embodiment 63. The cell penetrating complex of any one of embodiments 56-62, wherein said first cationic amphipathic polymer has the formula:

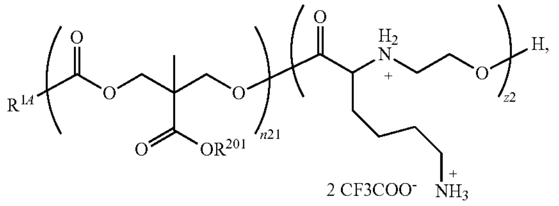

wherein n21 is 14, $R^{201}$ is dodecyl and z2 is 8; and wherein said second cationic amphipathic polymer has the formula:

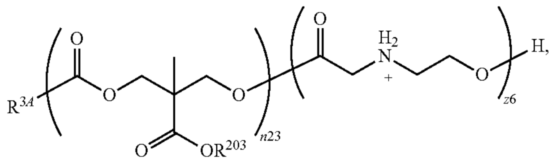

wherein n23 is 13, $R^{203}$ is dodecyl and z6 is 11.

Embodiment 64. The cell penetrating complex of any one of embodiments 56-62, wherein said first cationic amphipathic polymer has the formula:

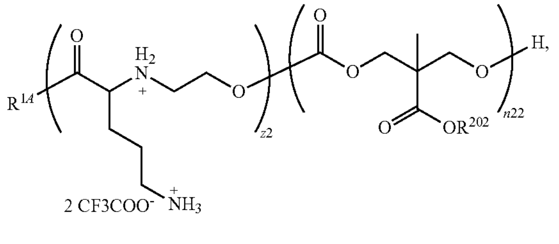

wherein n22 is an integer from 10-35, $R^{202}$ is dodecyl and z2 is 3-15; and wherein said second cationic amphipathic polymer has the formula:

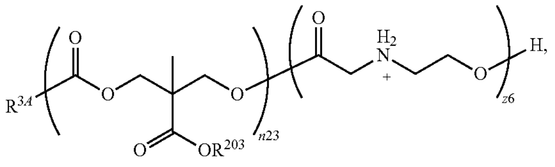

wherein n23 is 13, $R^{203}$ is dodecyl and z6 is 11.

Embodiment 65. A nanoparticle composition comprising a plurality of cell-penetrating complexes according to any one of embodiments 28-64.

Embodiment 66. A pharmaceutical composition comprising a cell-penetrating complex of any one of embodiments 28-64 and a pharmaceutical excipient.

Embodiment 67. A method of transfecting a nucleic acid into a cell, the method comprising contacting a cell with a cell-penetrating complex of any one of embodiments 28-64.

Embodiment 68. The method of embodiment 67, wherein said cell is a lung cell.

Embodiment 69. The method of embodiment 67, wherein said cell is a reticulocyte.

Embodiment 70. The method of embodiment 67, wherein said cell is a hematopoietic stem cell.

Embodiment 71. A method of transfecting a nucleic acid into a reticulocyte, the method comprising contacting a cell with a cell-penetrating complex of any one of embodiments 53-64.

Embodiment 72. A method of transfecting a nucleic acid into a hematopoietic stem cell, the method comprising contacting a cell with a cell-penetrating complex of any one of embodiments 53-64.

Embodiment 73. A method of delivering a nucleic acid to the lung of a subject in need thereof, said method comprising administering to said subject a cell-penetrating complex of any one of embodiments 28-64.

Embodiment 74. The method of embodiment 73, wherein said cell-penetrating complex is not directly administered to the lung.

Embodiment 75. The method of embodiments 73 or 74, wherein said cell-penetrating complex is administered intravenously.

Embodiment 76. A method of delivering a nucleic acid to a plurality of tissues in a subject in need thereof, said method comprising administering a cell-penetrating complex of any one of embodiments 53-64.

Embodiment 77. The method of embodiment 76, wherein said plurality of tissues include at least one of spleen, liver, lungs, kidney, heart, thymus, muscle, brain, ovaries, gut associated lymphoid tissue (GALT), pancreas, bone marrow, lymph nodes, circulating cells of hematopoietic origin or adrenal glands.

EXAMPLES

Example 1: Amino Acid Derived CARTs Potential Targets and Synthetic Methods

Amino acids provide an expansive chemical space for synthesizing a novel, diverse and demonstrably useful class of cyclic lactone monomers. We have developed a strategy for generating monomers of this type and shown that they offer remarkable biological activity when incorporated into CART mRNA delivery vehicles.

General strategy: The starting amino acid derivative in our current procedure are amino acid methyl ester HCl salts. This can be done with BOTH D and L enantiomers, which would allow us to generate chiral CARTs. In our current amino acid-based synthesis we perform an alkylation of amino acid methyl ester HCl salt followed by an N-Boc protection. This product is purified followed by acid catalyzed cyclization to generate the lactone monomer (Scheme 1).

Scheme 1. Amino acid derived monomer synthesis

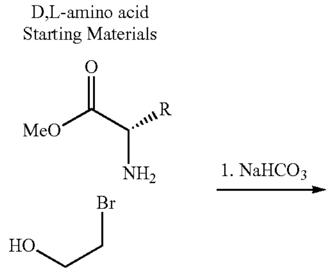

-continued

Method 1

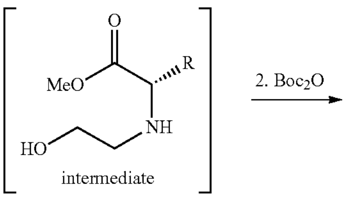

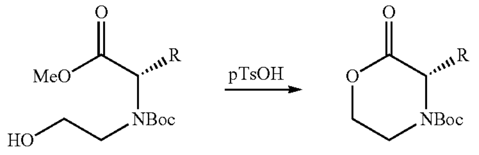

Example 2: Substrate Scope and Methodology of Amino Acid Derived CARTs

The amino acid derived monomers have relatively low reactivity but can be polymerized to moderate conversion by running the polymerization at low temperature using an ring-opening polymerization organocatalysts (Urea anion catalyst shown in Scheme 2).

Scheme 2. Synthetic procedure to generate amino acid functionalized CARTs.

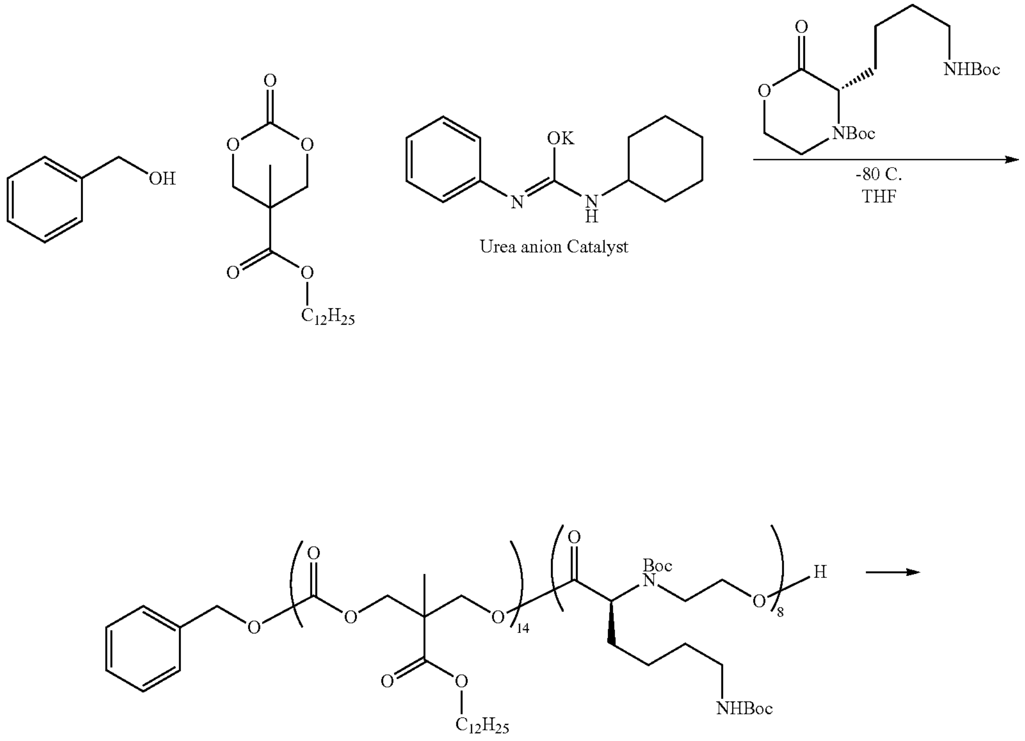

-continued

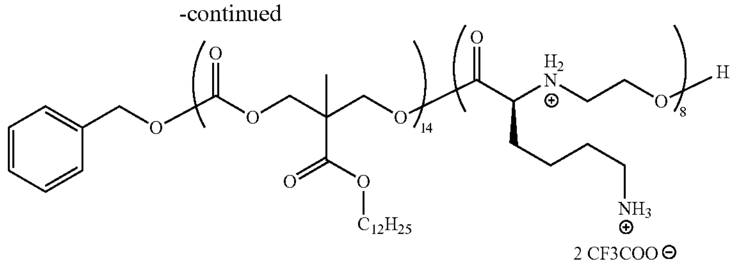

D:Lys 14:8

General Methods and Experimental

Materials

Reagents were purchased from Sigma-Aldrich and used as received unless otherwise indicated. 1-(3,5-Bis-trifluoromethyl-phenyl)-3-cyclohexyl-thiourea (*Macromolecules* 39(23):7863-7871), MTC-guanidine monomer (*J Am Chem Soc* 131(45):16401-16403), MTC-dodecyl monomer (*Proc Natl Acad Sci* 109(33):13171-13176), MTC-piperidine monomer (*Chem Commun* (1):114-116), N-Boc morpholinone monomer (*J Am Chem Soc* 136(26):9252-9255), and dansyl alcohol (*J Am Chem Soc* 131(45):16401-16403) were all prepared according to literature procedures. Unless otherwise noted, all commercial solvents and reagents were used without further purification. Methylene chloride ($CH_2Cl_2$) and tetrahydrofuran (THF) were passed through an alumina drying column (Solv-tek Inc.) using nitrogen pressure. Petroleum ether, pentane, hexane, ethyl acetate (EtOAc), and methanol (MeOH) were obtained from Fisher Scientific. Deuterated solvents were purchased from Cambridge Isotope Laboratories. Regenerated cellulose dialysis membranes (Spectra/Por® 6 Standard RC; MWCO 1000) were purchased from Spectrum Laboratories, Inc.

mRNAs

In all following examples, eGFP mRNA (5meC, Ψ, L-6101), Fluc mRNA (5meC, Ψ, L-6107), OVA mRNA (5meC, Ψ, L-7210) and Cy5-eGFP mRNA (5meC, Ψ, L-6402) were purchased from TriLink BioTechnologies Inc.

Instrumentation

Particle size was measured by dynamic light scattering on a Malvern Zetasizer Nano ZS90. Flow cytometry analysis was performed on a BD LSRII FACS Analyzer (Stanford University Shared FACS Facility). Laser scanning confocal microscopy was carried out using a Leica SP8 White Light Confocal microscope with a 40×HC PL APO, CS2 oil objective lens (Stanford University Cell Sciences Imaging Facility). Bioluminescence was measured using a charge-coupled device (CCD) camera (IVIS 100, Xenogen Corp., Alameda, CA) and analyzed using Living Image Software (Perkin-Elmer). Epifluorescence microscopy was performed on a Zeiss Axio Observer.Z1 with an X-Cite 120Q wide-field excitation light source and a GFP filter set. Images were acquired with a CoolSNAP HQ$^2$ camera and transferred to a computer for image analysis.

Example 3: Synthetic Methods

Example 3A. Synthetic Methods for the Lysine CART

Example 3A.1. Synthesis of (tert-butyl 3-(4-((tert-butoxycarbonyl)amino)butyl)-2-oxomorpholine-4-carboxylate, $M_{Lys}$ monomer

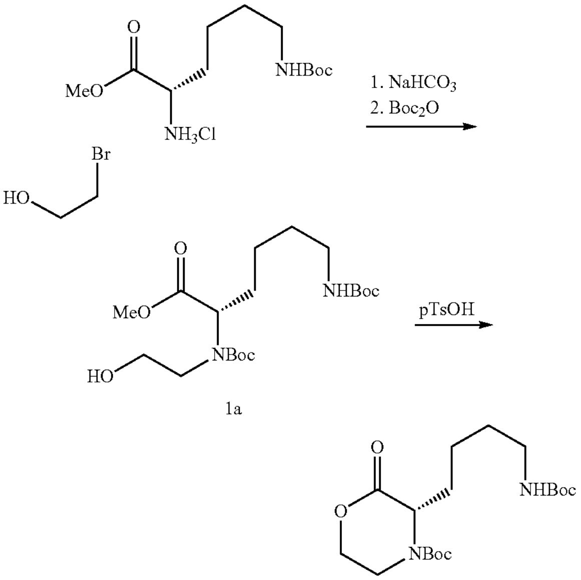

1a

Mlys

Synthesis of $M_{lys}$ precursor (methyl $N^2$,$N^6$-bis(tert-butoxycarbonyl)-$N^2$-(2-hydroxyethyl)lysinate, 1a): A round-bottom flask was charged with N-epsilon-Boc-L-Lysine methyl ester HCl (1.18 g, 4 mmol) and $NaHCO_3$ (750 mg, 8.9 mmol) in 12 mL acetonitrile. This mixture was refluxed for one hour at 85° C., then bromoethanol (300 uL, 4.4 mmol) was added in one portion. The reaction was stirred overnight, filtered, then concentrated. This residue was resuspended in 4 mL MeOH and stirred for 5 minutes before adding $Boc_2O$ in one portion (950 uL, 4.15 mmol). After stirring overnight, the reaction was concentrated under reduced pressure to give 1.7 g yellow residue as the crude product which was loaded onto silica gel and purified via flash chromatography using 2:1 DCM:EtOAc. Concentration of the relevant fractions yielded 857 mg clear residue (2.12 mmol, 53% yield). $^1H$ NMR (400 MHz, d-chloroform): 4.6-4.5 (br, 1H), 4.2-3.75 (m, 2H), 3.7-3.5 (m, 6H), 3.3-3.0 (m, 3H), 2.05-1.75 (m, 4H), 1.55-1.25 (m, 20H)

Synthesis of (tert-butyl 3-(4-((tert-butoxycarbonyl)amino)butyl)-2-oxomorpholine-4-carboxylate, $M_{Lys}$ monomer): The linear alcohol intermediate 1a (140 mg, 0.35 mmol) along with catalytic PTsOH (5 mg, catalytic) was taken up in 15 mL toluene and refluxed at 120° C., monitoring reaction progress by TLC (9:1 DCM:EtOAc). After a total of 20 minutes, the reaction was cooled to room temperature and concentrated under reduced pressure. The crude mixture was loaded onto silica gel and purified via flash chromatography using 9:1 DCM:EtOAc. Concentration of the relevant fractions yielded 115 mg clear residue (0.31 mmol, 89% yield). $^1H$ NMR (400 MHz, d-chloroform): 4.75-4.5 (br, 2H), 4.45-4.3 (br, 2H), 4.0-3.7 (br, 2H), 3.5-3.35 (br, 1H), 3.2-3.0 (br, 2H), 1.9-1.8 (q, 2H), 1.6-1.4 (m, 22H)

Example 3B. Synthesis of Homopolymers

Example 3B.1. Synthesis of p(HE-lysine)

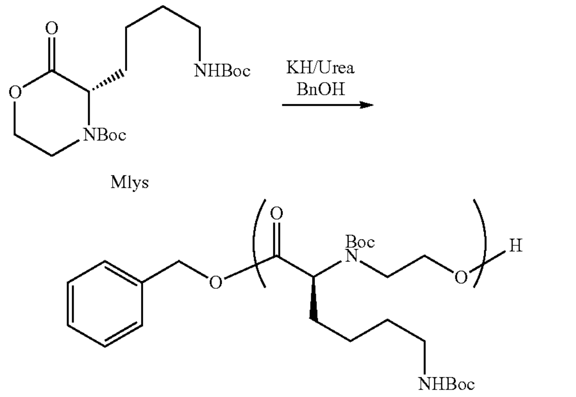

Mlys
p(HE-lys)

Urea/Alkoxide polymerization catalyst

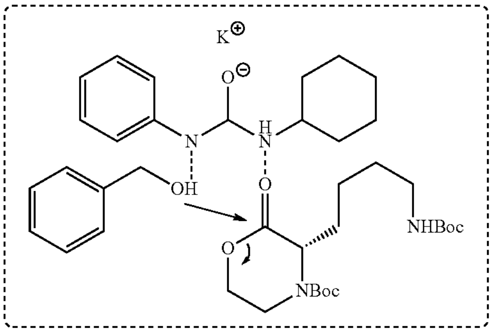

Synthesis of p(HE-lysine): A flame-dried vial was loaded with Mlys (38.5 mg, 0.103 mmol, 54 eq) in 75 uL THF. To this solution was added a mixture of KH (0.08 mg, 0.002 mmol, 1 eq), BnOH (0.2 mg, 0.002 mmol, 1 eq), and urea (1.3 mg, 0.006 mmol, 3 eq) in 25 uL THF. After stirring at R.T. for 30 s, the reaction mixture was submerged in an acetone/dry ice bath at −78° C. The reaction was allowed to stir for 20 minutes, then quenched with 5 uL AcOH in 100 uL THF. After stirring the quenched reaction at −78° C. for 2 minutes, the solution was warmed to room temperature and conversion was determined by $^1H$NMR. The product was then dialyzed in DCM/MeOH overnight (1 kDa dialysis bags). Concentration of dialyzed polymer 1 yielded 31.5 mg clear residue (81% yield). $^1H$ NMR (400 MHz, d-chloroform): 7.45-7.35 (br, 5H), 5.15-5.1 (s, 2H), 5.0-4.75 (br, 32H), 4.54-3.95 (m, 126H), 3.65-2.75 (m, 188H), 2.0-1.65 (br, 106H), 1.6-1.15 (1030H). $^1H$ NMR analysis revealed a homopolymer with block length of 42. This DP was determined by comparing imitator signal (7.35-7.3, 5H) to the signal of the amide proton of the lysine polymer (5.05-4.75, 32H). GPC: Mn=5457, PDI=1.20

Example 3B.2. Synthesis of Dodecyl Macroinitiator

D12

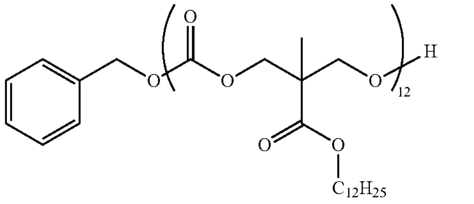

macroinitiator

Synthesis of Dodecyl macroinitiator: To a vial containing dodecyl carbonate (356 mg, 1.1 mmol) and BnOH (11 mg, 0.1 mmol) in 0.5 mL toluene was added a solution of DBU (7.5 mg, 0.05 mmol) and TU (18.5 mg, 0.05 mmol) in 500 uL toluene. The reaction was stirred for 1.5 hours then quenched with 5 drops of AcOH. The reaction was dialyzed in DCM/MeOH overnight. Concentration of the recovered polymer yielded 302 mg clear residue (82% yield). $^1H$ NMR (400 MHz, d-chloroform): 7.45-7.35 (br, 5H), 5.13 (s, 2H), 4.4-4.2 (m, 38H), 4.15-4.05 (t, 21H), 3.75-3.65 (m, 2H), 1.65-1.55 (br, 26H), 1.35-1.15 (220H), 0.9-0.8 (t, 32H)$^1H$ NMR analysis revealed a homopolymer with block lengths of 12. This DP was determined by comparing imitator signal (7.45-7.35, 5H) to the signal of the terminal methyl group of the dodecyl block (0.9-0.8, 32H). GPC Example 3C. Synthesis of Protected CARTs Example 3C.1. Synthesis of D:Lysine CART

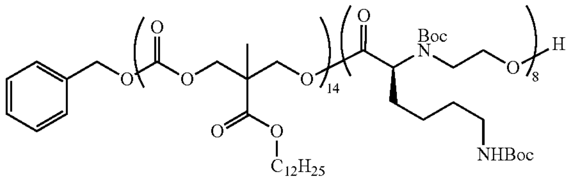

Synthesis of D:Lysine CART: A flame dried vial loaded with DP 12 dodecyl carbonate macroinitiator (58 mg, 0.012 mmol) and Mlys (45 mg, 0.12 mmol), was stirred in 62 uL THF at room temperature for 5 minutes to homogenize the reactants. To this mixture was added a solution of KH (0.6 mg, 0.012 mmol) and Urea 7 (3.3 mg, 0.15 mmol). In 60 uL THF. After stirring at R.T. for 30 s, the reaction was submerged in an acetone/dry ice bath. The reaction was allowed to stir at −78 C for 20 minutes, then quenched with 5 uL AcOH in 100 uL THF. After stirring the quenched reaction at −78 C for 2 minutes, the reaction was warmed to room temperature and analyzed for conversion by $^1$H NMR. The product was then dialyzed in DCM/MeOH overnight (1 kDa dialysis bags). Concentration of the recovered polymer yielded 84 mg clear residue (82% yield). 1H NMR (400 MHz, d-chloroform): 7.4-7.3 (m, 5H), 5.15-5.1 (m, 2H), 4.9-4.5 (br, 7H), 4.5-4.0 (m, 102H), 3.6-3.1 (m, 16H), 3.1-2.95 (br, 16H), 2.0-1.0 (526H), 0.9-0.8 (t, 42H). $^1$H NMR analysis revealed a diblock with dodecyl:$M_{lys}$ block lengths of 14:8. These DPs were determined by comparing initiator signal (7.45-7.35, 5H) to the signal of the lysine block (3.1-2.95, 16H), and signal from dodecyl block (0.9-0.8 ppm, 42H). GPC (in THF): $M_n$ =1.46 kDa, PDI=1.78.

Example 3D. Deprotection of CART Polymers

Example 3D.1. Deprotection of Homolysine

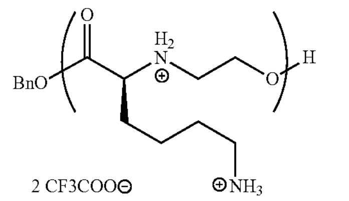

Deprotection of Homolysine: p(HE-lys) polymer (30 mg) was dissolved in 3 mL DCM. To this solution was added 0.3 mL TFA and allowed to stir under $N_2$. After 4 hours, the reaction was concentrated, yielding 33 mg of a foamy tan residue. $^1$H NMR (500 MHz in methanol-$d_4$): 7.45-7.35 (m, 5H), 4.7-4.6 (br, 41H), 4.6-4.5 (40H), 4.3-4.2 (m, 40H), 3.65-3.45 (br, 80H), 3.0-2.9 (br, 81H). 2.2-2.0 (br, 86H), 1.8-1.45 (m, 208H). $^1$H NMR analysis (500 MHz in methanol-$d_4$) revealed a block length of DP 40.

Example 3D.2. Deprotection of D:Lys 14:8

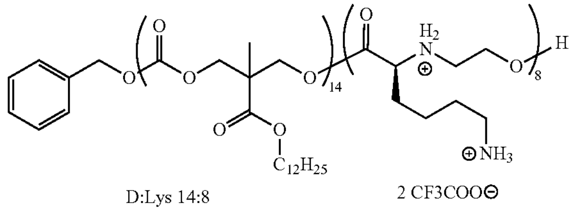

D:Lys 14:8

Deprotection of D:Lys 14:8: $CART_{lys}$ (35 mg) polymer was dissolved in DCM (3.5 mL). To this solution was added TFA (0.35 mL) and allowed to stir under $N_2$. After 4 hours, the reaction was concentrated, yielding 36 mg of a foamy tan residue. $^1$H NMR (500 MHz in methanol-$d_4$): 7.5-7.3 (br, 5H) 5.15 (br, 2H), 4.7-4.0 (m, 105H), 3.65-3.4 (br, 14H), 3.0-2.9 (t, 16H), 2.2-1.9 (br, 15H), 1.8-1.0 (m, 368H), 0.95-0.85 (t, 42H). $^1$H NMR analysis revealed a diblock with D:Mlysine block lengths of 14:8. These DPs were determined by comparing initator signal (5.15-5.1, 2H) to the signal of the lysine block (3.0-2.9, 16H), and signal from dodecyl block (0.95-0.85 ppm, 42H).

Example 3E. Synthetic Methods for the Ornithine-Derived CARTs

Example 3E.1. Synthesis of Ornithine-Derived Morpholinone (Morn) Monomer

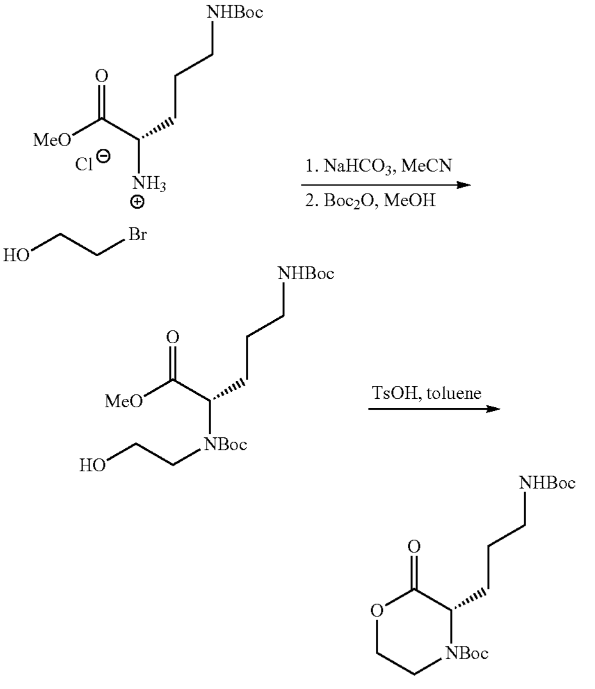

$M_{Orn}$ (56% yield)

Synthesis of ornithine-derived morpholinone. A solution of Nd-Boc-L-ornithine methyl ester hydrochloride (2.0 g, 7.07 mmol, 1.0 eq) and sodium bicarbonate (1.54 g, 18.38 mmol, 2.6 eq) in acetonitrile (21 ml) in a round-bottom flask was refluxed with stirring for 15 min. 2-Bromoethanol (601 μl, 8.49 mmol, 1.2 eq) was added in one shot. The reaction was stirred at reflux for 20 hours, until the consumption of 2-bromoethanol plateaued, as determined by $^1$H NMR. The crude product was cooled, diluted in acetone, and filtered through celite. The solution was concentrated to dryness under reduced pressure and the crude product was resuspended in methanol (7.8 ml). The solution was sparged with nitrogen for 5 minutes, and then to the solution was added di-tert-butyl dicarbonate (1.62 ml, 7.07 mmol, 1.0 eq). The reaction was stirred at room temperature for 15 hours. The solution was concentrated to dryness under reduced pressure to yield the crude product as a yellow oil. Purification by column chromatography (2:1 ethyl acetate:dichloromethane) yielded the product, di-Boc-protected N-hydroxyl ornithine methyl ester as a colorless oil.

A solution of the isolated di-Boc-protected N-hydroxyl ornithine methyl ester and p-toluenesulfonic acid (172 mg) was heated to reflux in toluene. The reaction was stirred at reflux for 45 minutes, after which the solution was concentrated to dryness. Purification by column chromatography (9:1 ethyl acetate:dichloromethane) yielded the product, the ornithine-derived morpholinone ($M_{Orn}$, 1.43 g, 56% yield over 3 steps) as a viscous, white oil We have developed two methods to isolate Ornithine-type CARTs: Reverse block (polymerize ornithine THEN lipid carbonate) and Endcap lipid-ornithine "forward" block with acetic anhydride Example 3E.2. Synthesis of Ornithine-Derived CARTs: Polymerization. Type A. Reverse Block Strategy

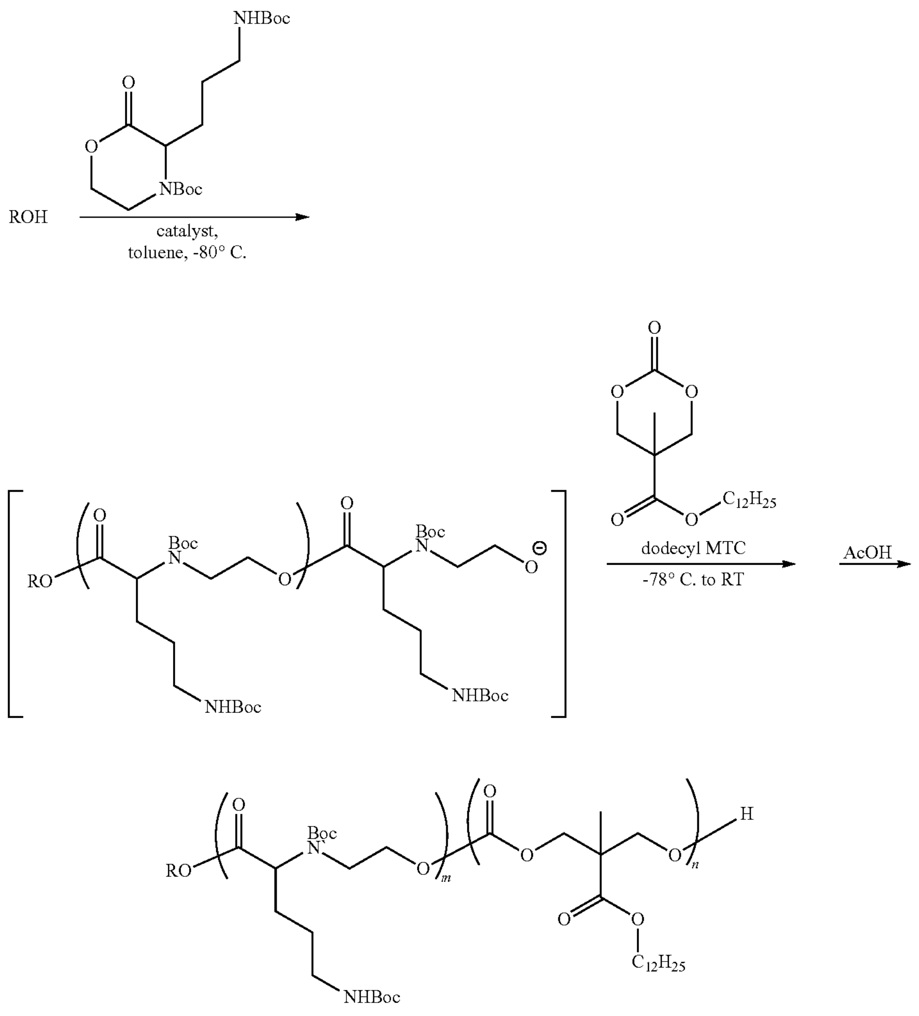

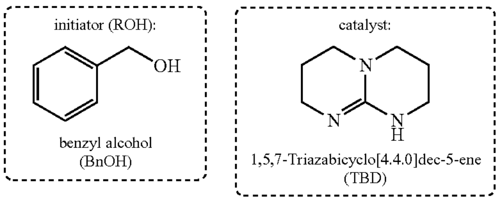

Synthesis of reverse block ornithine-derived CARTs. To a solution of the ornithine-derived morpholinone in toluene was added a solution of an alcohol initiator and a ring-opening polymerization catalyst in toluene under a nitrogen atmosphere. This solution was cooled to −78° C. After 20 min, a solution of lipid-functionalized monomer in toluene was added. The solution was stirred for 10 minutes at −78° C., and then warmed to room temperature and stirred for an additional 7 minutes. A solution of acetic acid in toluene was added. The solution was stirred for two minutes and then concentrated to dryness. The crude residue was redissolved in dichloromethane and then dialyzed (regenerated cellulose tubing, MWCO 1 kD) against methanol for 18 hours. The product was analyzed by $^1H$ NMR analysis to determine the degree of polymerization.

Representative procedure: To a solution of ornithine-derived morpholinone (17.9 mg, 0.05 mmol, 16 eq) in toluene (35 μl) was added a solution of benzyl alcohol (0.32 ul, 0.00313 mmol, 1 eq) and 1,5,7-triazabicyclo[4.4.0]dec-5-ene (0.35 mg, 0.0025 mmol, 0.8 eq) in toluene (15 μl) under a nitrogen atmosphere. The solution was cooled to −78° C. and stirred for twenty minutes, at which point a solution of dodecyl MTC (19.7 mg, 19.2 eq) in toluene (50 μl) was added. The solution was stirred for 10 minutes at −78° C., and then warmed to room temperature and stirred for an additional 7 minutes. A solution of acetic acid (5 drops) in toluene (100 μl) was added. The solution was stirred for two minutes and then concentrated to dryness. The crude residue was redissolved in dichloromethane and then dialyzed (regenerated cellulose tubing, MWCO 1 kD) against methanol for 18 hours to yield a clear oil (19.6 mg). $^{1}$H NMR analysis reveals an oligomer with 7 ornithine units and 14 dodecyl MTC units.

Example 3E.3. Synthesis of Ornithine-Derived CARTs: Polymerization. Type B. Forward Block, End-Capping Strategy

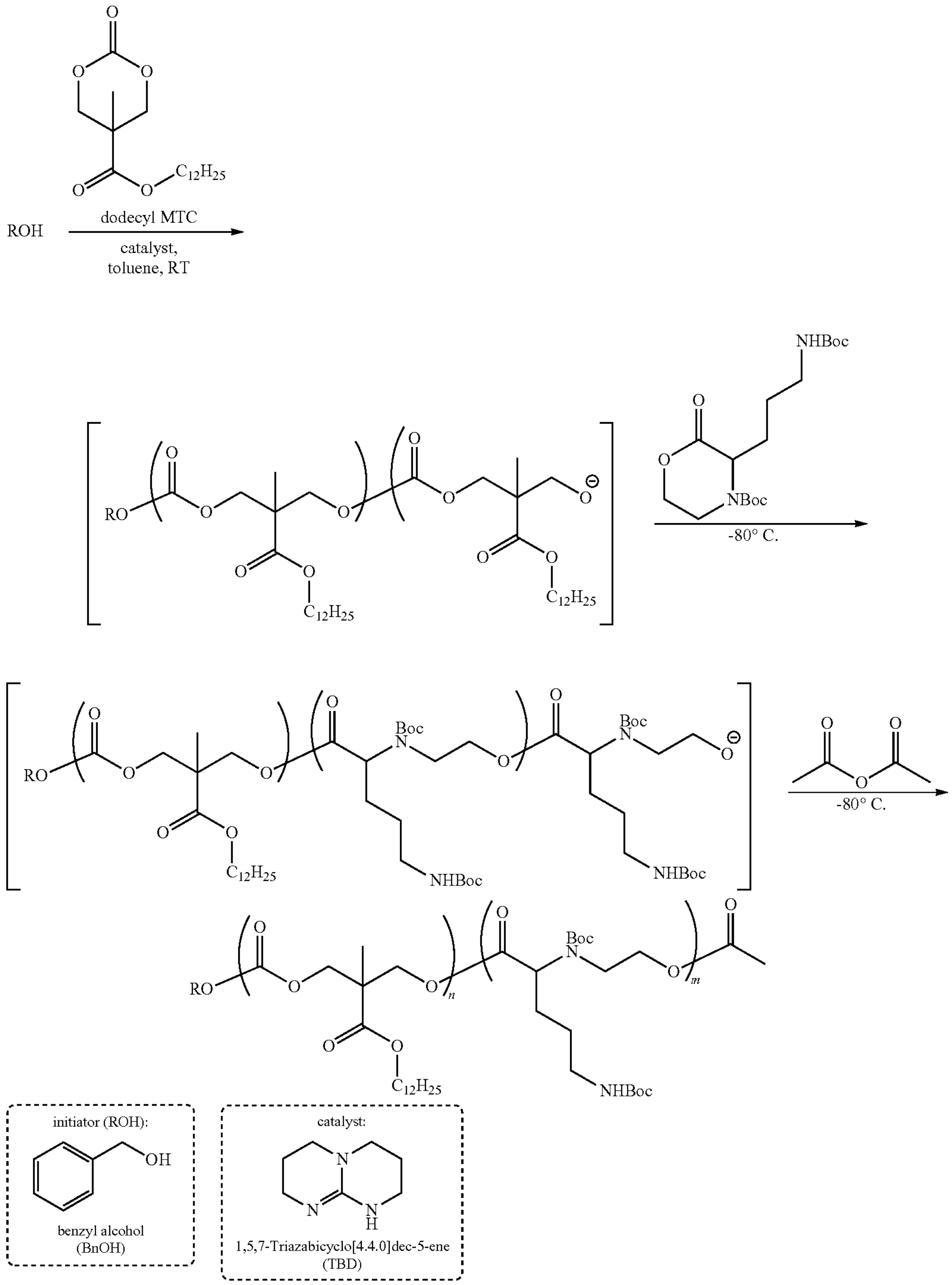

Synthesis of forward block ornithine-derived CARTs. To a solution of dodecyl MTC in toluene was added a solution of an alcohol initiator and a ring-opening polymerization catalyst in toluene under a nitrogen atmosphere. This solution was stirred at room temperature. After 7 min, the solution of dodecyl MTC, initiator, and catalyst was added to a solution of ornithine-derived morpholinone in toluene. The solution was cooled to −78° C. and stirred for 15 min, after which point a solution of acetic anhydride in toluene was added. This was allowed to warm to room temperature. The crude residue was redissolved in dichloromethane and then dialyzed (regenerated cellulose tubing, MWCO 1 kD) against methanol for 18 hours. The product was analyzed by $^1$H NMR analysis to determine the degree of polymerization.

Representative procedure: To a solution of dodecyl MTC (17.9 mg, 0.5 mmol, 13 eq) in toluene (35 µl) was added a solution of benzyl alcohol (0.40 d, 0.0038 mmol, 1 eq) and 1,5,7-triazabicyclo[4.4.0]dec-5-ene (0.35 mg, 0.0025 mmol, 0.8 eq) in toluene (15 µl) under a nitrogen atmosphere. This solution was stirred at room temperature. After 7 min, the solution of dodecyl MTC, initiator, and catalyst was added to a solution of ornithine-derived morpholinone (23.4 mg, in toluene. The solution was cooled to −78° C. and stirred for 15 min, after which point a solution of acetic anhydride (18 µl, 0.19 mmol, 50 eq) in toluene (40 µl) was added. This was allowed to warm to room temperature. The crude residue was redissolved in dichloromethane and then dialyzed (regenerated cellulose tubing, MWCO 1 kD) against methanol for 18 hours to yield a clear oil (25.4 mg). $^1$H NMR analysis reveals an oligomer with 15 ornithine units and 16 dodecyl MTC units.

Example 3E.4. Synthesis of Ornithine-Derived CARTs: Deprotection. Type A. Reverse Block

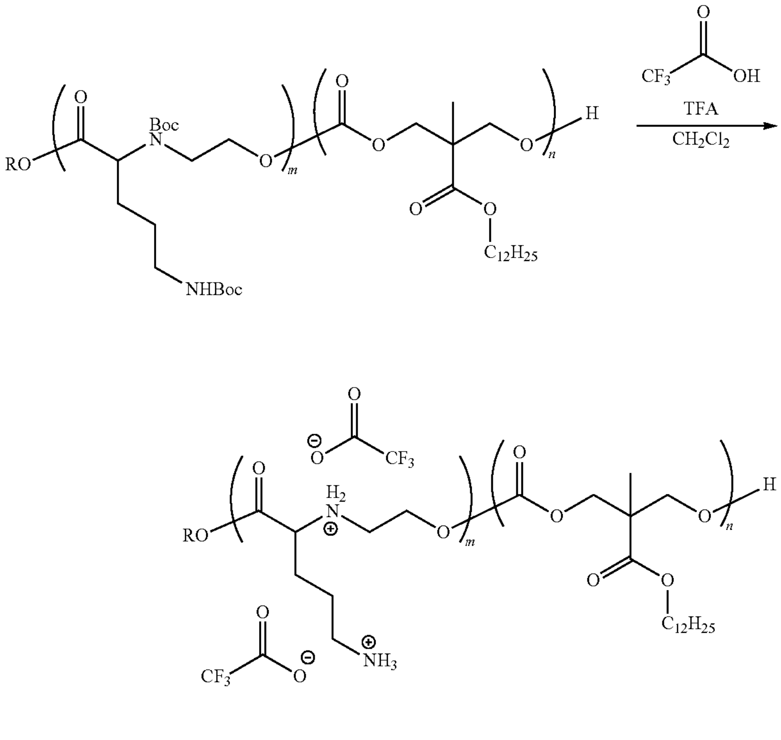

Deprotection of reverse block ornithine-derived CARTs. To a solution of a reverse block ornithine CART in dry, degassed dichloromethane was added trifluoroacetic acid. The solution was stirred under a nitrogen atmosphere for 4 hours, after which point the product was concentrated to dryness to yield a clear oil. The product was dissolved in dimethyl sulfoxide to make a 2 mM solution and was used in in vitro and in vivo experiments without further purification.

Representative procedure: To a solution of a reverse block ornithine CART (m=7, n=14, 6.0 mg, 0.83 mmol) in dry, degassed dichloromethane (600 µl) was added trifluoroacetic acid (60 µl). The solution was stirred under a nitrogen atmosphere for 4 hours, after which point the product was concentrated to dryness to yield a clear oil (4.1 mg). The product was dissolved in dimethyl sulfoxide to make a 2 mM solution and was used in in vitro and in vivo experiments without further purification.

Example 3E.5. Synthesis of Ornithine-Derived CARTs: Deprotection. Type B. Forward Block

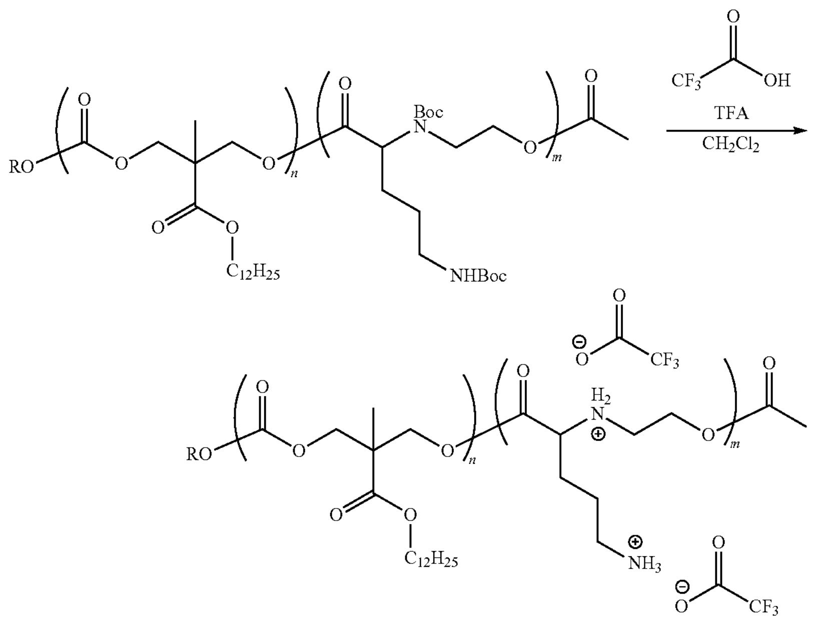

Synthesis of forward block ornithine-derived CARTs. To a solution of a forward block ornithine CART in dry, degassed dichloromethane was added trifluoroacetic acid. The solution was stirred under a nitrogen atmosphere for 4 hours, after which point the product was concentrated to dryness to yield a clear oil. The product was dissolved in dimethyl sulfoxide to make a 2 mM solution and was used in in vitro and in vivo experiments without further purification.

Representative procedure: To a solution of a forward block ornithine CART (n=16, m=15, 5.3 mg, 0.49 mmol) in dry, degassed dichloromethane (530 μl) was added trifluoroacetic acid (53 μl). The solution was stirred under a nitrogen atmosphere for 4 hours, after which point the product was concentrated to dryness to yield a clear oil (6.0 mg). The product was dissolved in dimethyl sulfoxide to make a 2 mM solution and was used in in vitro and in vivo experiments without further purification.

Example 4: Polymer Degradation Kinetics

Figure 1A:
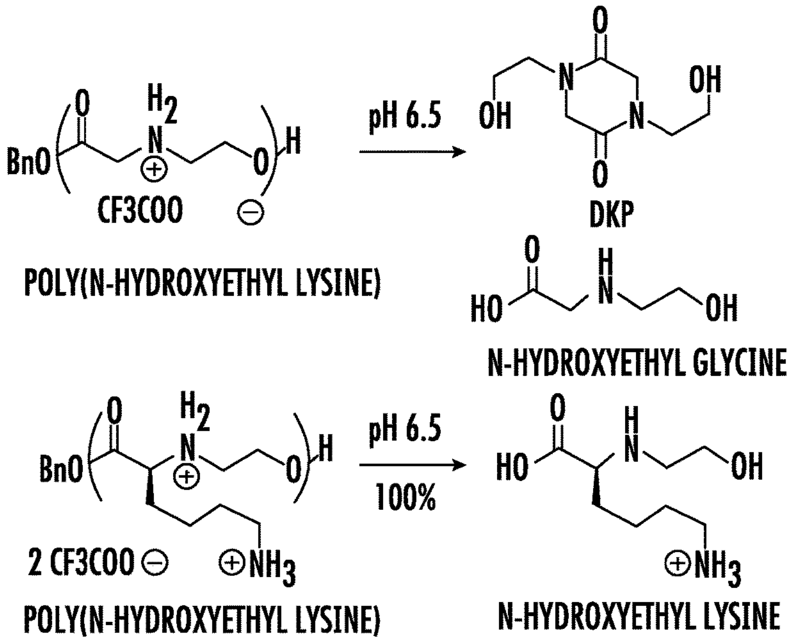
FIGS. 1A-1D shows polymer degradation kinetics.
Figure 1B:
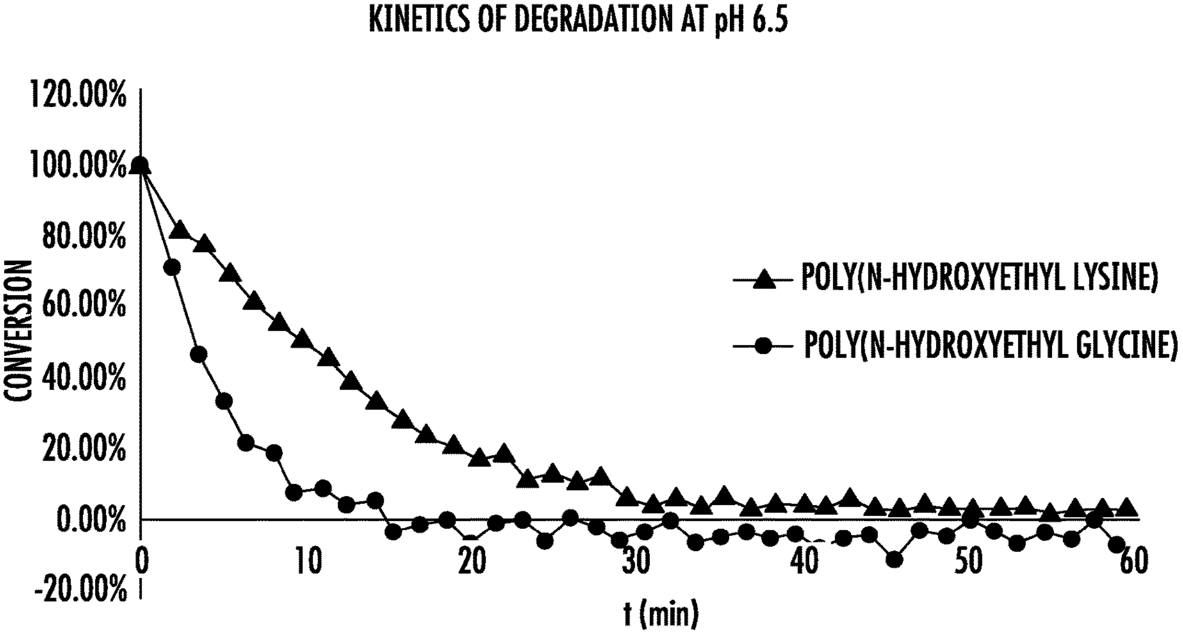
Figure 1C:
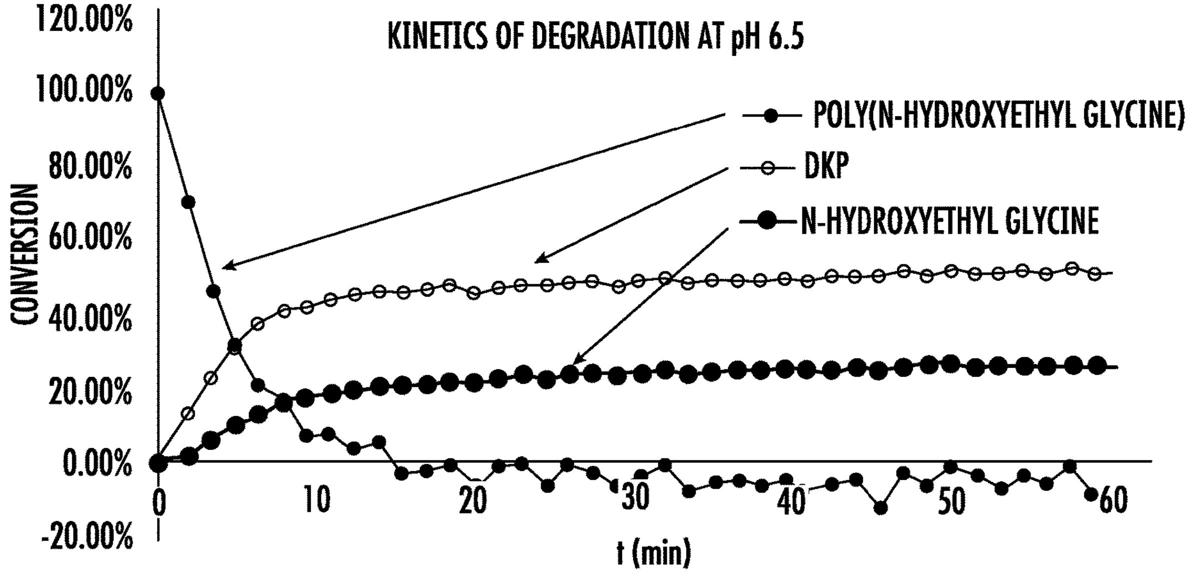
Figure 1D:
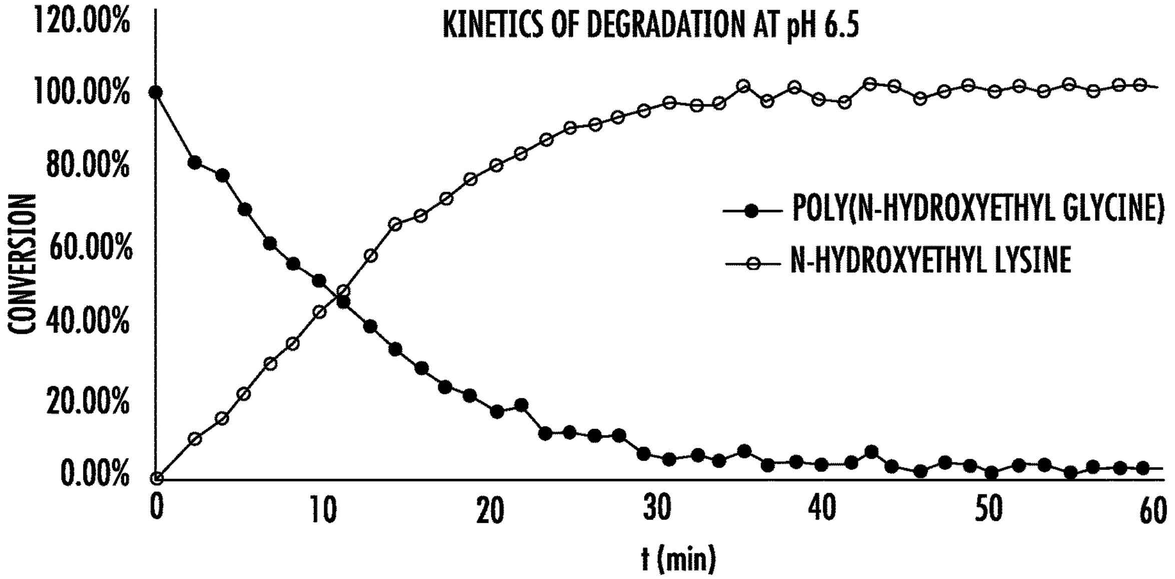

Several homo-polymers (FIG. 1A) were dissolved in pH 6.5 buffer and monitored for degradation products using 1H NMR. Both the rate of degradation and degradation product are different than the rate of degradation and degradation products that result from the original cationic poly-alpha aminoester backbone (FIG. 1B-D). Poly(N-hydroxyethyl lysine) shows a significantly different rate of degradation than poly(hydroxyethyl glycine). Poly(N-hydroxyethyl lysine) as a half-life of approximately 12 minutes, while poly(hydroxyethyl glycine) has a half-life of approximately 3 minutes.

Example 5: Nanoparticle (NP) Characterization

Figure 2A:
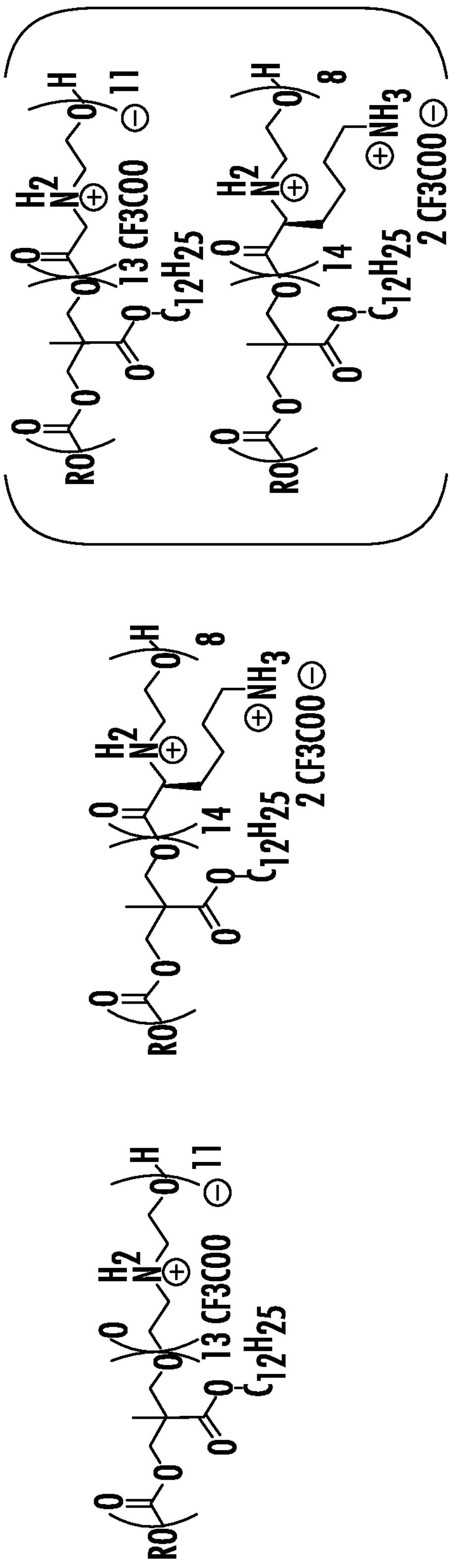
FIGS. 2A-2D show mRNA-CART (cationic charge altering releasable transporter) NP (nanoparticle) characterization data for CART-Gly (glycine), CART-Lys (lysine), and CART-Mix.
Figure 2B:
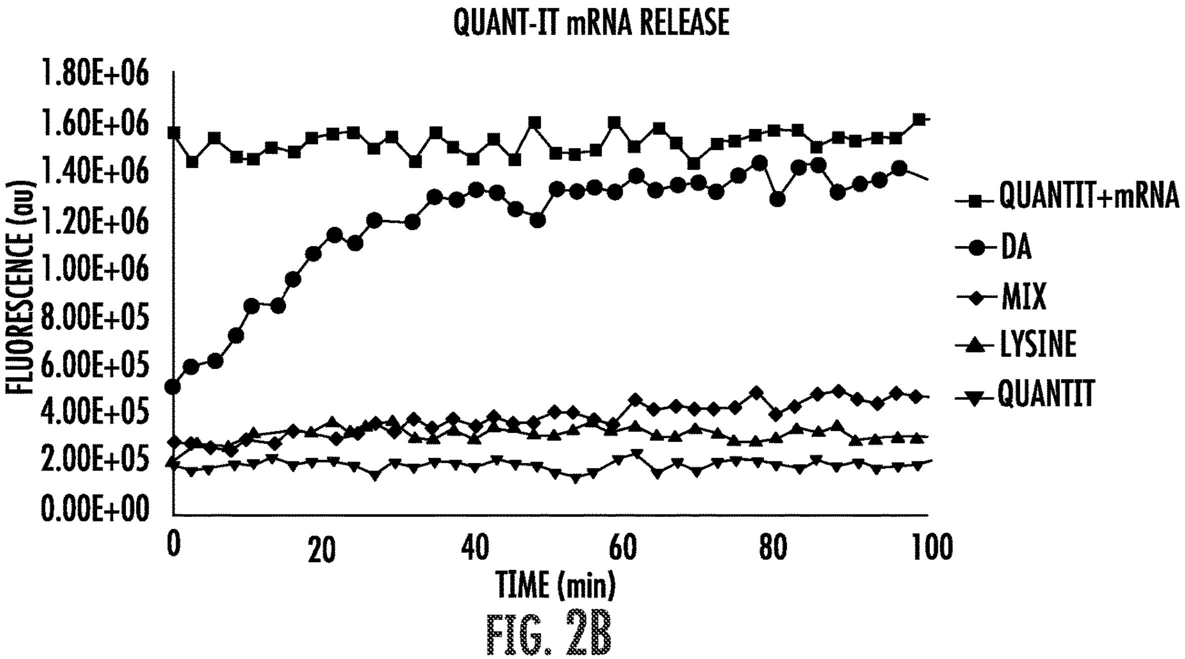
Figure 2C:
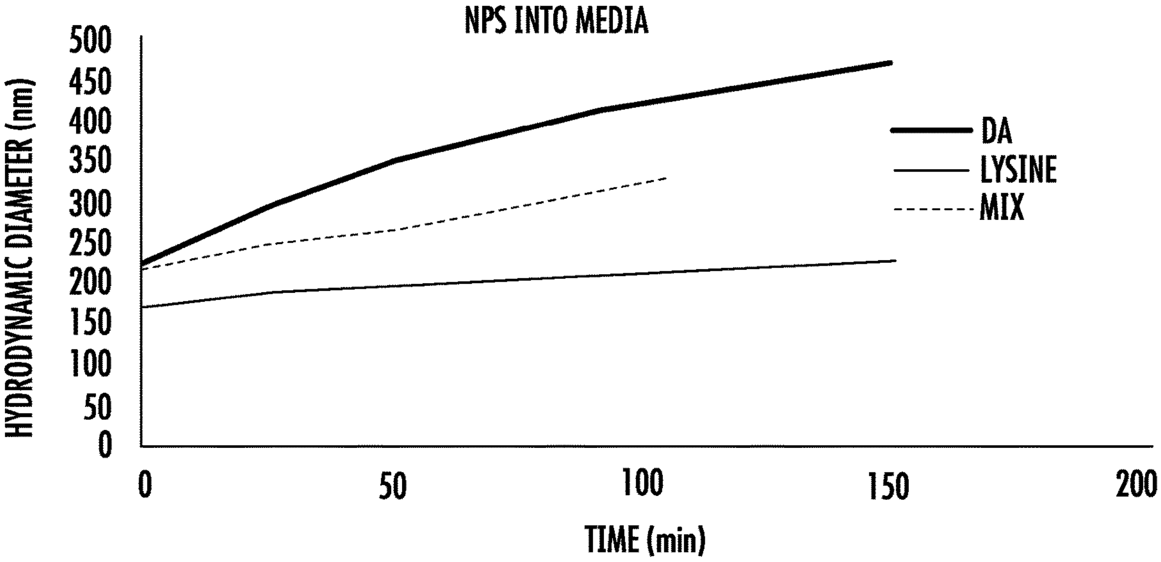
Figure 2D:
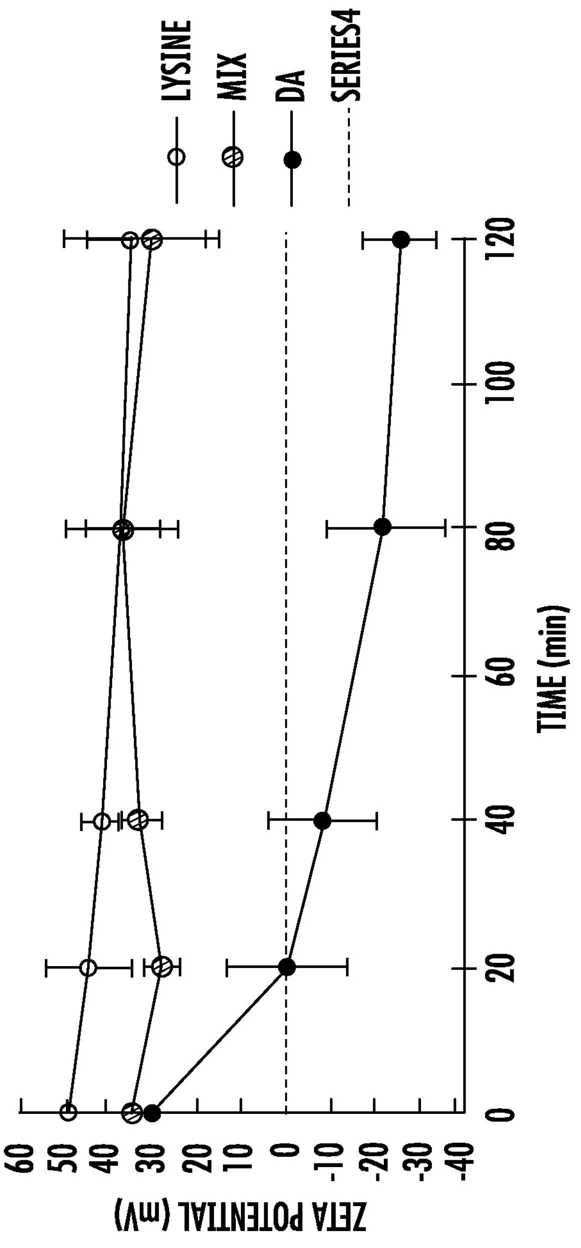

NP formation when complexed with mRNA was determined by DLS. A 1:1 mixture (CART-mix) of CART-gly and CART-lys was also studied. Both CART-lys and the 1:1 mixture of CART-gly and CART-lys form smaller NPs than CART-gly (FIG. 2A). Monitoring the change in size over time revealed that CART-lys and CART-mix maintained their initial size more than CART-gly (FIG. 2C). Zeta potential measurements show a rapid decrease in cationic character within 20 min for CART-gly, while CART-lys and CART-mix unexpectedly maintain a positive zeta potential for over 2 hours (FIG. 2D). An mRNA release assay shows a similar trend, where mRNA is released from the CART-gly-NPs within one hour and CART-lys and CART-mix maintain mRNA encapsulation over 100 minutes (FIG. 2B).

Example 6: In Vitro and Reporter Toxicity Assays

Figure 3A:
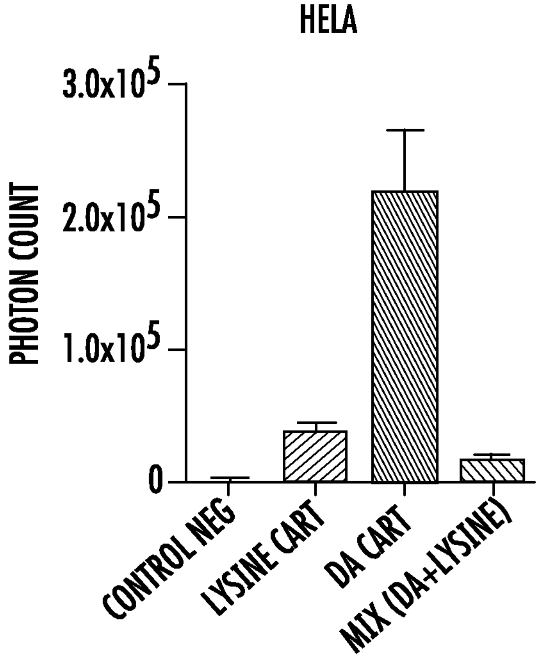
FIGS. 3A-3F show the in vitro reporter and toxicity assays. In vitro delivery assays: Treatment of HeLa, DC 2.4, and LLC (Lewis Lung Cell carcinoma) show a cell line specific transfection efficiency between CARTs; CART-Gly shows superior transfection in HeLa and DC2.4 cells; CART-lys shows superior transfection in LLCs. In vitro toxicity assays: MTT proliferation assay was performed after a 3 day incubation with: CART-Gly, CART-Lys, CART-mix, CART-Gly alone, CART-Lys alone and the lysine degradation product, hydroxyethyl lysine; Cellular viability was not affected by any of the conditions
Figure 3B:
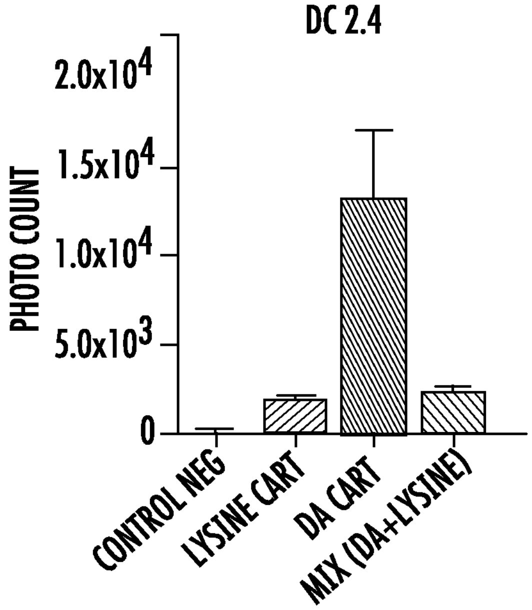
Figure 3C:
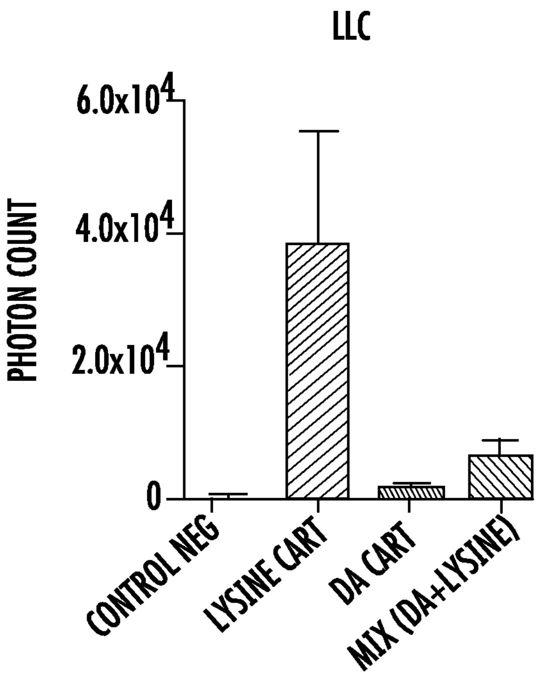

In vitro delivery assays: Treatment of HeLa, DC 2.4, and LLC (lewis lung cell carcinoma) show a cell line specific transfection efficiency between CARTs (FIG. 3A-C). CART-Gly shows superior transfection in HeLa and DC2.4 cells (FIG. 3B-C). CART-lys shows superior transfection in LLCs (FIG. 3C).

Figure 3D:
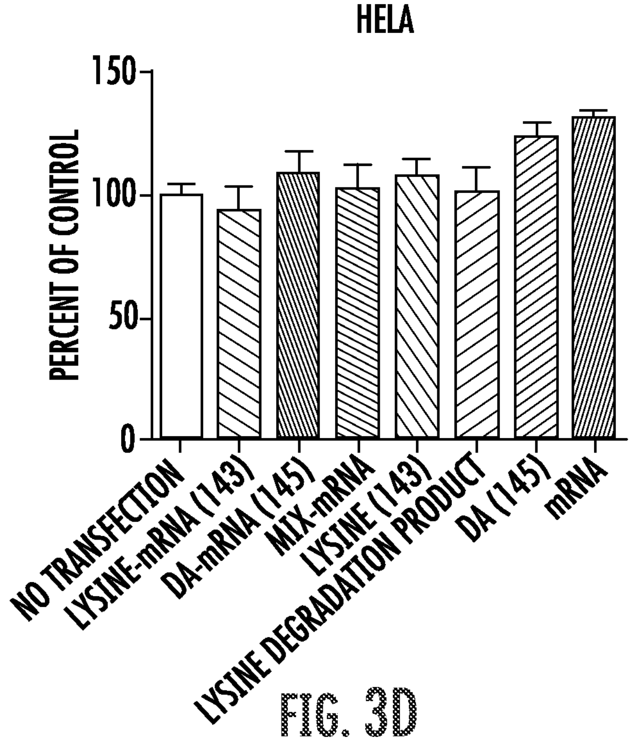
Figure 3E:
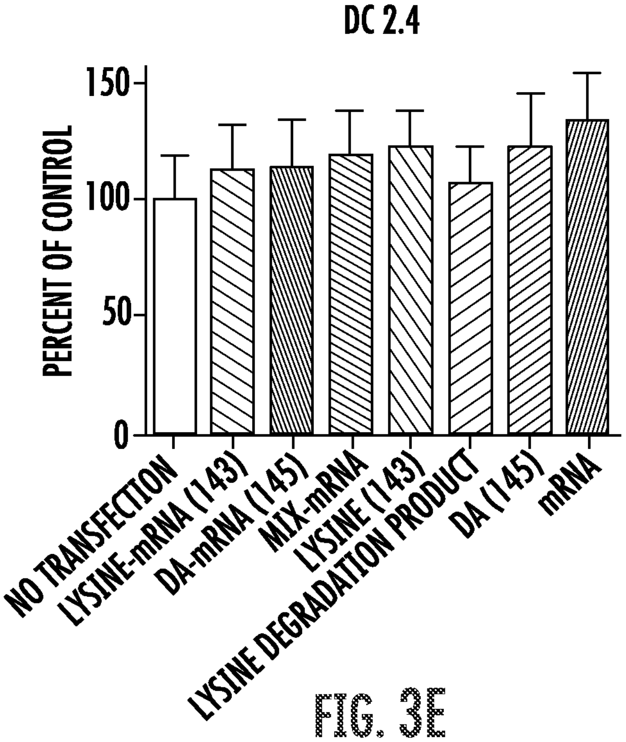
Figure 3F:
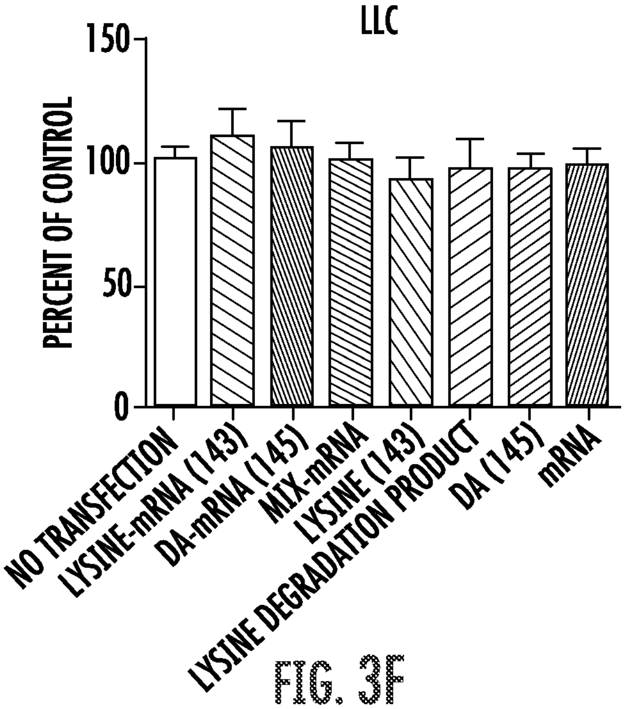

In vitro toxicity assays: MTT proliferation assay was performed after a 3 day incubation with: CART-Gly, CART-Lys, CART-mix, CART-Gly alone, CART-Lys alone and the lysine degradation product, hydroxyethyl lysine (FIG. 3D-F). Cellular viability was not affected by any of the conditions.

Example 7: In Vivo Cation Mixture Screen

Figure 4A:
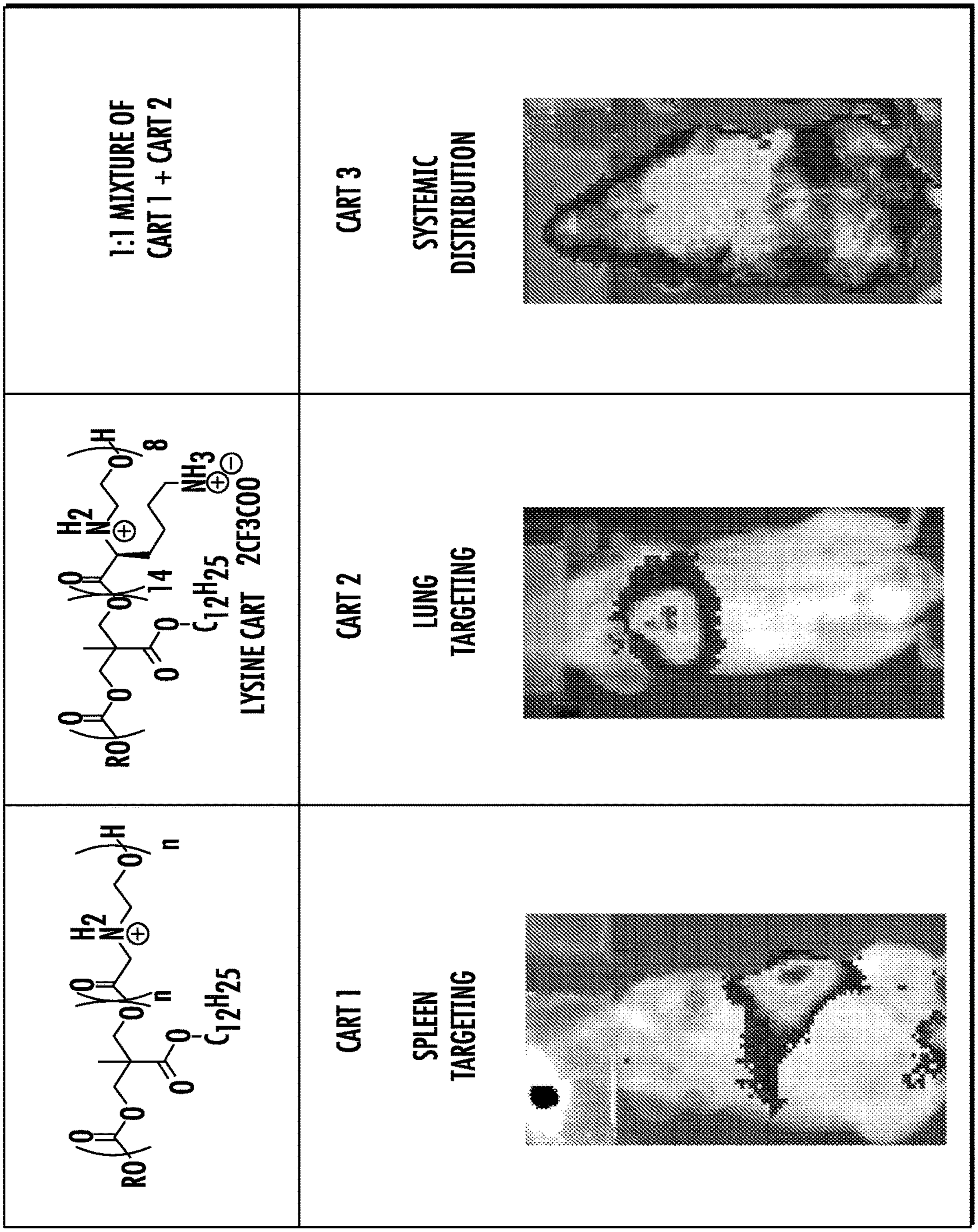
FIGS. 4A-4B show an in vivo cation mixture screen.
Figure 4B:
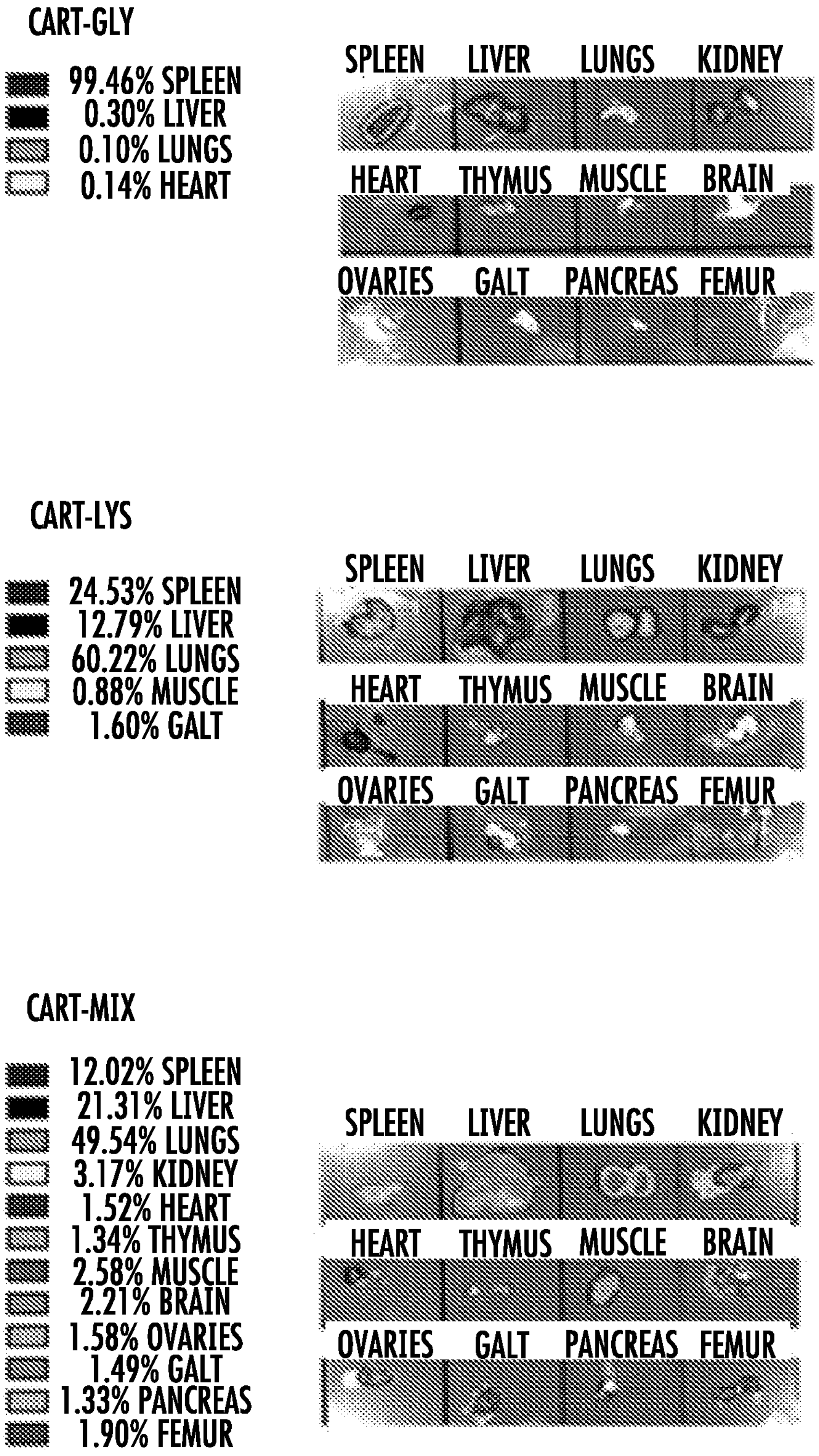

CART-lys targets the lung with high selectivity, which was not anticipated (FIG. 4A) In addition, CART-mix delivers mRNA systemically, which also was not anticipated (FIG. 4A).

Example 8: Fluorescent CARTs Used for Phenotyping

Previously shown that cellular signal from reporter gene and cellular signal from the CART fluorophore are strongly correlated. This fluorophore tag allows for cellular phenotyping by FACS.

IV administration of BDK-labeled CARTs: after 6 hours mice sacrificed, lung and spleen harvested then homogenized. Of the individual organs, high levels of cells were transfected with mRNA. In the spleen there are high percentages of CART-gly, with a small population when BDK-CART-lys is administered (FIG. 5A). A high population of lung cells are transfected with BDK-CART-lys (FIG. 5B).

Example 9: Pathological Studies and Histologic Findings

Microscopic Findings: Examined are sections of heart, lung, liver, spleen, kidney, cerebrum, cerebellum, eyes, reproductive tract, salivary gland, pancreas, tongue, trachea, thyroid gland, esophagus, stomach, small intestine, large intestine, white adipose tissue, brown adipose tissue, thymus, lymph nodes, and haired skin. All tissues examined are histologically within normal limits.

Diagnosis: Body as a whole within normal limits. Comments: sections from the various organs examined in this animal (see above for list of organs) were histologically within normal limits. There were no obvious changes that could be resolved by light microscopy in H&E-stained slides (FIG. 6A-B).

Example 10: Conclusions

We developed new chemistries to enable novel families of CARTs (polymerization unanticipated).

The cationic portion of new polymers degrade to different products at different rates than the original CARTs.

New CARTs form stable nanoparticles that retain cationic charge and encapsulate mRNA much longer than original CARTs (>2 h vs. ~20 min). This alters the physical properties of the CART NPs which could lead to the observed tissue selectivity.

In lung carcinoma cells, CART-lys outperforms CART-gly, but in HeLas and CART-gly performs much better.

In vivo IV administration of CART-gly selectively targeted the spleen (99%), while CART-lys targets the lungs (~60%) (COMPLETELY unanticipated).

Mixing the two CARTs in a 1:1 ratio results in SYSTEMIC DELIVERY after IV injection (2:1 has similar effect). This includes some transfection of the brain, which is to our knowledge has never been reported.

CARTs have no acute toxicity or pathology.

REFERENCES

Dove A P, Pratt R C, Lohmeijer B G G, Waymouth R M, Hedrick J L (2005) Thiourea-based bifunctional organocatalysis: Supramolecular recognition for living polymerization. J Am Chem Soc 127:13798-13799.

McKinlay C J, et al. (2017) Charge-altering releasable transporters (CARTs) for the delivery and release of mRNA in living animals. Proc Natl Acad Sci USA 114: E448-E456.

Geihe E I, et al. (2012) Designed guanidinium-rich amphipathic oligocarbonate molecular transporters complex, deliver and release siRNA in cells. Proc Natl Acad Sci USA 109:13171-13176.

Blake T R, Waymouth R M (2014) Organocatalytic ring-opening polymerization of morpholinones: New strategies to functionalized polyesters. J Am Chem Soc 136: 9252-9255.

What is claimed is:

1. A composition comprising a mixture of a first cationic amphipathic polymer of formula A or B:

Formula A

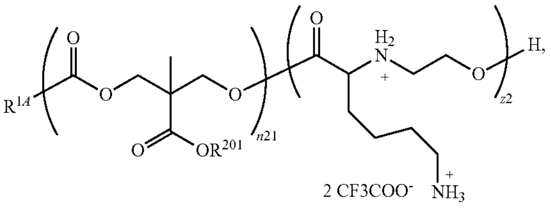

wherein n21 is 10-35 and z2 is 3-20;

or

Formula B

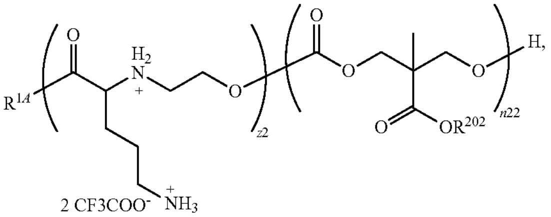

wherein n22 is 10-35 and z2 is 3-20;

wherein $R^{1A}$ is hydrogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and $R^{201}$, $R^{202}$ are each independently stearyl, oleyl, linoleyl, dodecyl, nonenyl, or cholesterol;

and a second cationic amphipathic polymer of formula C:

Formula C

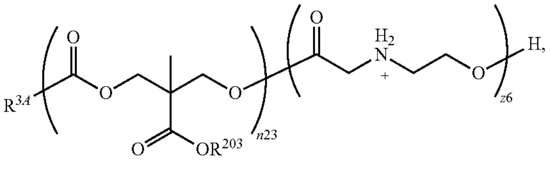

wherein n23 is 1-100, z6 is 5-15, $R^{3A}$ is hydrogen, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)

$NHNH_2$, —$NHC(O)NH_2$, —$NHSO_2H$, —NHC(O)H, —NHC(O)OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and $R^{203}$ is stearyl, oleyl, linoleyl, dodecyl, nonenyl, or cholesterol.

2. The composition of claim 1, wherein n21 is 10-20 and z2 is 3-15 or n22 is 10-20 and z2 is 3-15; and n23 is 10-20 and z6 is 5-15.

3. The composition of claim 2, wherein one or both of $R^{201}$ and $R^{202}$ is dodecyl.

4. The composition of claim 1, wherein the mixture comprises a 1:1 mixture of the first and second cationic amphipathic polymers.

5. The composition of claim 1 wherein each of the first and second cationic amphipathic polymers is non-covalently bound to a nucleic acid to form a plurality of cell-penetrating complexes.

6. The composition of claim 5, wherein the nucleic acid is messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, or genomic DNA (gDNA).

7. The composition of claim 6, wherein the nucleic acid is mRNA.

8. A pharmaceutical composition comprising the cell-penetrating complexes of claim 5, and a pharmaceutical excipient.

9. The pharmaceutical composition of claim 8, wherein the nucleic acid is messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, or genomic DNA (gDNA).

10. The pharmaceutical composition of claim 9, wherein the nucleic acid is mRNA.

11. The pharmaceutical composition of claim 8, wherein the first cationic amphipathic polymer is a polymer of formula A.

12. The pharmaceutical composition of claim 11, wherein n21 is 10-20 and z2 is 3-15, n23 is 10-20 and z6 is 5-15, $R^{201}$ is dodecyl, and $R^{203}$ is stearyl, oleyl, linoleyl, dodecyl, nonenyl, or cholesterol.

13. A method of transfecting a nucleic acid into a cell, wherein the method comprises contacting the cell with the cell-penetrating complexes of claim 5.

14. The method of claim 13, wherein the cell is a lung cell, a reticulocyte cell or a hematopoietic stem cell.

15. The method of claim 14, wherein the cell is in vitro or ex vivo.

16. The method of claim 15, wherein the nucleic acid is mRNA.

17. The method of claim 16, wherein the first cationic amphipathic polymer is a polymer of formula A.

18. The method of claim 17, wherein n21 is 10-20 and z2 is 3-15, n23 is 10-20 and z6 is 5-15, $R^{201}$ is dodecyl, and $R^{203}$ is stearyl, oleyl, linoleyl, dodecyl, nonenyl, or cholesterol.

19. The method of claim 18, wherein the cell is a reticulocyte cell.

20. A method of transfecting a nucleic acid into a reticulocyte cell of a subject, the method comprising administering to the subject the pharmaceutical composition of claim 12.

* * * * *